US011219432B2

(12) United States Patent
Harrison et al.

(10) Patent No.: US 11,219,432 B2
(45) Date of Patent: Jan. 11, 2022

(54) APPARATUS AND METHODS FOR LOADING SUTURE

(71) Applicant: Anchor Orthopedics XT Inc., Mississauga (CA)

(72) Inventors: Robert Harrison, Milton (CA); Andrew Oldham, Etobicoke (CA); Aye Nyein San, Mississauga (CA); Neil Godara, Milton (CA); Jeffery Arnett, Gilbert, AZ (US)

(73) Assignee: Anchor Orthopedics XT Inc., Mississauga (CA)

( * ) Notice: Subject to any disclaimer, the term of this patent is extended or adjusted under 35 U.S.C. 154(b) by 1277 days.

(21) Appl. No.: 14/853,095

(22) Filed: Sep. 14, 2015

(65) Prior Publication Data

US 2016/0000422 A1 Jan. 7, 2016

Related U.S. Application Data

(63) Continuation-in-part of application No. PCT/IB2014/059847, filed on Mar. 15, 2014.
(Continued)

(51) Int. Cl.
*A61B 17/04* (2006.01)
*A61B 17/00* (2006.01)
(Continued)

(52) U.S. Cl.
CPC .......... *A61B 17/00* (2013.01); *A61B 17/0469* (2013.01); *A61B 17/0483* (2013.01);
(Continued)

(58) Field of Classification Search
CPC .......... A61B 17/0469; A61B 17/06004; A61B 17/06114; A61B 17/0483; A61B 17/06;
(Continued)

(56) References Cited

U.S. PATENT DOCUMENTS 3,901,244 A    8/1975    Schweizer
4,841,888 A    6/1989    Mills et al.
(Continued)

FOREIGN PATENT DOCUMENTS

EP    0174843 B1    12/1991
EP    1839585 B1    10/2007
(Continued)

OTHER PUBLICATIONS

Corresponding European Application, Supplementary European Search Report, dated Sep. 30, 2016.
(Continued)

*Primary Examiner* — Katherine M Rodjom
(74) *Attorney, Agent, or Firm* — Nir Lifshitz; Glenn Arnold; Vincent Man

(57) ABSTRACT

Various embodiments of a cartridge for loading a suture onto a suturing instrument are disclosed. In some embodiments, the cartridge is operable for loading a pre-tied knot formed from the suture onto the suturing instrument. The suturing instrument is typically of the type having a suture passing member defining a suture receiving passage therein. In some embodiments, the cartridge comprises a housing defining a chamber, and a partially pre-tied knot mounted about the housing or the chamber. The cartridge additionally provides a base coupled to the housing, the base defining a seat for releasably holding a portion of a suture to be aligned with, and transferred to, the suturing instrument. The portion of the suture may be held independently, or it may be coupled to a component such as a ferrule or shuttle.

25 Claims, 74 Drawing Sheets

Related U.S. Application Data

(60) Provisional application No. 61/791,469, filed on Mar. 15, 2013.

(51) Int. Cl.
*A61B 17/062* (2006.01)
*A61B 90/00* (2016.01)
*A61M 25/01* (2006.01)
*A61B 17/06* (2006.01)

(52) U.S. Cl.
CPC .......... *A61B 17/0491* (2013.01); *A61B 17/06* (2013.01); *A61B 17/06004* (2013.01); *A61B 17/0625* (2013.01); *A61B 90/39* (2016.02); *A61M 25/0108* (2013.01); *A61B 17/0482* (2013.01); *A61B 2017/0053* (2013.01); *A61B 2017/0409* (2013.01); *A61B 2017/0419* (2013.01); *A61B 2017/0474* (2013.01); *A61B 2017/0477* (2013.01); *A61B 2017/06009* (2013.01); *A61B 2017/06052* (2013.01); *A61B 2090/3966* (2016.02)

(58) Field of Classification Search
CPC ............. A61B 2017/0474; A61B 2017/06009; A61B 2017/0477
See application file for complete search history.

(56) References Cited

U.S. PATENT DOCUMENTS

| | | | |
|---|---|---|---|
| 5,478,345 | A | 12/1995 | Stone et al. |
| 5,733,293 | A | 3/1998 | Scirica et al. |
| 5,814,069 | A | 9/1998 | Schulze et al. |
| 6,533,796 | B1 * | 3/2003 | Sauer ............... A61B 17/0469 606/144 |
| 6,638,283 | B2 | 10/2003 | Thal |
| 8,821,520 | B2 | 9/2014 | Schwemberger et al. |
| 9,370,354 | B1 | 6/2016 | Martin et al. |
| 2004/0092967 | A1 | 5/2004 | Sancoff et al. |
| 2004/0193217 | A1 | 9/2004 | Lubbers et al. |
| 2006/0142784 | A1 * | 6/2006 | Kontos .............. A61B 17/0057 606/139 |
| 2007/0162052 | A1 | 7/2007 | Hashimoto et al. |
| 2007/0203508 | A1 | 8/2007 | White et al. |
| 2007/0213745 | A1 | 9/2007 | Takemoto et al. |
| 2008/0275474 | A1 | 11/2008 | Martin et al. |
| 2010/0268274 | A1 | 10/2010 | Williams |
| 2011/0082471 | A1 * | 4/2011 | Holcomb ........... A61B 17/0401 606/139 |
| 2013/0023905 | A1 | 1/2013 | Kubalak |

FOREIGN PATENT DOCUMENTS

| | | |
|---|---|---|
| JP | S61122852 A1 | 6/1986 |
| JP | 2000116659 A | 4/2000 |
| JP | 2010525894 A | 7/2010 |
| JP | 2010525895 A | 7/2010 |
| JP | 2012523914 A | 10/2012 |
| WO | 97/22300 A1 | 6/1997 |
| WO | 0230294 A1 | 4/2002 |
| WO | 2008137537 A2 | 11/2008 |
| WO | 2013024466 | 2/2013 |
| WO | 2013142487 A1 | 9/2013 |

OTHER PUBLICATIONS

Corresponding European Application, European Search Opinion, dated Oct. 12, 2016.
Corresponding European Application, Communication pursuant to Art 94(3) EPC, dated Oct. 19, 2018.
Patent Corporation Treaty, International Search Report for PCT Application No. PCT/IB2014/059847, dated Aug. 21, 2014.
Patent Corporation Treaty, International Preliminary Report on Patentability, PCT Application No. PCT/B2014/059847, dated Sep. 15, 2015.
Patent Corporation Treaty, Written Opinion for PCT Application No. PCT/IB2014/059847, dated Aug. 21, 2014.
Corresponding Canadian Application, Examiner Requisition, dated Jun. 18, 2019.
Corresponding Japanese Application, Office Action, dated Dec. 27, 2017.
Corresponding Japanese Application, Office Action, dated Aug. 24, 2018.
Related U.S. Application, Non-Final Rejection, dated Sep. 6, 2019.
Related U.S. Application, Final Rejection, dated Mar. 18, 2020.
Related Application, Patent Corporation Treaty, International Search Report for PCT Application No. PCT/B2014/064608, dated Mar. 5, 2015.
Related Application, Patent Corporation Treaty, Written Opinion for PCT Application No. PCT/IB2014/064608, dated Mar. 5, 2015.
Related Application, Patent Corporation Treaty, International Preliminary Report on Patentability, PCT Application No. PCT/IB2014/064608, dated Sep. 20, 2016.
Related European Application, Supplementary European Search Report, dated Oct. 18, 2017.
Related European Application, European Search Opinion, dated Oct. 18, 2017.
Related European Application, Communication pursuant to Art 94(3) EPC, dated Jul. 27, 2018.
Related European Application, Communication pursuant to Art 94(3) EPC, dated Mar. 7, 2019.
Related European Application, Communication pursuant to Art 94(3) EPC, dated Feb. 14, 2020.
Related Japanese Application, Office Action, dated Jun. 29, 2018.
Related Japanese Application, Office Action, dated Jun. 21, 2019.
Corresponding Japanese Application, Notice of Refusal, dated Oct. 23, 2020.
Related U.S. Application, Non-Final Rejection, dated Jul. 23, 2020.
Related EP Application, Summons to Attend Oral Proceedings, dated Nov. 16, 2020.
Related Canadian Application, Examiner Requisition, dated Sep. 8, 2020.
Related Canadian Application, Examiner Requisition, dated Feb. 8, 2021.
Corresponding Canadian Application, Examiner Requisition, dated Jul. 7, 2020.

* cited by examiner

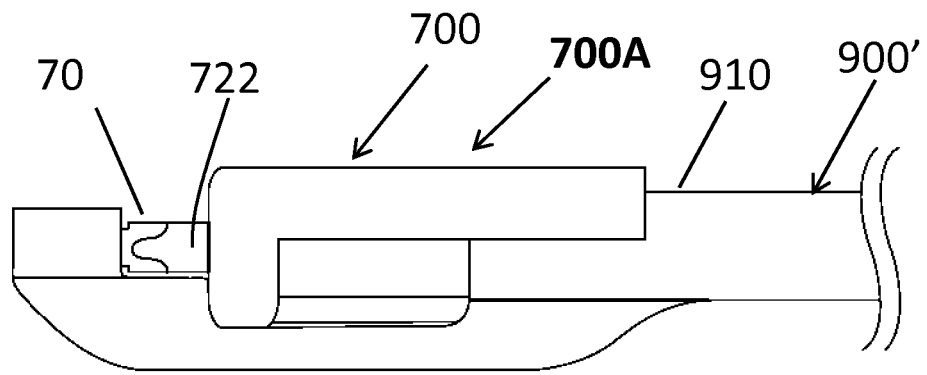
Fig. 7F
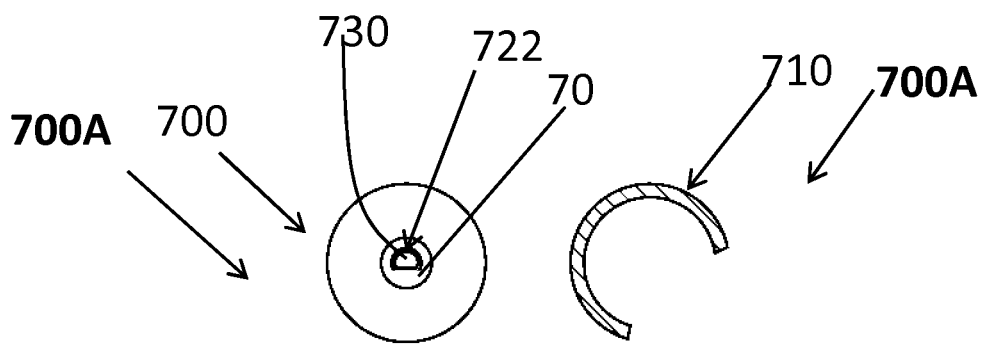
Fig. 7G
Fig. 7H
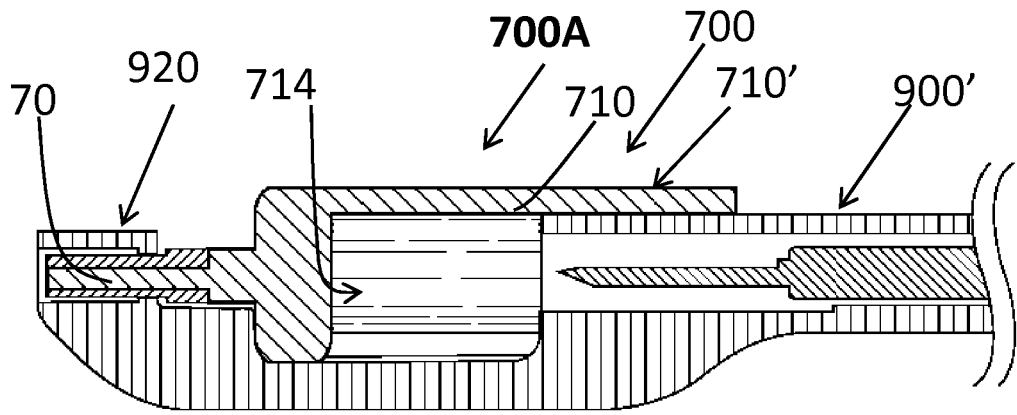
Fig. 7I

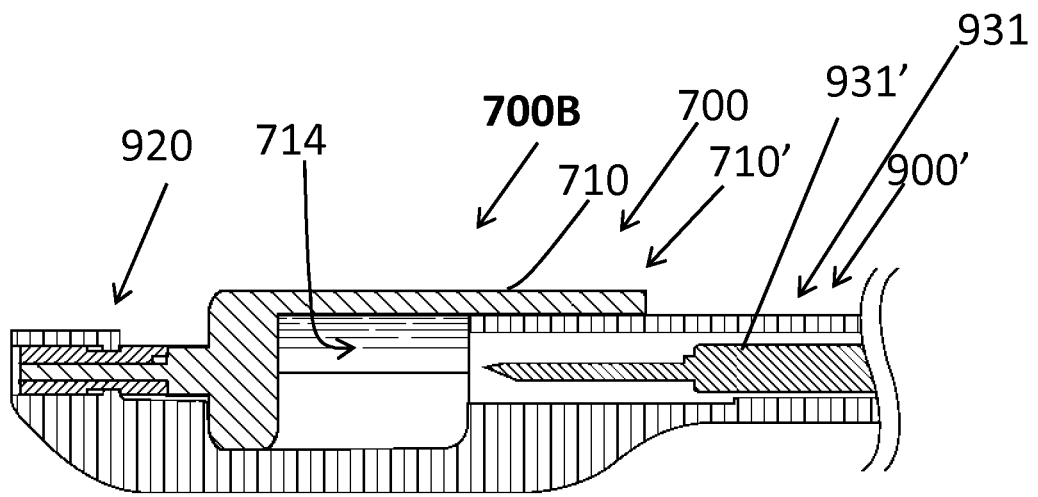
Fig. 7J
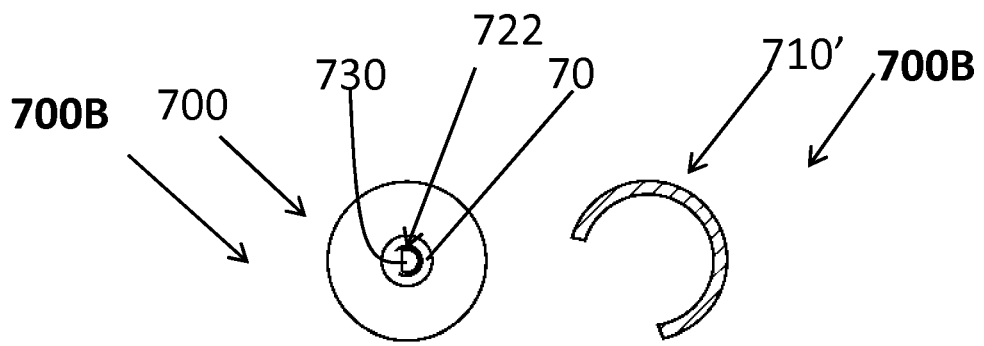
Fig. 7K
Fig. 7L
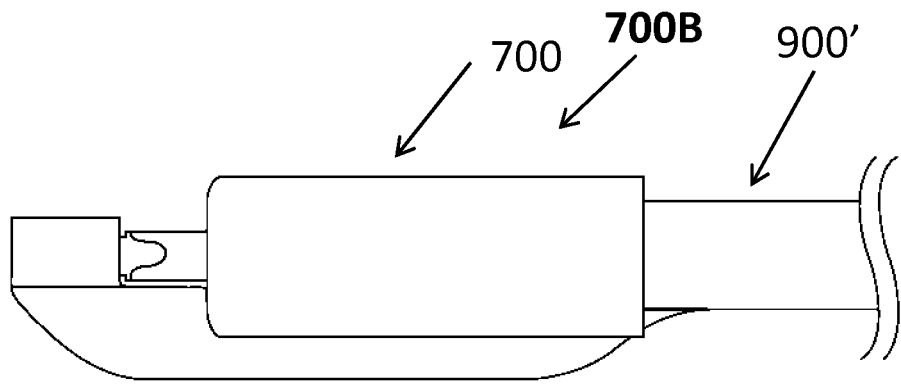
Fig. 7M

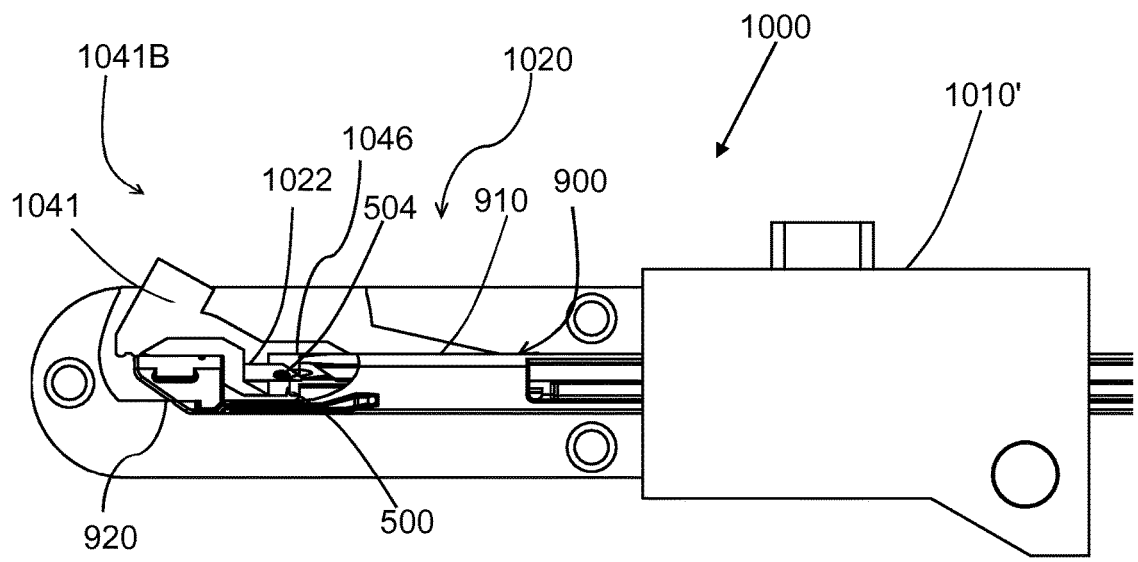
FIG. 10C(ii)
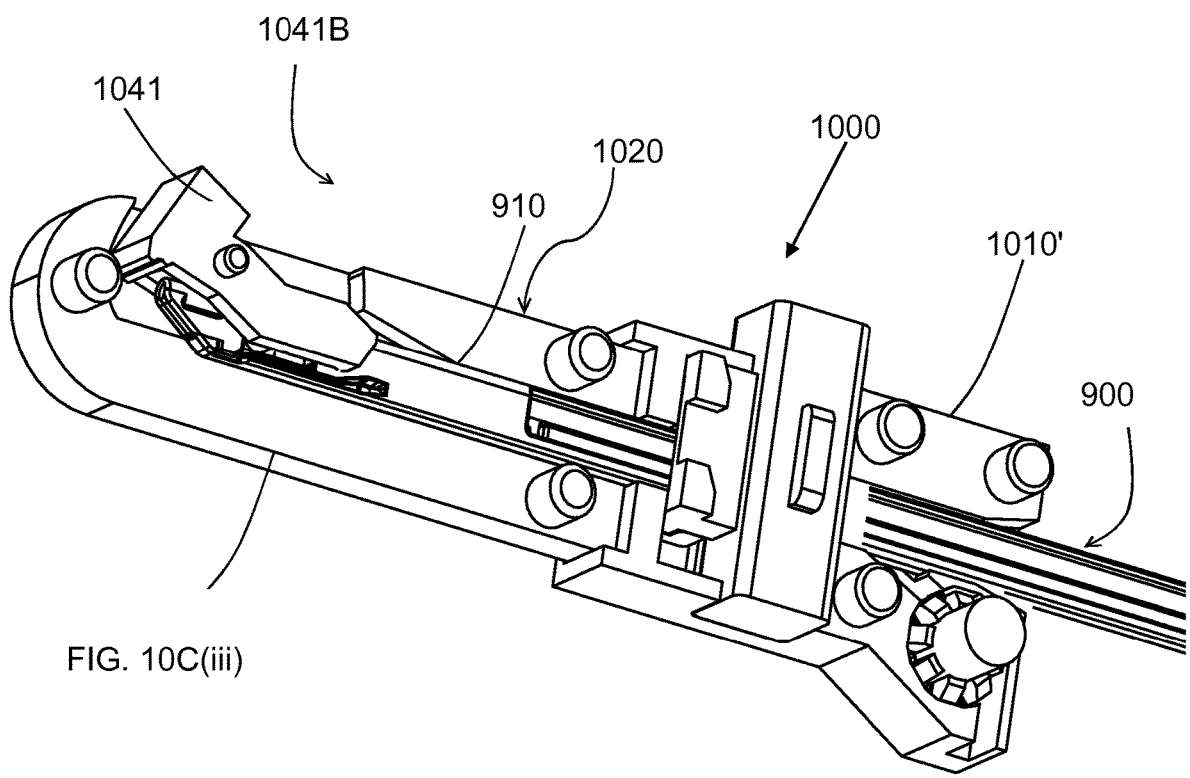
FIG. 10C(iii)

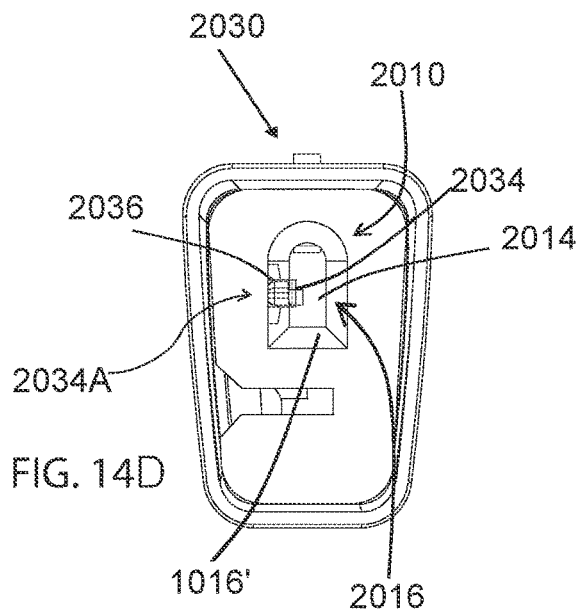
FIG. 14D
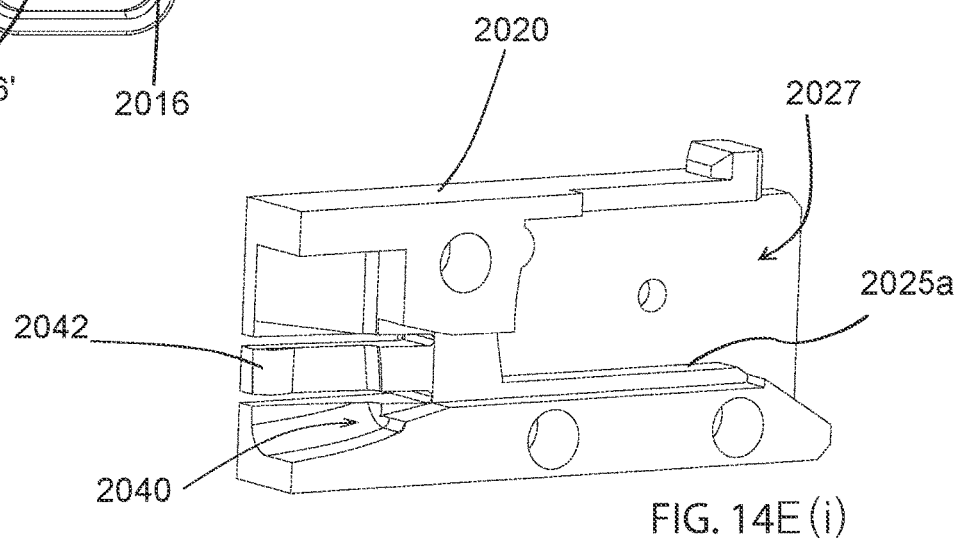
FIG. 14E(i)
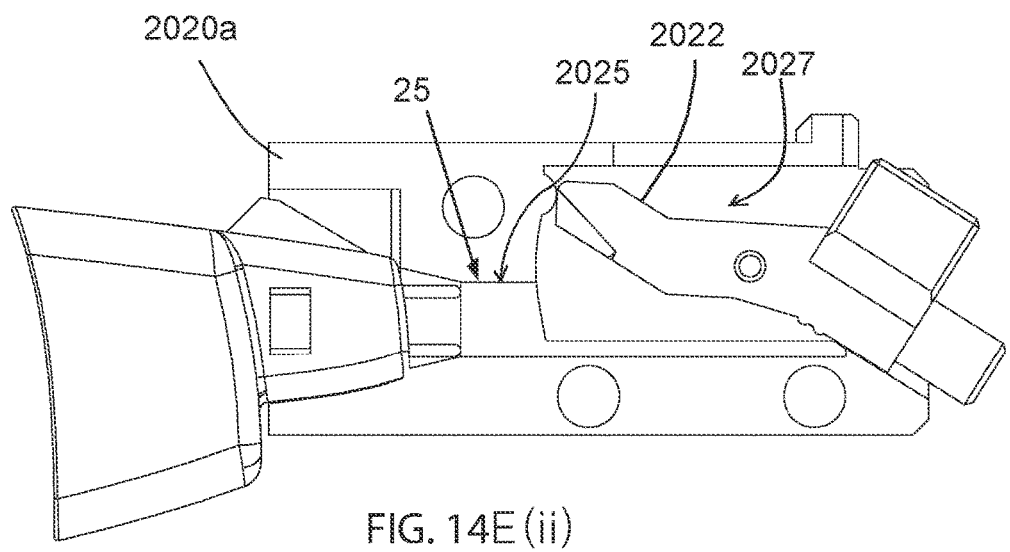
FIG. 14E(ii)

Fig. 14F(ii)

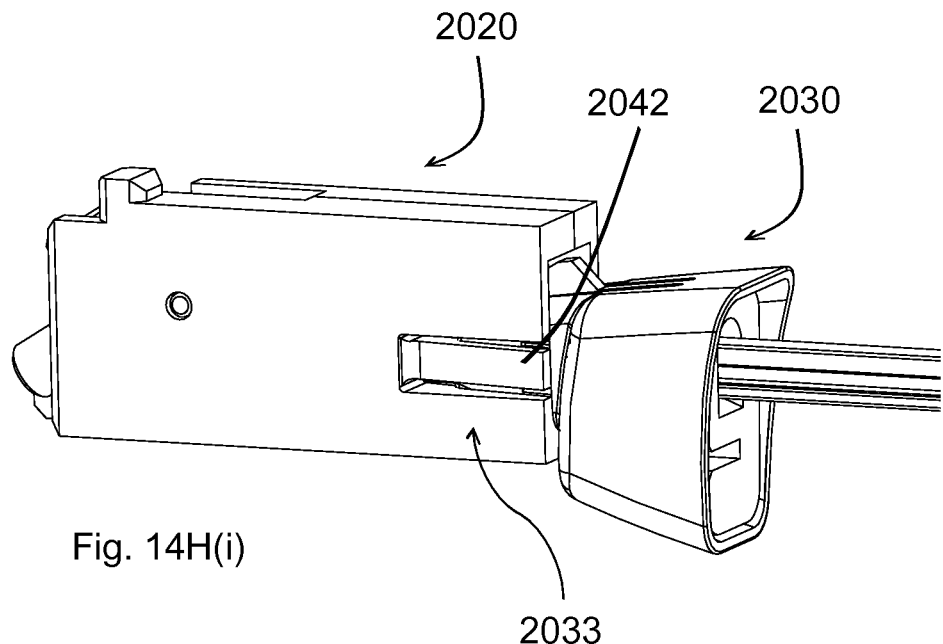
Fig. 14H(i)
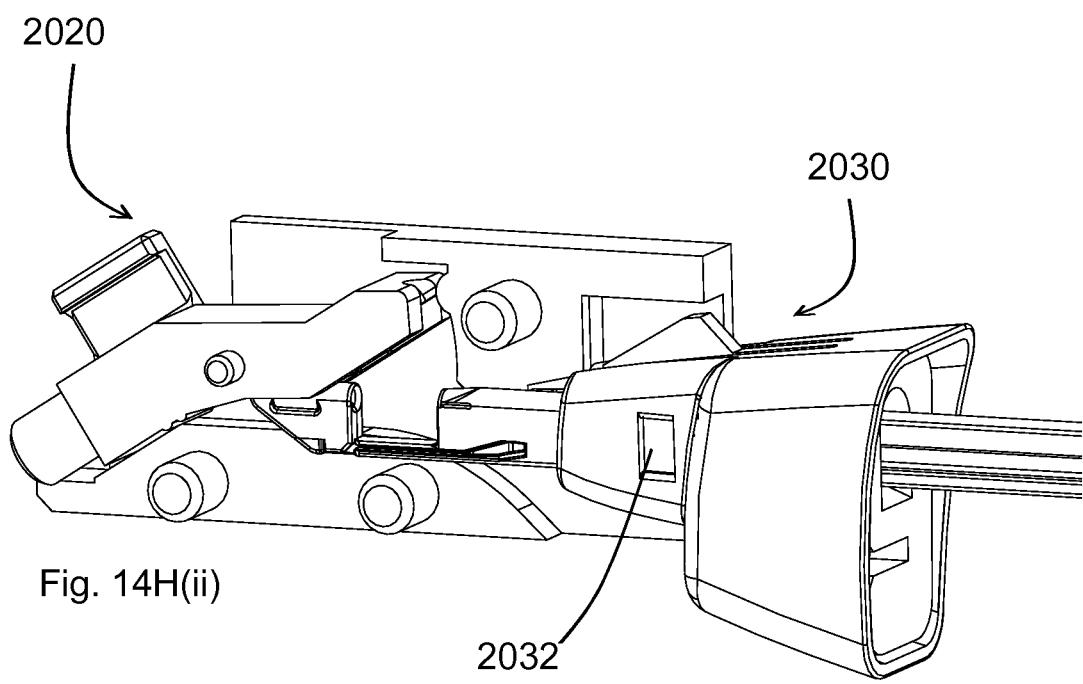
Fig. 14H(ii)

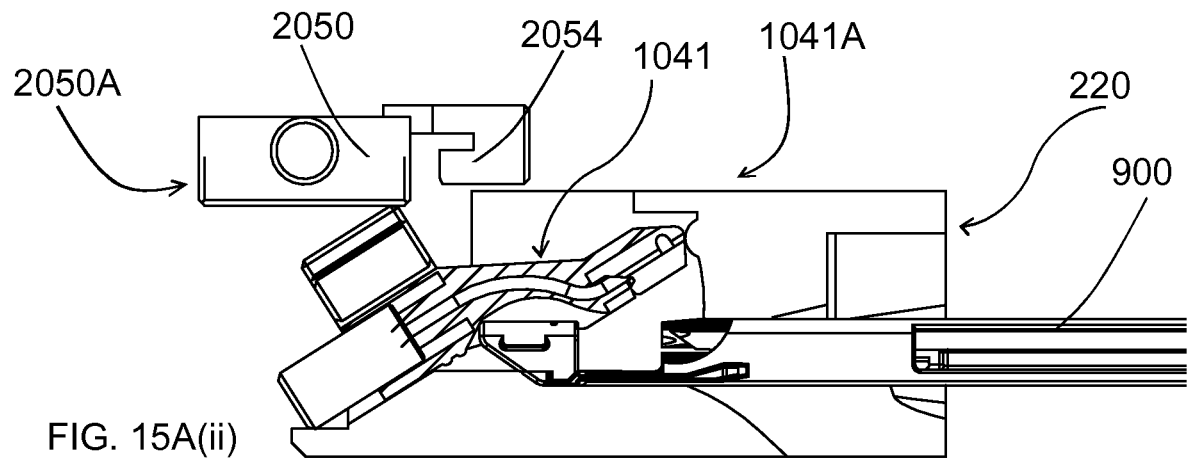
FIG. 15A(ii)
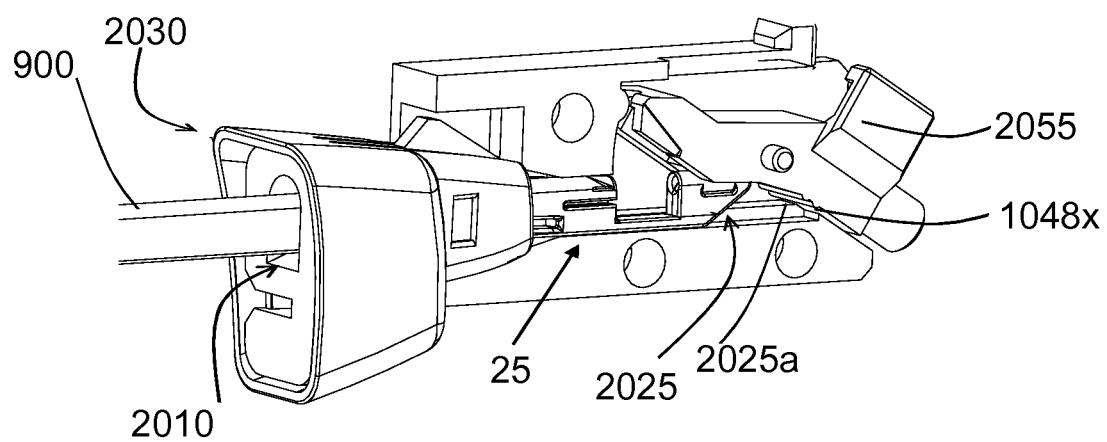
Fig. 15A(iii)

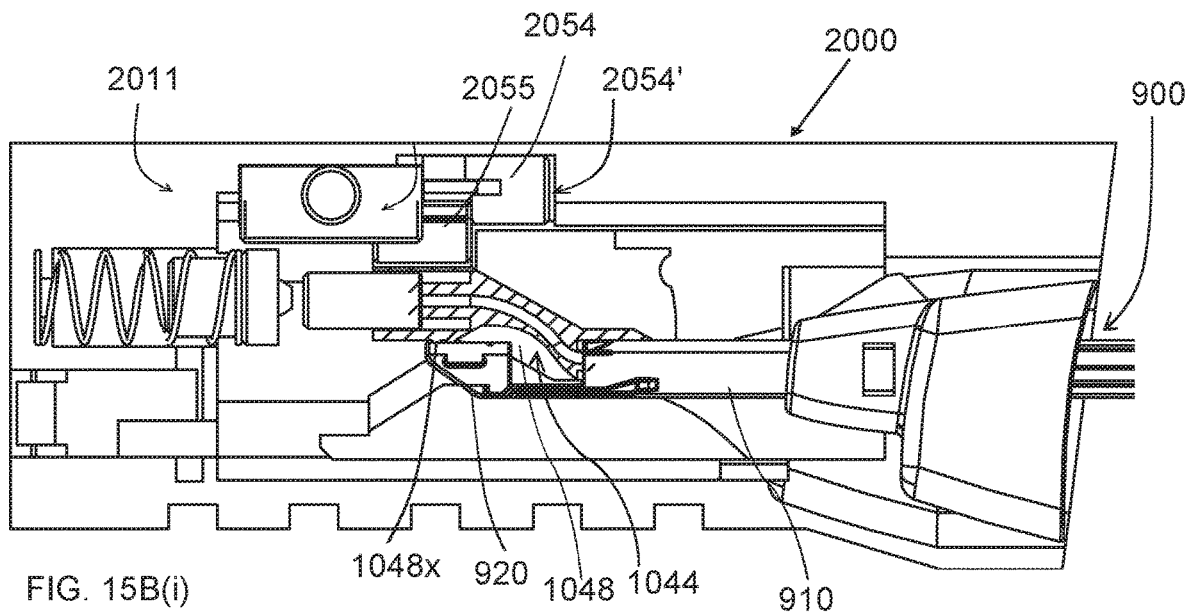
FIG. 15B(i)
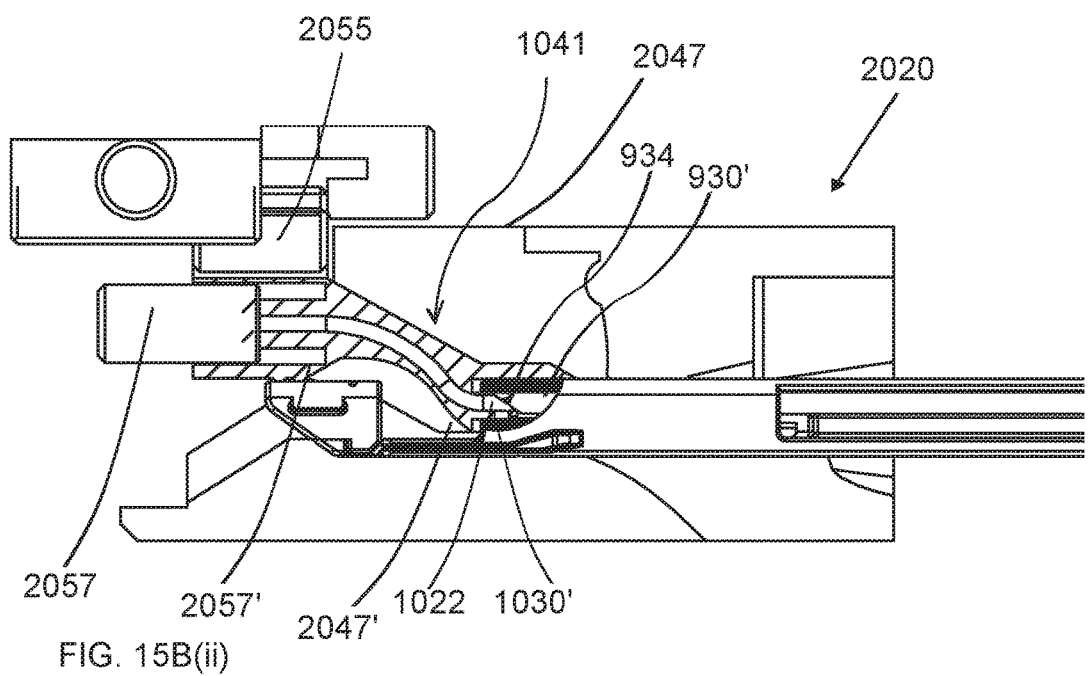
FIG. 15B(ii)

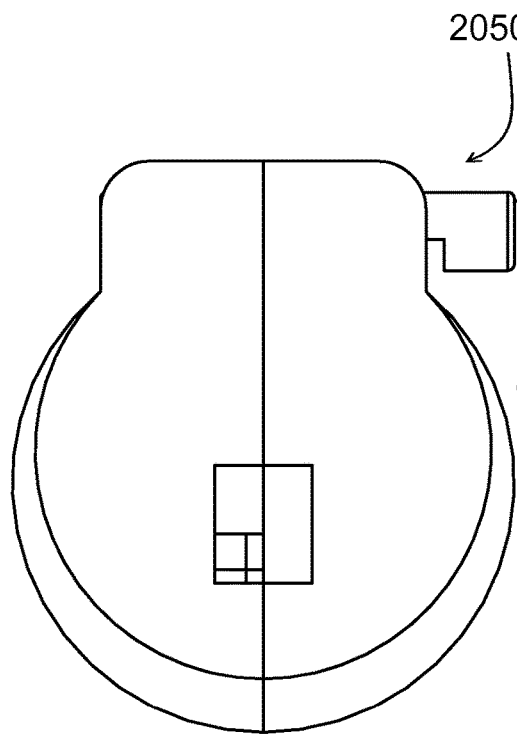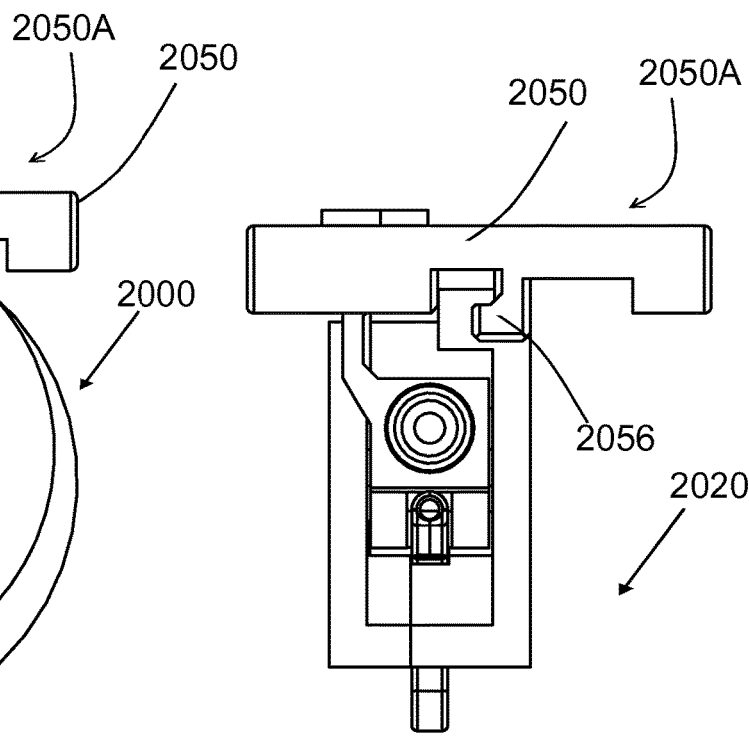
FIG. 15C(i)          FIG. 15C(ii)
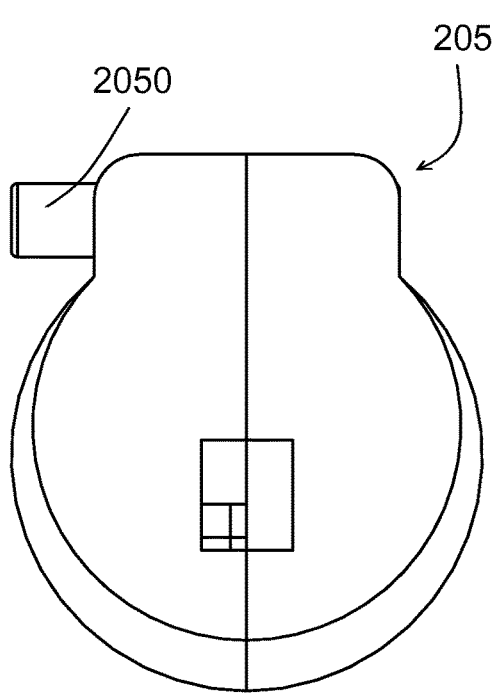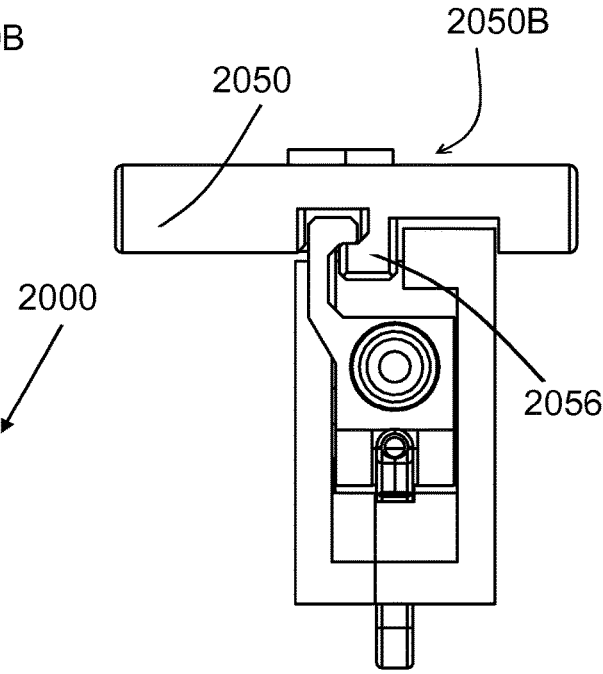
FIG. 15D(i)          FIG. 15D(ii)

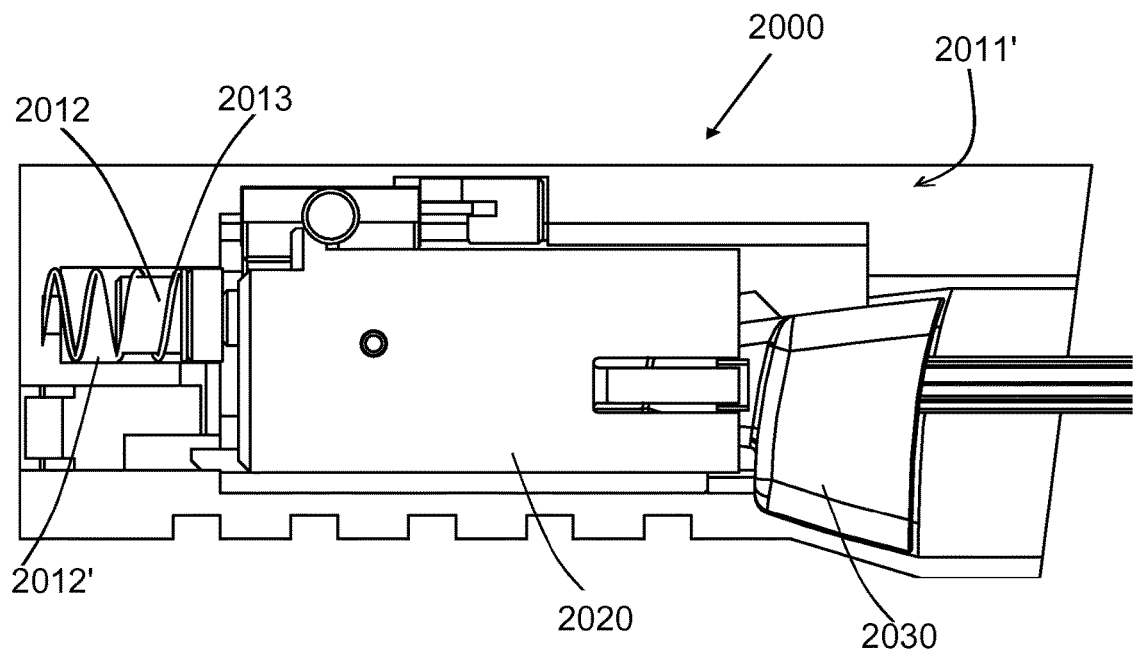
FIG. 15E(i)
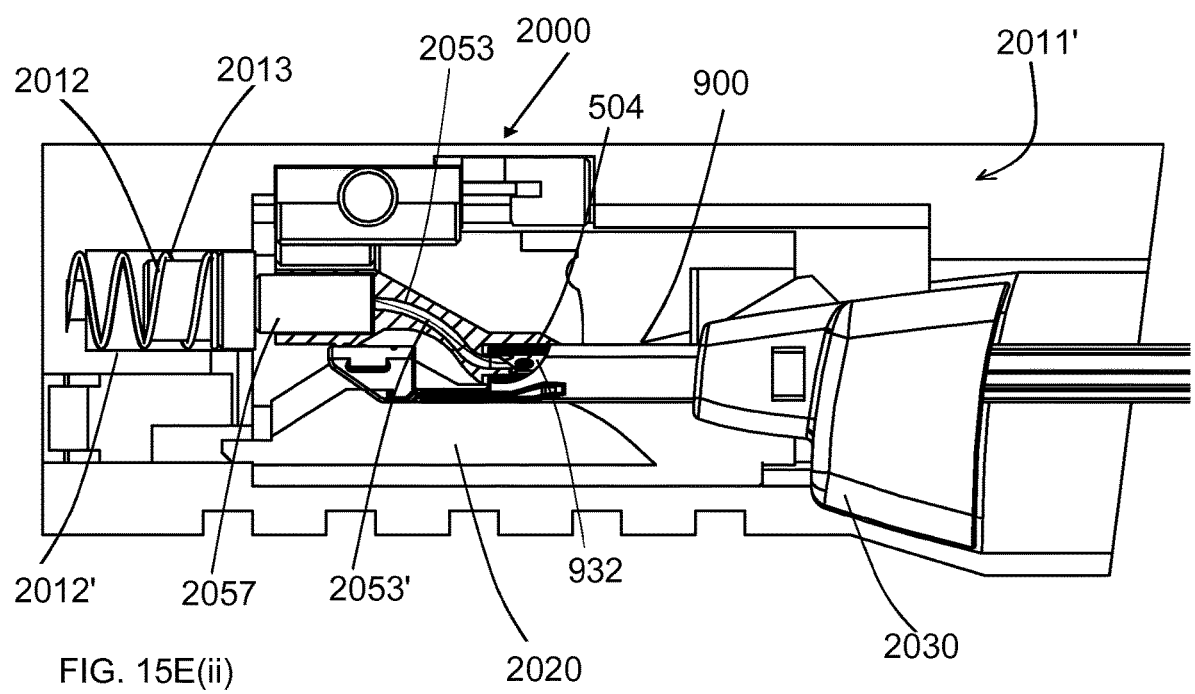
FIG. 15E(ii)

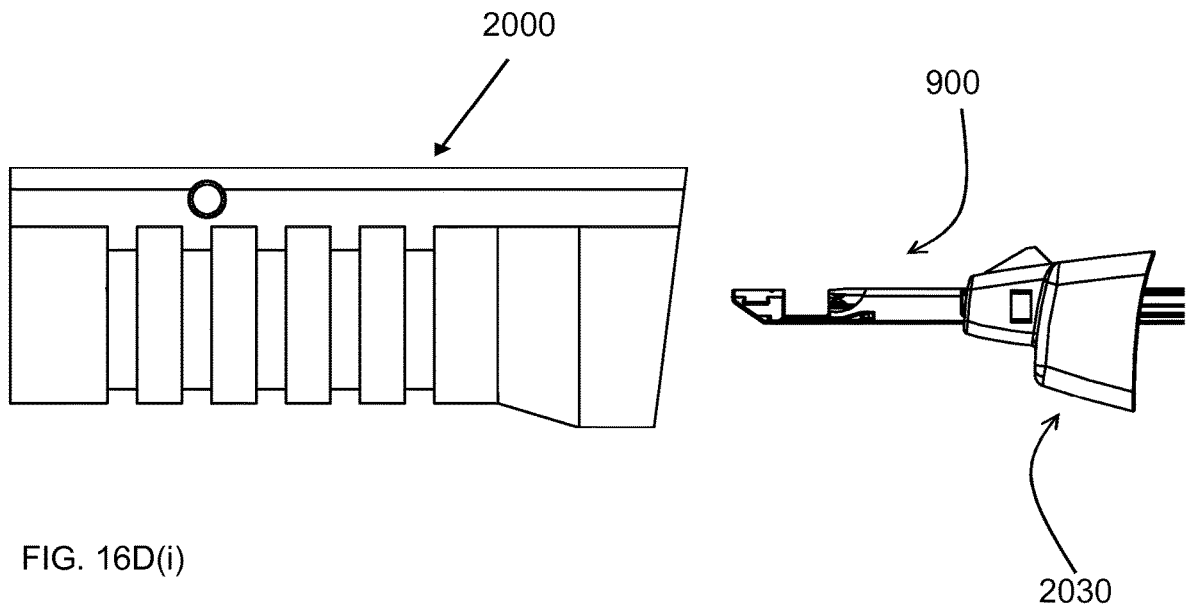
FIG. 16D(i)
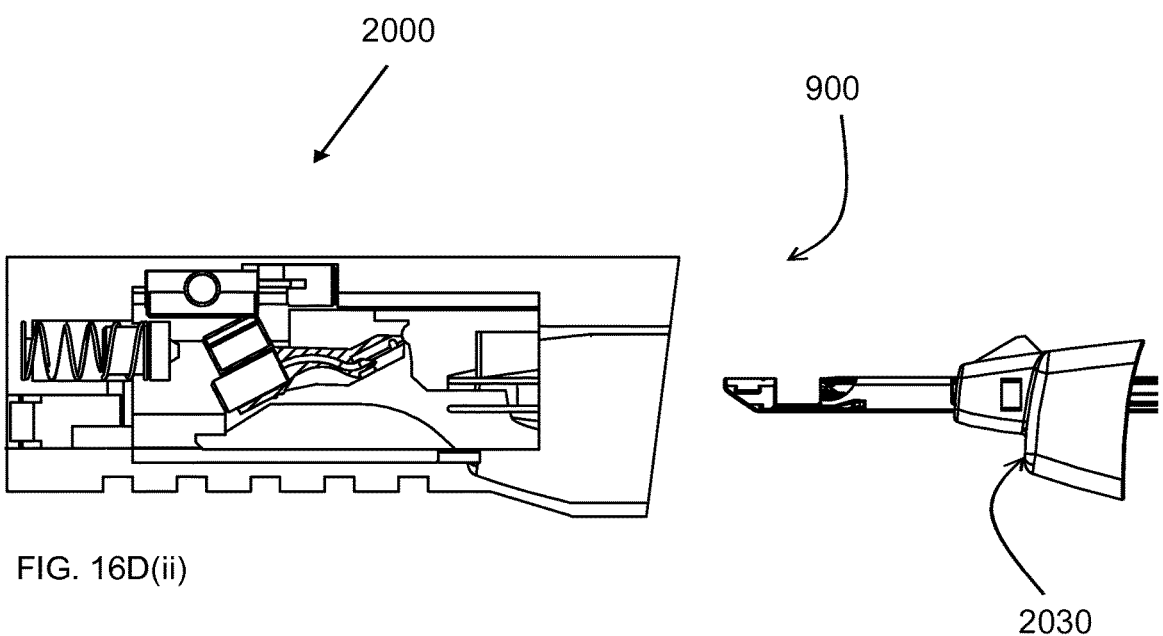
FIG. 16D(ii)

APPARATUS AND METHODS FOR LOADING SUTURE

TECHNICAL FIELD

The disclosure relates to an apparatus for loading suture onto a medical device, more specifically, to a cartridge for loading suture onto a surgical suturing instrument.

SUMMARY OF THE DISCLOSURE

Various embodiments of a cartridge are disclosed for loading a suture onto a suturing instrument. In some embodiments, a cartridge is disclosed for loading a pre-tied knot formed from the suture onto the suturing instrument. The suturing instrument is typically of the type having a suture passing member defining a suture receiving passage therein. In some embodiments, the cartridge comprises a housing defining a chamber and a partially pre-tied knot mounted about the housing or the chamber. The cartridge additionally provides a base coupled to the housing, the base defining a seat for releasably holding a portion of a suture to be aligned with, and transferred to, the suturing instrument. The portion of the suture may be held independently, or it may be coupled to a component such as a ferrule or shuttle.

In one broad aspect, embodiments of the present invention provide a cartridge for loading suture onto a suture passing instrument, the cartridge comprising: a base comprising a seat configured for releasably holding a portion of a suture; and a housing coupled to the base; the cartridge being configured to allow relative movement between the seat and the housing for aligning the suture portion with a suture passing instrument.

In another broad aspect, embodiments of the present invention provide a cartridge for loading a suture onto a suturing instrument, the cartridge comprising: a housing defining a chamber with a partially pre-tied knot releasably coupled to the housing, the pre-tied knot being formed from a suture, the chamber being configured to receive a suturing instrument there-through for deploying the pre-tied knot onto the suturing instrument; and a base coupled to the housing, the base defining a seat for releasably holding a portion of the suture, the seat being moveable to bring the suture portion into alignment with the suturing instrument for permitting transfer of the suture portion from the seat to the suturing instrument.

In still an additional broad aspect, embodiments of the present invention provide a cartridge for loading a suture onto a suturing instrument, the cartridge comprising: a housing defining a chamber with a partially pre-tied knot releasably coupled to the housing, the pre-tied knot being formed from a suture, the chamber configured for a suturing instrument to be received there-through for deploying the pre-tied knot onto the suturing instrument; and a base coupled to the housing, the base defining a seat for releasably holding a portion of the suture, the base comprising a restraint for constraining movement of the suturing instrument received through the chamber relative to the seat for facilitating alignment of the seat with the suturing instrument.

In a further broad aspect, embodiments of the present invention comprise a cartridge for loading suture onto a suturing instrument at a point of use, the cartridge comprising: a base for holding a portion of a suture for alignment with a suturing instrument receivable within the base; and a housing that is coupled to and moveable relative to the base and to the suturing instrument received therein for independently transferring the suture portion from the base onto the suturing instrument.

In still an additional embodiment, a cartridge is provided for axially loading suture onto a suturing instrument at a point of use, the cartridge comprising: a base comprising a seat for releasably holding a portion of a suture, the seat being moveable relative to a remaining portion of the base for aligning the suture portion relative to a suturing instrument received within the base; and a housing coupled to the base, the housing being moveable relative to the base and to the suturing instrument received within the base to independently transfer the suture portion from the seat onto the suturing instrument.

In still another broad aspect, embodiments of the present invention provide a cartridge for loading a suture onto a suturing instrument, the cartridge comprising: a chamber defining a recess for axially receiving a distal portion of a suturing instrument there-through; a seat adjacent the recess for releasably holding a portion of a suture; and a restraint configured for constraining movement of the suturing instrument relative to the seat, for facilitating alignment of the seat with the suturing instrument received through the recess to permit transfer of the suture portion from the seat into the suturing instrument.

In still another broad aspect, embodiments of the present invention provide a cartridge for linearly loading suture onto a suturing instrument at a point of use, the cartridge comprising: a chamber for receiving a suturing instrument and a seat for releasably holding a portion of a suture, the seat being moveable relative to the chamber upon advancement of the suturing instrument through the chamber for aligning the portion of the suture relative to a portion of the suturing instrument, to allow the suture portion to be independently transferred to the portion of the suturing instrument.

In still a further broad aspect, embodiments of the present invention provide a cartridge for loading a ferrule having a suture coupled thereto onto a suturing instrument, the cartridge comprising: a chamber defining a recess for receiving a portion of the suturing instrument, the recess configured for allowing axial movement of the suturing instrument there-through; and a seat adjacent the recess for releasably holding a ferrule having a portion of a suture coupled thereto; the chamber being configured to cooperate with the suturing instrument to align the seat with a portion of the suturing instrument to permit transfer of the ferrule from the seat into the portion of the suturing instrument.

In an additional broad aspect, embodiments of the present invention provide a cartridge for loading a ferrule having a suture coupled thereto onto a suturing instrument, the cartridge comprising: a housing defining a chamber, the housing configured to support a pre-tied knot about the chamber, the chamber defining a recess for receiving a distal end of a suturing instrument; and a base detachably coupled to the housing, the base defining a seat adjacent the recess for releasably holding a ferrule having a portion of a suture attached thereto; the cartridge being configured to allow the seat to be brought into alignment with a portion of the suturing instrument when the suturing instrument is positioned within the recess, for permitting transfer of the ferrule from the seat to the portion of the suturing instrument, the cartridge being further configured to enable the pre-tied knot to be mounted onto the suturing instrument.

In still a further broad aspect, embodiments of the present invention provide a cartridge for loading a suture onto a suturing instrument to enable the suturing instrument to form a pre-tied knot, the cartridge comprising: a chamber for receiving a suturing instrument, the chamber supporting loops of suture coupled thereto for transferring onto the suturing instrument upon advancement of the suturing instrument into the chamber, the loops of suture being configured to form a pre-tied knot upon deployment from the suturing instrument; and a seat for releasably holding a portion of the suture to enable transfer of the suture portion onto the suturing instrument, the suture portion comprising an end of the suture configured to define a post of the pre-tied knot upon deployment of the loops from the suturing instrument.

In another broad aspect embodiments of the present invention provide a cartridge for loading suture onto a suture passing instrument, the cartridge comprising: a base comprising a seat that releasably holds a portion of a suture; and a housing coupled to the base; the cartridge being configured to allow relative movement between the seat and the housing for aligning the suture portion with a suture passing instrument.

In still an additional broad aspect, embodiments of the present invention provide a method of loading suture onto a suturing instrument, the suture comprising suture loops and terminating in a suture end, the suturing instrument comprising a suture passing member defining a suture-receiving passage, the method comprising the steps of using a cartridge in accordance with an embodiment of the present invention as described herein to align a suture end with a suture receiving passage of a suturing instrument; and transferring suture loops onto the suturing instrument.

In still a further broad aspect embodiments of the present invention provide a method of loading suture onto a suturing instrument, the suturing instrument comprising a suture passing member defining a suture receiving passage therein, the method comprising the steps of: advancing a suturing instrument into a cartridge in accordance with an embodiment of the present invention as described herein, thereby causing a seat of the cartridge to move automatically to align a portion of suture with a suture receiving passage of the suturing instrument.

In another broad aspect embodiments of the present invention provide a method of loading suture onto a suturing instrument, the suturing instrument comprising a suture passing member defining a suture receiving passage therein, the method comprising the steps of: linearly advancing a suturing instrument into a cartridge in accordance with an embodiment of the present invention as described herein; and independently transferring an end of a suture from the cartridge into a suture receiving passage of the suturing instrument using a suture transferring component of the cartridge.

In a further broad aspect embodiments, of the present invention provide a method of suturing an intervertebral disc, the method comprising the steps of: loading a suture onto a suturing instrument using a cartridge in accordance with an embodiment of the present invention as described herein; and passing the suture through at least a portion of an intervertebral disc using the suturing instrument.

In still an additional broad aspect, embodiments of the present invention provide a method of suturing tissue in an intervertebral disc having a defect therein, the method comprising the steps of: loading suture onto a suturing instrument at a point of use using a cartridge in accordance with an embodiment of the present invention as described herein; and passing the suture through tissue using the suturing instrument to substantially approximate a defect in the tissue.

In still another broad aspect embodiments of the present invention provide a method of loading a ferrule with a suture attached thereto onto a suturing instrument, the method comprising the steps of: coupling a cartridge in accordance with an embodiment of the present invention as described herein to a suturing instrument such that the suturing instrument is received within the cartridge; and axially moving the cartridge relative to the suturing instrument to position a ferrule within a ferrule receiving passage defined by the suturing instrument.

In still another broad aspect, embodiments of the present invention provide a suturing system comprising: a suturing instrument defining a tissue receiving gap and comprising a suture passing member defining a suture receiving passage therein; and a cartridge, the cartridge comprising a base for releasably holding a suture portion, and a suture transferring component that is moveable relative to the base for independently transferring the suture portion from the cartridge to the suture receiving passage.

In still another broad aspect, embodiments of the present invention provide a suturing system comprising: a suturing instrument comprising a suture passing member; and a cartridge for releasably holding an end of a suture and defining a chamber for coupling a partially pre-tied knot thereabout, the chamber configured to receive the suturing instrument there-through; the cartridge being configured to transfer the suture end to the suture passing member and to transfer the partially pre-tied knot onto the suturing instrument; the suture passing member being configured to pass the suture end from a proximal side of a tissue to a distal side of the tissue in a first actuation of the suture passing member.

BRIEF DESCRIPTION OF THE DRAWINGS

In order that the invention may be readily understood, embodiments of the invention are illustrated by way of examples in the accompanying drawings, in which:

FIG. 7F illustrates a left side view of a cartridge for loading onto a surgical suturing instrument during use, in accordance with an embodiment of a method of the present invention;

FIG. 7G illustrates a front end view of a cartridge by itself during use of the cartridge to load suture onto a surgical suturing instrument in accordance with an embodiment of a method of the present invention;

FIG. 7H illustrates a cross-sectional view of a cartridge by itself during use of the cartridge to load suture onto a surgical suturing instrument in accordance with an embodiment of a method of the present invention;

FIGS. 7I-7J illustrate cross-sectional views showing steps of a method for loading suture onto a surgical suturing instrument using a cartridge in accordance with an embodiment of a method of the present invention;

FIG. 7K illustrates a front end view of a cartridge by itself during use of the cartridge to load suture onto a surgical suturing instrument in accordance with an embodiment of a method of the present invention;

FIG. 7L illustrates a cross-sectional view of a cartridge by itself during use of the cartridge to load suture onto a surgical suturing instrument in accordance with an embodiment of a method of the present invention;

FIG. 7M illustrates a left side view of cartridge during use of the cartridge for loading suture onto a surgical suturing instrument in accordance with an embodiment of the present invention;

FIGS. 14A-14H(ii) illustrate views of a cartridge in accordance with an alternate embodiment of the present invention;

FIGS. 16A-16D(ii) illustrate views of a cartridge and a method of using the same in accordance with an alternate embodiment of the present invention;

DETAILED DESCRIPTION

Figure 1A:
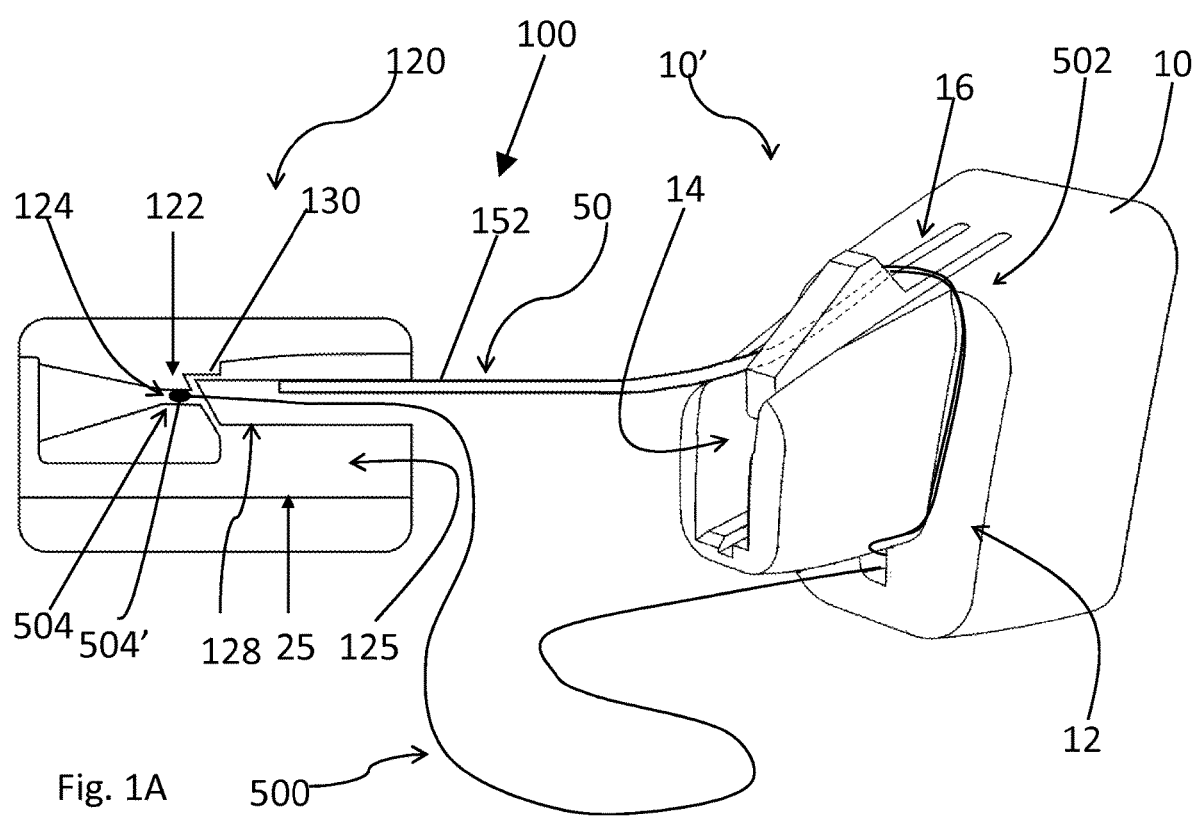
FIG. 1A illustrates a left side perspective view of a cartridge in accordance with an embodiment of the present invention.

In certain medical interventional procedures, a suturing instrument may be used by physicians to pass suture through a region of tissue having a cut or a defect in order to approximate the tissue to repair the defect. In some such procedures, there may be a need to load suture onto the surgical suturing instrument at the point of use. However, it may be difficult to load the suture using conventional loading mechanisms as they may require the user to perform several steps and may require user dexterity and concentration. Conventional loading mechanisms may also require a specific order of operation which if done out of order could result in a failure of the device and may be time consuming. Thus, there is a need in the art to provide a cartridge for loading suture onto a suturing instrument at the point of use that provides ease of use and allows the suture to be loaded in an efficient manner.

The present inventors have discovered, and reduced to practice, several embodiments of a novel apparatus and method that facilitates loading of suture onto a suturing instrument at the point of use. In general, in accordance with embodiments of the present invention, a cartridge is provided that permits loading of a suture onto a suturing instrument upon axial or linear movement of the suturing instrument at least partially through the cartridge. The cartridge may additionally comprise one or more features that facilitate alignment and transferring of the suture onto the instrument.

More specifically, some embodiments of the present invention provide a suture cartridge that is usable for loading suture onto a medical device, such as a surgical suturing instrument, at the point of use in a situation where suture is to be supplied separate from the device. In some such embodiments, a cartridge is provided that allows the physician to load the suture onto a surgical suturing instrument prior to a surgical procedure using an axial or front end loading mechanism. The cartridge defines a seat for holding a portion of the suture, and defines an opening extending longitudinally through at least a portion of the cartridge, which allows a portion of the surgical suturing instrument to be received axially there-through for aligning a portion of the suture held therein with the surgical suturing instrument. This allows direct transfer of the portion of the suture held within the seat from the cartridge onto the surgical suturing instrument, allowing it to be independently transferred to enable the surgical suturing instrument to suture therewith.

In some embodiments of the present invention, the cartridge may additionally comprise one or more features that facilitate transferring or loading the suture onto the device.

In some embodiments, the cartridge additionally provides one or more of the following: a means to mount a pre-tied knot onto a surgical instrument, a restraint to secure a position of the suturing instrument upon insertion into the cartridge, and an alignment feature to align the suture with the suturing instrument, such as a moveable seat. In some such embodiments, a cartridge is provided that is usable with a suturing instrument that defines a tissue receiving gap, where the cartridge is configured to position the seat within the tissue receiving gap to facilitate alignment of the portion of the suture held within the seat with a suture passing member of the suturing instrument.

In one particular embodiment, a cartridge is provided that provides a two-piece cartridge design that comprises (i) a base defining a seat for holding a portion of the suture and for aligning the portion of the suture (for example, an end of the suture) held therein with the surgical suturing instrument; and (ii) a chamber for receiving a surgical suturing instrument there-through. In some alternative embodiments outlined herein, the base and the chamber may be formed integrally with one another and may thereby form a one-piece device. Some embodiments may provide a suture with a ferrule coupled thereto rather than an independent suture portion. In some embodiments, the seat may be moveable with respect to the housing to enable alignment of the suture. In other embodiments, the seat may alternatively or additionally be moveable with respect to the base to facilitate alignment of the suture portion with the suturing instrument.

In some embodiments of the two-piece cartridge design, the cartridge comprises a housing that defines the chamber, where the chamber has a partially pre-tied knot coupled thereto for positioning onto the surgical suturing instrument that is received through the chamber. The pre-tied knot is formed from the suture and the cartridge is operable to mount the pre-tied knot onto the suturing instrument during use. In other embodiments of a two-piece cartridge design, at least a portion of the housing is detachable from the base to actively transfer the portion of the suture held within the seat, or the pre-tied knot coupled to the housing, onto the surgical suturing instrument. The portion of the housing used for transferring the partially pre-tied knot onto the suturing instrument may be referred to as a knot slider, and may be mountable on the suturing instrument for use in a suturing procedure. The suture may be coupled to the housing along a specific segment of the suture in order to allow the suture end to be moved out of the seat and into the suturing instrument as the housing is moved. In some such embodiments, the housing functions as a suture transferring component to transfer an end of the suture held within the seat of the cartridge to a suture passing member of the suturing instrument.

The cartridge may additionally comprise one or more features to assist in loading the suture from the cartridge directly onto the suturing instrument or device. For example, some embodiments provide a magazine moveable within the base for aligning the suture relative to the suturing instrument upon loading of the cartridge onto the suturing instrument prior to transferring suture. Additionally, some embodiments may provide a mechanism that automatically aligns the suture with the suturing instrument upon mounting of the cartridge onto the suturing instrument to facilitate subsequent transfer of the suture. Other embodiments may comprise one or more of the above mentioned alignment and transferring features. Such embodiments, as discussed further herein below, provide a means for loading suture directly onto a surgical suturing instrument prior to use.

Thus, embodiments of the present invention provide a suture cartridge for loading suture onto a suturing instrument, for example at a point of use, by efficiently aligning the suture with the suturing instrument. In some embodiments, the cartridge additionally provides one or more of a means to load a pre-tied knot onto a suturing instrument and a means for transferring the suture onto the suturing instrument.

Furthermore, several novel embodiments of methods for loading a suture onto a suturing instrument are described hereinbelow. In addition, methods of suturing tissue of an intervertebral disc including a cartridge for loading the suture onto a suturing instrument, are described as well.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Devices for Loading Suture

Example 1A

In accordance with an embodiment of the present invention, a suture-carrying cartridge is provided for loading suture onto a surgical suturing instrument, such as a suture passer, at the point of use. The cartridge may be used in instances where the suturing instrument requires a pre-tied knot and comprises a suture passing member, and where loading involves loading the suture onto the suture passing member and loading the pre-tied knot onto the surgical suturing instrument. The suture-carrying cartridge (having a pre-tied knot secured thereto) is coupled to the suture passer and allows coupling of the suture to the suture passing member by allowing the suture to be moved so that it is aligned with the suture passing member.

Figure 1B:
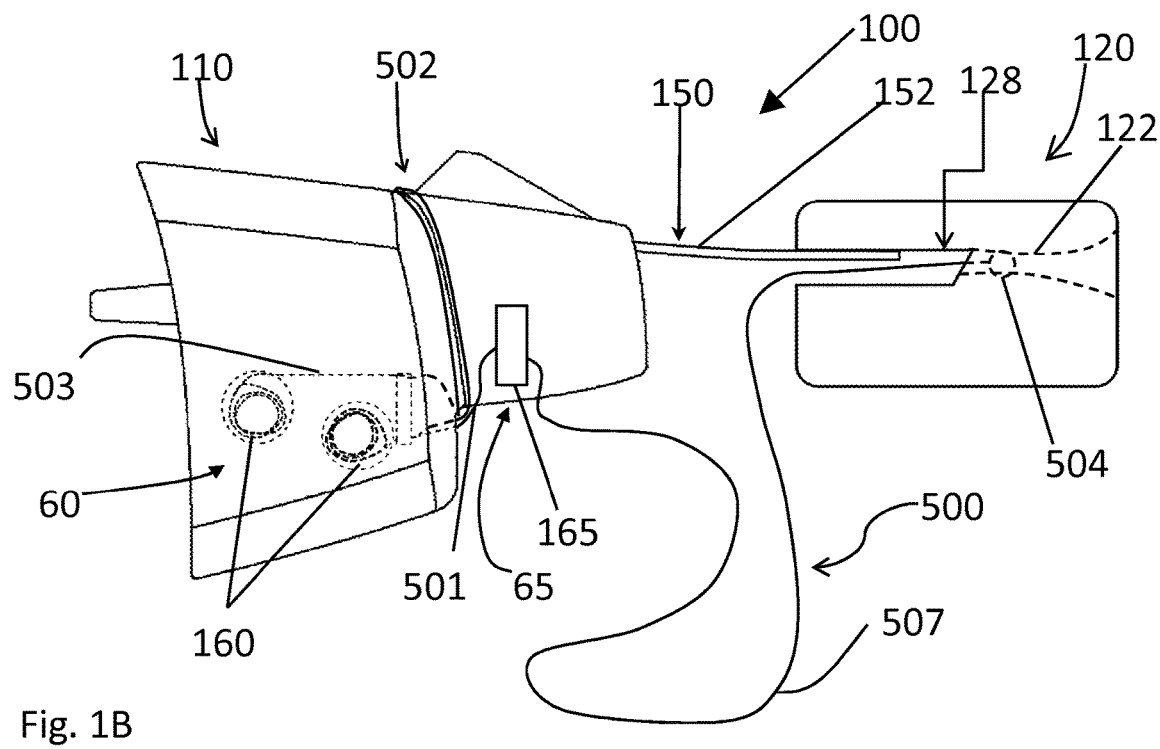
FIG. 1B illustrates a right side view of a cartridge in accordance with an embodiment of the present invention.

FIG. 1A illustrates a cartridge 100 in accordance with an embodiment of the present invention. The cartridge 100 is provided for loading a length of suture 500 onto a surgical suturing instrument, including loading a pre-tied knot 502 comprising suture loops (which in some embodiments is formed from and/or attached to the suture 500) onto the suturing instrument. In an exemplary embodiment shown, the suture 500 may define an end portion 504 (of the suture or suture end) 504, such as a knot 504'), for loading onto the surgical suturing instrument 900. As shown in FIG. 1B, the suture 500 emanating from the pre-tied knot 502 terminates in two strands of suture: a service loop 501 terminating in tug loop 507 that is connected to the suture end 504, and a locker 503. In some embodiments, the surgical suturing instrument is of the type defining a suture passing member defining a suture receiving passage therein for receiving the end portion 504 of the suture 500 from the cartridge 100.

Figure 1C:
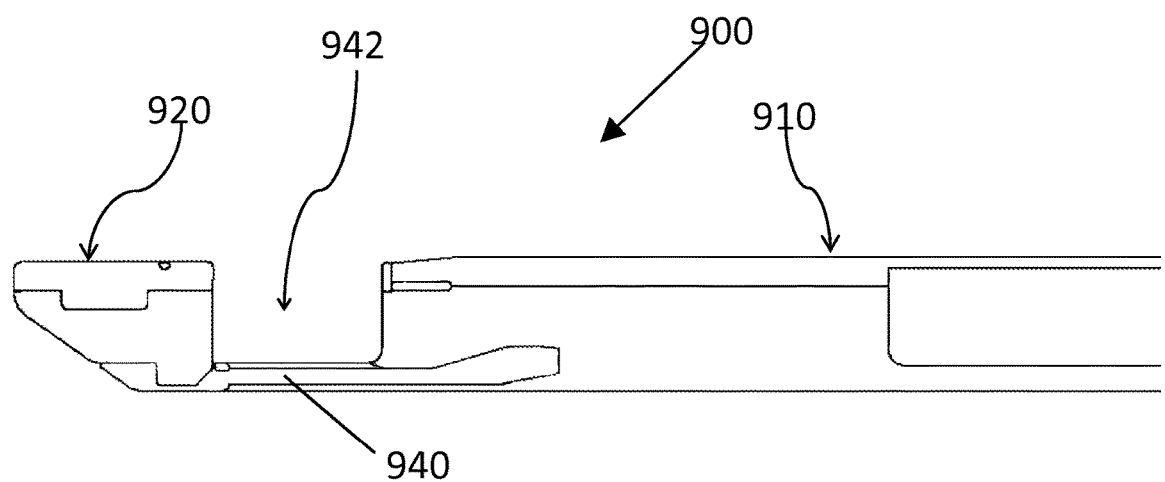
FIG. 1C illustrates a left side view of a portion of a surgical suturing instrument for use with a cartridge in accordance with an embodiment of a the present invention.
Figure 1D:
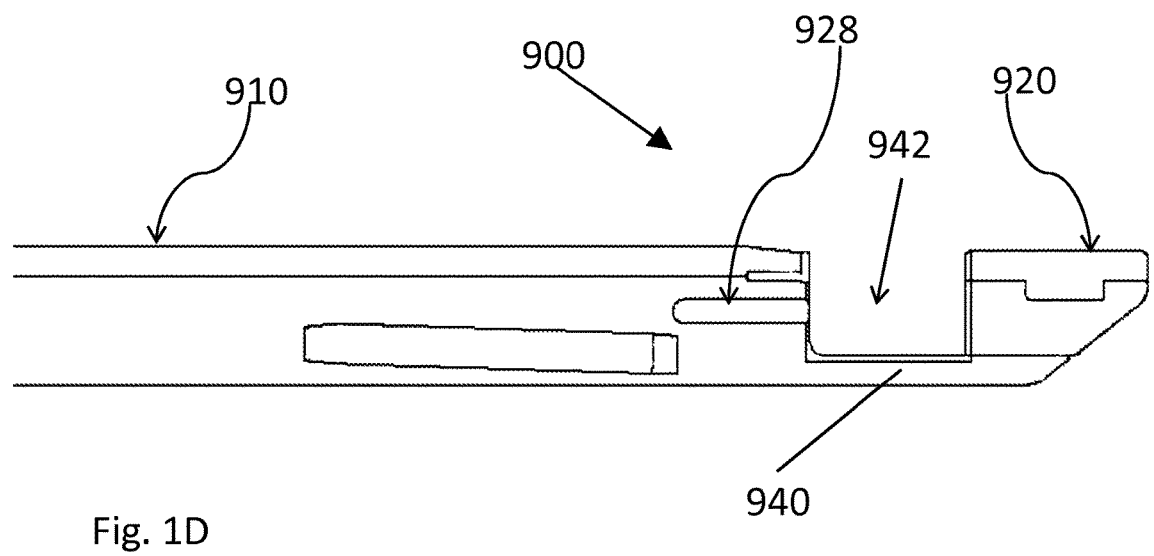
FIG. 1D illustrates a right side view of a portion of a surgical suturing instrument for use with a cartridge in accordance with an embodiment of the present invention.

In one example as illustrated in FIGS. 1C and 1D, the surgical suturing instrument or suturing instrument 900 is of the type having an instrument proximal portion (or shaft) 910 and an instrument distal portion 920 coupled thereto via a neck portion 940 and defining a tissue receiving gap 942 there-between. The instrument distal portion 920 may alternatively be referred to as the distal end or distal tip 920. As shown in the cross-sectional view of FIG. 1E, the suturing instrument 900 comprises a suture passing member 930 such as a hollow needle 930' housed within the instrument proximal portion 910. The suture passing member 930 defines a suture receiving passage 932 for receiving the end portion 504 of the suture. In some embodiments, the suture passing member 930 is reciprocally movable, for example, between the device proximal portion 910 and the device distal portion 920. In some embodiments, movement of the suture passing member 930 may assist in transferring the suture end portion 504 from the cartridge 100 to the suturing instrument 900. In a particular example, the suturing instrument 900 is of the type shown and described in the PCT application PCT/IB2012/054204, which is incorporated herein by reference in its entirety.

Referring again to the exemplary embodiment shown in FIG. 1A, a cartridge 100 is shown for loading suture 500 onto the surgical suturing instrument 900 is shown. In accordance with a general embodiment of the present invention, the cartridge 100 comprises a housing 10' defining a chamber 10 for receiving the surgical suturing instrument 900. The cartridge further comprises a base 120 coupled to the chamber 10.

In the specific example shown in FIG. 1A, the chamber 10 comprises a means for securing or mounting the pre-tied knot 502 about the chamber 10. In the illustrated embodiment, the means for securing the pre-tied knot 502 comprises a mount 12 for holding the pre-tied knot 502 about the chamber 10. More specifically, the mount 12 may form a part of the housing 10'. Additionally, the chamber 10 defines a channel 14 to allow passage of a portion of the suturing instrument 900 to be received through the pre-tied knot 502, to enable the pre-tied knot 502 to be deployed thereon.

In the exemplary embodiment shown in FIG. 1A, the base 120 defines a seat 122 for releasably holding a portion of a suture 500, such as an end 504 of the suture 500. In the specific example shown, the seat 122 defines a seat channel (recess or passage) 124 for retaining the suture end 504. More specifically, the cartridge 100 specifies a seat 122 for 'directly holding' the end 504 of the suture 500 such that the suture 500 by itself is held directly by the seat 122.

In accordance with a broad embodiment of the present invention, the cartridge 100 is structured to allow the seat 122 to be brought into alignment with and in some examples adjacent the suture receiving passage 932 of the suture passing member 930. In some embodiments, as will be discussed herein below with respect to FIG. 1F, the seat 122 is moveable (along with the base 120) relative to the chamber 10 and housing 10' to bring the suture end 504 into alignment with the suture receiving passage 932.

Figure 1E:
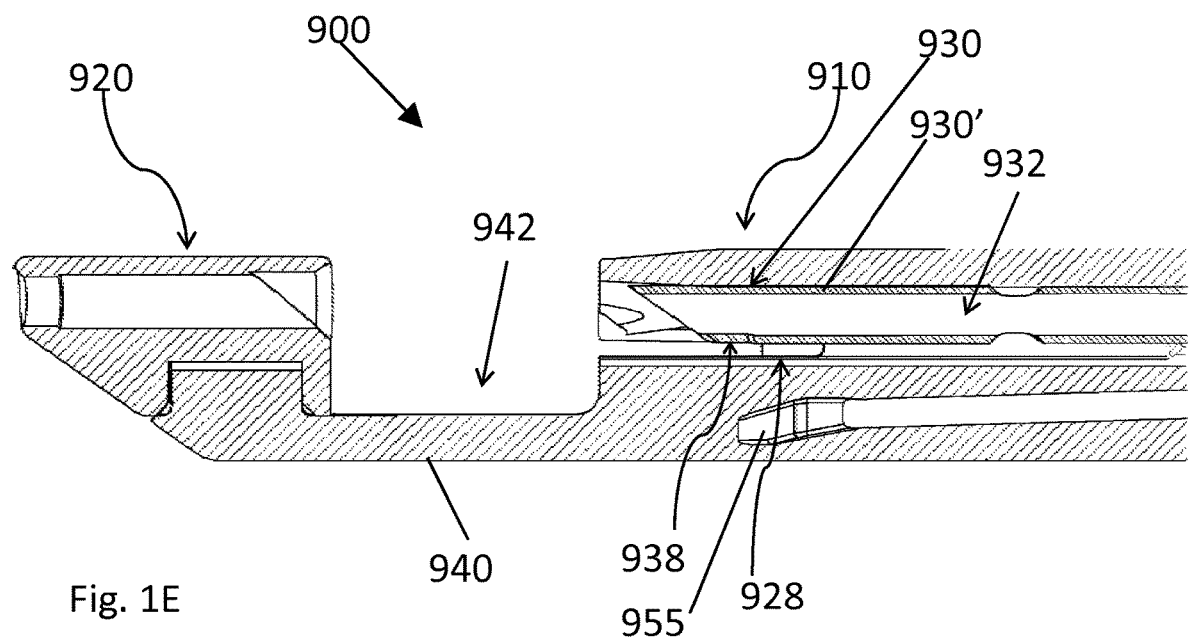
FIG. 1E illustrates a cross-sectional view of a portion of the surgical suturing instrument for use with a cartridge in accordance with an embodiment of the present invention.
Figure 1F:
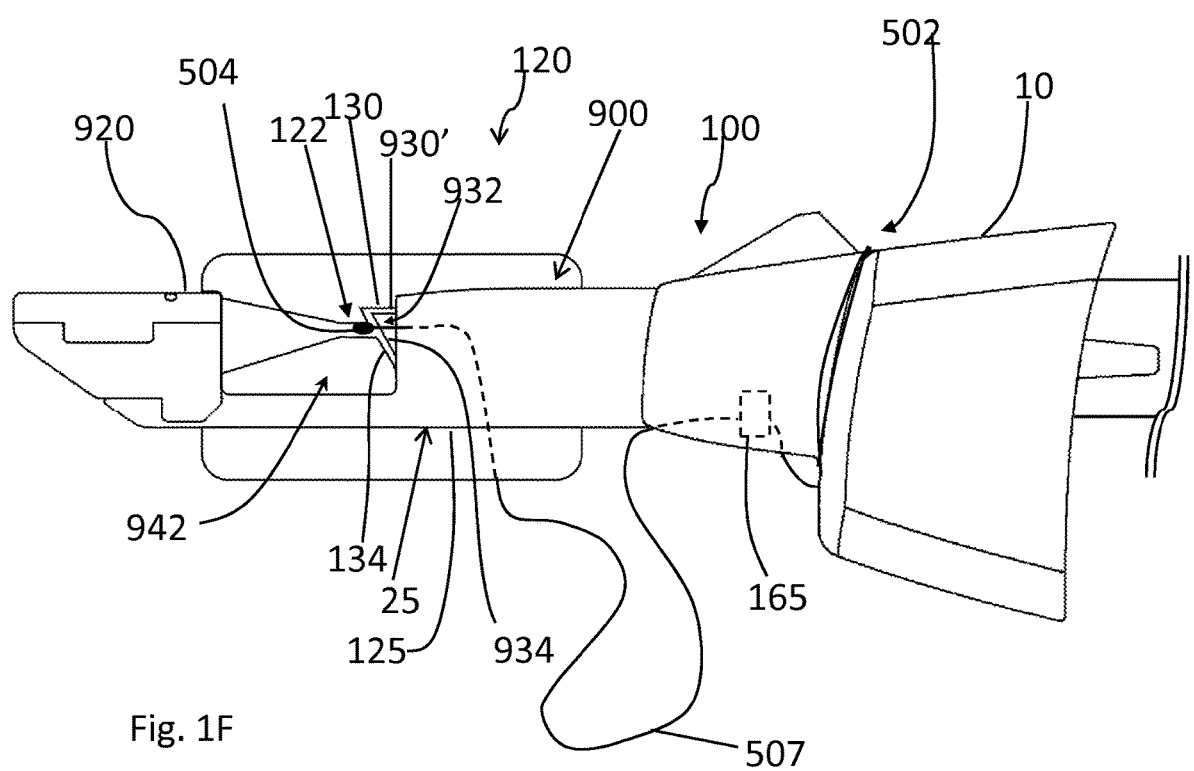
FIG. 1F illustrates a left side view of a cartridge mounted onto a surgical suturing instrument in accordance with an embodiment of the present invention.

In some embodiments of the present invention, as shown in FIG. 1A, the cartridge 100 includes an alignment feature that restrains or fixes/locks the position of the suturing instrument 900 relative to the cartridge to help align the seat 122 with suture receiving passage 932 of the of the suture passing member 930 such as a needle 930'. More specifically, the cartridge base 120 comprises a restraint 25 (means for restraining) for positioning a portion of the suturing instrument 900 received through the chamber 10 relative to the seat 122 for aligning the seat 122 with a suture receiving passage 932 of the suture passing member 930. In some embodiments, the restraint may function as a means for locking or snapping the cartridge 100 onto the suturing instrument, such as a locking feature. In the embodiment illustrated in FIG. 1A, the restraint 25 comprises a recess that functions as a locking recess 125 for receiving a portion of the surgical suturing instrument 900. As shown in FIG. 1F, the locking recess 125 receives the suturing instrument 900 and allows the base 120 of the cartridge 100 to be latched onto the suturing instrument 900. In other words, the locking recess 125 within the base 120 receives a portion of the surgical suturing instrument 900 (neck portion 940 and sections of the proximal and distal portions 910, 920) such that the base 120 press-fits around the portion of the suturing instrument 900, to lock the position of the surgical suturing instrument 900 relative to the base 120.

As shown in FIG. 1A, the cartridge 100 additionally comprises an alignment feature in the form of an alignment recess 130 located adjacent the seat 122. In a specific example, as shown in FIG. 1F, the alignment recess 130 is sized to allow the suture passing member 930 to be advanced therein to allow the suture receiving passage 932 to be aligned with the seat 122. As shown in FIG. 1F, the alignment recess 130 additionally comprises a bevel face 134 that matches the bevel face 934 of the needle 930' to further assist in aligning the needle 930' with the seat 122. Thus, in the exemplary embodiment, the alignment recess 130 receives a portion of the suture passing member 930, such as a needle 930', when it is advanced distally to allow the suture receiving passage 932 to be placed in line with the suture end 504 held within the seat 122. This permits suture 500 to be loaded onto the suturing instrument 900, for example, by allowing the tug loop 507 (that is connected to the end portion 504 of the suture 500) to be pulled to transfer the suture end 504 from the cartridge 100 into the suture receiving passage 932. The alignment recess 130 allows the seat 122 to be brought adjacent and in communication with the suture receiving passage 932 to allow the suture end 504 to be transferred into the lumen of the suture passing member 930.

The cartridge may additionally comprise features to assist in routing of the suture 500 to facilitate manipulation of the suture 500 in order to transfer the suture 500 from the cartridge 100 to the surgical suturing instrument 900. With reference now to FIGS. 1B and 1E, in some embodiments the base 120 of the cartridge 100 further defines a base channel or base slot 128 in communication with the seat 122 for routing the suture 500 to facilitate manipulation of the suture 500 in order to load the suture 500 onto/within the suture passing member 930. In some embodiments, once the cartridge 100 is loaded onto the suturing instrument 900, the base slot 128 may be aligned with a longitudinal opening 928 within the suturing instrument 900 (for example, within the instrument proximal portion 910). In some embodiments, the suture passing member 930 may also comprise a slit 938 that can line up with the base slot 128 so that it is in communication with the base slot 128. This facilitates loading of the suture 500 into the suture receiving passage 932 by allowing room for suture 500 to exit the cartridge 100, so that it may be manipulated, for example by tugging on the suture 500, to allow it to be transferred from the seat 122 to within the suture passing member 930.

In some embodiments, the cartridge 100 may comprise a base 120 that is formed integrally with the chamber 10 or housing 10'. In other embodiments, the base 120 may be detachably coupled to the housing 10' via a detachable coupling 50, as shown in FIG. 1A. This may allow the base 120 to be decoupled from the housing 10' after suture end 504 is loaded into a suturing instrument using the cartridge 100. The housing 10' may then be advanced or slid proximally to position the housing 10' and pre-tied knot 502 along the instrument proximal portion, to permit deployment of the pre-tied knot 502 after the suturing instrument is used to apply suture to a region of tissue (such as an inter-vertebral disc), to help secure the suture 500 within the region of tissue.

In some such embodiments, with reference now to FIGS. 1A and 1B, the base 120 is indirectly coupled to the housing 10' through a flexible coupling 150 such as a flexible tube or tether 152. In some examples, a first end of the flexible tube 152 may be affixed permanently to one of the base 120 and the housing 10', whereas a second end of the flexible tube 152 may be removably attached to the other of the base 120 and the housing 10'. In the example shown, one end of the flexible tube 152 is permanently secured to the base 120 within the base slot 128, and the second end of the flexible tube 152 is received within a groove 16 within the housing 10' to be removably attached thereto. Alternatively, both ends of the flexible tube 152 could be permanently affixed to each of the base 120 and the housing 10', and the flexible tube 152 may be designed with break lines to allow separation of the flexible tube 152 into two parts under application of force, allowing detachment of the base 120 from the housing 10'. In another example, the flexible coupling 150 may comprise a flexible or soft hinge. Alternatively, the base 120 may be directly coupled to the housing 10' as discussed herein below with reference to FIGS. 3A-3D.

In some embodiments, the cartridge 100 may additionally comprise a means to store a length of suture 500, such as suture storage 60, shown in FIG. 1B. The suture storage 60 may comprise one or more spools 160 held within the cartridge 100. More specifically, the one or more spools 160 may be held within the housing 10' to store the service loop 501 and the locker 503 of the suture 500. The one or more spools 160 may help prevent entanglement of the suture 500 during loading of the suturing instrument 900 and/or during use of the suturing instrument 900. Alternatively, the suture 500 may be held within suture payout tubes as discussed herein below with reference to FIG. 2E.

Example 1B

Referring again to FIG. 1B, in some embodiments the cartridge 100 comprises a suture retaining component 65 such as a suture retaining pin 165 for retaining a portion of the suture 500 to allow the tug loop 507 of the suture 500 to be pulled (to transfer the suture end 504 within the suture receiving passage 932 of the suture passing member 930) while minimizing or preventing force from being applied to the service loop 501. This may help prevent the service loop 501 from being pulled out prematurely from the suture storage 60. In the illustrated embodiment, the suture retention pin 165 is releasable, which allows the housing 10' (and thus chamber 10) to be advanced independently from the base 120 proximally along the proximal portion 910 of the surgical suturing instrument 900 in order to place the housing 10' in a position for deployment of the pre-tied knot 502 carried thereon.

Example 2

Figure 2A:
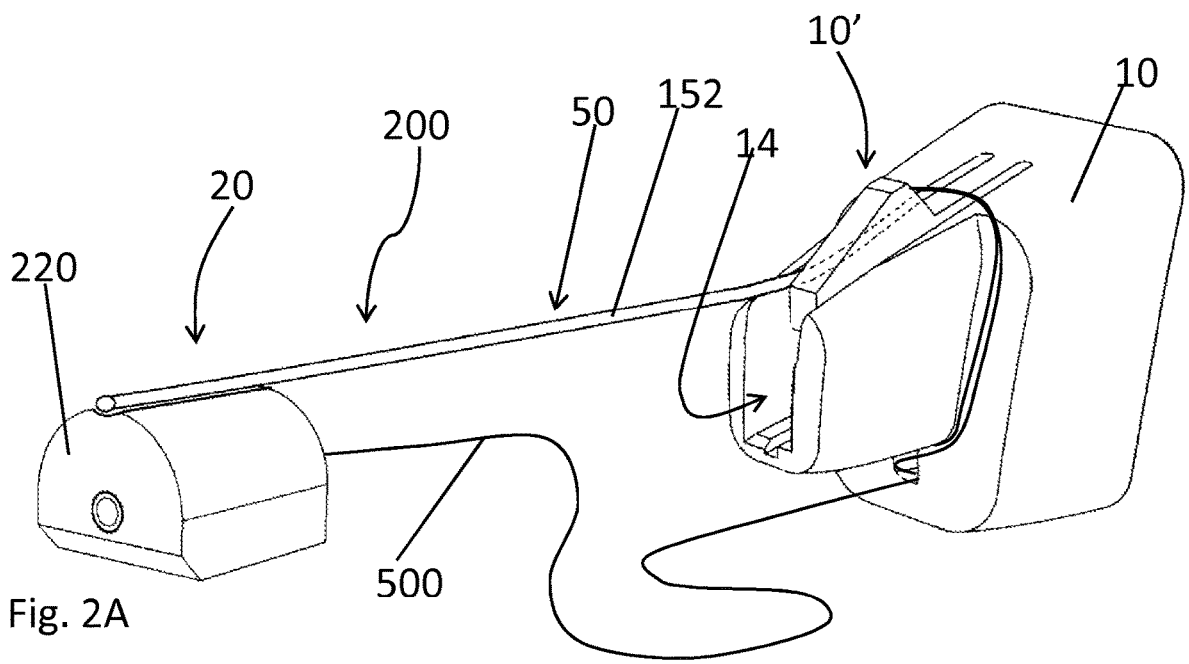
FIG. 2A illustrates a left side perspective view of a cartridge in accordance with an alternate embodiment of the present invention.

In an alternative embodiment of the cartridge, referring initially to FIG. 2A, a cartridge 200 is disclosed that similar to the previous embodiment, comprises a base 220 that is coupled to a housing 10' defining a chamber 10 (housing 10' may of the type shown previously with respect to FIGS. 1A and 1B). And similarly, the cartridge is structured to allow a seat 222 to be brought into alignment with and adjacent a suture receiving passage 932 of a suture passing member 930, to allow the suture 500 to be transferred to a suturing instrument. The suturing instrument 900 may be of the type described previously with respect to FIGS. 1C-1E. Furthermore, the cartridge 200 provides a base 220 that is moveable relative to the chamber 10 (housing 10') to bring the suture end 504 into alignment with the suture receiving passage 932.

Specifically with reference again to FIG. 2A, cartridge 200 comprises a base 220 that is coupled to the housing 10' via a detachable coupling 50 comprising a flexible tube/tether 152. The base 220 defines a seat 222 for releasably holding or retaining the suture end 504, as shown in FIG. 2C. In the illustrated embodiment, the seat 222 is defined by a projection 230 extending into an instrument receiving recess or groove/channel 225 of the cartridge 200. More particularly, the projection 230 comprises a hollow interior defining a seat channel 224 that the suture end 504 can be press-fit into. In a specific example, the suture end 504 is a knot 504' that can be press-fit into the seat channel 224.

Figure 2B:
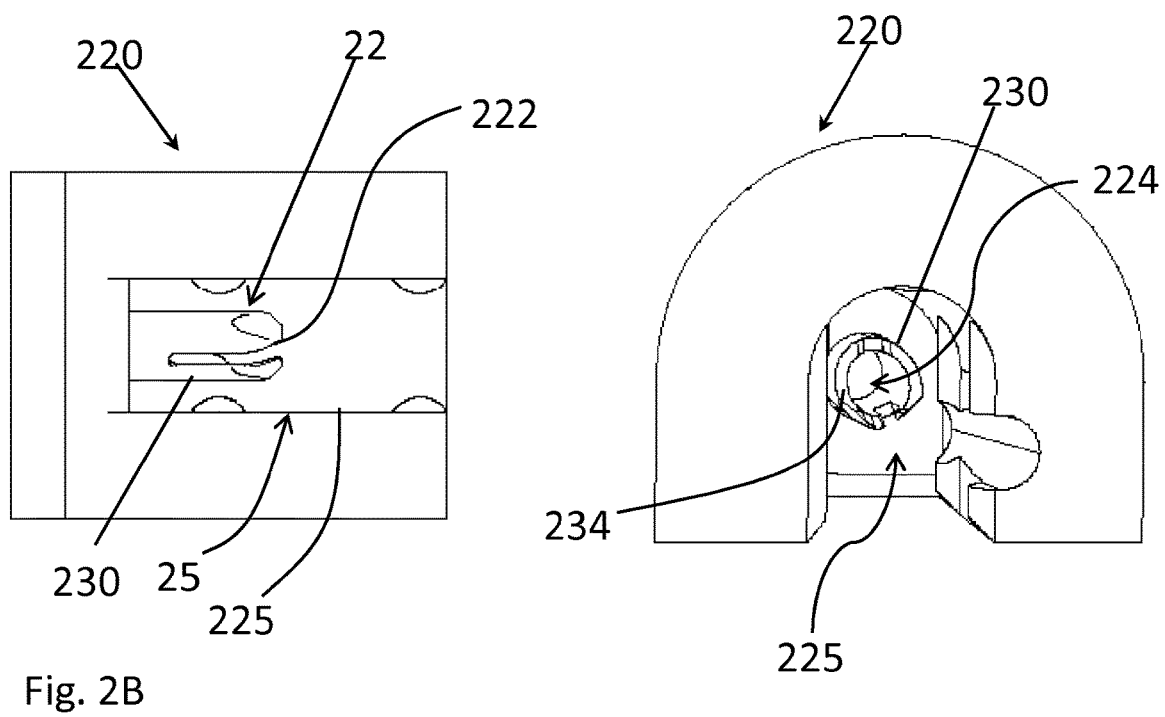
FIG. 2B illustrates a bottom view and a rear view of a cartridge base in accordance with an alternate embodiment of the present invention.
Figure 2C:
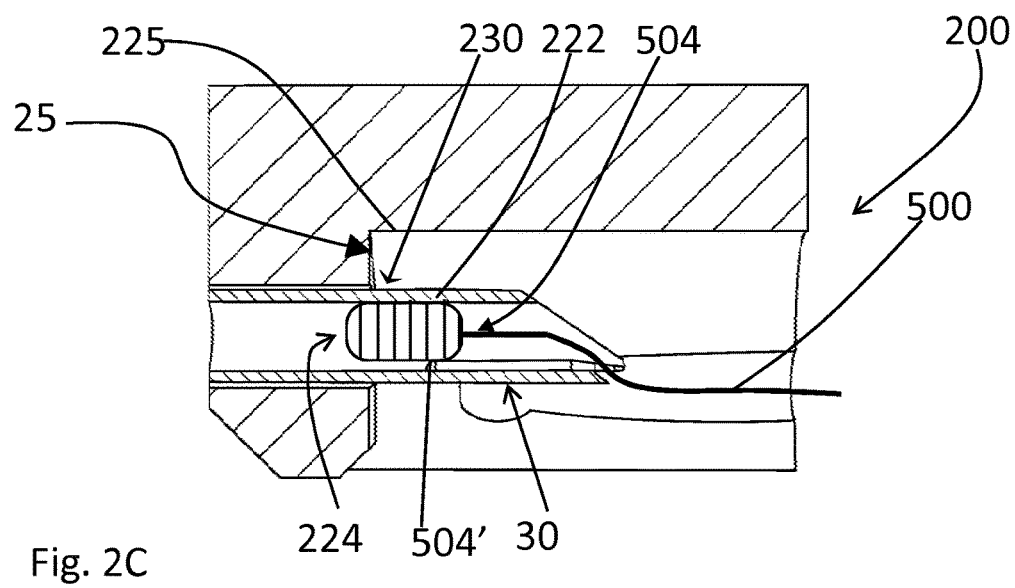
FIG. 2C illustrates a cross-sectional view of a cartridge base in accordance with an alternate embodiment of the present invention.

With reference now to FIGS. 2B and 2C, the cartridge 200 comprises an alignment feature comprising a restraint 25 (means for restraining) for positioning a portion of the suturing instrument 900 (received through the channel 14 within the chamber 10) relative to the seat 222 for aligning the seat with a suture receiving passage 932 of the suture passing member 930. The restraint 25 allows the cartridge 200 to be coupled to the suturing instrument 900. In the particular embodiment shown in FIGS. 2B-2D, the base 220 has a restraint 25 formed by the recess 225 that functions as a locking recess 225. The locking recess 225 receives a section 911 of the shaft 910 of the suturing instrument 900 in a press-fit sliding engagement such that the base 220 press-fits around the shaft 910. Once the shaft section 911 is received and positioned within the locking recess 225, the cartridge base 220 may be slid or translated proximally along the proximal portion or shaft 910 to align the seat 222 with the suture receiving passage 932 of the suturing instrument 900, for permitting transfer of the suture end 504 from the seat 222 within the cartridge into the suture receiving passage 932.

Figure 2D:
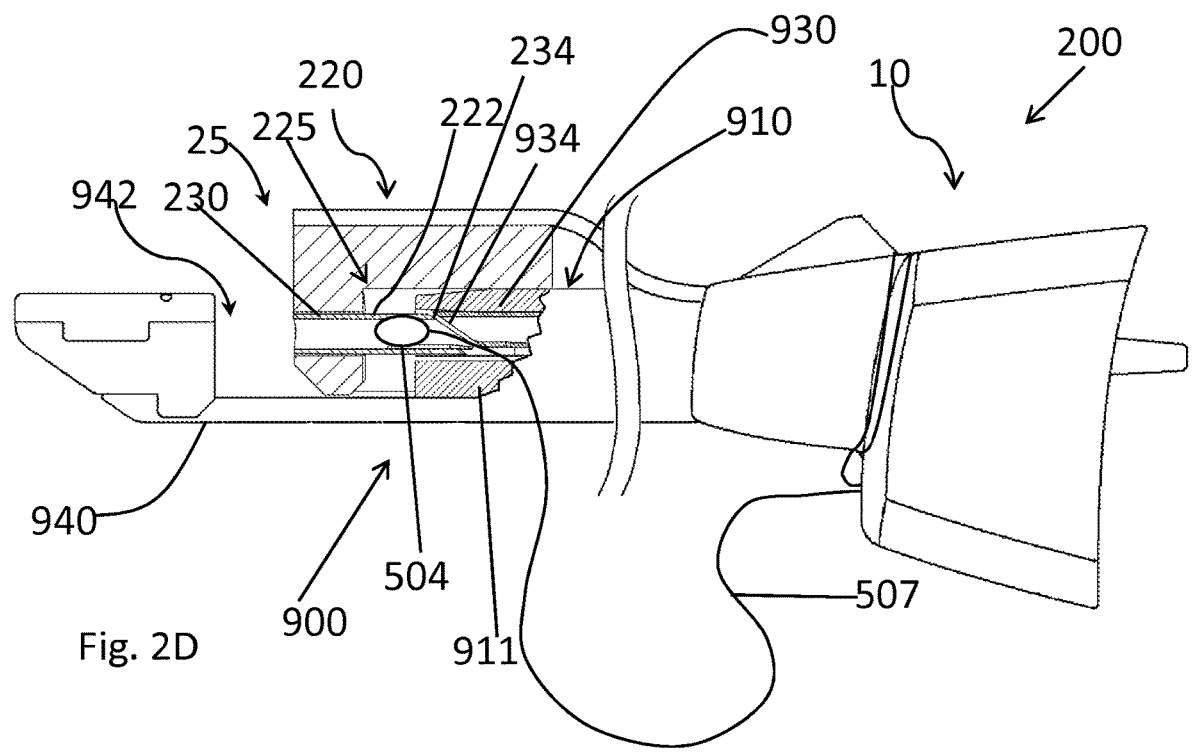
FIG. 2D illustrates a partial cross-sectional view of a cartridge base with the cartridge shown to be mounted onto a surgical suturing instrument in accordance with an alternate embodiment of the present invention.

As shown in FIG. 2D, in use, once a portion of the suturing instrument 900 is received through/within the chamber 10, the cartridge base 220 is loaded onto the surgical suturing instrument 900, and is moveable proximally (along with the seat 222) relative the chamber 10 to bring the suture end 504 into alignment with and adjacent the suture receiving passage 932 of the suture passing member 930.

In some embodiments, as illustrated in FIGS. 2C and 2D, an alignment feature in the form of a projection 230 is provided to further aid in aligning the seat 222 within the suture receiving passage 932. As outlined previously, the cartridge base 220 comprises a projection 230 that defines the seat 222. The projection 230 extends into the instrument receiving recess or locking recess 225. In one such embodiment, the projection 230 forms an alignment feature. More specifically, the projection 230 is capable of abutting against/mating with the suture passing member 930 (such as needle 930') when brought into engagement therewith. In the present embodiment illustrated in FIG. 2D, the base 220 of the cartridge 200 can be slid proximally along the shaft 910 so that the projection 230 abuts against the needle 930' to align the seat 222 with the suture receiving passage 932. More specifically, the projection segment 232 abuts against the needle 930' to co-operatively engage with and align the needle 930' to bring the seat 222 into alignment with the suture receiving passage 932. The seat 222 is brought into communication with the suture receiving passage 932. In one specific example as shown in FIG. 2B-2D, the projection 230 defines a bevel face 234 for engaging with a bevel face 934 of the needle 930' for docking the needle 930' to align the needle 930' with the seat 222 to permit transfer of the suture end 504 from the seat 222 into the suture receiving passage 932 of the needle 930', for example, by pulling on the tug loop 507. Additionally, the cartridge 200 may comprise a snap that can engage with an opening 955 (shown in FIG. 1E) within the shaft 910 as an alignment feature to help align the seat 222 with the suture receiving passage 932 of the suturing instrument 900.

Alternatively, an active mechanism, may be provided such as a push feature to push the suture end 504 from the seat 222 into the suture receiving passage 932. In some embodiments, the mechanism may comprise a plunger that can be activated to push the suture end 504 from the seat 222 into the suture receiving passage 932. In a particular example of this, the plunger may be advanced automatically into the seat channel 224 as the suturing instrument 900 is advanced distally with respect to the instrument receiving or locking recess 225. The plunger is capable of pushing the suture end 504 from the seat 222 and into the suture receiving recess 932 of the suturing instrument 900.

Figure 2E:
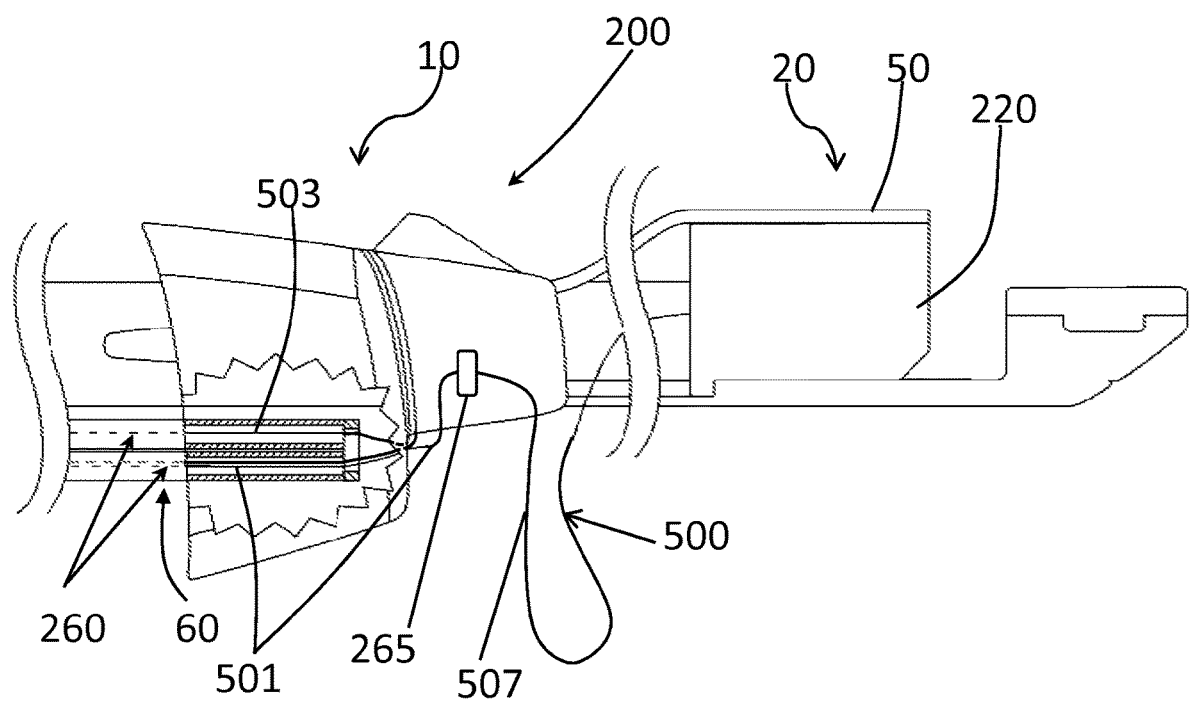
FIG. 2E illustrates a partial cross-sectional view of a cartridge housing with the cartridge shown to be mounted onto a surgical suturing instrument in accordance with an alternate embodiment of the present invention.

Referring now to FIG. 2E, in some embodiments the cartridge 200 comprises a means to store the length of suture 500, i.e. suture storage 60 in the form of one or more suture tubes or payout tubes 260. More specifically, each of the service loop 501 and the locker 503 (extending from the pre-tied knot 502 formed from the length of suture 500) is stored within payout tube 260. The payout tubes 260 may be coupled to the cartridge 200 or may be coupled to a component of the cartridge 200. In the illustrated embodiment, the payout tubes 260 are held within the housing 10' of the cartridge 200. The payout tubes 260 may help prevent entanglement of the suture 500 during handling and loading of the cartridge 200 onto the surgical suturing instrument, and/or during use of the surgical suturing instrument 900 to pass suture 500 within a region of tissue within a patient's body.

Referring again to FIG. 2E, in some embodiments, the cartridge 200 further comprises a suture retaining component 65 such as a suture retaining pin 265. The retaining pin 265 for retaining a portion of the suture 500 comprising the tug loop 507, so that when the tug loop 507 is pulled to transfer the suture end 504 from the seat 222 into the suture receiving passage 932 within the needle 930', forces exerted on the service loop 501 are minimized to prevent suture 500 from being pulled out of the suture storage 60 which in this particular example comprises a payout tube 260.

Example 3

With reference now to FIGS. 3A-3D, an alternative embodiment of the cartridge 300 is disclosed. Similar to the embodiments discussed previously a cartridge 300 is provided comprising base 320 that is coupled to a housing 10' defining a chamber 10 (housing 10' may of the type shown previously with respect to FIGS. 1A and 1B). The base defines a seat 322 for releasably holding or retaining the suture end 504. This alternative embodiment provides the same function as cartridge 100, 200, with the cartridge being structured to allow seat 322 to be brought into alignment with and adjacent a suture receiving passage 932 of a suture passing member 930 (the suturing instrument may be of the type described previously with reference to FIGS. 1C-1E). However, the present embodiment additionally provides a seat 322 that is moveable relative to the chamber 10 (housing 10'). More specifically, the base 320 (including the seat 322 it defines) may be moved relative to the chamber 10 to bring the suture end 504 into alignment with and adjacent the suture receiving passage 932 of the suture passing member 930 when a portion of the suturing instrument 900 is received through the channel within the chamber 10, to permit transfer of the suture end 504 from the seat 122 within the cartridge 100 into the suture receiving passage 932.

More specifically, the base 320 includes an alignment feature in the form of a moveable seat 322. The seat 322 is moveable to bring it into alignment with the suture receiving recess 932 of the suturing instrument 900. More specifically, base 320 houses a moveable magazine 321 that is coupled to the base 320 and is reciprocally moveable within the base 320, with the magazine 321 defining the seat 322. The magazine 321, and thus the seat 322 defined thereby are moveable relative to the chamber 10 to bring the suture end 504 into alignment with and adjacent the suture receiving passage 932 of the suture passing member 930. In one specific example as shown in FIG. 3A, the magazine 321 is moveable downwards with respect to the base 320 for bringing the seat 322 into alignment with the surgical suturing instrument 900.

Similar to embodiments discussed previously hereinabove, the cartridge 300 comprises an alignment feature in the form of a restraint 25 (means for restraining) for positioning a portion of the suturing instrument received through the chamber 10 relative to the seat 322, to align the seat 322 with a suture receiving passage 932 of the suture passing member 930. As shown in FIGS. 3A-3C, the restraint 25 comprises a tail hook 325. As shown in further detail in FIG. 3E, the tail hook 325 extends into an instrument receiving recess 325' of the cartridge 300. The tail hook 325 is engageable with a portion of the suturing instrument 900 to align the magazine 321 with a tissue receiving gap 942 of the suturing instrument 900. The restraint 25 additionally comprises the instrument receiving recess or locking recess 325' that receives a part of the suturing instrument 900.

In further detail, with specific reference now to FIG. 3C, once the cartridge 300 is loaded onto the suturing instrument 900, it may be advanced along the shaft 910 of the suturing instrument 900. As the cartridge is slid along the shaft of the suturing instrument 900, the tail hook 325 engages with the proximal portion or position or shaft 910 of the surgical instrument to restrain or position the cartridge 300 such that the magazine 321 is aligned with the tissue receiving gap 942. This may help ensure that the magazine 321 is in a position to permit movement of the seat 322 to bring the suture end 504 into alignment with the suture receiving passage 932. Thus, the magazine 321 and thus the seat 322 therein are moveable downwards into the tissue receiving gap 942 to bring the seat 322 into alignment with the suture receiving passage 932 of the surgical suturing instrument 900.

Figure 3A:
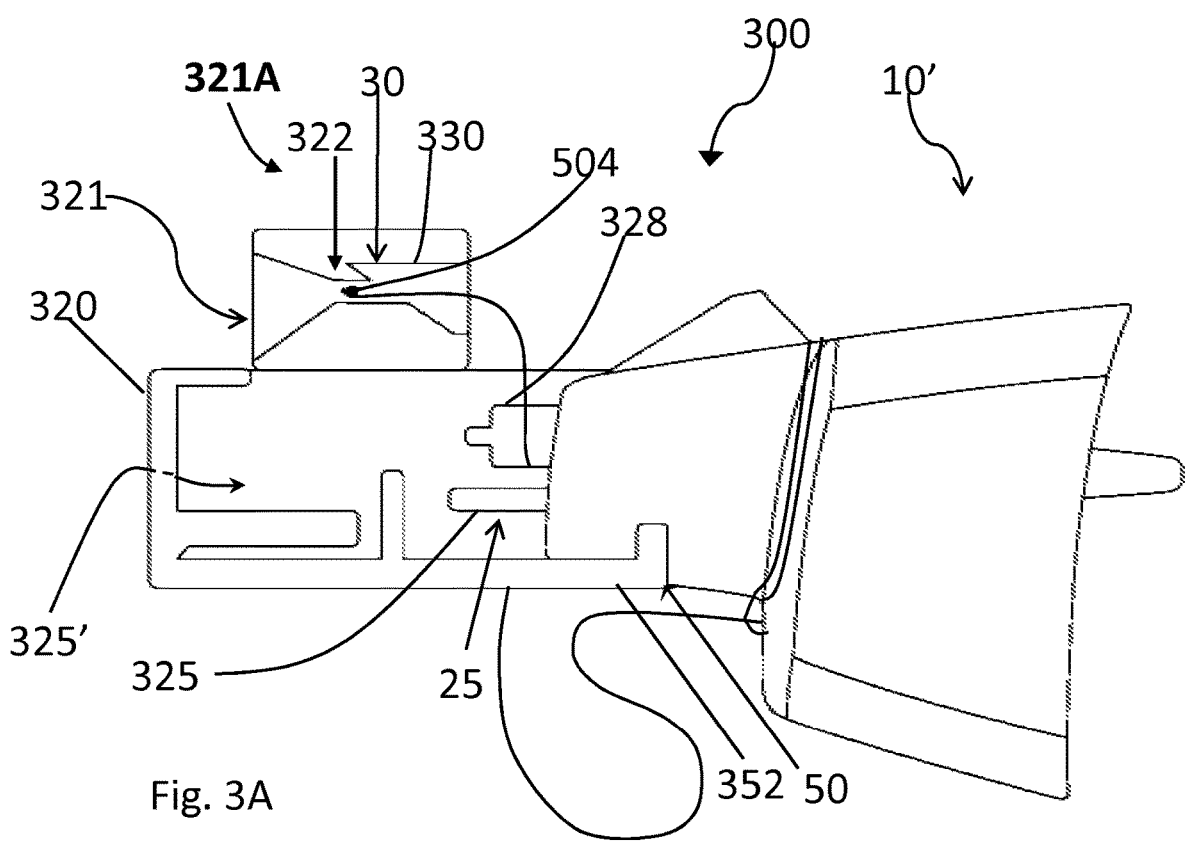
FIG. 3A illustrates a left side view of a cartridge in accordance with an embodiment of the present invention.
Figure 3B:
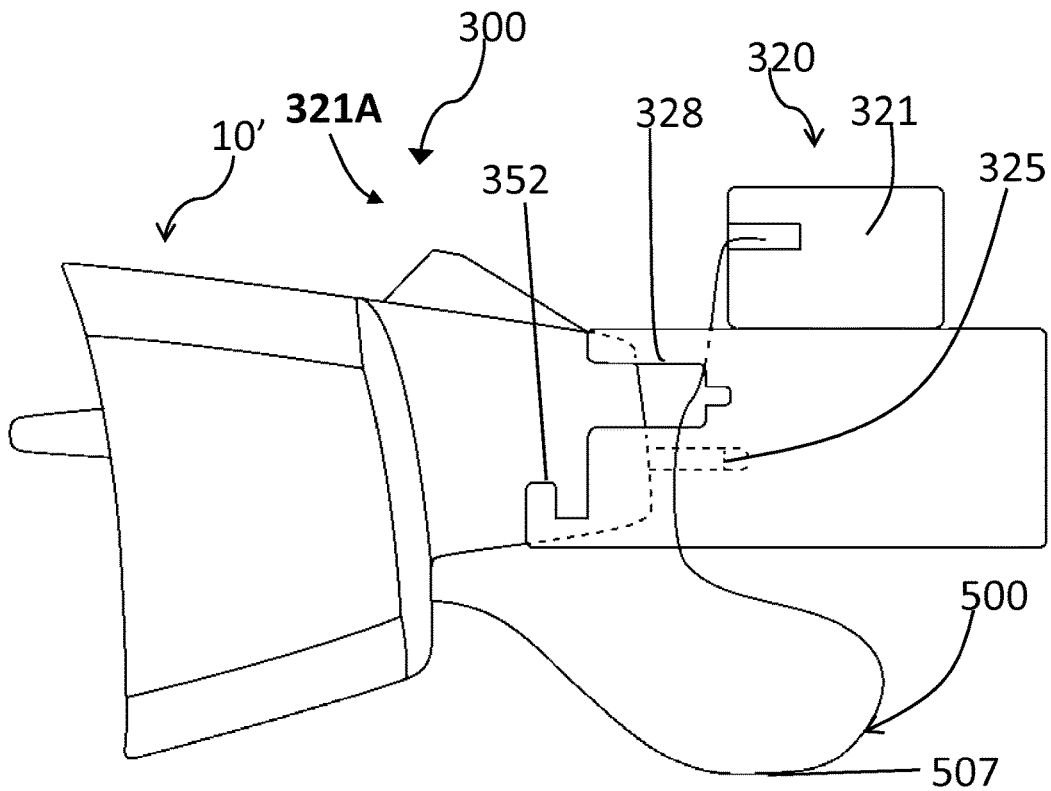
FIG. 3B illustrates a right side view of a cartridge in accordance with an embodiment of the present invention.
Figure 3C:
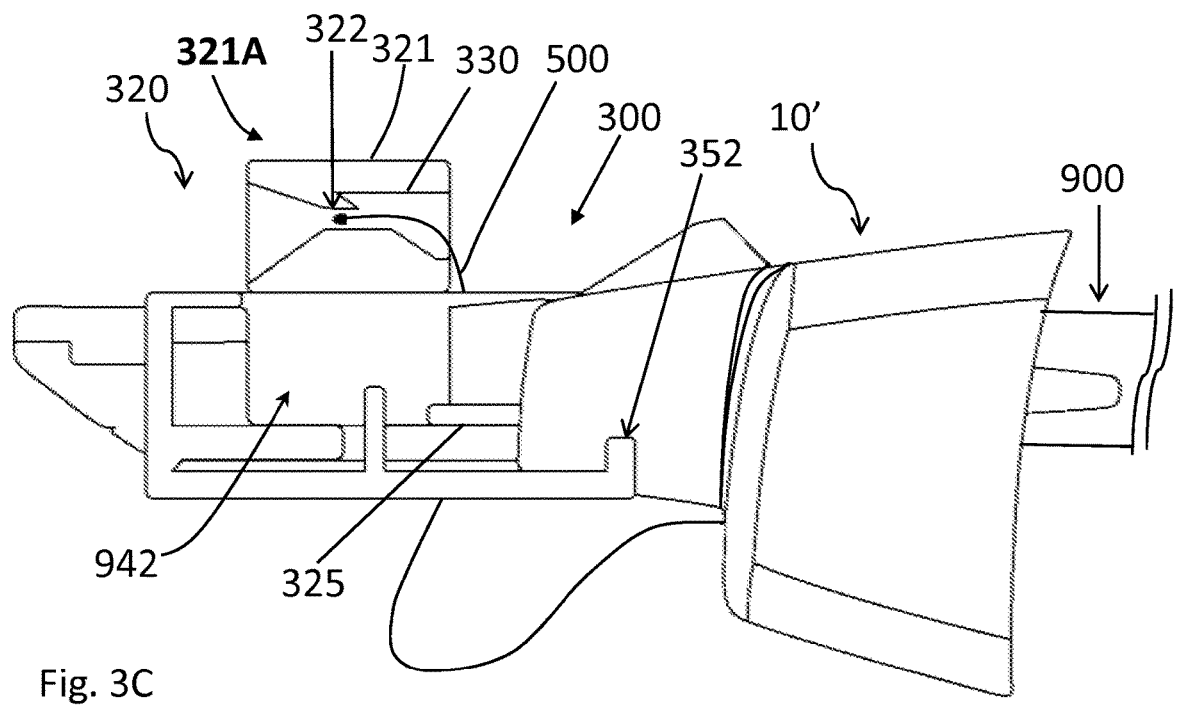
FIG. 3C illustrates a left side view of a cartridge mounted onto a surgical suturing instrument in accordance with an embodiment of the present invention.
Figure 3D:
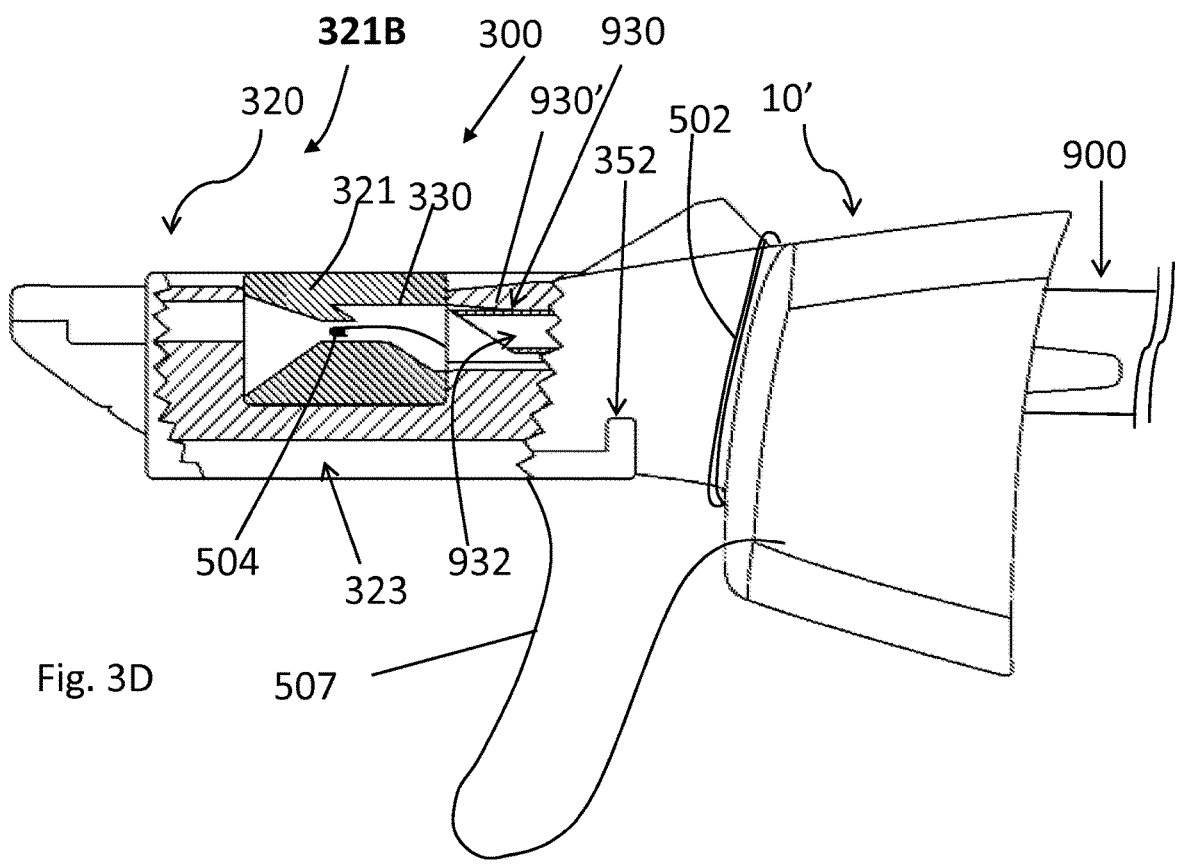
FIG. 3D illustrates a partial cross-section view of a cartridge mounted onto a surgical suturing instrument in accordance with an embodiment of the present invention.

Referring now to FIGS. 3A, 3C-3D, the magazine 321 defines an alignment feature in the form of an alignment recess 330 in communication with the seat 322. Once the magazine 321 is moved from its first or initial position 321A, as shown in FIG. 3C, to its second position 321B as shown in FIG. 3D, the alignment recess 330 is in line with the suture passing member 930, and is positioned for receiving the suture passing member 930 therein, to allow suture end 504 to be transferred from the seat 322 to the suture receiving passage 932 of the suture passing member 930. For example, the suture passing member 930 in the form of a needle 930' can then be advanced in the alignment recess, for example, upon actuation of a trigger. The suture end 504 can then be transferred by pulling the tug loop 507 of the suture 500.

As shown in FIGS. 3A and 3B, in some embodiments, the cartridge 300 comprises a base slot 328 to assist in routing of the suture to facilitate manipulation of the suture to transfer the suture 500 from cartridge 100 to surgical suturing instrument 900. The base slot 328 provides an exit point for the suture tug loop 507 to permit tug loop 507 to be pulled once the magazine 321 is positioned within the tissue receiving gap 942 of the suturing instrument 900 to permit loading of the suture end 504 into the suture receiving passage 932.

With reference again to FIG. 3A, the base 320 may be detachably coupled to the housing 10' via a detachable coupling 50. In some such embodiments, the base 320 is coupled directly to the housing 10'. In a particular example of this as shown in FIGS. 3A-3D, the base 320 is detachably coupled to the housing 10' (chamber 10) via a rigid coupling comprising an interlock or snap 352. In one example, the snap 352 comprises a tab that is receivable within an opening within the housing 10'. In some examples, the snap 352 is automatically releasable upon movement of the magazine 321 within the tissue receiving gap 942. For example, the magazine 321, as it fits into the tissue receiving gap 942, may disengage the tab from the opening.

As shown in FIG. 3D, the base 320 comprises an open slot (exit slot) 323 along a bottom portion 301 of the base 320 to permit removal of the base 320 from the top. The slot 323 functions to eliminate any hindrance from the instrument 900 as the base 320 is removed.

Example 4

In an alternate embodiment of the present invention, as shown in FIGS. 4A-4D, a cartridge 400 is disclosed. Similar to cartridge 300, cartridge 400 provides a seat 422 that is moveable relative to the chamber 10 (housing 10'). Additionally, cartridge 400 incorporates a seat 422 that is automatically moveable.

Figure 4A:
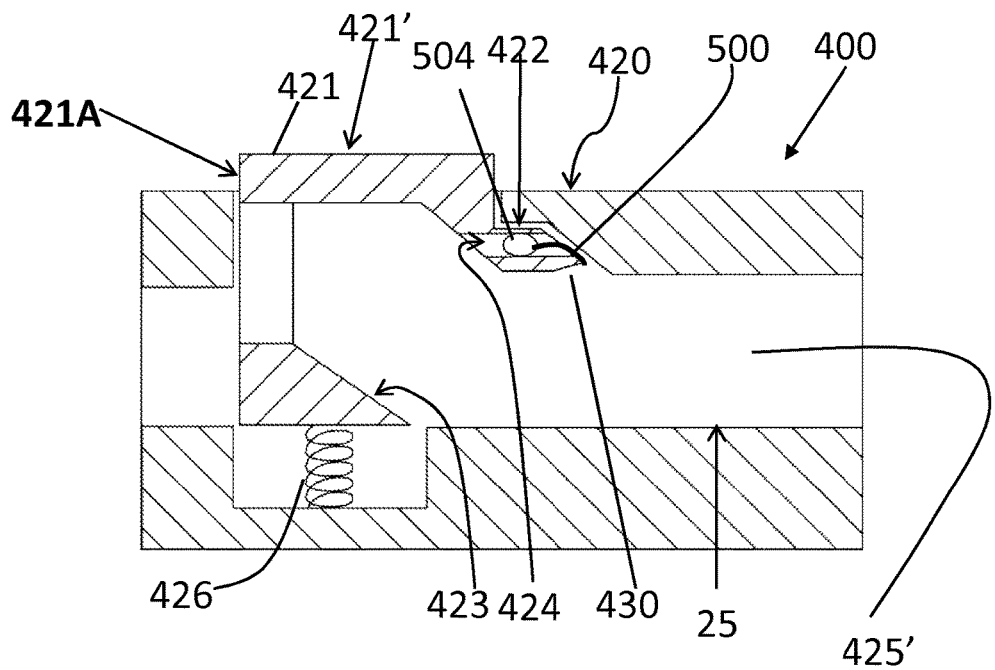
FIG. 4A illustrates a cross-sectional view of a cartridge in accordance with an alternate embodiment of the present invention.

With reference now to FIG. 4A, a cartridge 400 is disclosed comprising a cartridge base 420 that is coupled to a housing, for example a housing 10' of the type discussed previously herein above. In one example, the base 420 may be detachably coupled to the housing 10' (chamber 10). Base 420 comprises a magazine 421 which defines the seat 422 for releasably holding or retaining the suture end 504. More specifically, the magazine 421 comprises a projection 430 which defines the seat 422. In a specific example the seat 422 comprises a seat channel 424 and the suture end 504 is press-fit within the seat channel.

Figure 4B:
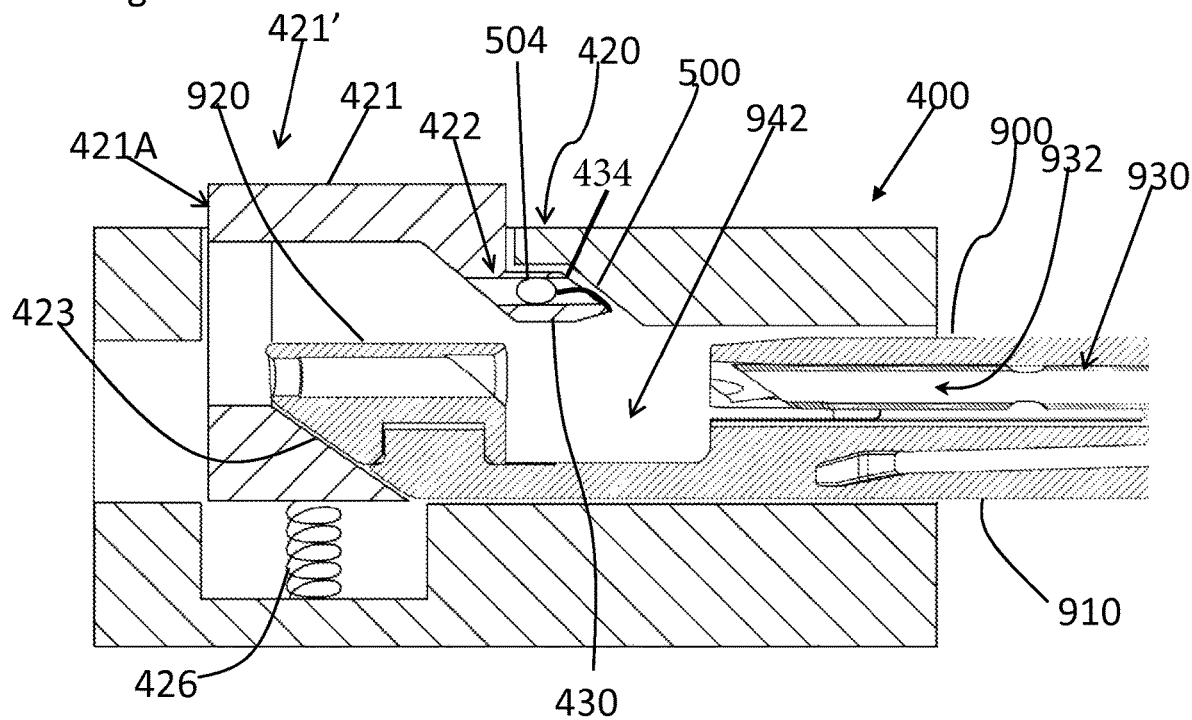
FIG. 4B illustrates a cross-sectional view of a cartridge with a surgical suturing instrument partially advanced therein, in accordance with an embodiment of the present invention.
Figure 4C:
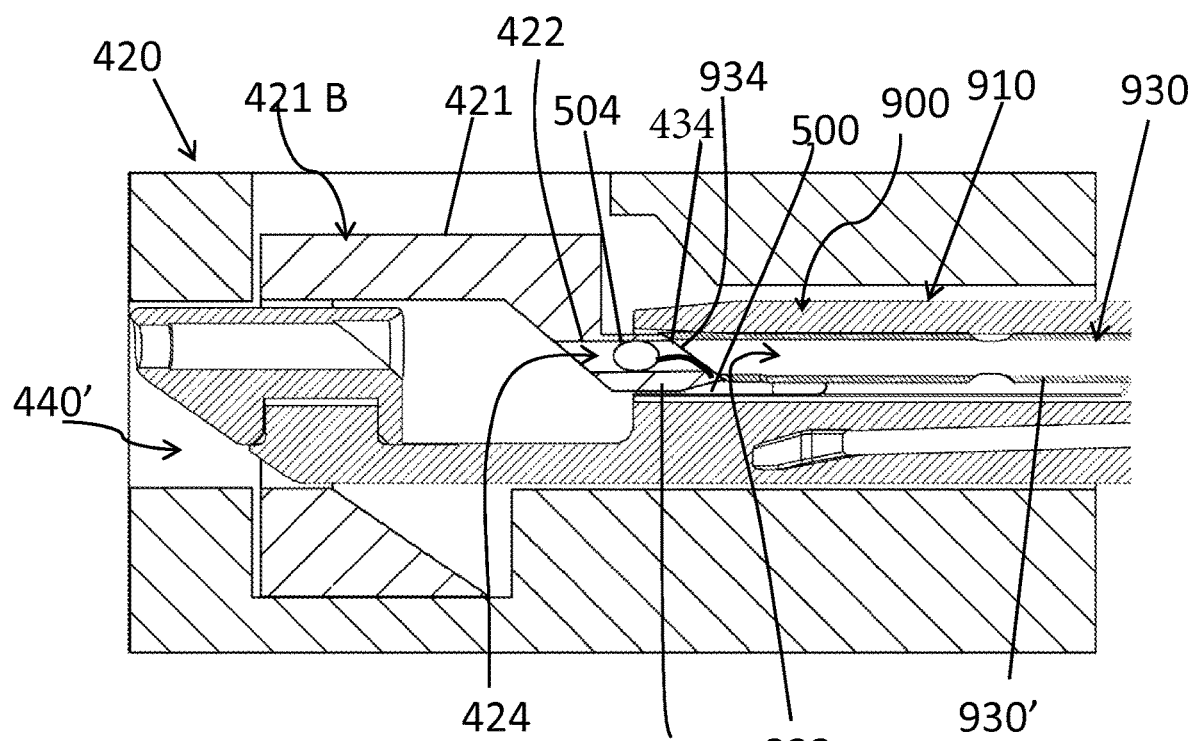
FIG. 4C illustrates a cross-sectional view of a cartridge with a surgical suturing instrument advanced therein, in accordance with an embodiment of the present invention.

In the embodiment shown in FIGS. 4A-4C, the cartridge 400 comprises an alignment feature in the form of a restraint 25 comprising an instrument receiving recess or locking recess 425' that allows the suturing instrument 900 to be positioned within the base 420 to allow the seat 422 to be aligned with the suture receiving passage 932. Additionally, the alignment feature comprises a moveable seat 422. The magazine 421 is mounted onto a spring 426 forming a spring biased interlock 421' which is automatically moveable upon advancement of the surgical suturing instrument 900 within an instrument receiving recess 425' of the base 420. Movement of the interlock 421' translates into a movement of the projection 430 defining the seat 422. Thus, the seat 422 is moveable upon advancement of the suturing instrument 900 to bring the suture into alignment with the suture receiving passage 932.

More specifically, referring now to FIG. 4B, the spring biased interlock 421' is shown in its initial position 421A. As shown in FIG. 4C, the interlock 421' is moveable from its first or initial position 421A, into its second position 421B upon advancement of the suturing instrument 900 within the instrument receiving recess 425'. Movement or depression of the interlock 421' into its second position 421B allows the seat 422 to be brought into alignment with the suture passing member 930 and the suture receiving passage 932. More specifically, the interlock 421' comprises a ramp 423 (shown in FIGS. 4A, 4B) that is engaged by the distal tip 920 of the suturing instrument 900 as the suturing instrument 900 is advanced to automatically move the interlock 421'. For example ramp 423 is engaged by a tapered surface of the distal tip 920. As a result seat 422 (defined by projection 430) is automatically moveable and travels downwards into the tissue receiving gap 942 to bring the seat 422 (and thus the suture end 504 it retains) into alignment with the suture receiving passage 932 of the surgical suturing instrument 900. In other words, the (magazine 421) and thus seat 422 is automatically moveable upon relative movement between the cartridge base 420 and the surgical suturing instrument 900.

In some embodiments, an additional alignment feature is provided to further aid in aligning the seat 422 with the suture receiving passage 932. As mentioned previously, cartridge base 420 comprises a projection 430 that defines the seat 422. The projection 430 extends into the instrument receiving recess 425' and defines an alignment feature. The projection 430 is capable of abutting against/mating with the suture passing member 930 such as needle 930' when brought into engagement therewith. In the present embodiment illustrated in FIG. 4C, as the surgical suturing instrument 900 is advanced, the magazine 421 moves downwards into the tissue receiving gap. Magazine 421, and thus projection 430 and the seat 422 it defines, all move proximally with respect to the suturing instrument 900, so that the projection 430 abuts against the needle 930' to align the seat 422 with the suture receiving passage 932. More specifically, the projection 930 abuts against the needle 930' to co-operatively engage with and align the needle 930' to bring the seat 422 into alignment with the suture receiving passage 932. The seat 422 is brought into communication with the suture receiving passage 932. In the specific example shown in FIGS. 4B-4C, the projection 430 defines a bevel face 434 for engaging with a bevel face 934 of the needle 930' for docking the needle 930' to align the needle 930' with the seat 222 to permit transfer of the suture end 504 from the seat 222 into the suture receiving passage 932 of the needle 930', for example, by pulling on the tug loop 507. Alternatively, in some embodiments, the suture end 504 may be transferred automatically from the seat 422 into the suture receiving passage 932, for example using a plunger.

In one particular embodiment, the cartridge 400 may comprise a mechanism to permit automatic decoupling of the cartridge base from the suturing instrument 900 and/or the housing 10'. In the illustrated embodiment, once the suturing instrument 900 is withdrawn from the cartridge base 420, the spring biased interlock 421' is capable of automatically returning from its second position 421B (shown in FIG. 4C) to its original position 421A (shown in FIG. 4A) to permit de-coupling of the base 420 from the suturing instrument 900 and/or housing 10' (chamber 10).

Example 5

Figure 5A:
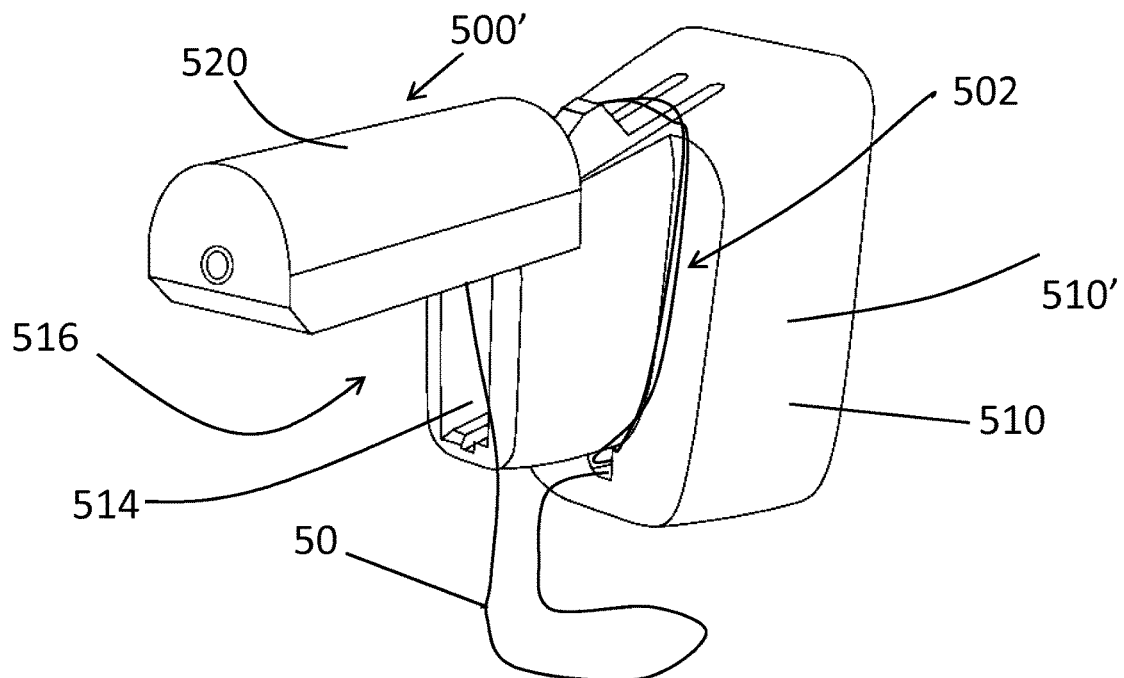
FIG. 5A illustrates a left perspective view of a cartridge in accordance with an embodiment of the present invention.
Figure 5B:
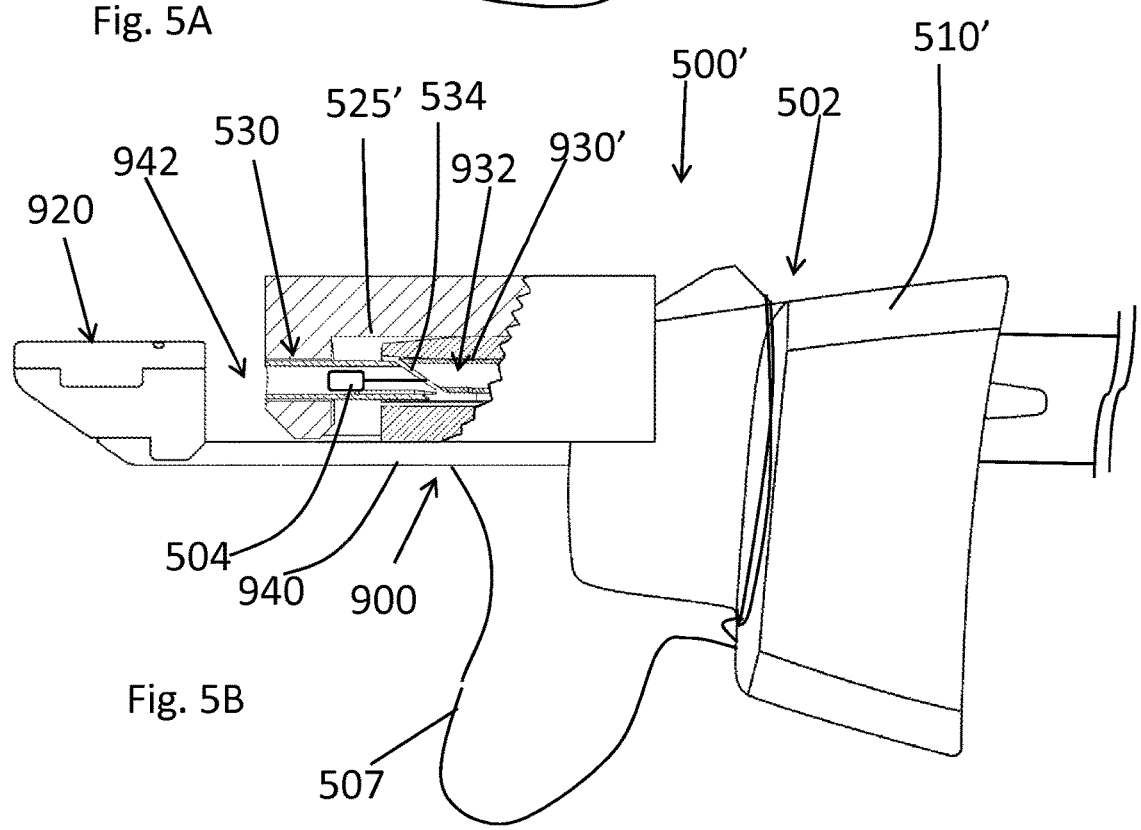
FIG. 5B illustrates a partial cross-sectional view of a cartridge an accordance with an alternate embodiment of the present invention.

In accordance with an additional broad embodiment of the present invention, a cartridge is provided that is configured to bring suture into alignment with and adjacent the suture receiving passage of a suturing instrument. As illustrated in FIGS. 5A and 5B, the cartridge 500' provides a base 520 that is coupled to a housing 510' defining a chamber 510 comprising a channel 514 for allowing the suturing instrument 900 to be received there-through. The cartridge 500' further comprises a projection 530 that defines the seat 522 for releasably holding an end of the suture end 504. Similar to the cartridge 200, the cartridge 500' is structured to allow a seat 522 and thus suture end 504 held therein, to be brought into alignment with the suture receiving passage 932 of the suture passing member 930. The cartridge 500' additionally comprises alignment features to assist in aligning the seat 322 with the suture receiving passage 932 of the suturing instrument 900. The cartridge 500' further comprises a cut-out 516 below the base 520 to enable the cartridge base 520 to be snapped into the tissue receiving gap 942 of the suturing instrument 900. The cut-out 516 functions as an alignment feature to align the seat 522 with the suture passing member 930, as shown in FIG. 5B. The cartridge base 520 further comprises an alignment feature in the form of an instrument receiving recess or locking recess 525'. Additionally, projection 530 extends into the locking recess 525' and also forms an alignment feature. Projection 530 may be referred to as the alignment projection 530. The method of using cartridge 500' is outlined further herein below.

In one broad embodiment of the present invention, a cartridge is provided for enabling axial loading of the cartridge onto a suturing instrument to load suture and/or a ferrule coupled to the suture onto the surgical suturing instrument. In some such embodiments, a cartridge is provided that can be loaded onto a front end of the surgical suturing instrument. In other embodiments, a cartridge is provided that comprises a component that can be lowered into the tissue receiving gap of the suturing instrument and can be advanced axially within the gap to load the suture and/or ferrule.

Example 6

Figure 6A:
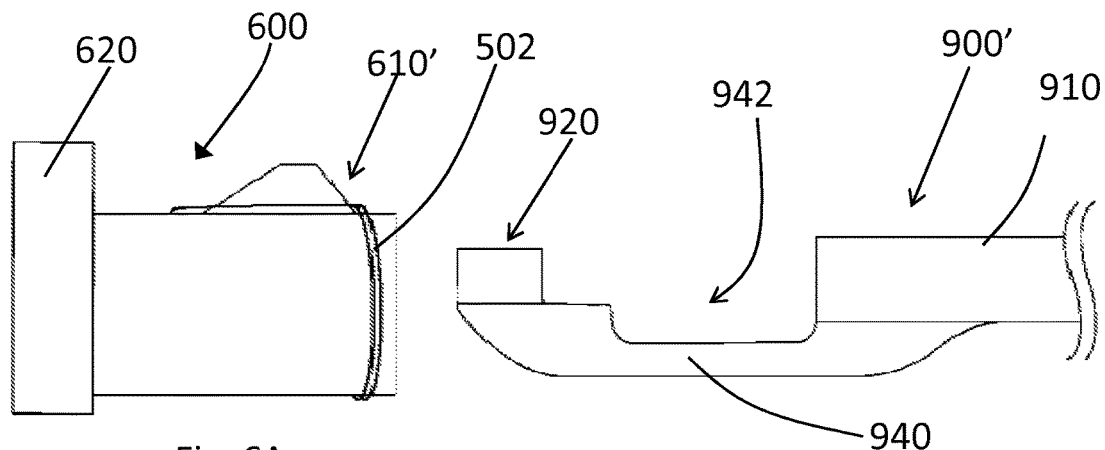
FIG. 6A illustrates a left side view of a cartridge for mounting on a surgical suturing instrument in accordance with an embodiment of the present invention.
Figure 6B:
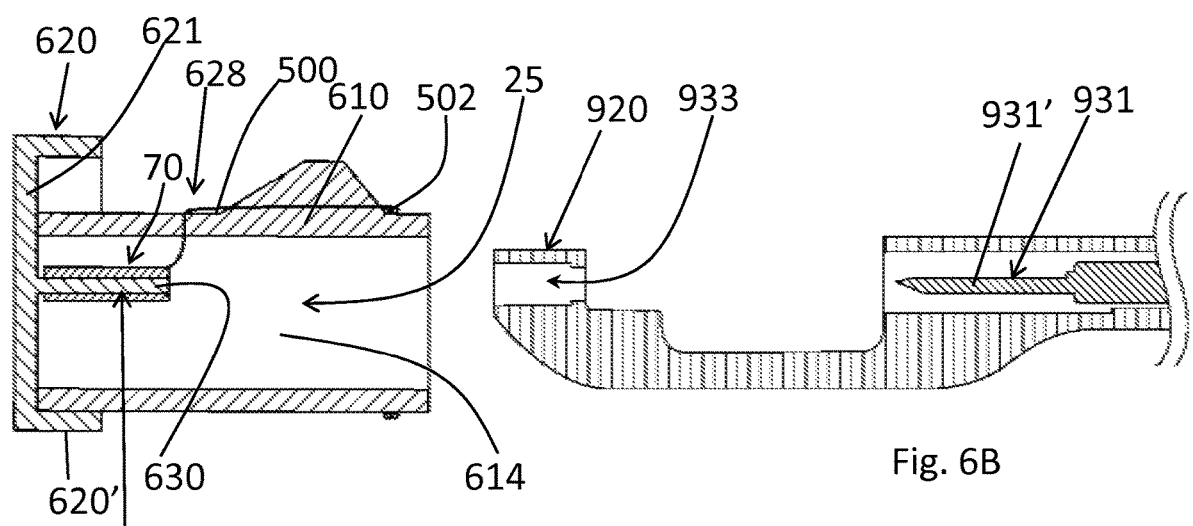
FIGS. 6B-6G illustrate cross-sectional views of a cartridge and the method of using the same to load suture onto a surgical suturing instrument in accordance with an embodiment of the present invention.

As illustrated in FIGS. 6A-6B, in accordance with a specific example of an embodiment of the present invention, a suture loading apparatus (cartridge 600) is provided for loading a ferrule 70 onto a surgical suturing instrument 900'.

The suturing instrument 900' is of the type comprising an instrument distal portion 920 coupled to an instrument proximal portion or shaft 910 via a neck portion 940 defining a tissue receiving gap 942 therebetween. The instrument distal portion 920 may alternatively be referred to as the distal end or distal tip 920. The suturing instrument 900' defines a ferrule receiving passage 933 within the instrument distal portion 920 and a ferrule passing member 931 (such as needle 931') held within the shaft 910.

In accordance with the illustrated embodiment shown in FIGS. 6A-6J, the cartridge 600 comprises a base 620 that defines a seat 622 for releasably holding a ferrule 70. With specific reference to FIG. 6B, in some embodiments, the base 620 comprises a hollow locking ring 620' that is attached to a cap 621. The cap 621 comprises a projection 630 in the form of a pin that defines the seat 622 for mounting the ferrule 70 thereon. In a particular example, the pin may comprise a D-shaped cross-section and the ferrule 70 may comprise a lumen having a matching cross-sectional shape to enable rotational coupling of the ferrule 70 to the seat 622 to allow the ferrule 70 to be rotated along with the seat 622. In the example shown, the locking ring 620' is formed integrally with the cap 621. Alternatively, the cap 621 may be coupled to the locking ring 620' through rotational coupling. The cartridge further comprises a housing 610' defining a chamber 610 for holding a pre-tied knot 502 mounted about the chamber 610. The pre-tied knot 502 is formed from a suture 500, with the one end of the suture having the ferrule 70 attached thereto.

In some embodiments as shown in FIG. 6B, the base 620 is detachably coupled to the housing 610' via a detachable coupling. In some embodiments, the base 620 is coupled to the housing 610' via a rotational coupling. In a specific example, the base 620 receives the housing 610' and is rotatably locked to the housing 610' by rotating the locking ring 620' by about 90 degrees clockwise to engage the housing 610'. This enables both rotational and translational locking of the base 620 to the housing 610'. In an alternate example, the base 620 may be detachably coupled to the housing 610' via a snap fit arrangement.

Referring again to FIG. 6B, in some embodiments, the cartridge housing 610' comprises a chamber 610 that defines a channel 614. Channel 614 allows the suturing instrument 900' to be passed therethrough to be positioned through the suture loops or pre-tied knot 502 mounted on the housing 610' (and more specifically on a mount 612). Furthermore, in some examples, the channel 614 is also a means for restraining (restraint) 25 and forms the instrument receiving recess or locking recess for positioning the portion of the suturing instrument 900' (received through the chamber 610) relative to the seat 622 for aligning the seat 622 with the ferrule receiving chamber 933 of the suturing instrument 900'.

In some embodiments, the cap 621 of the cartridge base 620 functions as a restraint by preventing further distal advancement of the suturing instrument 900' in order to position the suturing instrument relative to the seat after it is received through the chamber 610, in order to align the seat 622 with the ferrule receiving passage 933.

Figure 6C:
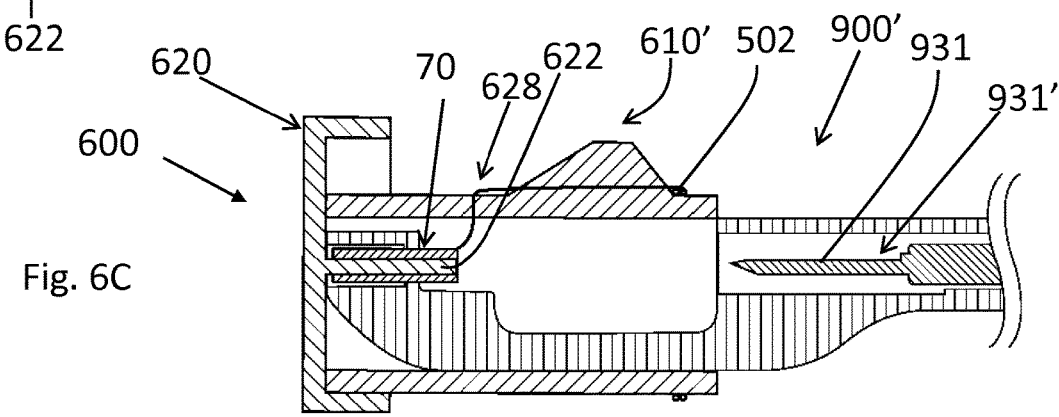

As mentioned previously, the base 620 comprises a projection 630 which defines the seat 622 having a ferrule 70 mounted thereon. In one specific example, the projection 630 comprises a pin. With reference now to FIG. 6B, in some embodiments, the projection 630 additionally forms an alignment feature and extends into the channel or instrument receiving recess 614. The projection 630 (and the ferrule 70 mounted thereon) are positionable within the ferrule receiving passage 933 of the instrument 900' as it is advanced distally with respect to the cartridge 600, as shown in FIG. 6C. Thus, the projection 630 functions to align the seat 622 with the ferrule receiving passage 933. Furthermore, the seat 622 is also brought in line with the (longitudinal axis of the) ferrule passing member 931 comprising needle 931' held within the shaft 910.

Figure 6D:
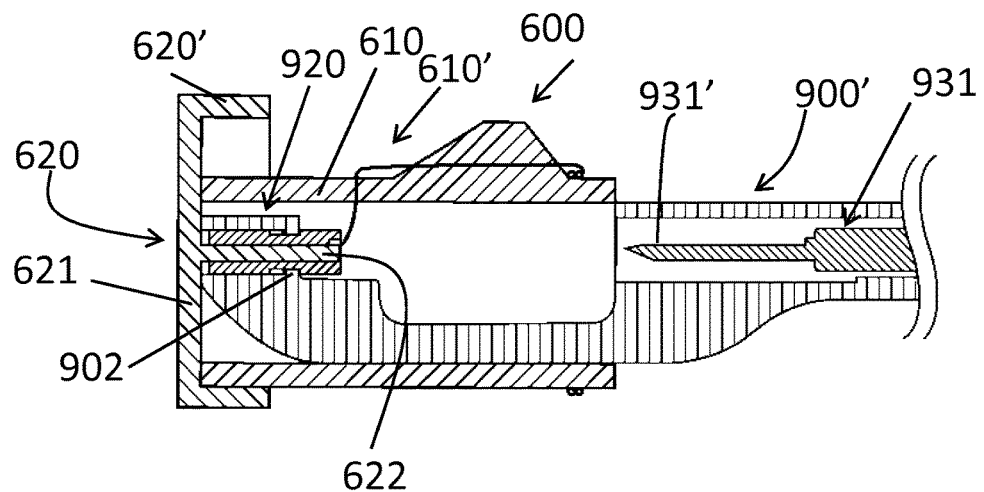
Figure 6E:
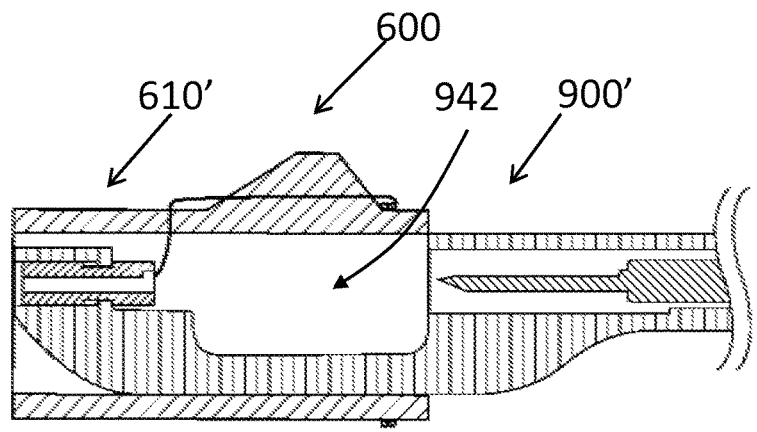
Figure 6F:
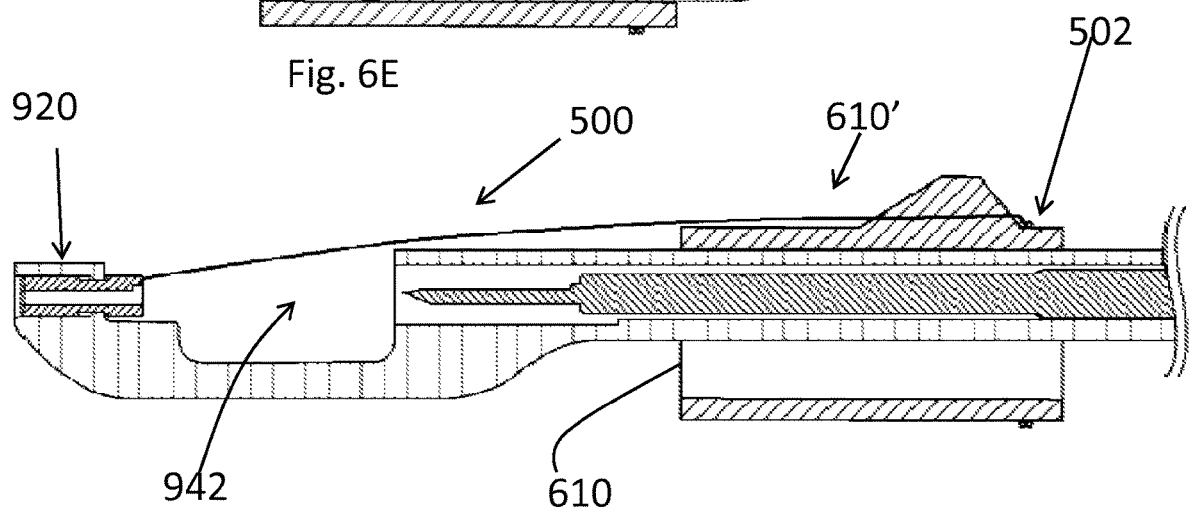
Figure 6G:
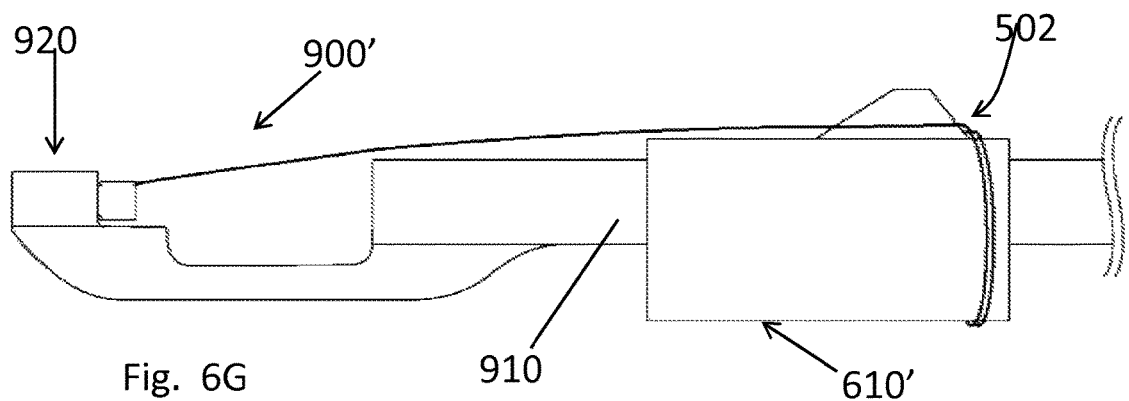
Figure 6H:
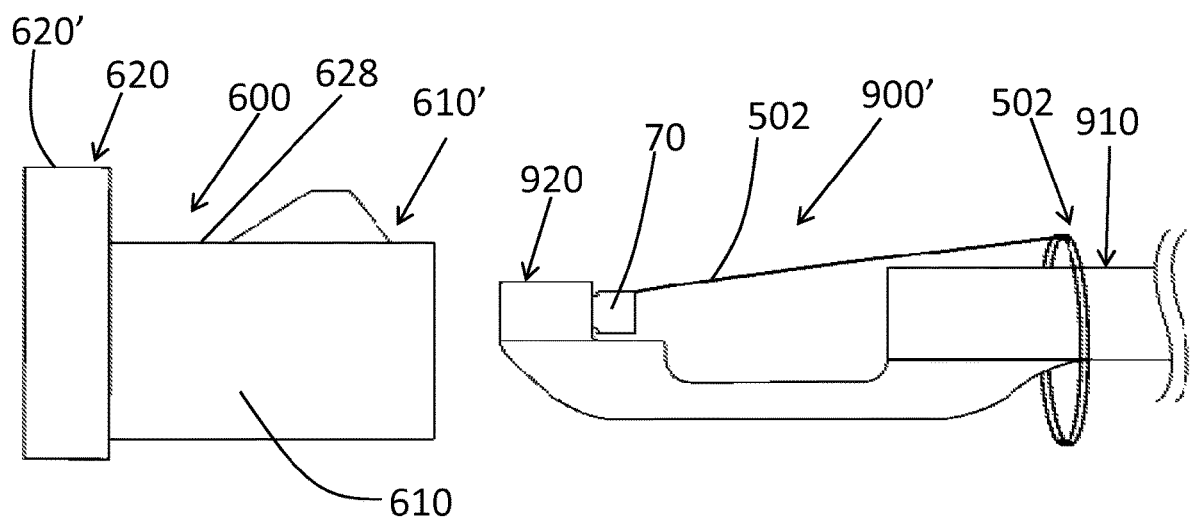
FIG. 6H illustrates a cartridge and a method of using the same to load suture onto a surgical suturing instrument in accordance with an alternate embodiment of the present invention.
Figure 6I:
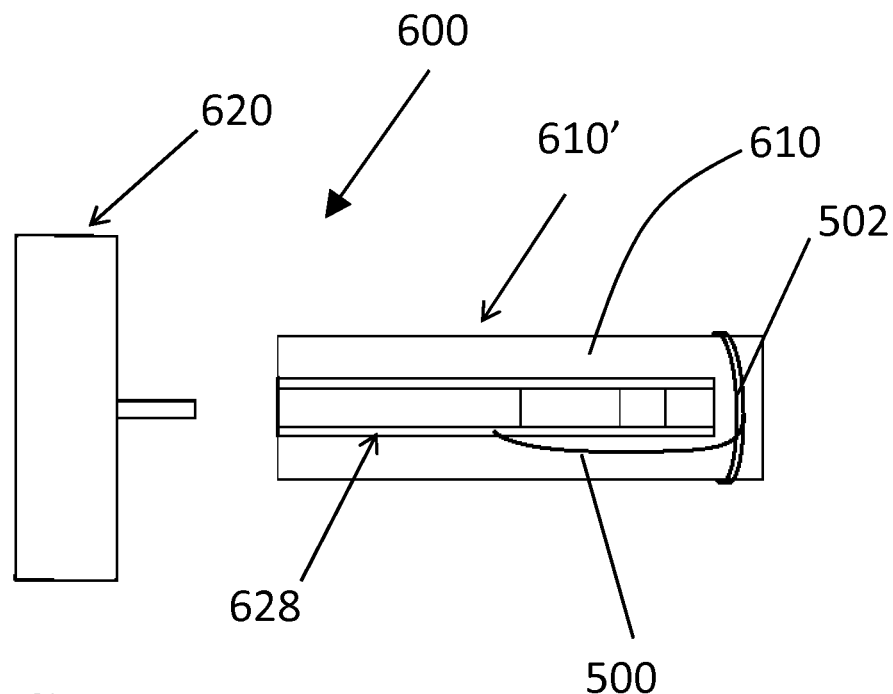
FIG. 6I illustrates a top view of a cartridge in accordance with an embodiment of the present invention.
Figure 6J:
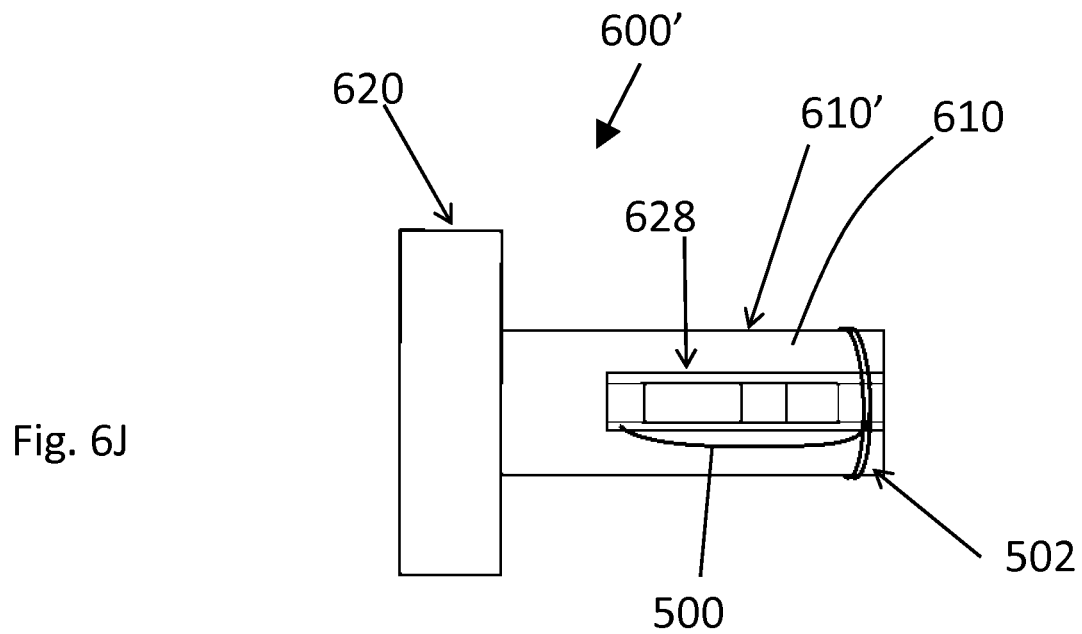
FIG. 6J illustrates a top view of a cartridge in accordance with an alternate embodiment of the present invention.

In some embodiments, as shown in FIG. 6I, the cartridge housing 610' may additionally comprise a slot 628 to facilitate manipulation of the suture to aid in transferring the suture 500 from cartridge 600' to the surgical suturing instrument 900. FIG. 6I illustrates a slot 628 in the exemplary embodiment where the base 620 and housing 610' are detachable. Whereas, FIG. 6J illustrates a slot 628 in the alternative embodiment where the base 620 remains coupled to the housing 610'.

Example 7

In an alternative embodiment of the present invention, a cartridge is disclosed for mounting a ferrule and suture onto a surgical suturing instrument such as surgical suturing instrument 900' described herein above. The cartridge enables axial loading of the suturing instrument by allowing the cartridge to be received within the tissue receiving gap 942 of the suturing instrument 900'.

Figure 7A:
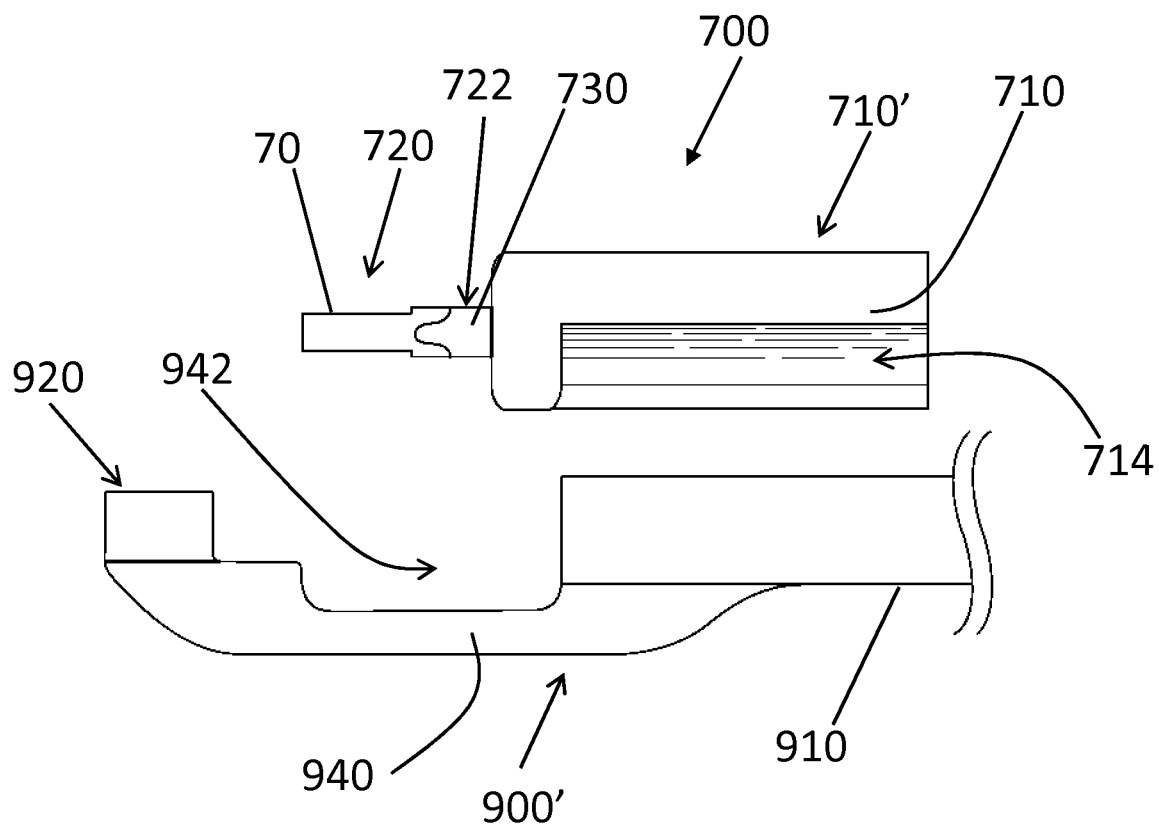
FIG. 7A illustrates a left side view of a cartridge for loading onto a surgical suturing instrument in accordance with an embodiment of the present invention.
Figure 7B:
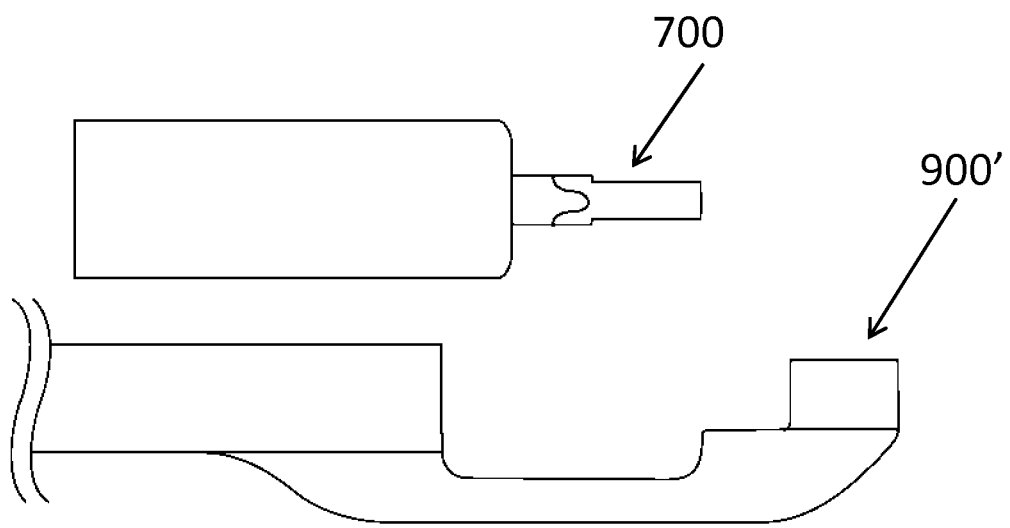
FIG. 7B illustrates a right side view of a cartridge for loading onto a surgical suturing instrument in accordance with an embodiment of the present invention.

With reference now to FIGS. 7A and 7B, a cartridge 700 is disclosed that comprises a housing 710' coupled to a base 720. In the particular example shown, base 720 is formed integrally with the housing 610'. The housing 710' defines a chamber 710 defining a channel or recess 714 therein. The base 720 defines a seat 722 in the form of a projection 730 for releasably holding the ferrule 70. In a particular example, as shown in FIG. 7G, the seat 722 comprises a projection 730 comprising a pin having a D-shaped cross-section, and the ferrule 70 has a matching inner profile to enable rotational coupling of the two.

Figure 7C:
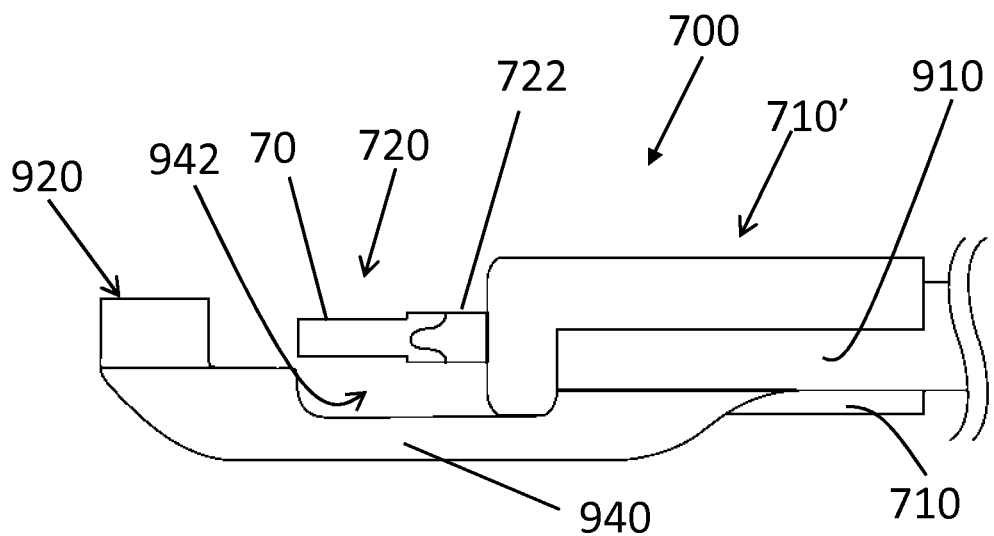
FIGS. 7C-7D illustrate steps of a method for loading suture onto a surgical suturing instrument using a cartridge in accordance with an embodiment of the present invention.
Figure 7D:
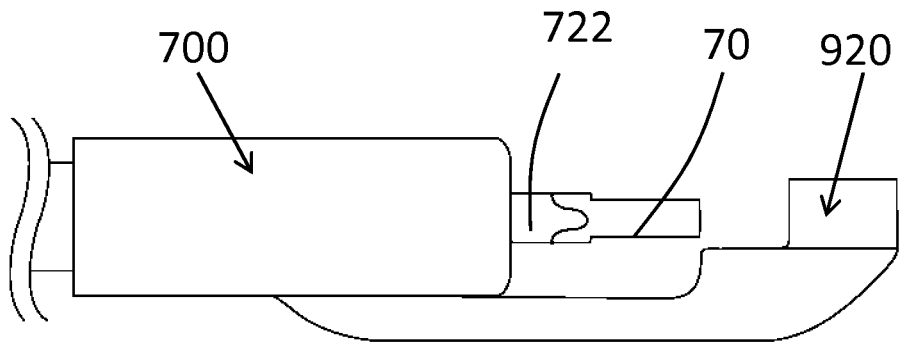
Figure 7E:
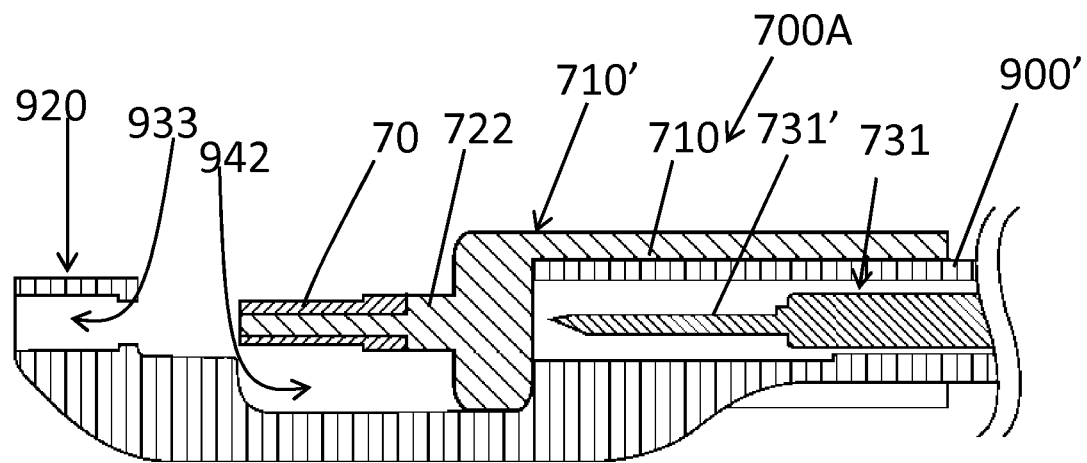
FIG. 7E illustrates a cross-sectional view of a cartridge for loading onto a surgical suturing instrument in accordance with an embodiment of a method of the present invention.

As shown in FIG. 7A, the channel or recess 714 is in the form of a channel cut-out. This configuration enables the seat 722 of the cartridge 700 to be dropped into the tissue receiving gap 942 as illustrated in FIG. 7C. The channel or recess 714 functions as a restraint to position the surgical suturing instrument 900' that is received through it relative to seat 722. As shown in FIGS. 7D-7E, this enables alignment of the seat 722 with the ferrule receiving passage 933 of the suturing instrument 900. The seat 722 can then be advanced axially to transfer the ferrule 70 within the distal end 920 of the suturing instrument 900, as shown in FIGS. 7F-7I. Furthermore, the cartridge 700 may be rotatable from its initial orientation 700A as shown in FIGS. 7F-7I, into its second orientation 700B, as shown in FIGS. 7J-7M to lock the ferrule 70 within the ferrule receiving passage 733. The method of using cartridge 700 to load a ferrule having an end of a suture coupled thereto, is described further herein below.

Example 8

Figure 8A:
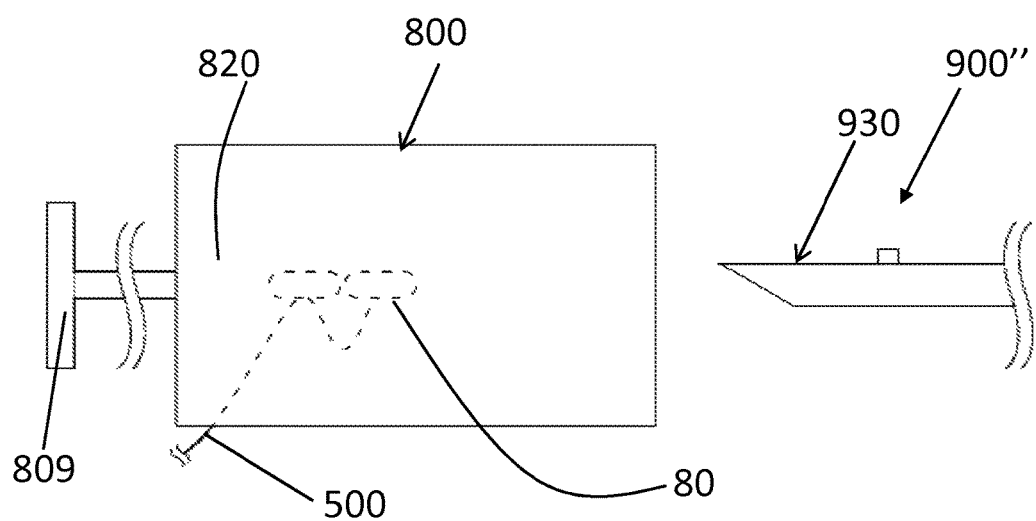
FIG. 8A is a left side view of cartridge in accordance with still another embodiment of the present invention.
Figure 8B:
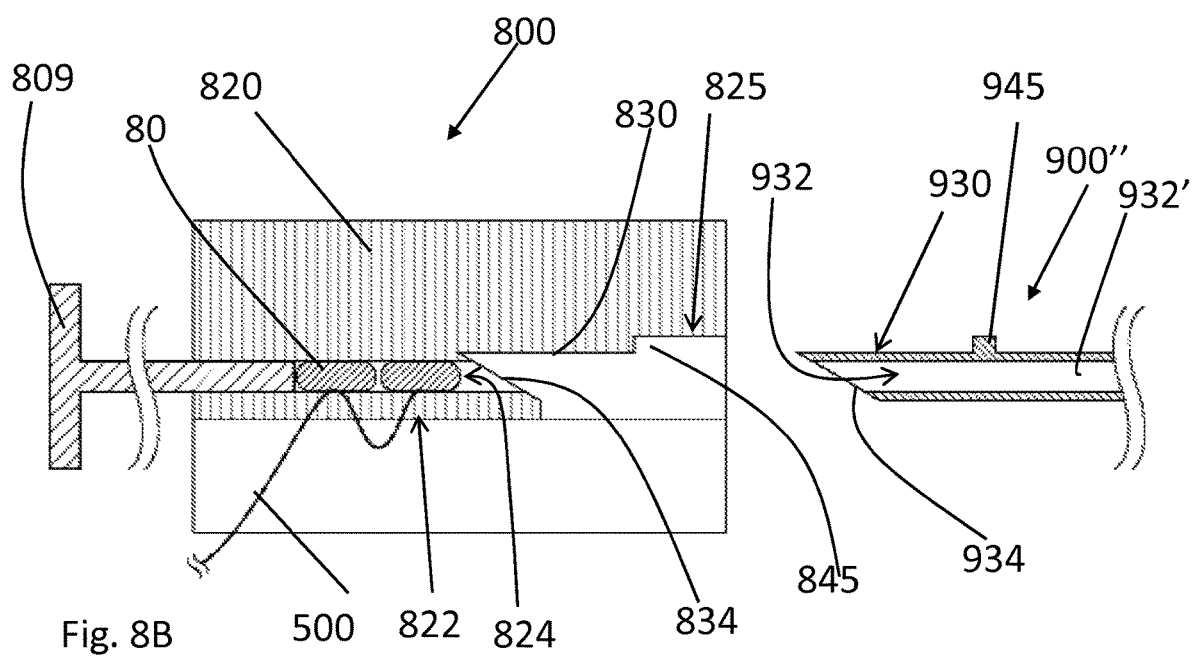
FIG. 8B is a cross-sectional view of a cartridge in accordance with an embodiment of the present invention.

In accordance with a further alternative of the present invention, a cartridge 800 is disclosed as shown in FIGS. 8A-8B. The cartridge 800 is provided for loading suture 500 (that is coupled to one or more tabs 80) onto a surgical suturing instrument 900". In a particular example, the suturing instrument 900" is a suture passing member 930 that comprises a hollow needle 930' defining a suture receiving passage 932 therein. In this particular embodiment, the suture receiving passage may alternatively be referred to as the tab receiving passage 932'. In the particular example shown, the suture receiving passage 932 is wide enough to allow insertion of the tabs 80 therein.

Referring again to FIGS. 8A-8B, the cartridge 800 comprises a base 820 that defines a seat 822 for releasably holding the one or more tabs 80. In the particular example shown, the seat 822 including a seat channel 824. The tabs 80 may be held in frictional engagement within the seat channel 824. The tabs 80 are coupled to a suture 500.

Referring again to FIGS. 8A and 8B, in some embodiments, the cartridge 800 defines a chamber for receiving the suturing instrument 900". In the particular embodiment shown, the chamber defines an instrument receiving channel 825 which additionally functions as a restraint (means for restraining) for positioning (a portion of) the suturing instrument 900'' (received through the chamber) relative to the seat 822 for aligning the seat 822 with a suture receiving passage 832 of the suturing instrument 900''. In some embodiments, the suture passing member 930 is received in frictional engagement within the channel 825. The base 820 additionally comprises an alignment feature in the form of an alignment recess 830 (which may be a part of the instrument receiving channel 825). The alignment recess 830 is positioned adjacent the seat 822 for receiving the needle 930' to align the needle 930' with the seat 822. More specifically, the alignment recess 830 is defined by an edge wall of the seat 822, which forms a bevel face 834 for engaging with a bevel face 934 of the needle 930' for docking the needle 930' to align the needle 930' with the seat 822. This allows for transfer of the tabs 80 and the suture coupled thereto, from the seat 822 into the suture receiving passage 932.

Figure 8C:
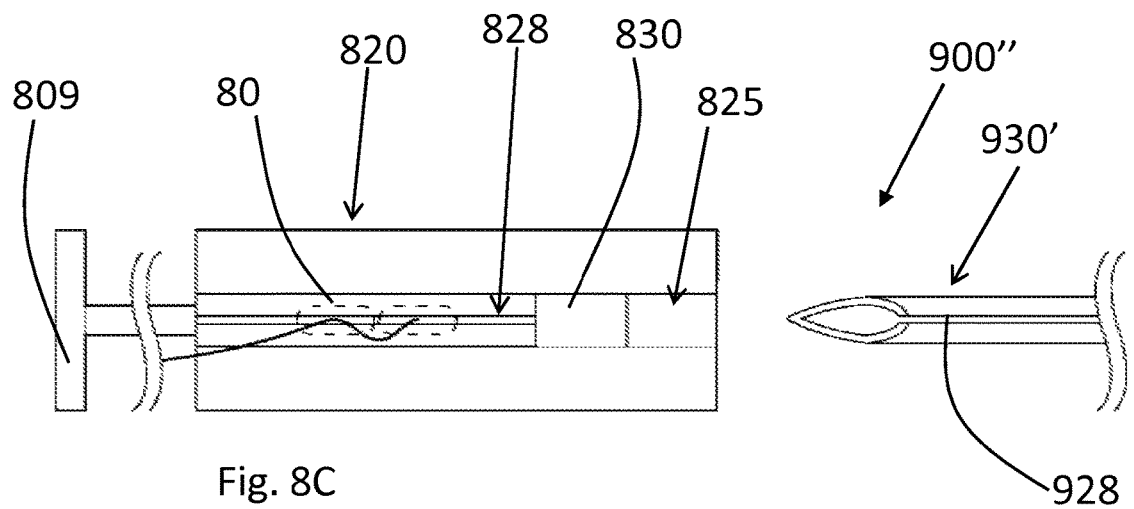
FIG. 8C is a bottom view of a cartridge in accordance with an embodiment of the present invention.

In a further example, the base 820 may comprise a feature to engage with a depth stop 945 of the suturing instrument, such as a depth stop cavity 845, (which may be a part of the instrument receiving channel 925. The depth stop cavity 845 helps to further align the needle 930' with the seat 822. More specifically, the depth stop cavity 845 helps to rotationally align the needle 930' with the cartridge 800 so that a slot 928 of the needle is aligned with a slot 938 of the cartridge 800 (as shown in FIG. 8C). This alignment permits transfer of the suture 500 from the cartridge slot or slit 938 to the longitudinal opening or needle slot 928. The depth stop cavity 845 additionally functions as a restraint to help position the suturing instrument 900'' with respect to the seat 822.

Figure 8D:
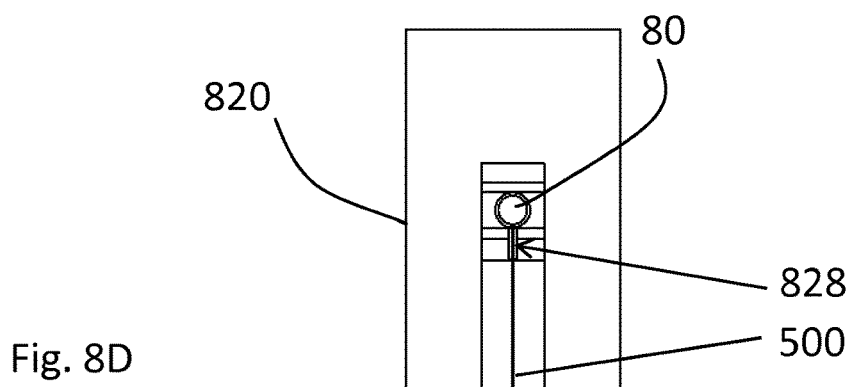
FIG. 8D is a rear end view of a cartridge in accordance with an embodiment of the present invention.

In some embodiments, the cartridge 800 additionally comprises a feature to facilitate routing of the suture. As illustrated in FIGS. 8C and 8D, the cartridge 800 comprises a slot 828 along the bottom wall of the cartridge 800 to facilitate manipulation of the suture 500 to aid in transferring the tabs 80 from the seat 822 within the cartridge 800 to the surgical suturing instrument 900''. The slot 828 provides clearance/room for suture 500 to be positioned within the slot 828 as the tabs 80 (along with the suture 500) are being transferred into the needle 930'. This allows the suture 500 to slide proximally within the slot 828 to be transferred into the slot 928 of the needle 930'.

In some embodiments, as illustrated in FIGS. 8A-8G, the cartridge 800 additionally comprises a means for transferring the tabs 80 from the seat 822 into the suture receiving passage 932. In an example, an active mechanism may be provided such as a push feature to push the tabs 80 from the seat 822 into the suture receiving passage 932. In some embodiments, the mechanism may comprise a plunger 809 that can be activated to push the tabs 80 from the seat 822 into the suture receiving passage 932. In a particular example of this, the plunger may be advanced automatically into the seat channel 824 as the suturing instrument 900'' is advanced distally with respect to the instrument receiving or locking recess 225. The plunger pushes the tabs 80 from the seat 822 and into the suture receiving recess 932 of the suturing instrument 900''.

In order to load suture into a surgical suturing instrument or suture passer, in accordance with some embodiments of the present invention as outlined herein below in Examples 9 and 10, two events or functions are required to take place: (1) alignment of the suture portion held within the cartridge with a suture receiving feature within the surgical suturing instrument or suture passer, and (2) insertion of the suture portion into the suture receiving feature within the suturing instrument or suture passer.

Example 9

In an alternate embodiment of the present invention, as shown in FIGS. 9A-9I, a cartridge 1000 is disclosed for loading suture onto a surgical suturing instrument, for example a suturing instrument 900 as discussed previously herein above with reference to FIG. 1E. The cartridge 1000 carries suture therein and functions to align the suture with the suturing instrument 900 upon insertion and axial advancement of the suturing instrument 900 within the cartridge 1000, in order to allow transfer of suture onto the surgical suturing instrument 900. In some such embodiments, the cartridge 1000 additionally functions to transfer the suture onto the suturing instrument 900.

Figure 9A:
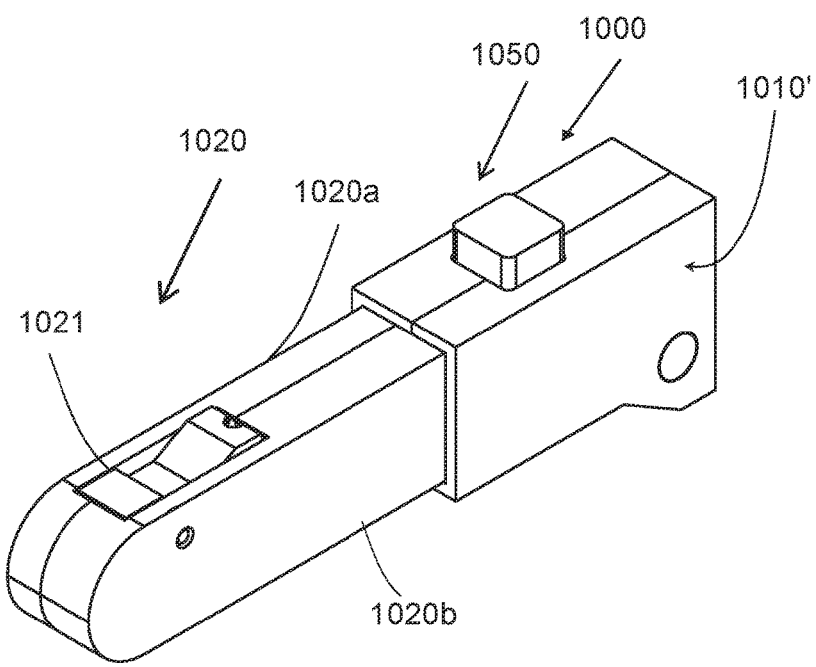
FIGS. 9A-9O illustrate views of a cartridge in accordance with an alternate embodiment of the present invention.
Figure 9C:
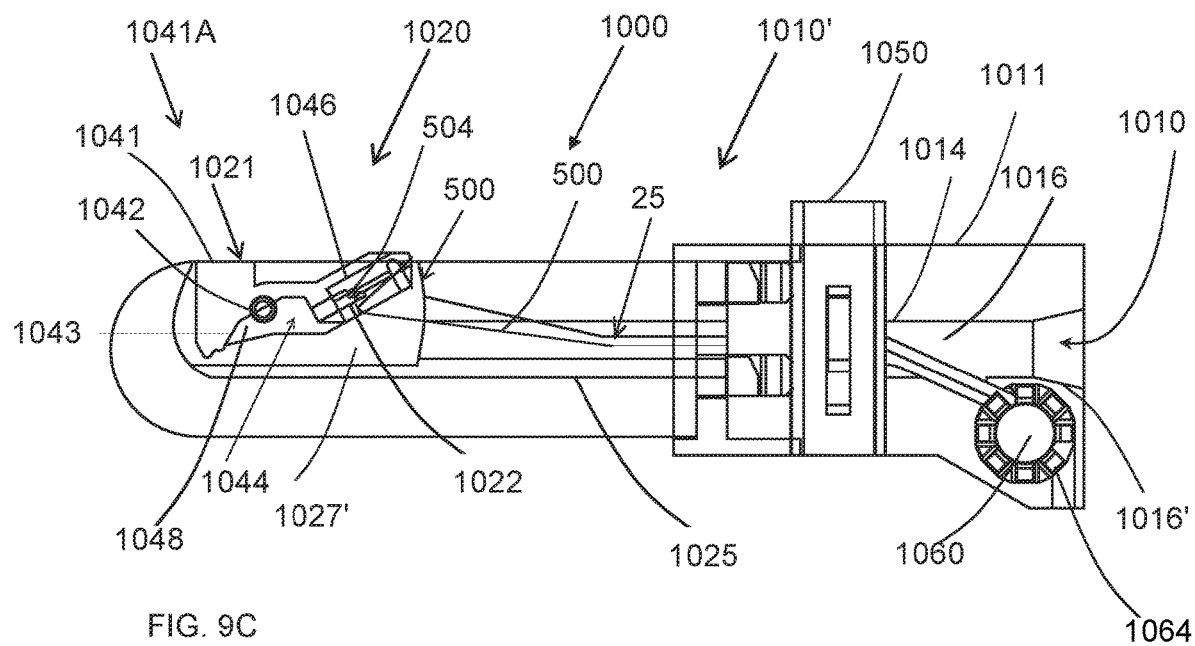
Figure 9G:
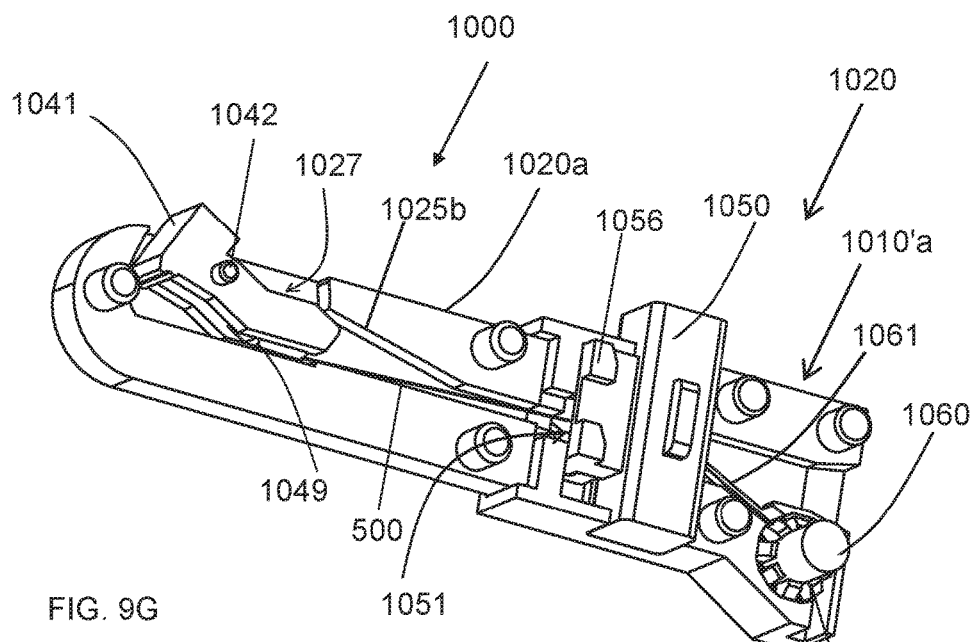
Figure 9B:
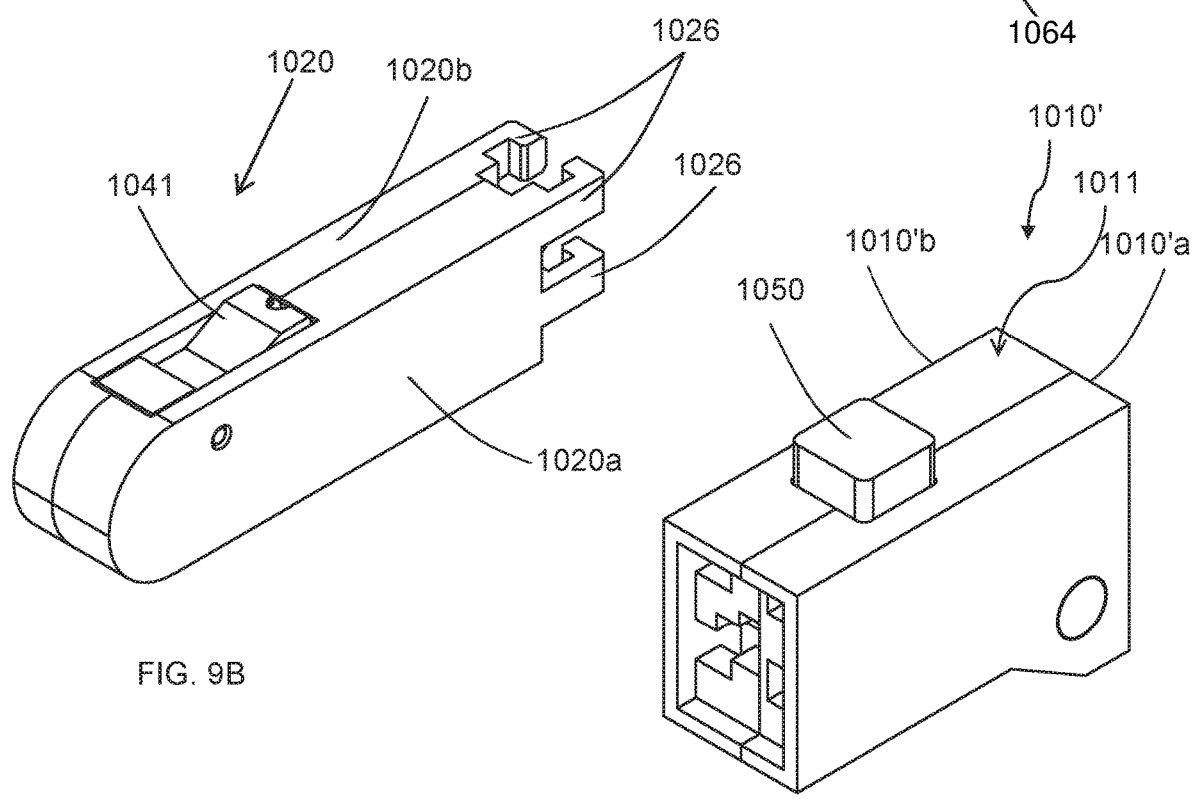

In the specific example shown in FIGS. 9A and 9B, a cartridge 1000 is provided that is functional to carry suture for loading onto a surgical suturing instrument 900. The cartridge comprises a housing 1010' that defines a chamber for axially receiving the surgical suturing instrument 900. Additionally, the chamber 1010 includes a recess or channel that is a part of the chamber 1010 that receives the suturing instrument 900. As such in some embodiments, as discussed herein, the channel may be referred to as a channel or a recess. In the particular example discussed herein the chamber 2010 defines a channel for receiving the suturing instrument. The cartridge further comprises a base 1020 that is detachably coupled to the housing 1010' that defines a seat for releasably holding the suture therein and enables alignment of the suture with the suture passing member 930 of the suturing instrument 900. The housing 1010' additionally comprises a means to secure a portion of the suture thereto, and is detachable from the base 1020 to function as a suture transferring component to transfer suture from the cartridge onto the suturing instrument 900. Thus, in some embodiments as shown in FIG. 9B, the base 1020 and the housing 1010' comprise separate components of the cartridge 1000 that are coupled to one another to assist in loading suture and may be detachable therefrom to assist in transferring suture. In other embodiments, the housing 1010' may be integrally formed with the base 1020. In some examples, the base 1020 may be formed from two halves 1020a and 1020b, and the housing similarly may also be formed from two halves 1010'a and 1010'b. The housing 1010' and the base 1020 collectively provide alignment features to assist in alignment of the suture upon loading of the cartridge 1000 onto the suturing instrument 900 to facilitate transfer of suture from the cartridge 1000 onto the suturing instrument 900 using the suture transferring component. The detailed mechanism and operation of the base 1020 and the housing 1010' in aligning and transferring the suture are described further herein below.

With reference now to FIG. 9C, in some embodiments the housing 1010' of the cartridge defines a chamber 1010 that comprises a channel 1014 for receiving the suturing instrument there-through. In some examples, the channel 1014 comprises a proximal opening 1016 that narrows towards the interior of the cartridge housing 1010' as defined by a beveled interior edge 1016'. The beveled interior edge 1016' functions as a lead in to guide the suturing instrument 900 into the channel 1014. The channel 1014 extends longitudinally through the housing 1010' and is in communication with a recess 1025 that defines an instrument receiving recess or locking recess formed within the base 1020. In some embodiments the channel 1014 may be formed continuously with the recess 1025 within the cartridge base 1020. The channel 1014 defines an opening through which the suturing instrument 900 may be advanced though the housing 1010' into the base 1020. The channel 1014 and the recess 1025 each function as a restraint 25 to constrain or restrict the lateral and transverse movement of the suturing instrument 900 within the cartridge 1000 while allowing the suturing instrument 900 to be advanced linearly or axially therein in sliding engagement to maintain the position of the suturing instrument 900 along the longitudinal axis as it is advanced. As such the restraint 25 constraints or limits the movement of the suturing instrument 900 in the transverse and lateral directions as well along a longitudinal path defined thereby. Thus the restraint 25 facilitates alignment of the suturing instrument 900 with a portion of the suture 500 that is held within a seat 1022 defined by the base 1020. More specifically, the channel 1014 and the recess 1025 allow the suturing instrument 900 to be advanced therein in sliding engagement therein, and additionally function to restrain the suturing instrument 900 in a linear path as it is advanced along the cartridge 1000 to allow the seat 1022 to be aligned with the suture receiving passage 932 of the suture passing member.

Therefore, the cartridge 1000 comprises an alignment feature in the form of a restraint 25 that comprises an instrument receiving recess defined by channel 1014 and recess 1025. The alignment feature allows the suturing instrument 900 to be positioned within the base 1020 to allow the seat 1022 holding a portion of the suture to be aligned with the suture passing member 930 of the suturing instrument 900.

Figure 9D:
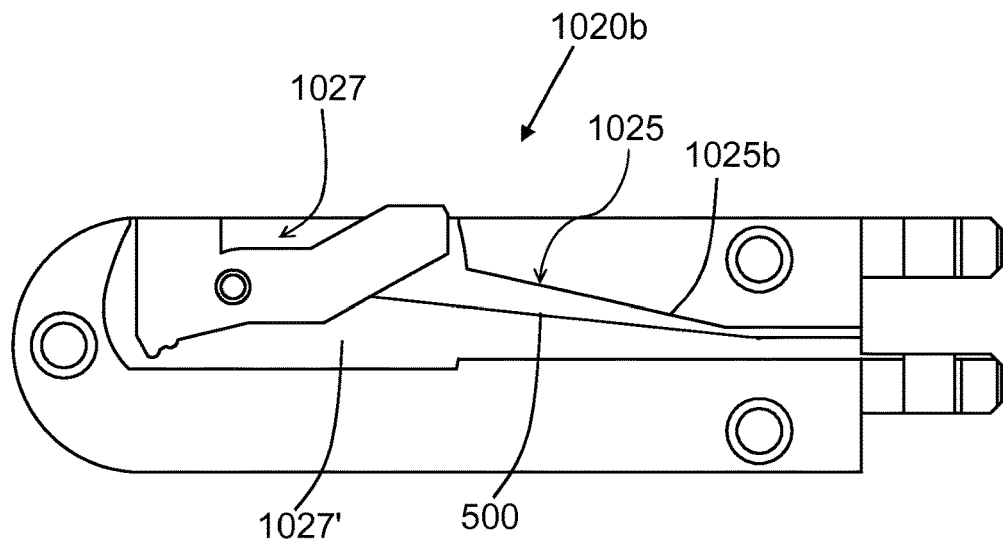
Figure 9E:
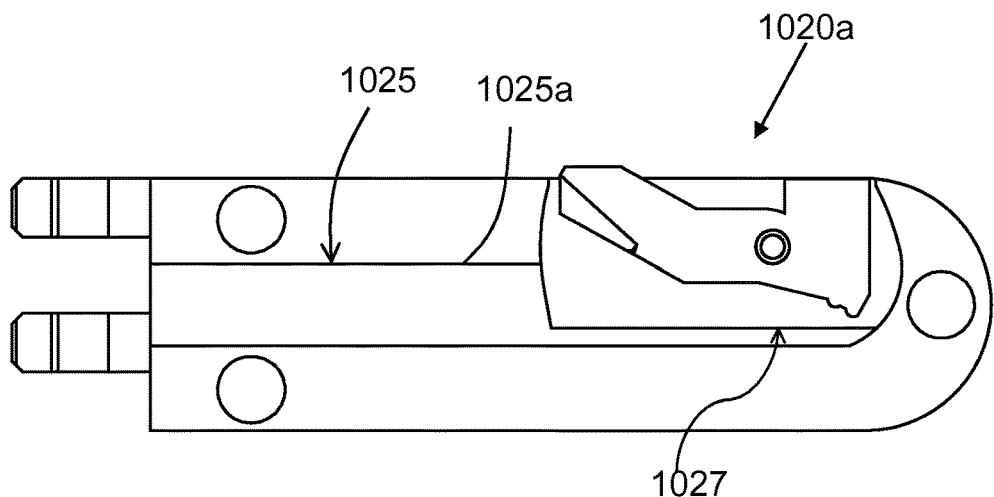
Figure 9F:
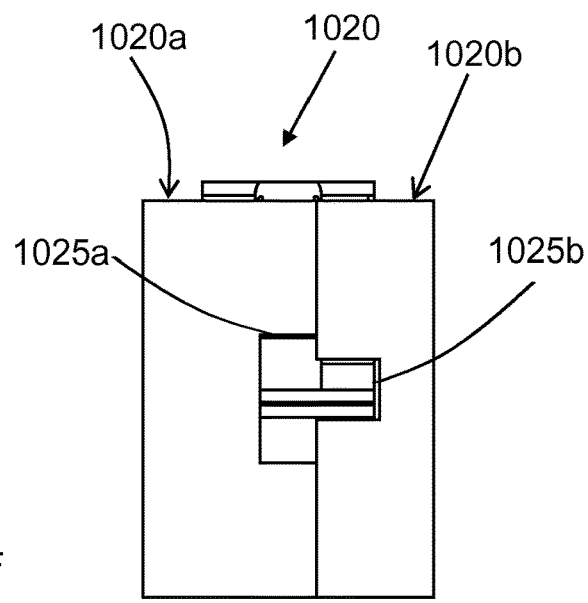
Figure 9H:
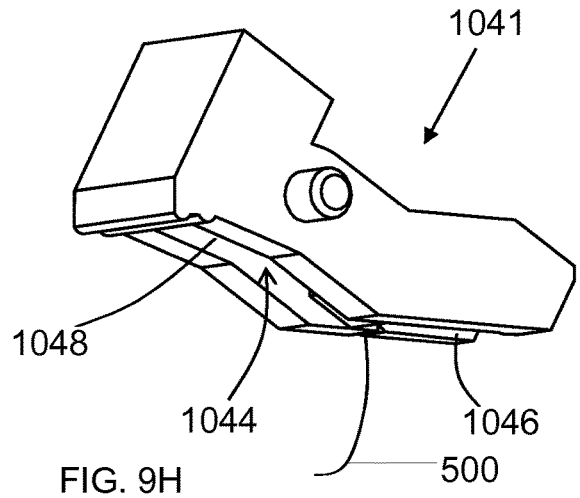
Figure 9I:
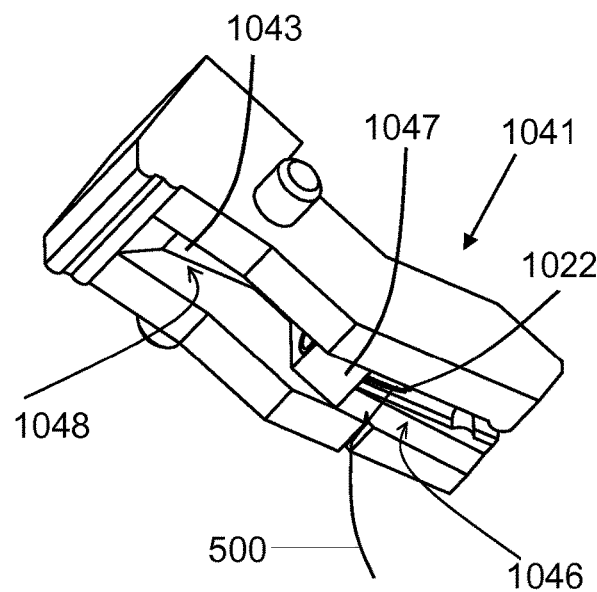

Furthermore, in some embodiments as shown in FIGS. 9C, 9D and 9E, the recess 1025 within the base is formed from two grooves: an instrument receiving groove 1025*a* defining an instrument receiving recess, and a suture receiving groove 1025*b* defining a suture receiving recess. The instrument and suture receiving grooves 1025*a* and 1025*b*, respectively are formed within the opposing halves 1020*a*, and 1020*b* of the base 1020 (also illustrated in FIG. 9B).

Figure 10A:
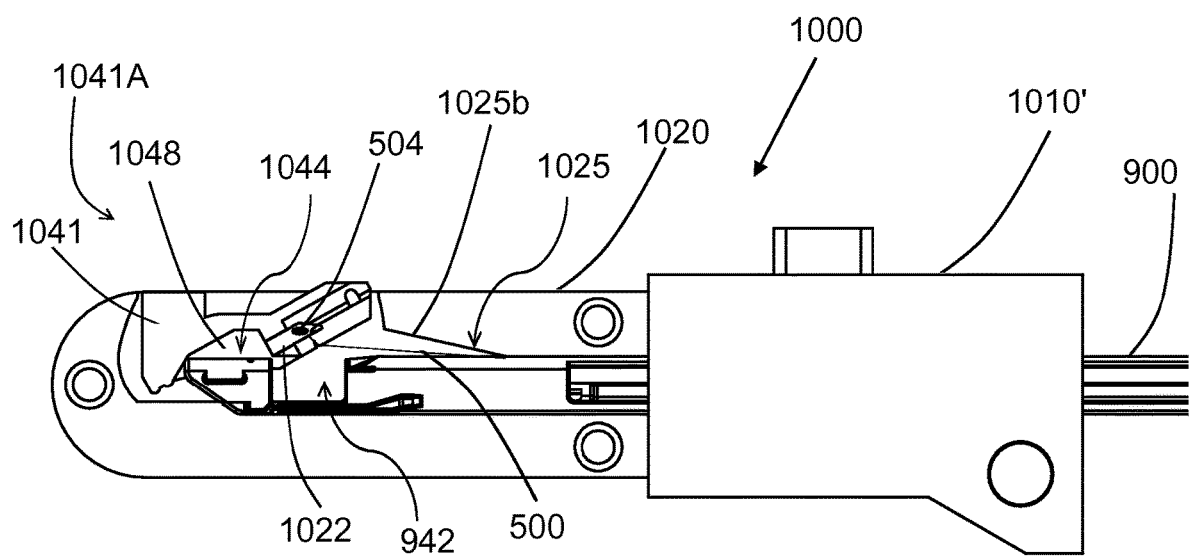
FIGS. 10A-10D illustrate views of a cartridge and a method of using the same in accordance with an embodiment of the present invention.

With reference again to FIG. 9D, the instrument receiving groove 1025*a* provides a track that functions as a restraint 25 to allow the suturing instrument 900 to be advanced therein, whereas suture groove or suture receiving groove 1025*b* provides a track to guide the portion of the suture held within the seat into the suture passing member 930 of the suturing instrument 900, as further illustrated in FIG. 9E. Suture receiving groove 1025*b* guides the portion of the suture by maintaining/routing the suture 500 therein such that it is adjacent to and in line with the shaft or proximal portion 910 of the suturing instrument 900 that is receivable within the instrument receiving groove 1025*a*. More specifically, the suture receiving groove 1025*b* allows the suture to be routed such that when the suturing instrument is received within the instrument receiving groove 1025*a*, the suture 500 is held adjacent the groove 928 within the shaft or the instrument proximal portion 910, as well as groove 938 within suture passing member 930 such as needle 930' (shown in FIG. 1E). Furthermore, the suture receiving groove 1025*b* provides room for routing the suture without excess tension being placed in the suture by providing a wider opening into a rocker recess 1027, as shown in FIGS. 9D and 10A. As such, the suture receiving groove 1025*b* accommodates the suture 500 as it enters a rocker recess 1027 in both a final position 1041B, as well as an initial position 1041A of a rocker 1041 (discussed further herein below). As such, the suture receiving groove 1025*b* enables the suture 500 to be maintained out of the way of the advancing suturing instrument 900 during use of the cartridge 1000. Additionally, suture receiving groove 1025*b* is in line with grooves 928, 938 of the suturing instrument 900 to further facilitate transfer of suture from the seat 1022 within the base 1020 into the needle 930'. In the illustrated embodiment, both the instrument receiving groove 1025*a* and the suture receiving groove 1025*b* exit into the rocker recess 1027.

With reference now to FIG. 9C, in some embodiments of the present invention the cartridge 1000 additionally provides an alignment feature comprising a moveable seat 1022. In some such embodiments, the cartridge 1000 comprises a magazine 1021 defined by the base 1020 that functions to align the suture with a portion of the surgical suturing instrument 900 that is receivable within the cartridge 1000. The magazine 1021 defines the seat 1022 for releasably holding or retaining a portion of the suture 500. More specifically, the seat 1022 is configured to hold an end portion 504 of the suture 500, as shown. The magazine 1021 is moveable with respect to the cartridge 1000 and as such defines a moveable seat 1022 for aligning the suture end 504 held therein with a portion of the surgical suturing instrument 900 that is received within the cartridge 1000. More particularly, as shown in FIG. 9C, the seat 1022 is moveable with respect to the base 1020. (Alternatively, in some embodiments the seat 1022 may be moveable relative to the chamber 1010 defined by housing 1010', for example, in embodiments where the base 1020 may be formed integrally with the housing 1010' forming a unitary cartridge 1000).

Figure 10B:
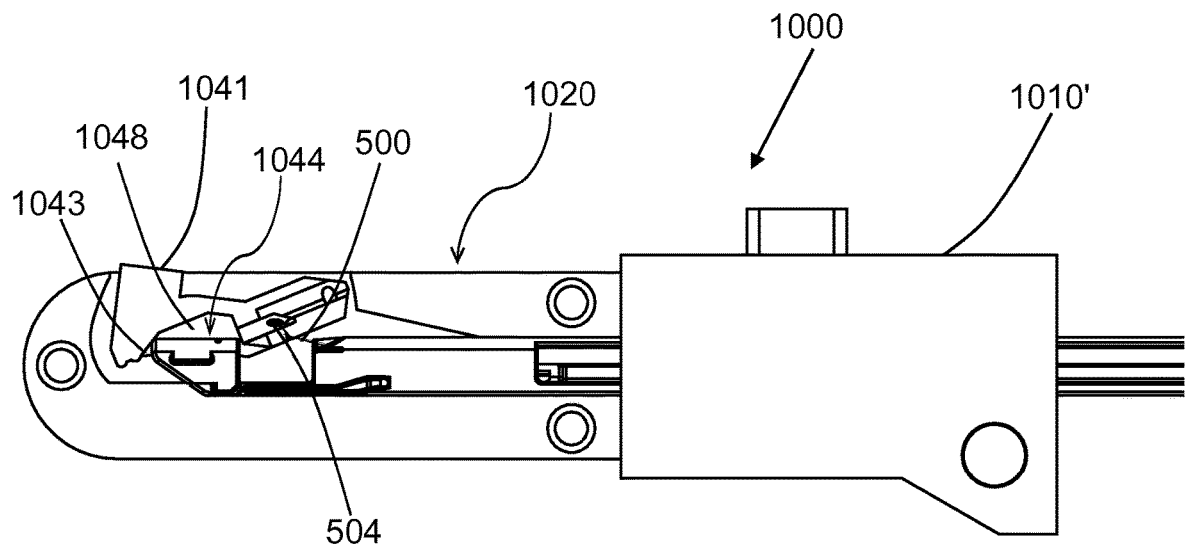
Figure 10C:
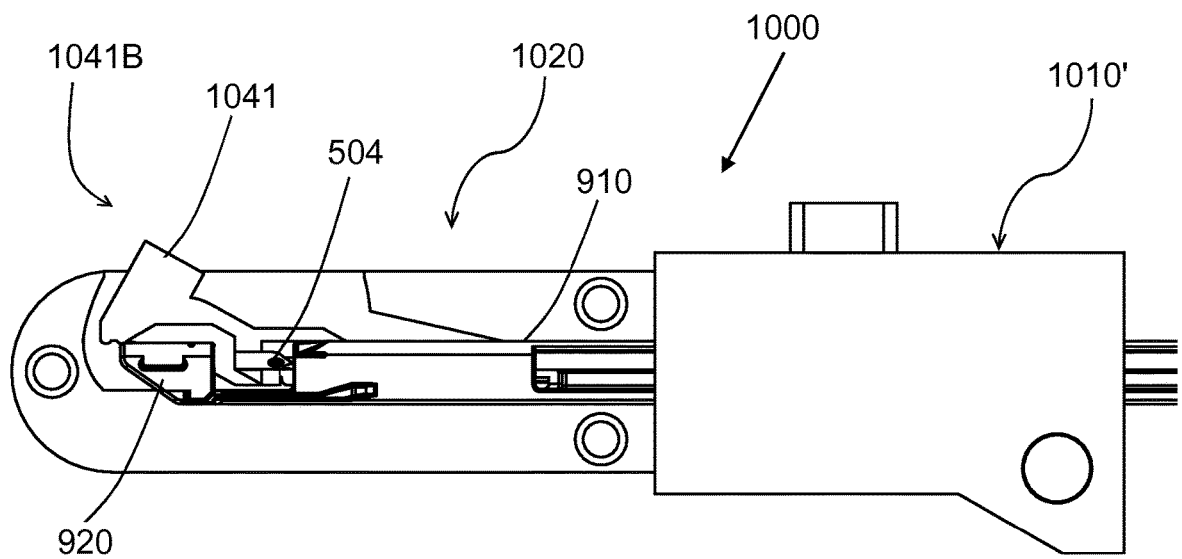

In some embodiments of the present invention, particularly with reference to FIG. 9C, the seat 1022 is automatically moveable upon insertion of the suturing instrument 900 within the cartridge 1000. In the particular example shown, the magazine 1021 comprises a rocker 1041 that is rotatable about a pivot 1042, and the base 1020 defines a rocker recess 1027 for enabling pivotal movement of the rocker 1041 therein. In the illustrated embodiment, also shown in FIG. 9G, the pivot 1042 is formed by laterally extending pins 1043 of the rocker 1041 that are held within pivot support openings 1023 of the base 1020 and are moveable freely therein. The rocker 1041 is moveable about the pivot 1042 from its initial position 1041A (as shown in FIG. 9C) to its second position (as shown in FIG. 10C(i)) in order to align the seat 1022 and the suture end 504 held therein with the path of an advancing suturing instrument 900 that is inserted within the cartridge 1000.

In some embodiments, the rocker 1041 is held in its initial position 1041A within the rocker recess 1027 through frictional engagement. For example, the rocker 1041 may be kept in its initial position 1041A by an engagement feature such as a raised tab or detent (not shown) that is formed within the base 1020 and may extend or jut into the rocker recess 1027. The tab may be engageable with a portion of the rocker 1041 to maintain the rocker in its initial position 1041A during shipment and prior to use. In other embodiments, the rocker 1041 may be held in its initial position 1041A through frictional engagement via a spring based mechanism. The frictional force may be sufficient to keep the rocker 1041 in its initial position 1041A when the cartridge is empty, but may be overcome upon contact with the suturing instrument 900. Thus, the rocker 1041 may be released from engagement with the base 1020 upon advancement of the suturing instrument 900 within the cartridge 1000, allowing the rocker 1041 to move into its second position 1041B to align the portion of the suture held therein with a portion of the suturing instrument 900. In its second position 1041B, the rocker 1041 moves into a cavity defined by the rocker recess 1027. More specifically, as defined herein the rocker 1041 is moveable into a rocker cavity 1027' of the rocker recess 1027 to align the seat 1022 with the suturing instrument 900. The rocker cavity 1027' is defined as a portion of the rocker recess 1027 that corresponds to a tissue receiving gap 942 of the suturing instrument 900, upon loading of the cartridge 1000 onto the suturing instrument 900 (FIG. 9C).

In some embodiments, the cartridge may comprise additional features that assist in aligning the seat 1022 with a portion of the suturing instrument 900 (such as the suture passing member 930 held within the shaft or instrument proximal portion or shaft 910). In one such example, referring again to FIG. 9C, the rocker 1041 additionally defines an instrument receiving or locking recess defined by a groove 1044 that is designed for receiving the suturing instrument 900 as it is advanced distally. The groove 1044 functions as a restraint to position the suturing instrument 900 in a desired position relative to the seat 1022 to assist in aligning the seat 1022 with a suture passing instrument 900. The groove 1044 enables the rocker 1041 to pivot down into its second position 1041B while allowing the suturing instrument 900 to be advanced into the cartridge 1000 to permit loading the suture into the suturing instrument 900. [The operation of the groove 1044 is discussed further herein below with reference to Figs. 10A-10D that illustrate the operation of the device]. As further shown in FIGS. 9H and 9I, the groove 1044 comprises a groove proximal portion 1046 for receiving the instrument proximal portion or shaft 910 of the suturing instrument 900, and additionally comprises a groove distal portion 1048 for receiving the instrument distal portion or tip 920.

Additionally, the rocker 1041 comprises a median 1047 that is defined by the groove 1044. The groove proximal and distal portions 1046, 1048 are separated by the median 1047 that functions to hold or define the seat 1022 to enable the seat to be brought down into the tissue receiving gap 942. The median 1047 functions as an alignment feature by holding and aligning the seat 1022 with the suture passing member such as needle 930' of the suturing instrument 900. As such, median 1047 enables the seat 1022 to be brought down into the cavity 1027' corresponding to the tissue receiving gap 942 upon reception of the suturing instrument within the cartridge.

Still furthermore, the groove 1044 defines an additional alignment feature in the form of an interior bevel face 1043 that is defined by the groove distal portion 1048 of the rocker 1041, along a distal end thereof. The bevel 1043 enables the distal portion 920 of the suturing instrument to pivot the rocker 1041 from its initial position 1041A into its aligned position or second position 1041B. This function enables alignment of the seat 1022 and the suture held therein with the suture passing member 930 of the suturing instrument.

Figure 9J:
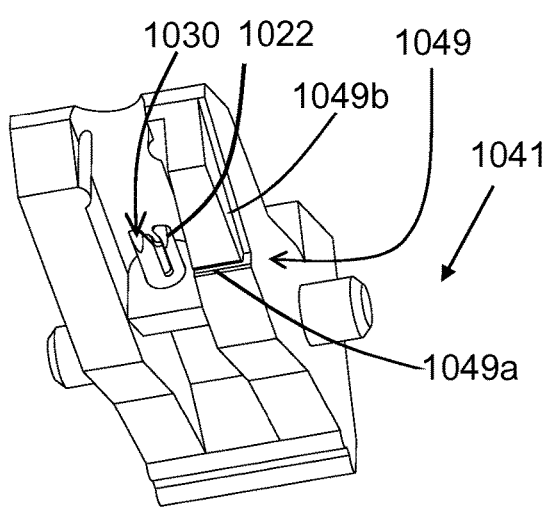
Figure 9K:
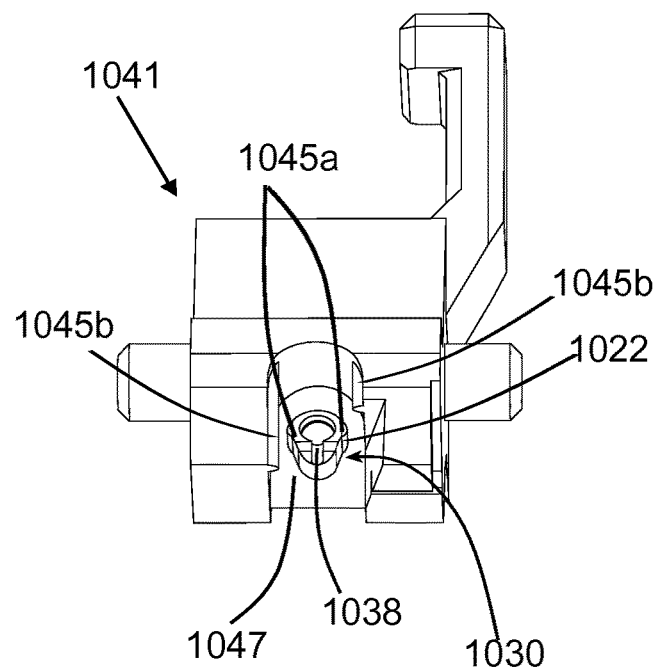
Figure 9L:
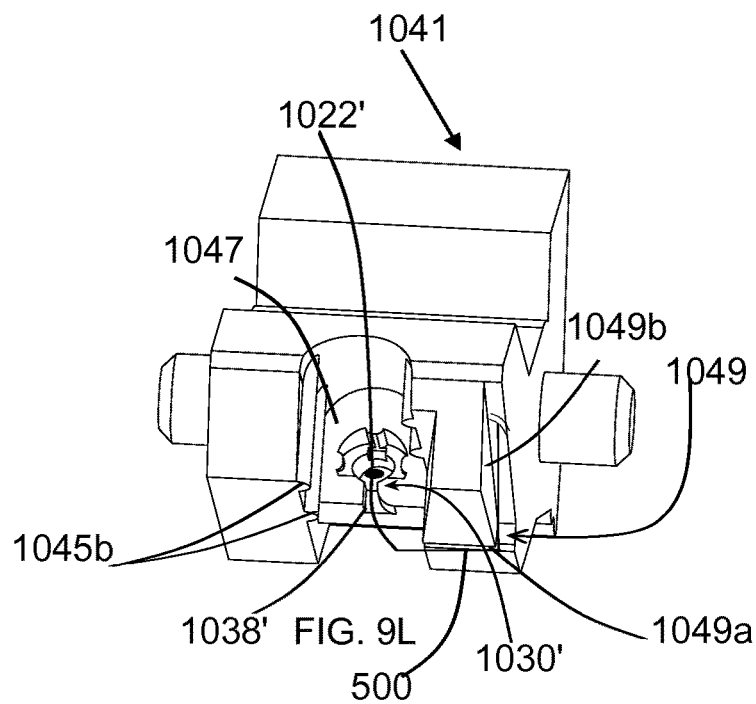

In some embodiments, as shown in FIGS. 9J and 9L, the rocker 1041 additionally defines another alignment feature in the form of a slot 1049 within the groove 1044, to assist in alignment and transfer of the suture end 504 into the suture passing member 930. The slot 1049 comprises a slit or channel 1049a that is formed within a wall 1044' of the rocker 1044 and extends transversally along the base of the wall 1044' to route the suture there-through upon exiting the seat 1022. The slit or channel 1049a functions to retain the suture 500 therein as it exits the seat 1022 within the rocker 1041, to aid in routing the suture 500 within the suture receiving groove 1025b of the base 1020 (FIG. 9D). The slit or channel 1049a additionally functions to align the suture with the suture receiving slot 928 in the shaft. The slit or channel 1049 exits into a cut-out portion defined within the exterior wall of the rocker 1041. The cutout defines a side slot 1049b defining a space enabling the suture 500 to be routed there-through to be guided into the suture receiving groove 1025b of the base 1020. The slit or groove 1049a is in communication with the rocker side slot 1049b to hold the suture to the side within the suture receiving groove 1025b of the base. This allows the suture to be held to the side of the suturing instrument 900 during advancement of the suturing instrument within the cartridge base 1020.

Figure 9M:
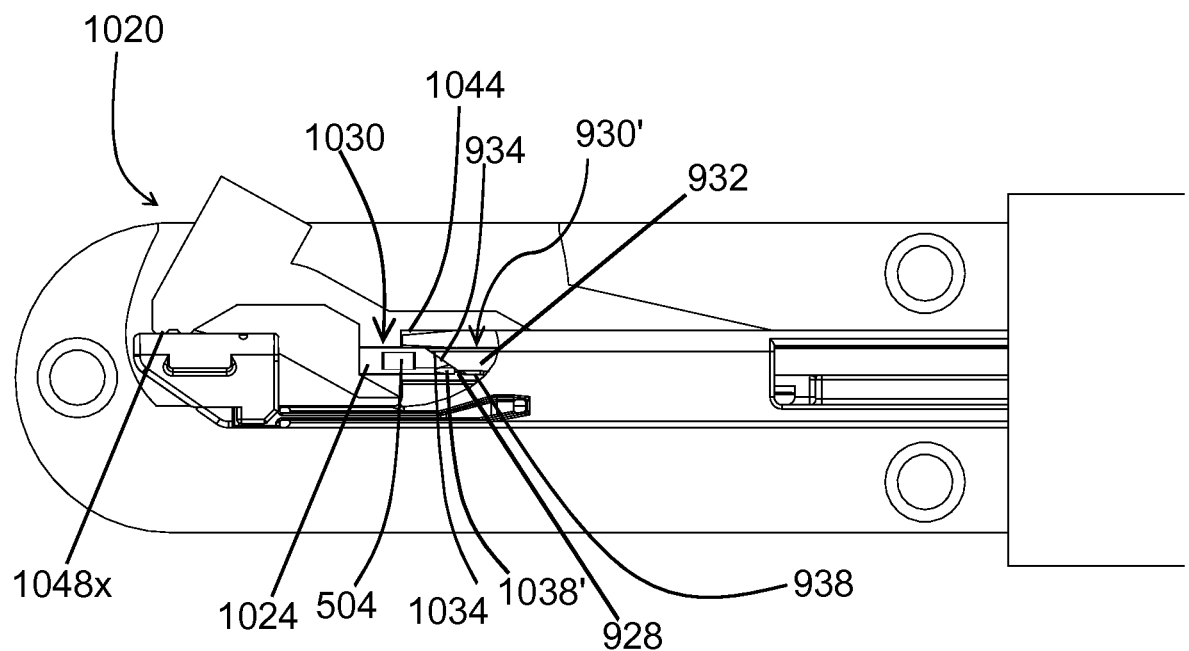
Figure 10D:
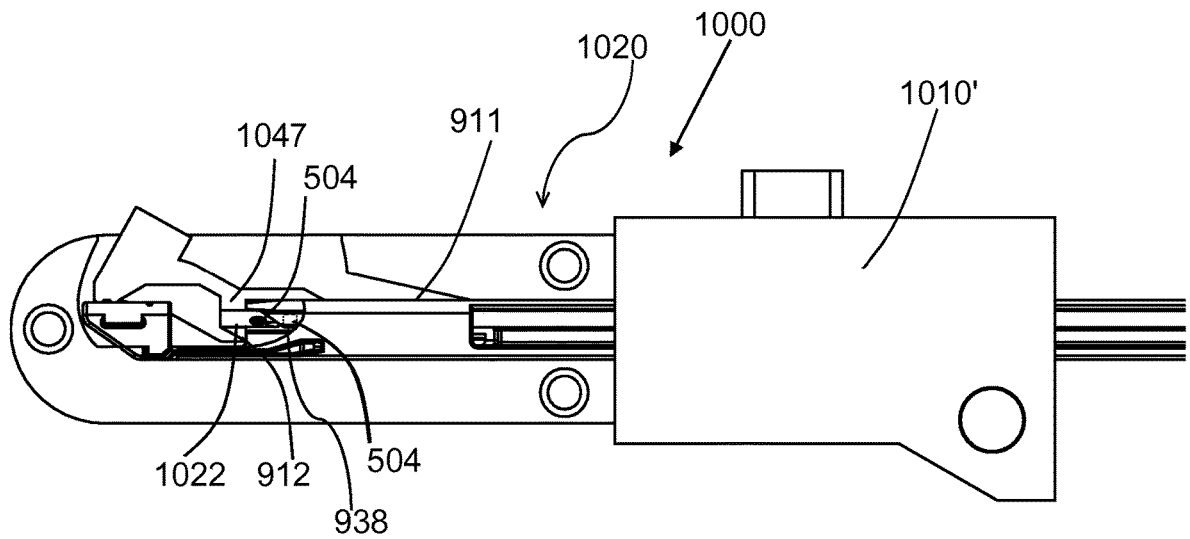

In one specific example, as shown in FIGS. 9J and 9K, the seat 1022 is defined by a projection 1030 that is housed within the magazine 1021, specifically within the rocker 1044. In one specific embodiment, the median 1047 comprises an axially extending channel or opening therein for receiving and retaining a projection 1030 that defines the seat 1022. In some embodiments, the projection may be press-fit within the channel or opening. In other embodiments it may be coupled to the median using an adhesive. In other embodiments the projection 1030 defining the seat 1022 may be formed in one piece as part of the rocker. The projection 1030 defines a hollow interior forming a seat channel 1024. The suture end 504 is press-fit within the seat channel 1024 to be held therein. As such, the projection 1030 forms an alignment feature to further aid in aligning the seat 1022 with the suture receiving passage 932 of the suture passing member 930 such as the needle 930' within the shaft 910. As shown in FIGS. 9M and 10D, the projection 1030 extends into the instrument receiving recess defined by the groove 1044. More specifically, the projection 1030 is capable of abutting against/mating with the suture passing member 930 (such as needle 930') when brought into engagement therewith. In one specific example, the projection 1030 defines a bevel face 1034 for engaging with a bevel face 934 of the needle 930' for docking the needle 930' to align the seat 1022 with the needle 930' with and to permit transfer of the suture end 504 from the seat 1022 into a suture receiving passage 932 of the needle 930'. In one specific example, the projection 1030 is receivable into the instrument proximal portion or shaft 910 to facilitate alignment of the seat 1022 with the needle 930'.

In some such embodiments, as shown in FIG. 9K, the rocker 1041 comprises additional alignment features to assist in alignment of the seat 1022. In one such example, the projection 1030 comprises interference features in the form of raised bumps 1045a on the exterior of the projection 1030. The raised bumps 1045a are configured to frictionally engage the interior of the instrument proximal portion or shaft 910 with the needle 930' as the projection 1030 is received within the shaft 910. In additional embodiments, as shown in FIGS. 9K and 9M, the cartridge 1000 defines a suture groove or slot to allow the suture to exit the seat 1022. In some such embodiments, the rocker 1041 defines a suture slot that is in communication with the seat 1022 for allowing the suture to exit the seat 1022. In the specific example shown, the rocker 1041 comprises additional raised bumps 1045b along the interior of the proximal groove portion 1046 for frictionally engaging the exterior of the instrument proximal portion or shaft 910 once it is received within the proximal groove portion 1046 in order to align the seat 1022 with the needle 930'. This may be referred to as the needle-in configuration of cartridge 1000 as the needle 930' remains inside the shaft 910 during loading of the suturing instrument 900.

In some embodiments, projection 1030 defines a suture slot 1038 therein allowing the suture 500 to exit therefrom to enable alignment of the suture end 504 with the suture receiving passage 932 within the needle 930'. More specifically, the suture slot 1038 provides a path that enables the suture to be to be routed through it upon exiting the seat 1022, such that suture is aligned with the needle slot 928 and shaft slot 938. This facilitates transfer of the suture end into the suture receiving passage 932 of the needle 930 using a suture transferring component of the cartridge 1000. Once the suture exits the suture slot 1038, it is routed though the slot 1049 of the rocker 1041 to enable suture be held to the side of the rocker such that it is off to the side of the path of the suturing instrument 900 as it is advanced into the cartridge 1000.

Figure 9N:
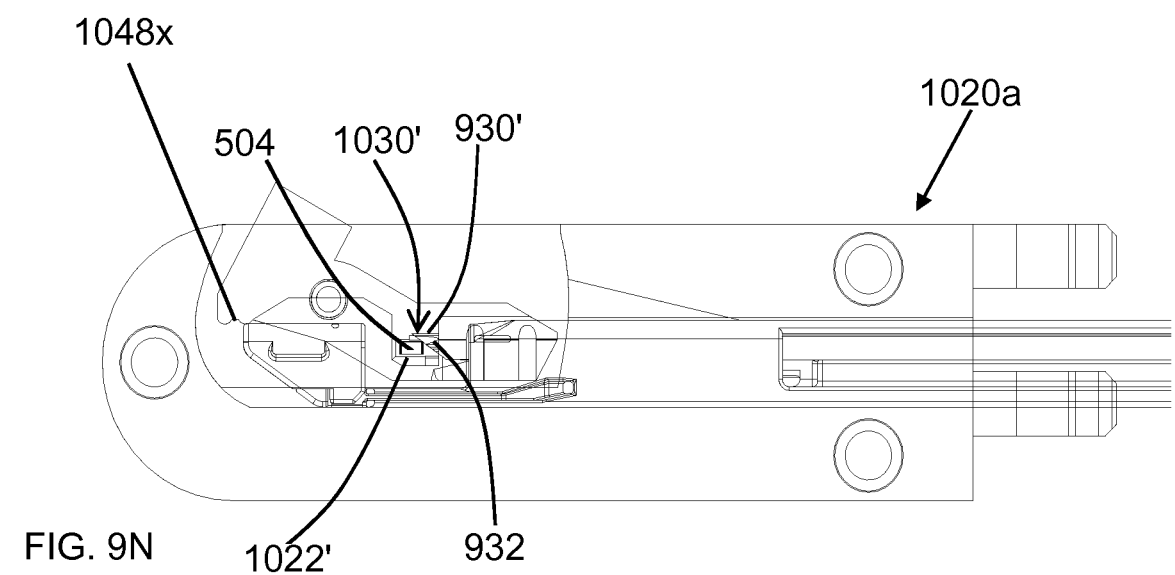

In an alternate embodiment of the present invention, as shown in FIGS. 9L and 9N, the magazine for example the rocker 1041 comprises an alignment recess 1030' that is located adjacent the seat, for holding the suture therein. In some such embodiments, the rocker 1041 defines an opening/space such as a seat recess or seat channel that forms the seat 1022' for holding the suture end 504 in frictional engagement therein. The alignment recess 1030' is positioned adjacent the seat 1022' and is in line with the suture passing member 930. The alignment recess 1030' is configured for receiving the suture passing member 930 (such as needle 930') therein, to allow suture end 504 to be transferred from the seat 1022' to the suture receiving passage 932 of the suture passing member 930. The present configuration of the cartridge 1000 may be referred to as the needle-out configuration, as the needle 930' is maintained in a partially extended position during loading of the cartridge 1000 onto the suturing instrument 900, as shown in FIG. 9N. In other words, a distal portion of the needle 930 extends distally outside the shaft 910 of the suturing instrument at the time of loading the cartridge 1000 onto the suturing instrument. For example, the suture passing member 930 such as the needle 930' can be held in a partially extended position to allow the needle 930' to be received within the alignment recess 1030' for loading of suture therein. In some embodiments, a needle lock is provided that is mounted along the instrument proximal portion or shaft 910 of the suturing instrument 900. The needle lock is engageable with an aperture 935 within the needle 930' in its locking position to maintain the needle 930' in the partially extended position during loading of the cartridge 1000 onto the suturing instrument 900. The needle lock may be disengaged thereafter to allow the needle 930' to be retracted to its nominal position prior to use of the suturing instrument 900.

Figure 9O:
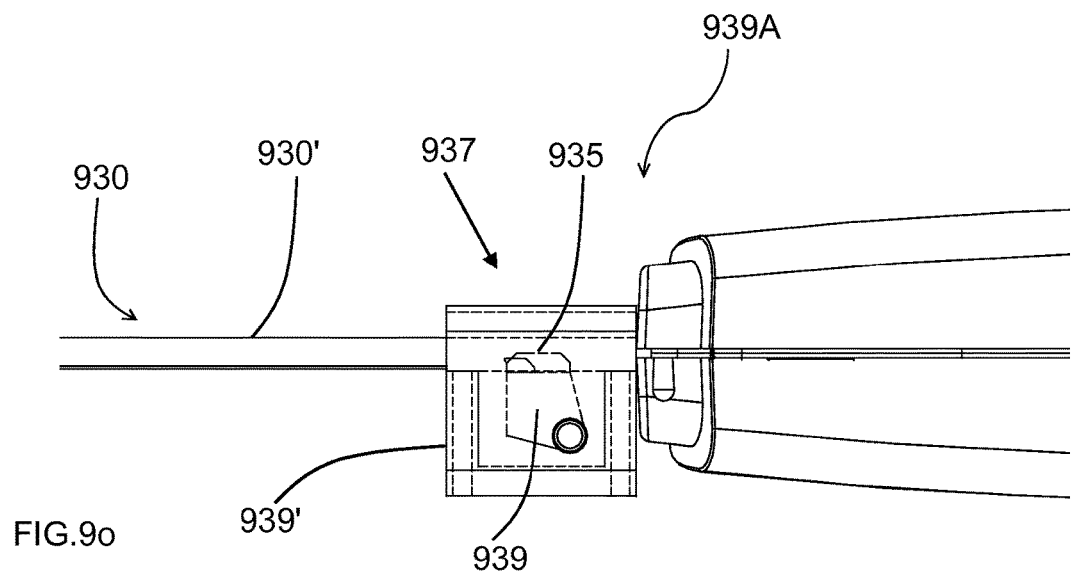

In one specific example, as shown in FIG. 9o, the needle lock comprises a cam lock 937 comprising a cam 939 within a cam housing 939'. In its locked position 939A as shown, the cam is engaged with the aperture 935 of the needle 930', preventing the needle 930' from retracting into the instrument proximal portion or shaft 910. As such, the cam 939 allows the needle 930' to remain in its partially extended position, to allow the needle 930' to be received within the alignment recess 1030' of the cartridge 1000 thereby facilitating alignment and transfer of suture end from the seat 1022' into the needle 930'. The cam 939 may then be disengaged from the needle aperture 935 thereafter moving the cam lock 937 into its unlocked position, which allows the needle 930' to retract back into the shaft or instrument proximal portion 910. In some examples, a component of the cartridge 1000, such as a component of the cartridge housing 1010', may be moveable proximally along the instrument proximal portion of shaft 910 to disengage the cam lock, moving it into its unlocked position to allow the needle to move into its unactuated/nominal position.

In some such embodiments as shown in FIG. 9L, the rocker 1041 comprises additional alignment features to assist in alignment of the seat 1022'. In one such example, the alignment recess 1030' adjacent to the seat 1022' comprises interference features for frictionally engaging an exterior of the needle 930' of the suturing instrument 900, upon advancement of the needle 930' into the alignment recess 1030'. More specifically, the cartridge 1000 comprises interference features in the form of raised bumps 1045a on the inner surface of the wall defining the alignment recess 1030'. The raised bumps 1045a extend proximally along the inner surface of the wall of the alignment recess 1030' and are configured to frictionally engage the exterior of the needle 930' as the needle 930' is received within the alignment recess 1030'. As outlined previously herein above for the embodiment illustrated in FIG. 9K, the rocker 1041 shown in FIG. 9L also comprises additional raised bumps 1045b along the interior of the proximal groove portion 1046 for frictionally engaging the exterior of the instrument proximal portion or shaft 910 once it is received within the proximal groove portion 1046, in order to align the seat 1022 with the needle 930'. This may be referred to as the needle-out configuration of the cartridge 1000 as the needle 930' remains partially extended outside the distal end of the shaft 910, during loading of the cartridge 1000 onto the suturing instrument 900.

In some embodiments, as shown in FIG. 9L, the cartridge 1000 defines a suture groove or slot to allow the suture to exit the seat 1022. In some such embodiments, the rocker 1041 defines a suture slot that is in communication with the seat 1022 for allowing the suture to exit the seat 1022. In the specific example shown in FIG. 9L, the alignment recess 1030' defines a suture slot 1038' therein allowing the suture 500 to exit therefrom to enable alignment of the suture end 504 with the suture receiving passage 932 within the needle 930'. More specifically, the suture slot 1038' provides a path and enables the suture to be to be routed through it upon exiting the seat 1022, such that the suture is aligned with the needle slot 928 and shaft slot 938. This facilitates transfer of the suture end into the suture receiving passage 932 of the needle 930 using a suture transferring component of the cartridge 1000. Once the suture exits the suture slot 1038', it is routed though the slot 1049 of the rocker 1041 to enable suture be held to the side of the rocker such that it is off to the side of the path of the suturing instrument 900 as it is advanced into the cartridge 1000.

In some embodiments of the present invention, the rocker 1041 additionally comprises interference tabs 1048x (as shown in FIG. 9M) for engagement with the suturing instrument 900. Interference tabs 1048x allow the rocker 1041 to over-rotate to ensure alignment of the rocker 1041 with the instrument proximal portion or shaft 910 of the suturing instrument 900 to allow advancement of the rocker 1041 along the shaft 910. In other words, the interference tabs 1048x may allow the rocker 1041 to rotate sufficiently to enable the seat 1022 to be positioned adjacent the suturing instrument 900 by ensuring that the shaft 910 is received within the rocker groove proximal portion 1046. For example, where the seat 1022 is defined by the projection 1030, the interference tabs allow the rocker 1041 to rotate sufficiently to enable the projection 1030 to be received within the instrument shaft 910. Whereas, where the seat 1022 is positioned adjacent an alignment recess (as discussed earlier with reference to FIG. 9N), the interference tabs allow the rocker 1041 to rotate sufficiently such that the alignment recess and the seat 1022 adjacent to it are both aligned with the needle 930'.

As outlined previously herein, with reference to FIG. 9A-9C, some embodiments of the present invention define a base 1020 that is detachably coupled to the housing 1010', enabling the base 1020 and the housing 1010' to operate as a single unit upon loading of the cartridge 1000 onto the suturing instrument 900. In such embodiments, the base 1020 and the housing 1010' provide features to assist in alignment of a portion of the suture 500, such as a suture end 504, with the suture passing member 930. In some such embodiments, the housing 1010' additionally comprises a means to frictionally engage a portion of the suture, and is detachable from the base 1020 after alignment of the suture portion with the suture passing member 930 to transfer the suture portion into the suture passing member. In one such example as described further herein below, the means to frictionally engage a portion of the suture comprises a suture lock.

In some embodiments, the cartridge housing 1010' defines a suture transferring component 1011 to transfer the suture end 504 into the suture passing member 930. In one embodiment as shown and described herein the suture transferring component 1011 is operable to pull the portion of the suture that is held in frictional engagement in order to transfer the suture portion such as suture end 504 held within the seat 1022, onto the suturing instrument 900. As such, the cartridge 1000 comprises a suture transferring component 1011 that forms or defines a pull mechanism as described further in the method outlined herein below. The pull mechanism is defined as the mechanism of the cartridge that enables a pulling force to be exerted or applied to the suture portion (such as the suture end) to transfer the suture portion from the seat into the suturing instrument. In some embodiments, the housing 1010' may additionally comprise suture loops that form a partially pre-tied knot that are mounted about the housing 1010'. Additionally, in some embodiments the housing 1010' may provide a means to house excess suture. In one example, the excess suture may be provided on spools that are carried by housing 1010'.

Figure 11A:
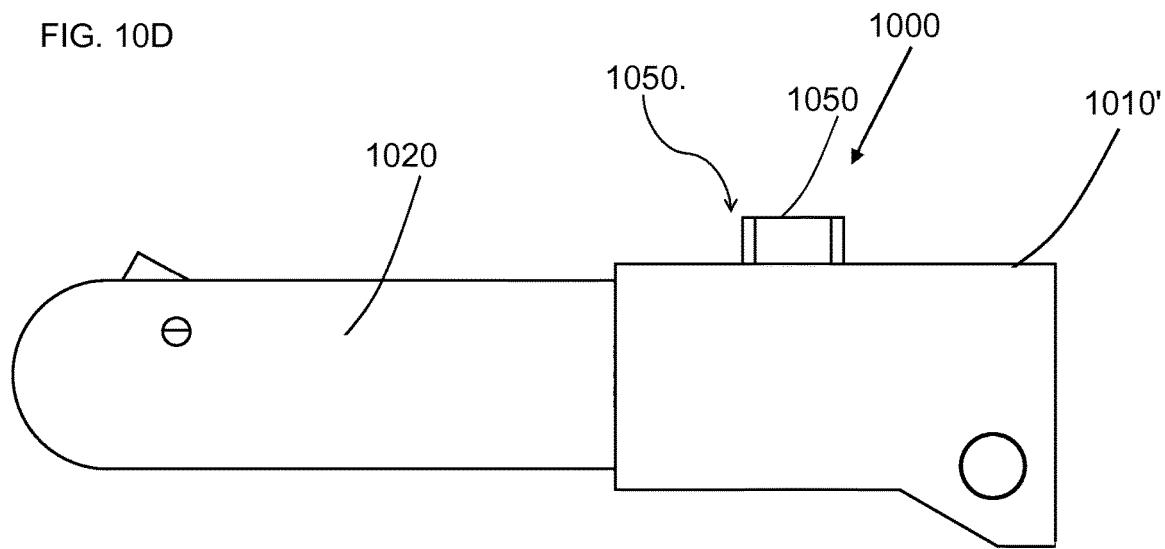
FIGS. 11A-11C illustrate views of an interlock mechanism of a cartridge in accordance with an embodiment of the present invention.
Figure 11B:
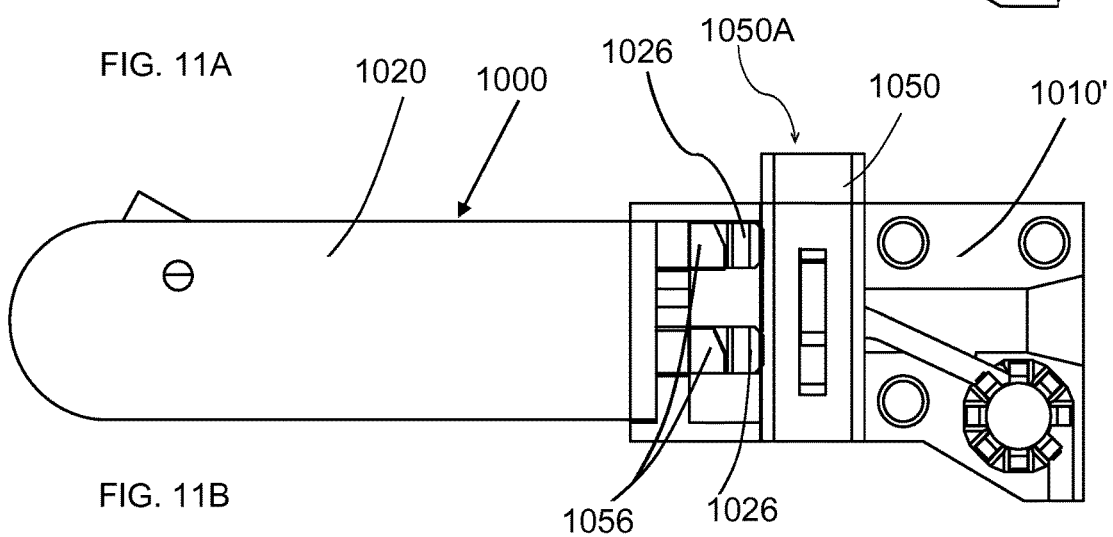
Figure 11C:
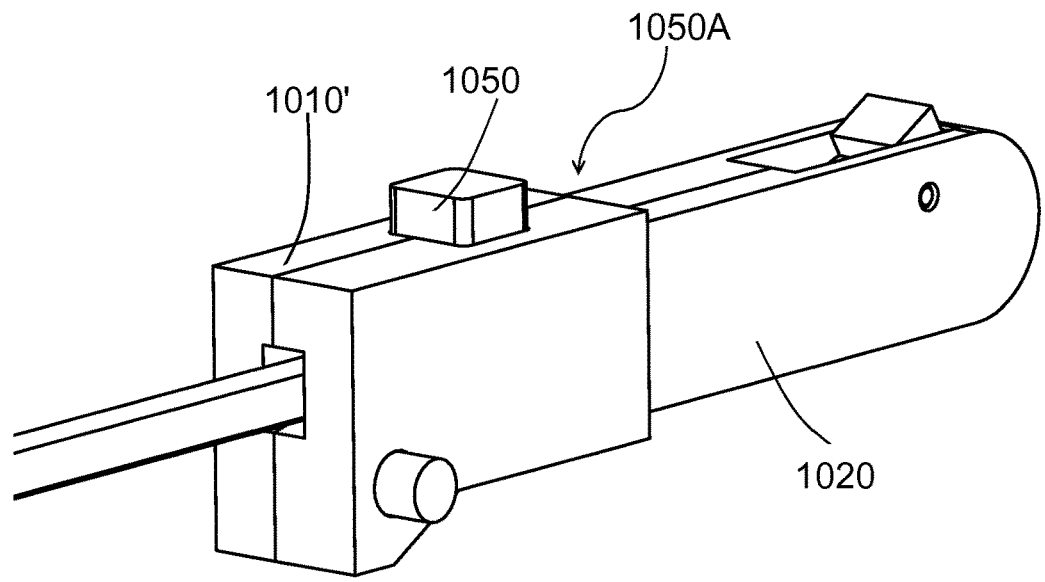

In some embodiments of the present invention as shown in FIGS. 9B, 9C and 9G, the cartridge base 1020 is detachably coupled to the cartridge housing 1010' via an interlock. In the specific example shown, the cartridge housing 1010' defining the suture transferring component 1011 comprises an interlock 1050. The interlock 1050 secures the base 1020 to the housing 1010' (and thus the suture transferring component) allowing the cartridge 1000 to operate as a single functional unit upon loading of the cartridge 1000 onto the suturing instrument 900, until the seat 1022 is aligned with the suturing passing member 930. The interlock 1050 may then be disengaged to allow the housing 1010' that defines the suture transferring component 1011 to translate independently along the suturing instrument 900 to transfer the suture end 504 from the seat 1022 into the suture passing member 930 of the suturing instrument 900. FIGS. 11A-11C illustrate the interlock 1050 in its initial locked position 1050A, with the interlock arms 1056 of the interlock 1050 being axially aligned with the locking arms 1026 of the base. The interlock arms 1056 prevent movement of the housing 1010' with respect to the base 1020 to form a cartridge unit 1000 by blocking longitudinal movement of the locking arms 1026 of the base 1020 (and as such block the longitudinal movement of the base 1020). The function of the interlock 1050 is described further herein below with respect to FIGS. 11A-12B. The interlock 1050 is moveable into its unlocked position 1050B to allow the housing 1010' to be disengaged from the base 1020. In some embodiments, the interlock 1050 comprises a manual interlock that is moveable into the unlocked position 1050B to manually disengage the housing 1010' (and thus the suture transferring component 1011 defined thereby) from the base 1020 upon alignment of the seat 1022 with the suture passing member 930.

Still furthermore, suture transferring component defined by the housing 1010' comprises a means to hold a portion of the suture 500 in frictional engagement with the housing 1010'. This allows the housing 1010' to move the suture 500 therewith to enable the housing 1010' to transfer the suture end 504 held within the seat 1022 of the base to the suture passing member 930. In the embodiment shown in FIGS. 9C and 9G, a portion or segment of the suture is held in frictional engagement with a suture lock 1060 to secure the suture 500 thereto to enable the housing to pull the suture end 504 from the seat 1022 into the suture passing member 930.

Figure 13A:
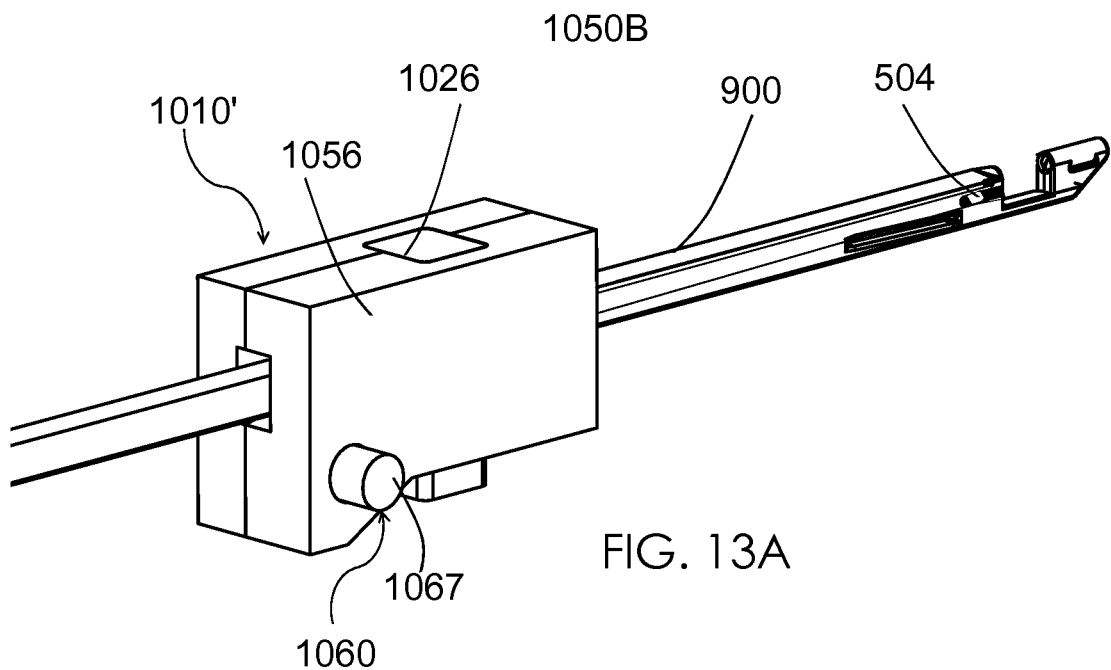
FIGS. 13A-13F illustrate views of a suture lock mechanism of a cartridge in accordance with an embodiment of the present invention.
Figure 13C:
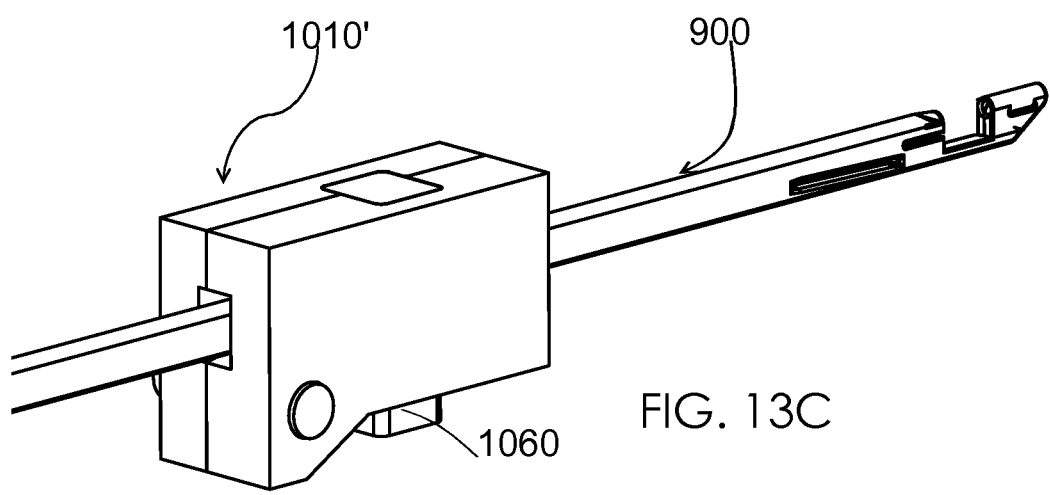
Figure 13B:
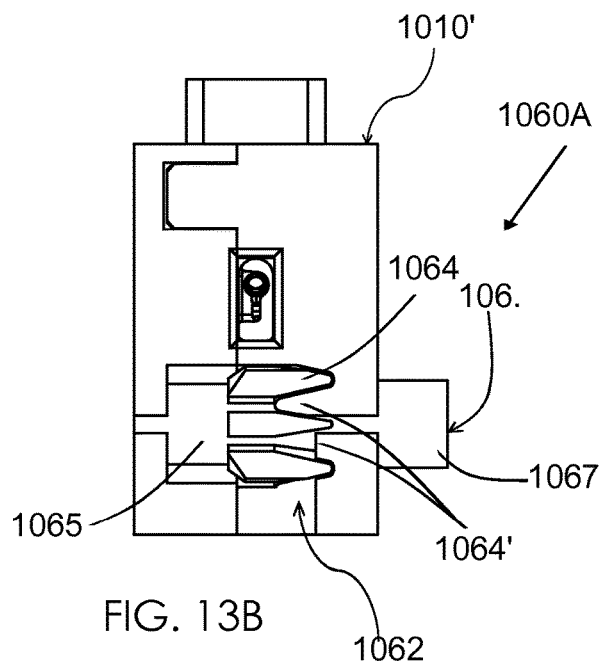
Figure 13D:
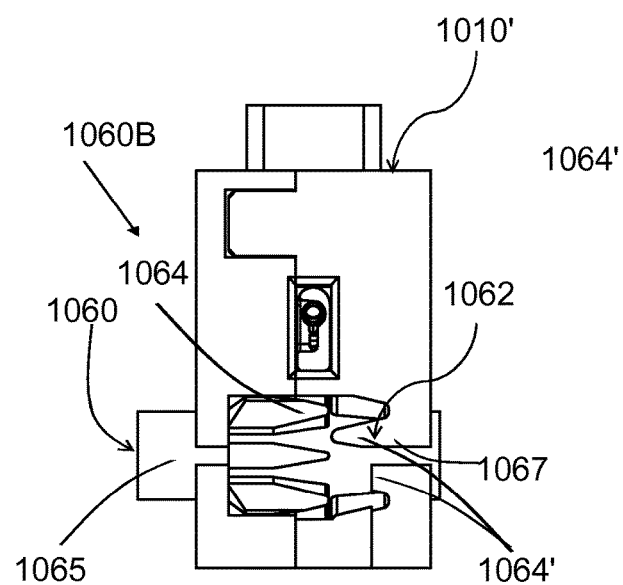
Figure 13E:
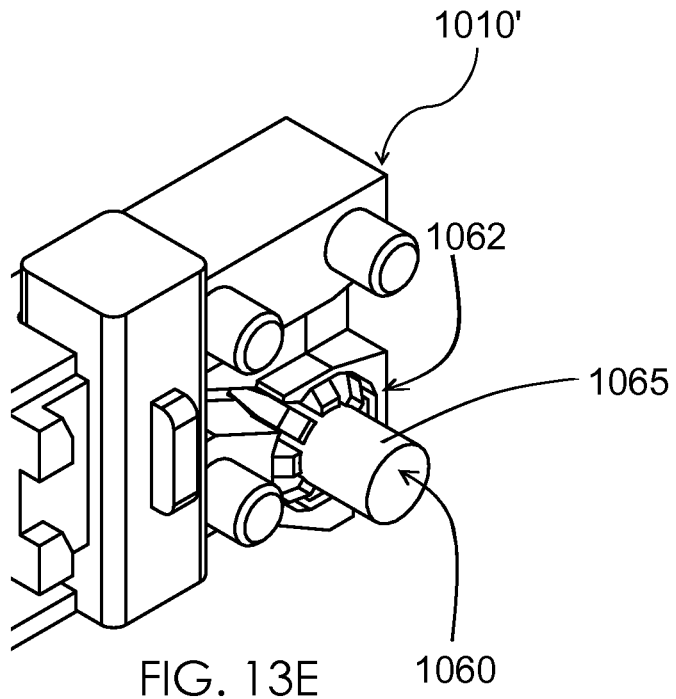
Figure 13F:
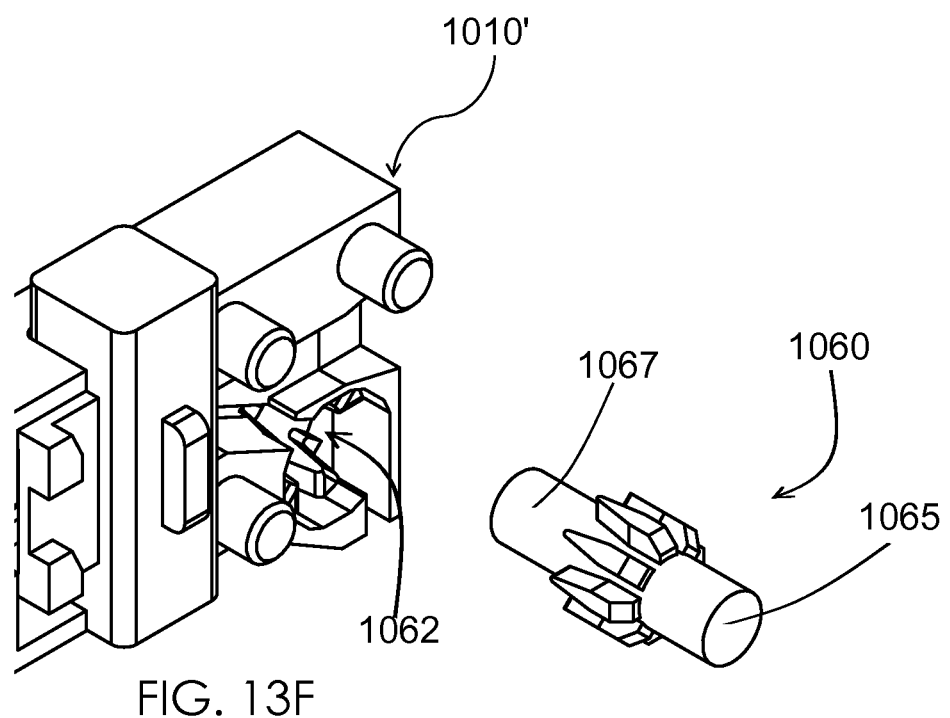

More specifically, in the embodiment shown, the suture 500 is held within the cartridge 1000 such that the suture 500 is routed from the suture end 504 within the seat 1022 upon exiting the seat slot 1038 such that it enters the slot 1049 of the rocker to be routed there-through. More specifically, in some examples the suture passed through and pinched within the slit or channel 1049 such that it is held therein in a force fit engagement. The suture 500 then enters the side slot 1049b on the exterior face of the rocker 1041 (FIGS. 9J and 9L). The suture 500 exits the rocker 1041 into the rocker recess 1027 and is routed through the recess groove 1025b within the base 1020, which allows the suture 500 to be maintained within recess groove 1025b adjacent to and out of the way of the path of the suturing instrument 900 to be inserted through the recess groove 1025a (FIG. 9D). The suture is then routed through an opening 1051 within the interlock and guided into a suture channel 1061 to engage with the suture lock 1060. In one particular embodiment, as shown in FIGS. 13A-13E, the suture lock 1060 comprises projections or teeth 1064 defining contours or ridges and valleys that are configured to engage corresponding features in the form of projections or teeth 1064 within a suture lock engaging component 1062 of the housing 1010'. The suture 500 is routed through the suture lock engaging component 1062 of the housing 1010' and the suture lock 1060 is press fit to engage with the suture lock engaging component 1062, pressing the suture between the two, and as such coupling the suture to the housing 1010'. FIGS. 13B and 13E show the lock in its initial locked configuration 1060A. The lock 1060 remains in its locked configuration until the suture portion such as the end of the suture has been loaded into the suturing instrument 900. The lock is moveable thereafter into its second or unlocked configuration (as shown in FIGS. 13D and 13F) to allow the suture 500 to be disengaged from the housing 1010'.

In some embodiments, as described herein above in example 9, the movement of the suturing instrument 900 may be a relative movement with respect to the cartridge 1000. In other words, the user may move the cartridge 1000 axially over the suturing instrument 900 in a proximal direction while the suturing instrument is held by the user in order to create a relative advancement of the suturing instrument 900 with respect to the cartridge 1000 in order to load the suture onto the suturing instrument 900. This may be referred to as loading of suture using pumping action. As such, the mechanism of loading the suture may remain as described above, but the movement may be created either by the proximal movement of the cartridge over the suturing instrument or the distal movement of the suturing instrument within the cartridge.

In some embodiments of the present invention as described herein, the cartridge is configured to align and transfer the suture upon a single linear motion of the cartridge with respect to the suturing instrument. In some such embodiments, the interlock 1050 may be automatically disengaged upon alignment of the suture end within the seat with the suture passing member. Automatic disengagement of the interlock 1050 enables automatic transfer of the suture end 504 into the suture passing member as the housing 1010' is continued to be pulled proximally. Additionally, the suture lock 1060 may be automatically disengaged thereafter upon transfer of the suture end from the seat 1022 into the suture passing member 930, which would allow the suturing instrument to be able to pass the suture in order to suture therewith. In some such embodiments, the cartridge is loaded onto the suturing instrument 900 with a single linear movement. In some such embodiments, a single pumping action is used involving a single linear relative movement of the cartridge onto the suturing instrument and removal of the base 1020 (for example via a linear movement in the opposing direction to the loading direction) thereafter leaving the housing coupled to the suturing instrument, for example to mount a pre-tied knot held therein onto the suturing instrument.

Example 10

Figure 14A:
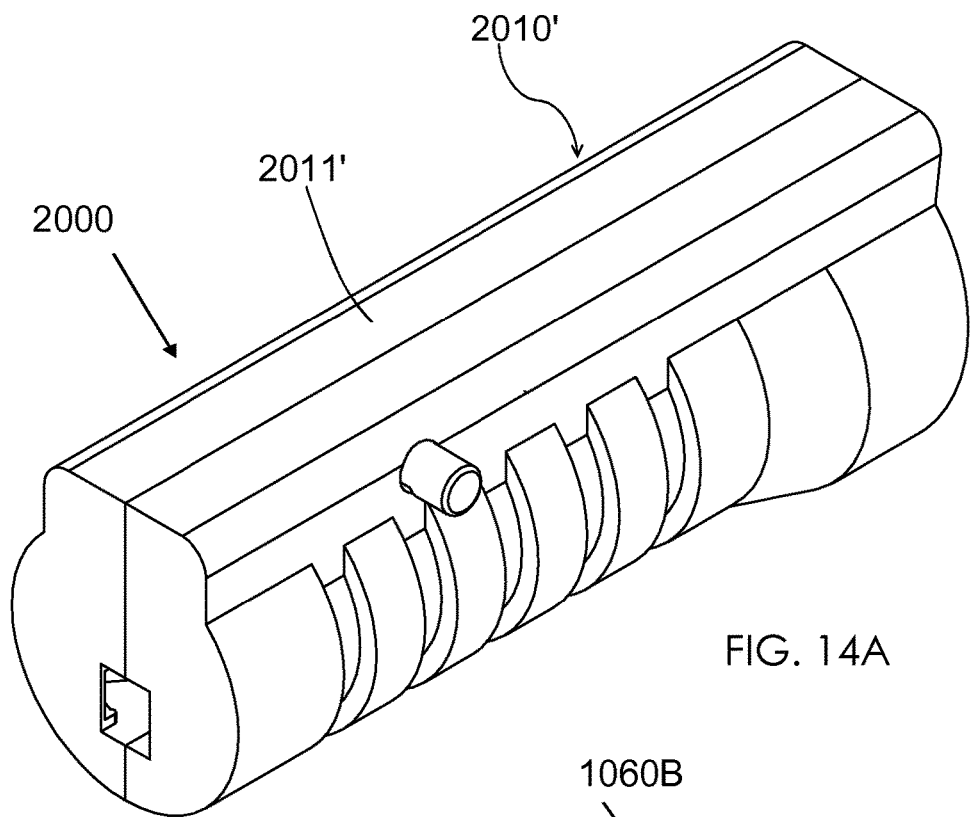
Figure 14B:
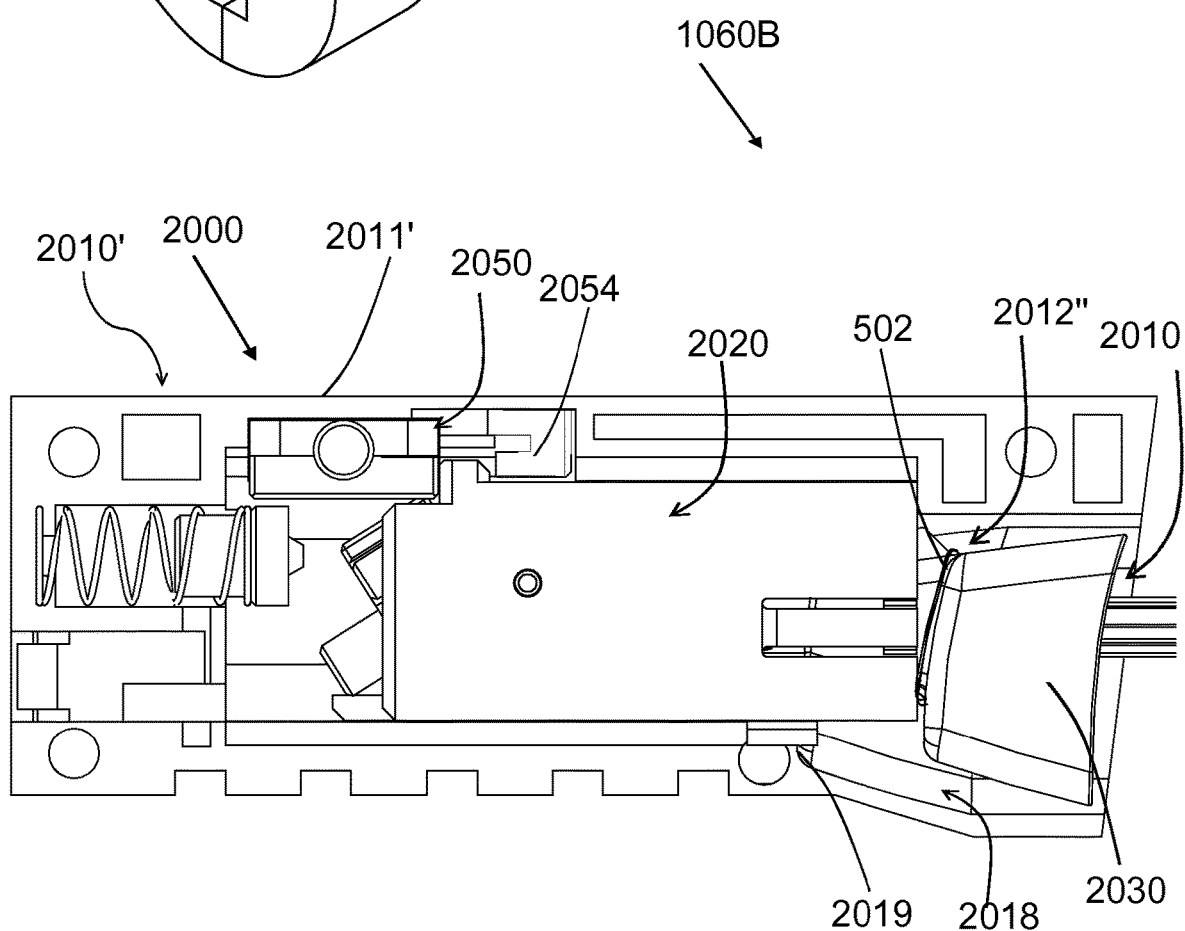
Figure 14C:
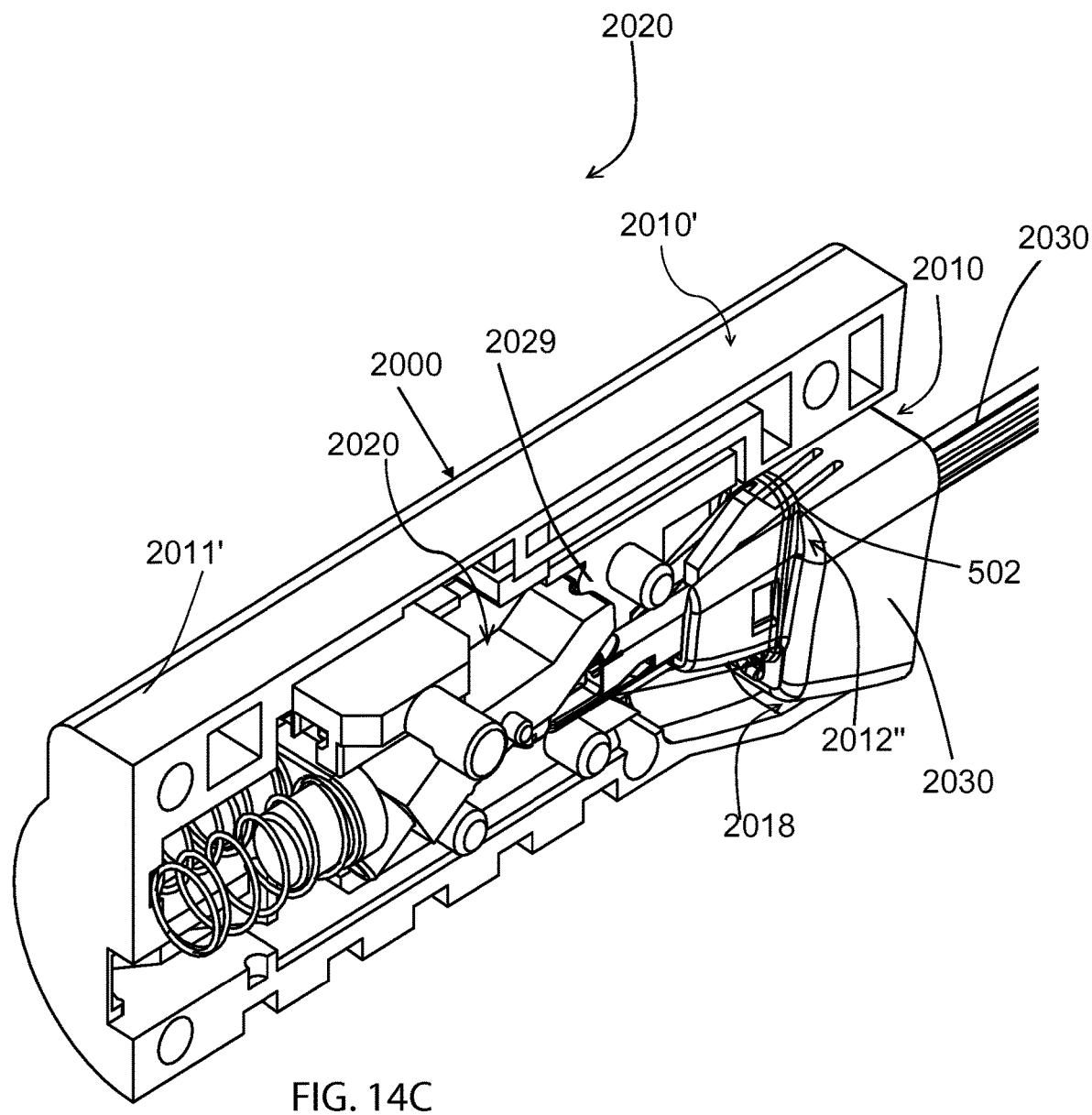

In an alternate embodiment of the present invention, as shown in FIGS. 14A-14C(i), a cartridge 2000 is disclosed for loading suture onto a surgical suturing instrument, for example a suturing instrument 900 as discussed previously herein above with reference to FIGS. 1D and 1E. Similar to embodiments described previously herein above, the cartridge 2000 carries suture therein and allows suture to be loaded onto a surgical suturing instrument 900, for example at the point of use. The cartridge 2000 functions to align the suture with the suturing instrument 900 upon insertion and relative axial advancement of the suturing instrument 900 within the cartridge 2000, and additionally functions to transfer the suture onto the surgical suturing instrument 900. In some such embodiments, either the suturing instrument 900 may be advanced distally into the cartridge 2000 or the cartridge 2000 may be pulled proximally over the suturing instrument. As described herein, either of these techniques may be utilized to provide the functionally described herein for creating relative axial movement between the cartridge 2000 and the suturing instrument 900 for loading the suture onto the suturing instrument 900. This is also applicable to embodiments described herein above in example 9. In some such embodiments, the cartridge 2000 additionally provides a pre-tied knot therein and enables the pre-tied knot to be loaded onto the suturing instrument 900. In some embodiments, the pre-tied knot may comprise loops that substantially form a pre-tied knot. In other words, a pre-tied knot may comprise a partially pre-tied knot. In some such embodiments, the partially pre-tied knot is configured to be deployed from the suturing instrument after suturing to form a knot to secure the suture.

With reference now to FIGS. 14B and 14C, the cartridge comprises a housing 2010' that defines a chamber 2010 for axially receiving the surgical suturing instrument 900. The cartridge 2000 further comprises a base 1020 that is detachably coupled to the housing 1010', the base 2020 defining a seat 2022 for releasably holding the suture therein (as shown in FIG. 14E(ii)). The base 2020 enables alignment of the suture held therein with the suture passing member 930 of the suturing instrument 900. The housing 2010' additionally comprises a suture transferring component to transfer suture from the base 2020 onto the surgical suturing instrument 900. Thus, in some embodiments, as shown in FIG. 14B, the base 1020 and the housing 2010' comprise separate components of the cartridge 1000 that are coupled to one another to assist in loading suture and may be detachable therefrom to assist in transferring suture. The housing 2010' additionally comprises a chamber 2010 therein and a means for securing or mounting a pre-tied knot 502 about the chamber 2010, to enable the pre-tied knot to be mounted onto the suturing instrument 900. The housing 2010' and the base 2020 collectively provide alignment features to assist in alignment of the suture upon loading of the cartridge 1000 onto the suturing instrument 900 to facilitate transfer of suture from the cartridge 1000 onto the suturing instrument 900 using the suture transferring component. In some embodiments, the housing 2010' comprises a knot slider 2030 that defines the chamber 2010. The knot slider 2030 includes suture loops coupled thereto, and the suture loops are configured to form a knot upon deployment thereof from the knot slider 2030, wherein the suturing instrument 900 is receivable within the chamber 2010 for mounting the suture loops onto the suturing instrument.

In some such embodiments, a suturing system is provided that comprises a suturing instrument 900 comprising a suture passing member 930; and a cartridge (such as cartridge 2000) for releasably holding an end of a suture and defining a chamber 2010 for coupling a partially pre-tied knot thereabout, the chamber 2010 is configured to receive the suturing instrument 900 there-through. The cartridge 2000 is configured to transfer the suture end 504 into the suture passing member 930 and to transfer the partially pre-tied knot (for example 502) onto the suturing instrument. In some such examples, the suture passing member 930 is configured to pass the suture end 504 from a proximal side of a tissue to a distal side of the tissue in a first actuation of the suture passing member.

In an additional embodiment, a cartridge (such as cartridge 2000) is provided for loading suture onto a suturing instrument 900 to enable the suturing instrument to form a pre-tied knot. The cartridge comprises: a chamber 2010 for receiving a suturing instrument 900, the chamber 2010 supporting loops of suture coupled thereto (such as loop 502 shown in FIG. 14B) for transferring onto the suturing instrument 900 upon advancement of the suturing instrument into the chamber 2010, the loops 502' of suture being configured to form a pre-tied knot upon deployment from the suturing instrument; and a seat 1022 for releasably holding a portion of the suture to enable transfer of the suture portion 504 onto the suturing instrument, the suture portion comprising an end of the suture configured to define a post of the pre-tied knot upon deployment of the loops from the suturing instrument.

In one particular embodiment, the cartridge housing 2010' is detachably coupled to the base 2020 and defines a chamber 2010 for receiving the surgical suturing instrument 900 there-through. In some such embodiments, the chamber 2010 additionally comprises a means for storing a pre-tied knot about the chamber. In some embodiments, the housing 2010' additionally comprises a knot slider 2030 defining the chamber 2010 having a pre-tied knot mounted thereon. In such embodiments, the surgical suturing instrument is receivable within the chamber 2010 to mount the pre-tied knot onto the surgical suturing instrument 900. In one particular example, the cartridge housing 2010' comprises an outer housing sleeve 2011' that defines a hollow interior for holding the knot slider 2030 therein. The knot slider 2030 is detachably coupled to the housing sleeve 2011' and forms a part of the housing 2010'. In a particular example as shown in FIG. 14B, the knot slider 2030 is detachably coupled to the housing 2010' via the base 2020 for holding a pre-tied knot about the chamber 2010.

Additionally, the chamber 2010 includes a recess or channel 2014 that is a part of the chamber that receives the suturing instrument. In the particular example discussed herein, the chamber 2010 defines a channel 2014 as shown in FIG. 14D which illustrates a rear view of the knot slider 2030 to allow a portion the suturing instrument 900 to be received there-through. As such the channel 2014 defines an instrument receiving recess for receiving the suturing instrument 900 that additionally functions as a restraint for maintaining the position of the suturing instrument 900 as it is advanced through the cartridge 1000. Similar to Example 9 described previously herein above, in some examples, the channel 2014 comprises a proximal opening 2016 that narrows towards the interior of the knot slider 2030 as defined by a beveled interior edge 2016'. The beveled interior edge 2016' functions as a lead in to guide the suturing instrument 900 into the channel 2014.

The channel 2014 extends longitudinally through the knot slider 2030 of the housing 2010' and is in communication with a base recess 2025 within the base 2020. As shown in FIGS. 14A-14C, the base 2020 is detachably coupled to the housing 1010'. More specifically, the base 2020 is held within the housing sleeve 2011'. In some examples, the channel 2014 may be formed continuously with the base recess 2025 within the cartridge base 2020. One example of this is discussed further herein below. The channel 1014 and the base recess 1025 both function as a restraint 25 (FIG. 14E (i)), to constrain or restrict the lateral and transverse movement of the suturing instrument 900 within the cartridge 1000 while allowing the suturing instrument 900 to be advanced linearly or axially therein in sliding engagement to maintain the position of the suturing instrument 900 along the longitudinal axis as it is advanced. As such, the restraint 25 constraints or limits the movement of the suturing instrument 900 in the transverse and lateral directions as well as along a longitudinal path defined thereby. Thus, the restraint 25 facilitates alignment of the suturing instrument 900 with a portion of the suture 500 that is held within a seat 1022 defined by the base 1020. More specifically, the channel 1014 and the recess 1025 allow the suturing instrument 900 to be advanced therein in sliding engagement therein, and additionally function to restrain the suturing instrument 900 in a linear path as it is advanced along the cartridge 1000 to allow the seat 1022 to be aligned with the suture receiving passage 932 of the suture passing member 930.

Figure 14F:
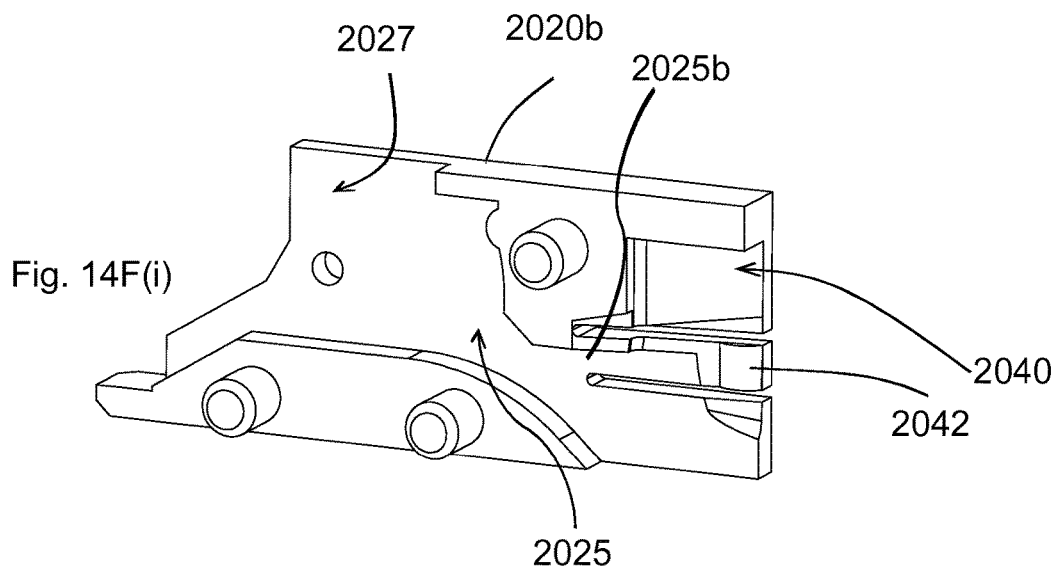
Figure 14G:
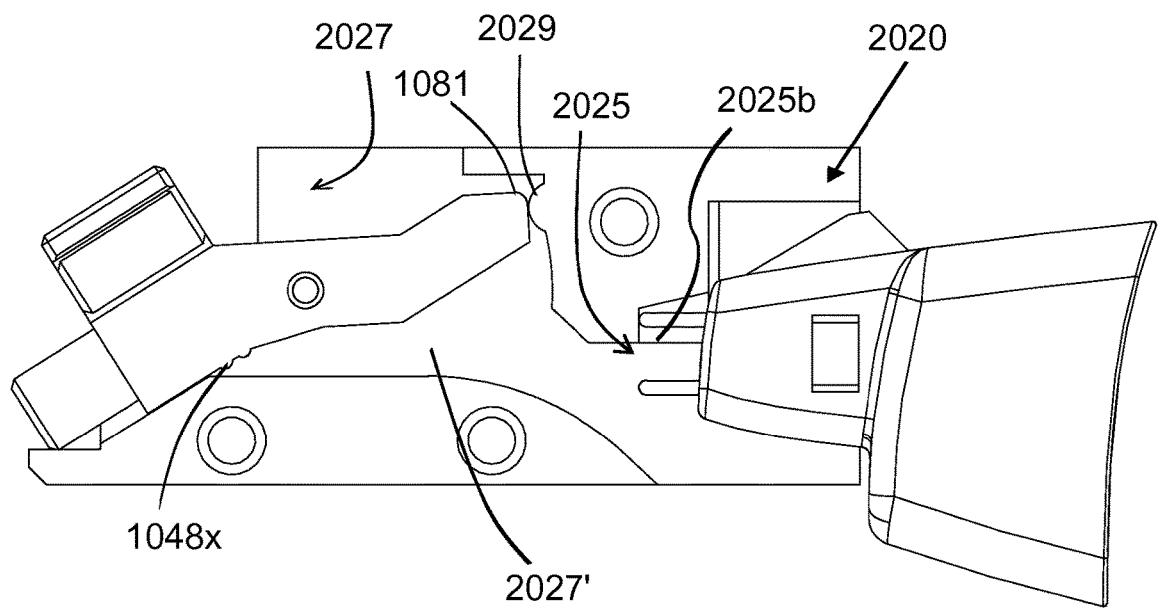
Figure 14G:
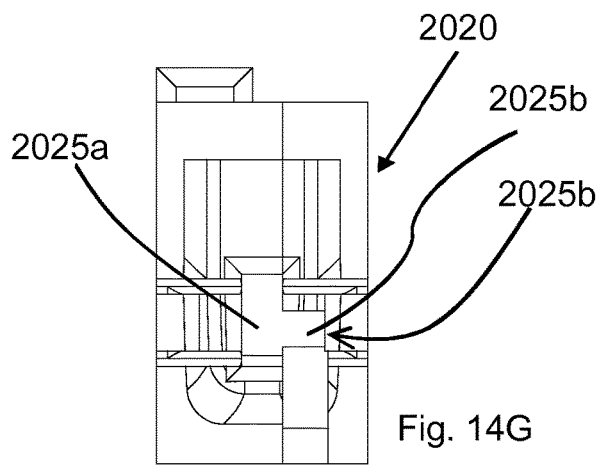

Furthermore, similar to embodiments discussed previously with respect to Example 9 herein above, the recess 2025 within the base is formed from two grooves, an instrument receiving groove 2025a defining an instrument receiving recess as shown in FIG. 14E(i) and FIG. 14E(ii), and a suture receiving groove 1025b defining a suture receiving recess, as shown in FIG. 14F(i) and FIG. 14F(ii). The instrument and suture receiving grooves 2025a and 2025b, respectively, are formed within the opposing halves 2020a and 2020b of the base 2020 (as illustrated in FIG. 14E(i)-FIG. 14F(ii)).

With reference again to FIGS. 14E(i),(ii) the instrument receiving groove 2025a defines an instrument receiving recess by providing a track that functions as a restraint 25 to allow the suturing instrument 900 to be advanced therein, whereas suture groove 2025b (FIG. 14F(i)) provides a track to guide the portion of the suture held within the seat into the suture passing member 930 of the suturing instrument 900 by maintaining/routing the suture 500 therein such that it is adjacent to and in line with the shaft or proximal portion 910 of the suturing instrument 900 that is receivable within the instrument receiving groove 2025a, as further illustrated in FIGS. 14F(ii) and 14G. More specifically, the suture receiving groove 2025b allows the suture to be routed such that when the suturing instrument is received within the instrument receiving recess 2025b, the suture 500 is held adjacent to the groove 928 within the shaft or the instrument proximal portion 910 as well as groove 938 within suture passing member 930 such as needle 930' (shown in FIG. 1E). Furthermore, the groove 2025b provides room for routing the suture without excess tension being placed in the suture by providing a wider opening into a rocker recess 2027, as shown by FIG. 14F(ii). As such, the groove 2025b accommodates the suture as it enters a rocker recess 2027 in both a final position 1041B as well as an initial position 1041A of a rocker 1041 (discussed further herein below). The suture receiving groove 2025b enables the suture 500 to be maintained out of the way of the advancing suturing instrument 900 during use of the cartridge 1000. Additionally, recess groove 2025b is in line with grooves 928, 938 within the suturing instrument 900 to further facilitate transfer of suture from a seat 2022 for example within the rocker 1041 within the base 2020 into the needle 930'. In the illustrated embodiment, both the instrument receiving groove and the suture receiving groove exit into the rocker recess 2027.

In some embodiments, as provided herein the cartridge 2000 additionally provides a pre-tied knot and a means to load the pre-tied knot onto the suturing instrument 900. In some such embodiments, the cartridge defines a chamber 2010 and a means to mount or retain a pre-tied knot about the chamber 2010. In one such example, as shown in FIG. 14C and as discussed herein, a knot slider 2030 is provided that enables a pre-tied knot to be mounted thereon so that it is held about and surrounds or circumscribes the chamber 2010. This enables the suturing instrument 900 to be received through a channel 2014 within the chamber 2010 such that it passes through the pre-tied knot to allow the pre-tied knot to be mounted thereon. In one specific example, the knot slider forms a mount 2012" for holding the pre-tied knot 502 about the chamber 2010, as shown in FIGS. 14B and 14C. The pre-tied knot 502 may be of the type as previously illustrated herein in FIG. 1A. In some embodiments, the knot slider 2030 forms an instrument mounted component of the cartridge 2000.

Additionally, some embodiments of the present invention provide a means to hold the knot slider 2030 within the cartridge 2000 to permit the knot slider 2030 to be held therein until a suturing instrument 900 is inserted within the cartridge 2000 to enable the knot slider 2030 to be detached from the rest of the cartridge 2000 to be coupled to the suturing instrument 900 thereafter. In some such embodiments, the knot slider 2030 is held within a knot slider recess 2018 within the outer sleeve 2011' (shown in FIG. 14B and FIG. 14C), and is detachably coupled thereto via the base 2020. In one particular example, the knot slider 2030 is detachably coupled to the base 2020 via a knot slider release interlock 2033 that for example comprises a snap fit arrangement as shown in FIG. H(i). As additionally illustrated in FIGS. 14E(i), 14F(i), the base comprises snap arms 2042 that are receivable within and engageable with grooves formed within the knot slider 2030 that may be referred to as snap grooves 2032 to couple knot slider 2030 therein, forming the knot slider release interlock 2033. In order to facilitate coupling between the knot slider 2030 and the base 2020, the base 2020 additionally comprises a knot slider cavity 2040 therein that is configured for receiving a portion of the knot slider 2030 therein.

In the illustrated embodiment, the knot slider 2030 is detachable from the base to enable loading of the knot slider 2030 and thus the pre-tied knot 502 onto the suturing instrument 900 upon disengagement of the knot slider release interlock 2033. In one specific embodiment, the knot slider 2030 is detachable from the base 2020 upon relative movement of base 2020 with respect to the housing 2010'. In one such example, the knot slider 2030 is moveable distally along the knot slider recess 2018 within the housing sleeve 2011' upon distal movement of the base 2020 within the housing sleeve 2011'. However, the wall 2019' of the housing sleeve 1011' adjacent the tapered inner wall 2019 (shown in FIG. 14B) of the knot slider recess 2018 functions as a stop to prevent further distal movement of the knot slider 2030 to disengage snap arms 2042 of the base 2020 from the snap grooves of the knot slider 2030, and as such disengages the knot slider release interlock 2033.

Figure 15A:
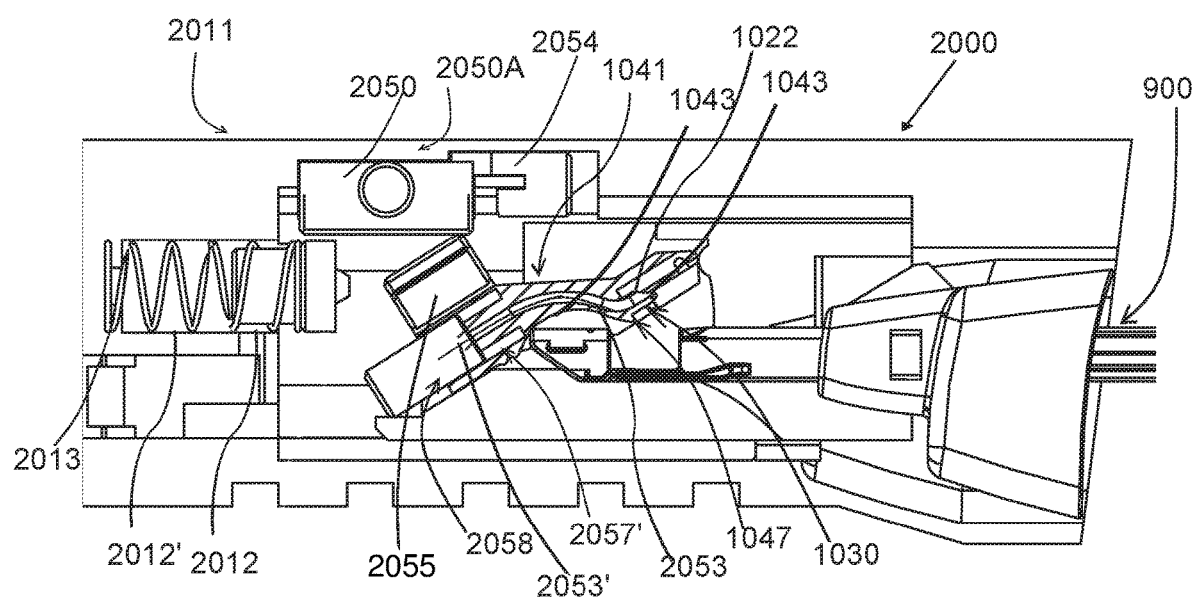
FIGS. 15A(i)-15F illustrate views of a cartridge and a method of using the same in accordance with an alternate embodiment of the present invention.

In some embodiments of the present invention, the cartridge 2000 defines a moveable seat 1022 as previously described herein above with reference to FIG. 9C, the seat 1022 is automatically moveable upon insertion of the suturing instrument 900 within the cartridge 1000. In the particular example shown, the cartridge 2000 comprises a magazine 1021 comprising a rocker 1041 that is rotatable about a pivot, and the base 2020 defines a rocker recess 2027 for enabling pivotal movement of the rocker 1041 therein. Similar to the embodiments illustrated in FIGS. 9C and 10C(i), the rocker 1041 is moveable about the pivot 1042 from its initial position 1041A (as shown in FIG. 15A(i),(ii)) to its second position 1041B (as shown in FIG. 15B(i),(ii)) in order to align the seat 1022 and the suture end 504 held therein with the path of an advancing suturing instrument 900 that is inserted within the cartridge 1000. As outlined previously in example 9, and as defined herein the rocker 1041 is moveable within the rocker recess 2027. The rocker 1041 is moveable from its first position 1041A into a rocker cavity 2027' to its second position 1041B, as shown in FIG. F(ii). The rocker cavity 2027' is defined as a portion of the rocker recess 2027 that corresponds to the tissue receiving gap 942 of the suturing instrument 900 once suturing instrument 900 is positioned within the base 2020 of the cartridge 2000 upon loading of the cartridge 2000 onto the suturing instrument.

In some embodiments, the rocker 1041 is held in its initial position 1041A within the rocker recess 2027 through frictional engagement. For example the rocker 1041 may be kept in its initial position 1041A by an engagement feature such as a raised tab or detent 2029 as shown in FIGS. 14C and 14F(i), that frictionally engages the rocker 1041. The tab or detent 2029 is formed within the base 2020 and may extend or jut into the rocker recess 2027. The tab 2029 is engageable with a portion of the rocker 1041 (for example a nose portion 1081) of the rocker 1041 as shown in FIG. 14F(ii), to maintain the rocker in its initial position 1041A during shipment and prior to use.

As outlined previously for Example 9, in some embodiments as additionally provided in Example 10, the cartridge 2000 may comprise additional features that assist in aligning the seat 1022 with a portion of the suturing instrument 900, such as the suture passing member 930 held within the shaft or instrument proximal portion or shaft 910. In one such example, with reference to FIG. 9C that was discussed earlier, the rocker 1041 additionally defines an instrument receiving or locking recess defined by a groove 1044 that is designed for receiving the suturing instrument 900 as it is advanced distally. The groove 1044 functions as a restraint to position the suturing instrument 900 in a desired position relative to the seat 1022 to assist in aligning the seat 1022 with a suture passing instrument 900. As shown and discussed previously with reference to FIGS. 9H and 9I, the groove 1044 comprises a groove proximal portion 1046 for receiving the instrument proximal portion or shaft 910 of the suturing instrument 900, and additionally comprises a groove distal portion 1048 for receiving the instrument distal portion or tip 920.

As discussed earlier in Example 9, the rocker 1041 of Example 10 additionally comprises a median 1047 (shown in FIG. 15A(i)). Median 1047 is defined by the groove 1044 that functions as an alignment feature by holding and aligning the seat 1022 with the suture passing member such as needle 930' of the suturing instrument 900.

Still furthermore, the groove 1044 defines an additional alignment feature in the form of an interior bevel face 1043 (shown in FIG. 15A (i)) within the distal groove portion 1048. Bevel face 1043 enables the distal portion 920 of the suturing instrument to pivot the rocker 1041 from its initial position 1041A into its aligned position or second position 1041B to enable alignment of the seat 1022 and the suture held therein with the suture passing member 930 of the suturing instrument.

In some embodiments, in cartridge 2000, the rocker 1041 additionally defines another alignment feature in the form of a rocker slot 1049 (as shown earlier in FIGS. 9J, 9L) within the groove 1044 to assist in alignment and transfer of the suture end 504 into the suture passing member 930. The slot 1049 comprises a slit or channel 1049a (also shown in FIG. 15A(i)) that exits into a side slot 1049b within the rocker 1041, to aid in routing the suture 500 within the suture receiving groove 2025b (shown in FIG. 14F(ii)) of the base 2020 to assist in aligning the suture with the suture receiving slot 928 in the shaft. This feature allows the suture to be held to the side of the suturing instrument 900 out of the way of the path of the advancing suturing instrument during advancement of the suturing instrument within the cartridge base 2020. As such, the rocker 1041 defines a rocker slot 1049 for routing the suture 500 there-through to enable the suture 500 to be kept out of the way of a path of the suturing instrument 900 upon advancement of the suturing instrument 900 therein (For example when a portion of the instrument proximal portion 910 is received within the groove proximal portion 1046 of the rocker groove 1044).

In one specific example as shown in FIGS. 9J and 9K, the seat 1022 is defined by a projection 1030 that is housed within the magazine 1021, specifically within the rocker 1044. As shown in FIGS. 9M and 10D, the projection 1030 extends into the instrument receiving recess defined by the groove 1044 (specifically, the groove proximal portion 1046). More specifically, the median functions to hold the projection 1030 within the groove proximal potion 1046 of the rocker. In some embodiments, the projection 1030 defining the seat 1022 may be formed in one piece as part of the rocker. The projection 1030 additionally defines a bevel face 1034 for engaging with a bevel face 934 of the needle 930' for docking the needle 930' to align the seat 1022 with the needle 930' to permit transfer of the suture end 504 from the seat 1022 into a suture receiving passage 932 of the needle 930'. In one specific example, the projection 1030 is receivable into the instrument proximal portion or shaft 910 to facilitate alignment of the seat 1022 with the needle 930'.

Alternatively, the rocker may define a seat recess or seat channel and an alignment recess 1030' that is located adjacent to the seat 1022. As shown and described further herein with respect to FIGS. 9L and 9N, the alignment recess 1030' is configured for receiving the suture passing member 930 such as needle 930' in its needle-out configuration to align the seat with the suture passing member.

In some such embodiments, as shown in FIG. 9K, the rocker 1041 comprises additional alignment features such as interference features in the form of raised bumps 1045a on the exterior of the projection 1030. Raised bumps 1045a are configured to frictionally engage the interior of the instrument proximal portion or shaft 910 with the needle 930' as the projection 1030 is received within the shaft 910. The rocker 1041 additionally comprises additional raised bumps 1045b along the interior of the proximal groove portion 1046 for frictionally engaging the exterior of the instrument proximal portion or shaft 910 once it is received within the proximal groove portion 1046. The raised bumps 1045a, 1045b help to align the seat 1022 with the needle 930'.

In some embodiments projection 1030 defines a suture slot 1038, therein allowing the suture 500 to exit therefrom to enable alignment of the suture end 504 with the suture receiving passage 932 within the needle 930'.

In some embodiments of the present invention, the rocker 1041 additionally comprises interference tabs 1048x (as shown in FIG. 15A (iii), and FIG. 15B (i), and as discussed earlier with respect to FIG. 9M) for engagement with the suturing instrument 900. Interference tabs 1048x allow the rocker 1041 to over-rotate to ensure alignment of the rocker 1041 with the instrument proximal portion or shaft 910 of the suturing instrument 900 to allow advancement of the rocker 1041 along the shaft 910. In other words, the interference tabs 1048x may allow the rocker 1041 to rotate sufficiently to enable the seat 1022 to be positioned adjacent the suturing instrument 900 by ensuring that the shaft 910 is received within the rocker groove proximal portion 1046. For example, where the seat 1022 is defined by the projection 1030, the interference tabs allow the rocker 1041 to rotate sufficiently to enable the projection 1030 to be received within the instrument shaft 910. Where the seat 1022 is positioned adjacent an alignment recess (as discussed earlier with reference to FIG. 9N), the interference tabs allow the rocker 1041 to rotate sufficiently such that the alignment recess and the seat 1022 adjacent to it are both aligned with the needle 930'.

As outlined previously herein with reference to FIG. 14A-14C, some embodiments of the present invention provide a housing sleeve 2011' that is detachably coupled to the base 2020 and remains coupled to the base 2020 to operate as a single unit upon loading of the cartridge 2000 onto the suturing instrument 900. The housing sleeve 2011' remains coupled to the base 2020 until the seat 1022 is aligned with the suture passing member 930 of the suturing instrument 900. The cartridge sleeve 2011' is detachable from the base 2020 thereafter to transfer suture from the base 2020 into the suturing instrument 900. As such, the cartridge housing 2010' defines a suture transferring component 2011.

In some embodiments of the present invention as shown in FIG. 14B, the cartridge base 2020 is detachably coupled to the suture transferring component 2011 of the housing 2010' via an interlock 2050. The interlock 2050 secures the base 2020 to the housing 2010' in its initial position 2050A, and may then be disengaged to move into its second position 2050B (shown later in FIGS. 15D(i), (ii)). Disengagement of the interlock 2050 allows the housing sleeve 2011' that comprises the suture transferring component 2011, to translate independently relative to the base 2020 to transfer the suture end 504 from the seat 1022 into the suture passing member 930 of the suturing instrument 900. FIGS. 15B(i), (ii) and 15C(i),(ii), illustrate the interlock 2050 in its initial locked position 2050A, with an interlock arm 2056 being axially aligned with and being positioned distal to the base 2020, preventing longitudinal movement of the base 2020 with respect to the housing 2010'. The interlock 2050 is moveable to its unlocked position 2050B (as shown in FIGS. 15D(i), (ii)) to disengage the transferring component from the base to enable relative movement there-between upon alignment of the seat with a suture passing member of the suturing instrument. The function of the interlock 2050 is described further herein below with respect to FIGS. 15C(i)-15D(ii). In some embodiments, the interlock 2050 comprises a manual interlock that is moveable into the unlocked position 2050B to manually disengage the suture transferring component 2011 from the base 2020 upon alignment of the seat 1022 with the suture passing member 930.

In some embodiments, the interlock 2050 comprises an automatic interlock (as shown in FIG. 15A(i)), that functions to automatically disengage the suture transferring component 2011 from the base 2020 upon alignment of the seat 1022 with the suture passing member 930. In some such embodiments, the operation of the interlock 2050 is partially automatic wherein the interlock 2050 comprises an interlock tab 2054 (as shown in FIG. 15A(i)), that is automatically disengaged upon alignment of the seat 1022 with the suture passing member 930 to enable the interlock 2050 to be moved manually into its unlocked position 2050B (as shown in FIG. 15E(i)). This enables the base 2020 to be disengaged from the suture transferring component 2011. More specifically, the rocker 1041 comprises a rocker bar 2055 that is moveable upon alignment of the seat 1022 to disengage the interlock tab 2054. This is discussed further herein below with reference to FIGS. 15A(i)-15B(ii).

In some embodiments, as shown in FIG. 15A(i), the suture transferring component 2011 comprises a push rod 2058. In such embodiments, the suture transferring component 2011 is moveable with respect to the base 2020 to enable movement of the base 2020 therein to engage a push rod 2058 to push the suture end 504 held within the seat 1022 to transfer it to the surgical suturing instrument 900. In some such embodiments, the push rod 2058 comprises a push rod hub 2057 that is configured to translate within push rod cavity 2057'. In some such embodiments, the suture transferring component 2011 comprises a sleeve push hub 2012 (which can also be referred to as a push sleeve hub) to push the push rod hub 2057 once in engagement therewith. In some embodiments, the sleeve push hub 2012 is moveable within a sleeve cavity 2012' and is biased towards the base 2020. In one specific example, the sleeve push hub 2012 is biased via a spring mechanism. In a specific instance of this example, the spring mechanism comprises two springs 2013. The sleeve push hub 2012 is configured to push the push rod hub 2057 upon translation of the suture transferring component 2011 with respect to the base 2020. As such, the suture transferring component 2011 comprises a hub, such as sleeve push hub 2012 that is biased towards the base 2020 to push the push rod 2058 upon engagement with the push rod 2058 upon translation of the base 2020 within the housing sleeve 2011'. In one example, the sleeve push hub 2012 is biased via a spring mechanism.

In one specific example, the push rod 2058 comprises a longitudinally extending wire 2053' coupled to the push rod hub 2057 that is translatable within a wire channel 2053 in communication with the seat 1022. The wire channel 2053 is configured for receiving the wire 2053' therein to push the suture end 504 held within the seat 1022 into a suture receiving passage 932 of the suturing instrument 900. As such, the cartridge 2000 comprises a suture transferring component 2011 that defines a push mechanism as described herein above. The push mechanism is defined as the mechanism of the cartridge that enables a pushing force to be applied to the suture portion, such as the suture end, to transfer the suture portion from the seat into the suturing instrument. In one such example the push mechanism comprises a push rod 2058 as described above.

In some embodiments, the cartridge 200 is configured to align and transfer the suture end 504 upon a single linear movement of the cartridge 2000 with respect to the suturing instrument 900. As outlined above, in some such embodiments surgical suturing instrument 900 comprises a suture passing member 930 defining a suture receiving passage 932 wherein the suture transferring component 2011 is operable to transfer an end of the suture 500 from the seat 1022 within the base 2020 into the suture receiving passage 932 of the suturing instrument 900.

Figure 17A:
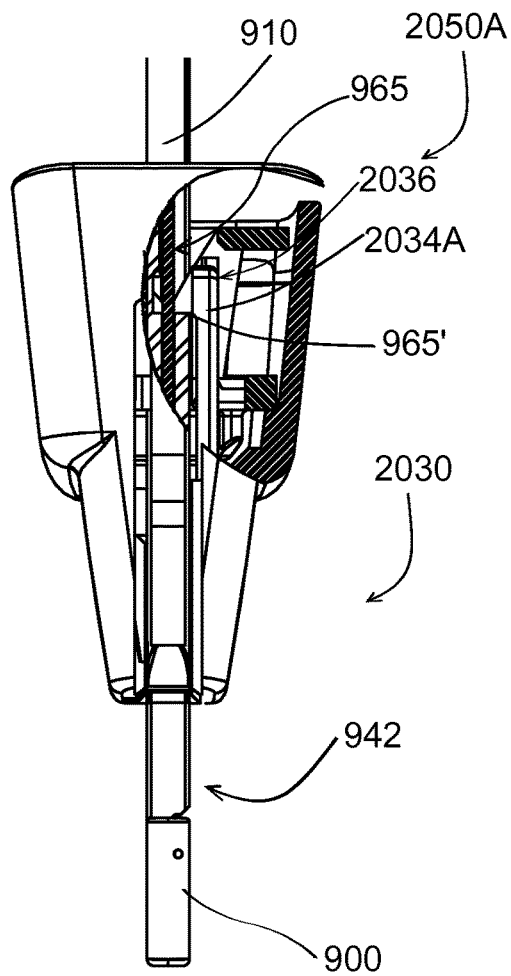
FIGS. 17A-17D illustrate views of a knot slider of a cartridge and a method of using the same in accordance with an alternate embodiment of the present invention.
Figure 17B:
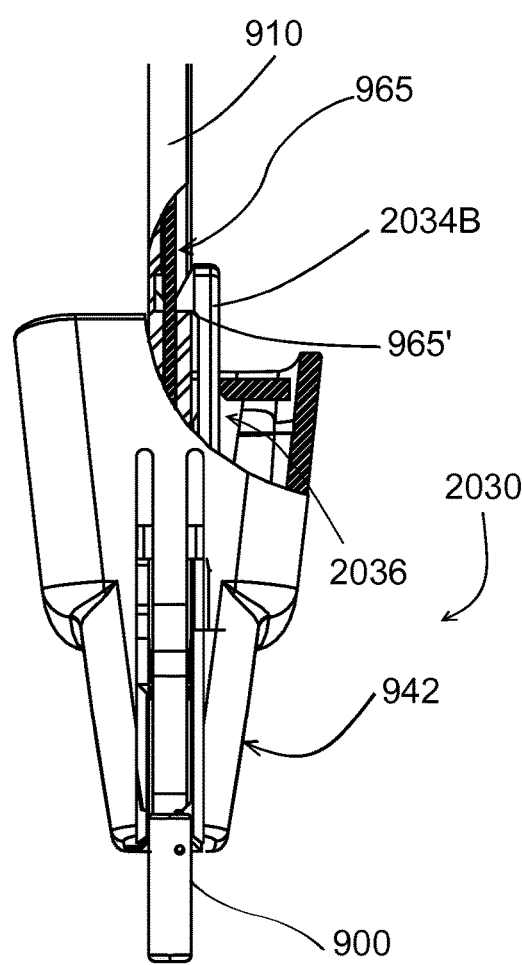
Figure 17C:
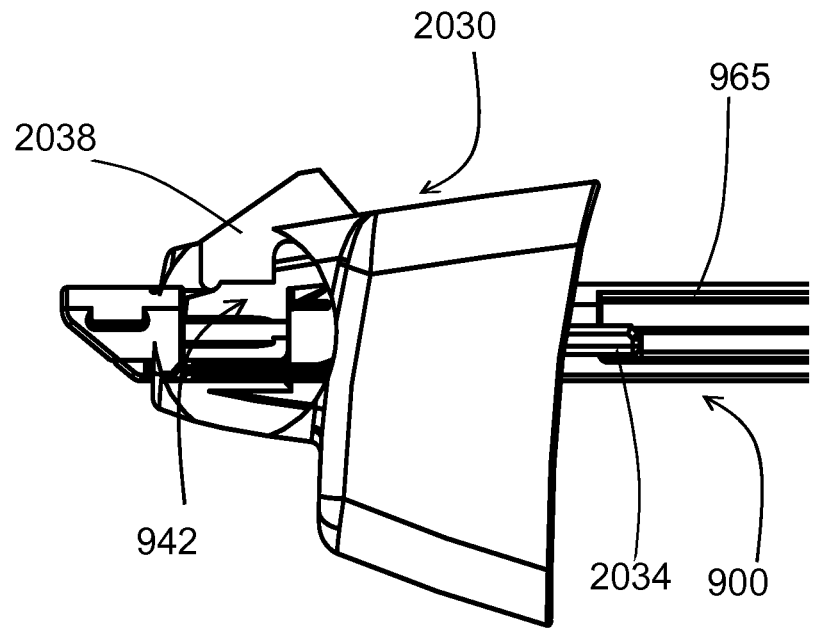

In some embodiments of the present invention as shown in FIG. 14C, the knot slider 2030 is coupled to the suturing instrument 900. In one such example, the knot slider 2030 is configured to be slidably engaged with a portion of the surgical suturing instrument to allow the knot slider 2030 to be mounted thereon. In one particular example, the knot slider 2030 is engageable in sliding contact with a portion of the suturing instrument 900 for positioning the knot slider 2030 along the suturing instrument to facilitate deployment of the pre-tied knot 502 from the knot slider 2030. In one specific example, the knot slider 2030 is engageable in sliding contact with the suturing instrument via an arm 2034 that is receivable within an opening/window or groove 965 (as shown in FIG. 17C) along the side of the instrument proximal portion 910. The knot slider arm 2034 enables positioning of the suturing instrument along the tissue receiving gap 942 to facilitate deployment of the pre-tied knot from the suturing instrument 900 during use. Furthermore, in some embodiments, the knot slider arm 2034 is housed within a slider groove 2036 and comprises an inner position 2034A where it is housed within the slider groove 2036 (as shown in FIG. 14D, FIG. 17A)]. The knot slider arm 2034 additionally and an outer position 2034B where it extends proximally (at least partially) from the slider groove 2036 (as shown in FIG. 17B) to allow the knot slider 2030 to be positioned over the tissue receiving gap 942.

Figure 17D:
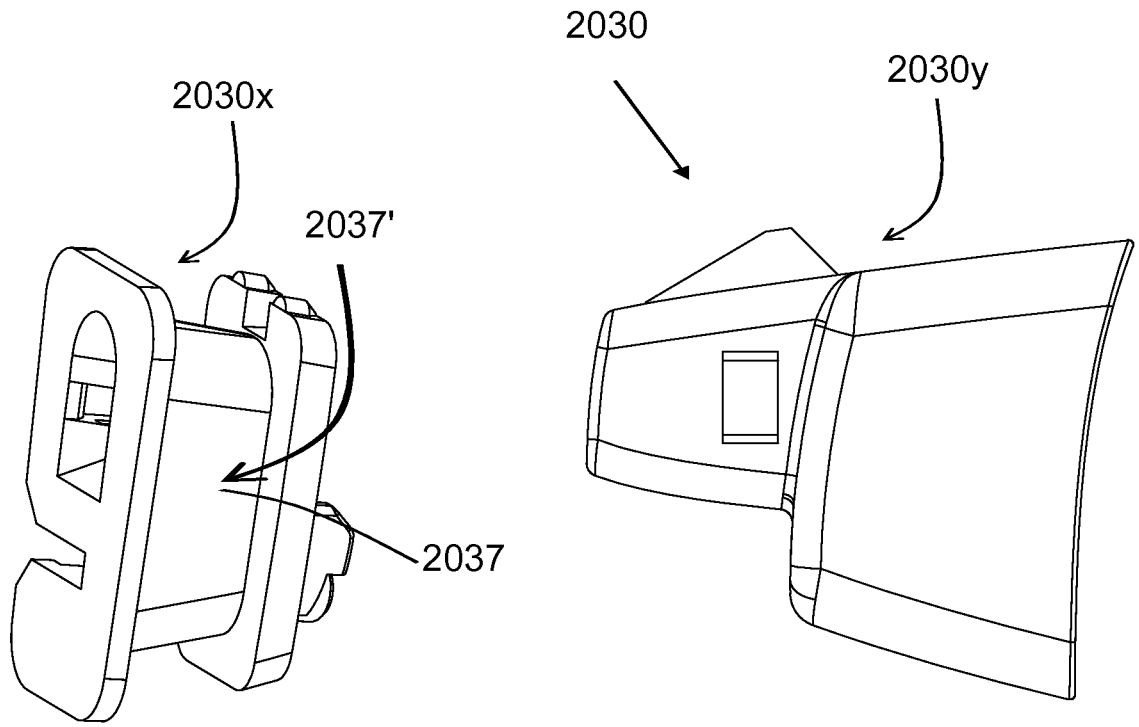

In some embodiments, the suture is contained within tubing mounted on the inside the knot slider 2030. The cartridge 2000 stores the suture limbs within the knot slider 2030, for example, inside a PTFE tube that may be coiled and mounted about an internal post 2037 of an internal knot slider 2030x that defining a passage 2037' about it once it is press fit inside the external knot slider 2030y, as shown in FIG. 17D. The PTFE tube allows the suture to be released with a small, constant force. In some embodiments, a silicone O-ring provides a dampening effect on the release of the suture to achieve a smoother, more constant release force and to retain tautness in the suture throughout the procedure.

In some embodiments with reference now to example 10 as shown and described in FIGS. 14A-17D, the movement of the suturing instrument 900 may be a relative movement with respect to the cartridge 2000. This may also be the case in some embodiments described previously herein above in example 9. In other words, the user may move the cartridge 2000 axially over the suturing instrument 900 in a proximal direction while the suturing instrument is held by the user in order to create a relative advancement of the suturing instrument 900 with respect to the cartridge 2000 in order to load the suture onto the suturing instrument 900. This action may be referred to as loading of suture using pumping action. As such, the mechanism of loading of the suture may remain as described above, but the movement may be created either by the proximal movement of the cartridge over the suturing instrument or the distal movement of the suturing instrument within the cartridge.

In some embodiments of the present invention as described herein, the cartridge is configured to align and transfer the suture upon a single linear motion of the cartridge with respect to the suturing instrument. In some such embodiments, an interlock 2050 may be automatically disengaged upon alignment of the suture end within the seat with the suture passing member. Disengagement of the interlock 2050 enables automatic transfer of the suture end 504 into the suture passing member (due to advancement of the base and activation/engagement of the push rod) as the housing 1010' is continued to be pulled proximally. Additionally, the cartridge enables a pre-tied knot be mounted onto the suturing instrument during the same linear movement of the cartridge. The mechanism provided may be similar to the mechanism described herein above with respect to the knot slider 2030. Thus, embodiments of the present invention may comprise a cartridge that is operable to transfer a suture portion, such as the suture end 504, from the seat 1022 into the suture passing member 930, which allows the suturing instrument to pass the suture in order to suture therewith. The cartridge additionally enables a pre-tied knot to be mounted onto the suturing instrument. In some such embodiments, the cartridge is loaded onto the suturing instrument 900 with a single linear movement. In some such embodiments a single pumping action is used involving a single linear relative movement of the cartridge onto the suturing instrument (to transfer the suture end mount the pre-tied knot) and linear movement the cartridge 2000 (in a direction opposite to the loading direction) thereafter leaving the knot slider 2030 coupled to the suturing instrument 900 for example to mount a pre-tied knot held therein onto the suturing instrument. As such the remainder of the cartridge 2000 other than the knot slider 2030 is removed.

Thus, as outlined herein above with reference to FIGS. 9 and 10, in accordance with some embodiments of the present invention, a mechanism is provided for providing both alignment and insertion that may facilitate ease of use by reducing the number of user steps required, and the requirements for user dexterity and concentration. In some embodiments, the mechanism additionally facilitates use by providing only one possible order of performing the user steps.

In order to load suture into a surgical suturing instrument or suture passer, in accordance with some embodiments of the present invention as outlined herein below in Examples 9 and 10, two events or functions are required to take place: (1) alignment of the suture portion held within the cartridge with a suture receiving feature within the surgical suturing instrument or the suture passer, and (2) insertion of the suture portion into the suture receiving feature within the suturing instrument or suture passer.

In some embodiments of the present invention, a cartridge configuration is provided that is fully automated—requiring a single "pump-action" user step while completing all mechanical events to load the suture into the suturing instrument. In one such example, a user step to actuate the suture passer trigger to load the suture may not be required.

In addition, the suture cartridge device includes a pre-tied knot and integrated features to store the suture limbs, which may reduce the required user attention to manage the suture and may help eliminate the complex knot-tying step required by existing devices. In some such embodiments, a cartridge configuration is provided that contains a detachable knot slider containing a pre-tied knot and storage of the suture.

In some embodiments, the cartridge has a side slot for securing the suture out of the way of the suture passer shaft when it is inserted into the cartridge.

In some such embodiments, the cartridge may be constructed of Medical Grade plastic/metal components such as ABS for the cartridge base, seat, suture lock, interlocks and other mechanical components. In some embodiments, stainless steel may be utilized for the seat, silicone in O-rings for holding the suture. In some embodiments the suture contained in the cartridge may comprise polyethylene.

Furthermore, embodiments of the present invention as outlined herein allow the suture end to be positioned or constrained in the following degrees for alignment to occur in order to allow the suture to be loaded onto the suturing instrument. The suture portion is positioned such that its position is maintained along the X-axis (lateral direction), Y-axis (vertical or up and down directions), Z-axis (linear or longitudinal direction) as well along the Y-rotational axis and the Z-rotational axis. Further details of the alignment mechanism are provided herein below.

In some embodiments of the present invention, in order to align the suture with a suture receiving feature of the suture passer (such as a suture receiving passage within suture passing member) a magazine defining a seat is provided that is operable to be mechanically interlocked with the suture passer such that when the suture cartridge is inserted over the suture passer and pressed, the magazine and thus the seat is configured to rotate down, aligning the suture portion within the seat with the suture passer. In some such embodiments, the magazine defining the seat, grabs onto the suture passer to align the suture portion in the X-axis and Y-axis, and constrain X-rotation and Y-rotation of the suture. Furthermore, the seat mates with and is pushed up to the suture passer to align the suture in the Z-axis.

In some embodiments, as outlined in examples 9 and 10, the magazine comprises a feature to hold/lock the suture to the side and align it with the suture slot in the suture passer shaft. In some embodiments as outlined above in examples 9 and 10, a cartridge base interlock is provided in the form of a button that the user presses to allow the cartridge base to move. Furthermore, some embodiments provide a suture lock using which the suture is manually unlocked by the user at a specified time In some embodiments as described herein above with reference to examples 9 and 10, embodiments of the present invention provide an alignment mechanism that comprises a magazine defining a seat that automatically pivots into place from the top to align the suture with the suture passer. The magazine is mechanically interlocked with the suture passer such that when the cartridge containing the magazine that defines the seat, is inserted onto the suture passer, the geometry of the suture passer presses a bevel on the magazine and causes the magazine, and thus the seat defined thereby, to pivot into place. In one such example, the seat is a part of a rocker as outlined in further detail herein above as discussed in examples 9 and 10.

In some embodiments, aligning of the seat using a pivoting rocker is beneficial when the suture passer has complex features around the site where the suture is loaded, which may limit the alignment of the seat to be purely linear. As well, the rocker is beneficial when an automatic mechanism is desired, that does not require user interaction to align the seat). This is because it may generally be easier to move a pivoting part through a desired displacement on an arc, than a sliding part through a desired displacement along an axis, (this is due to reduced friction/binding and increased mechanical advantaged gained in a pivoting system.

In some embodiments, the seat is configured such that it is defined by a tubular member (seat defining member or projection) that extends out from the body of the magazine, such as the rocker, and is receivable into the hole on the suture passer and up against the feature in the suture passer (such as the suture passing member such as the needle) into which the suture is loaded. The projection that extends into the hole in the suture passer has an interference fit with the inner walls of the hole to align the seat/suture within a repeatable tolerance zone relative to the feature on the suture passer that receives the suture. Having this interference fit may reduce the tolerance stack-up of misalignment.

In some embodiments the magazine is configured such that the magazine, and thus the seat defined thereby, aligns perfectly with the corresponding features on the suture passer such that the mechanism cannot possibly ever jam because the geometry does not allow that to happen.

In some embodiments, the magazine is configured such that it has an interference fit with reference features on the suture passer to positively align the seat defining member or projection within a repeatable tolerance zone relative to the hole that contains the suture passing member, such as the needle on the suture passer. Having this interference fit may reduce the tolerance stack-up of misalignment.

Furthermore, as described herein above, in some embodiments of the present invention, an alternative seat is provided, the seat containing a cavity that has an interference fit with the outer diameter of the needle and the needle is configured to come out of the hole in the suture passer to mate with this cavity in the cartridge. This may provide an alternative to a mechanism that requires a member (such as a projection defining the seat) to extend into the hole defined by the suture passer (or suturing instrument) shaft and up to the needle that is in the hole. As described previously, the needle is then held in the "out" position during shipping with a lock such as cam lock that hooks the needle, or a trigger lock that holds the trigger slightly depressed. In a manual version, the user is required to press the trigger to cause the needle to move out and into the seat cavity before the suture is pulled. In some such embodiments, having the "Needle-out" configuration may have a reduced tolerance stack-up of misalignment compared to the "Needle-In" configuration.

Alternatives

In alternative embodiments of the present invention, as described herein below in further detail, as an alternative to a top pivoting magazine (and as such a top pivoting seat), some embodiments of the present invention may provide a seat that pivots from the side. Alternatively, a seat may be provided that slides from the side(s) or from the top. Furthermore, instead of an automatic alignment seat, a magazine may be provided that is pushed into place by the user at a specified time to push the seat into place. Furthermore, as an alternative in some embodiments where the magazine comprises a rocker as described above, a button may be provided that the user may press to enable the rocker to rotate.

In some embodiments of the present invention, the alignment feature comprises a moveable seat as outlined above. In some such embodiments, the seat is moveable relative to the base. In other embodiments, the seat is moveable relative to the chamber defined by the housing of the cartridge. In such embodiments, the seat may be automatically moveable (upon advancement of the suturing instrument within the cartridge).

Figure 18A:
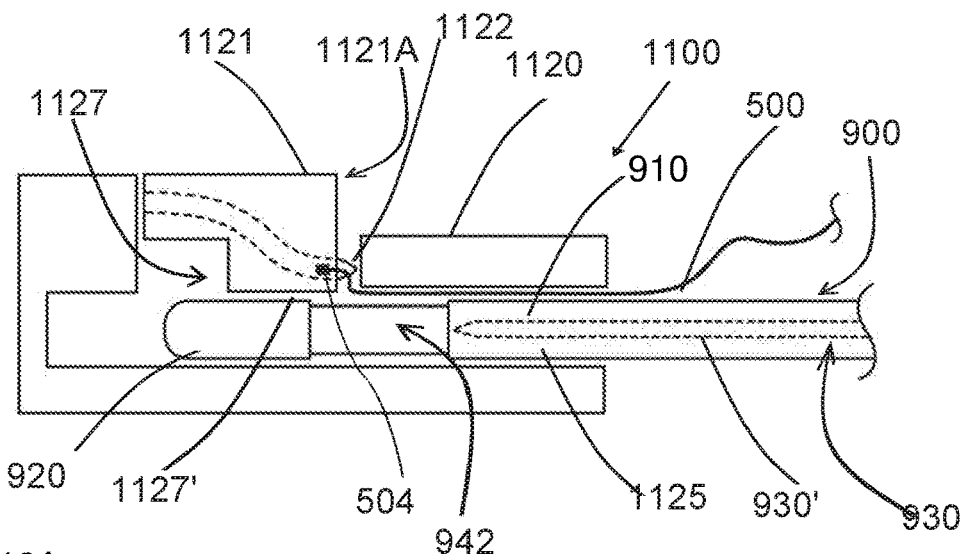
FIGS. 18A-18C illustrate an alignment mechanism of a cartridge and a method of using the same in accordance with an alternate embodiment of the present invention.
Figure 18B:
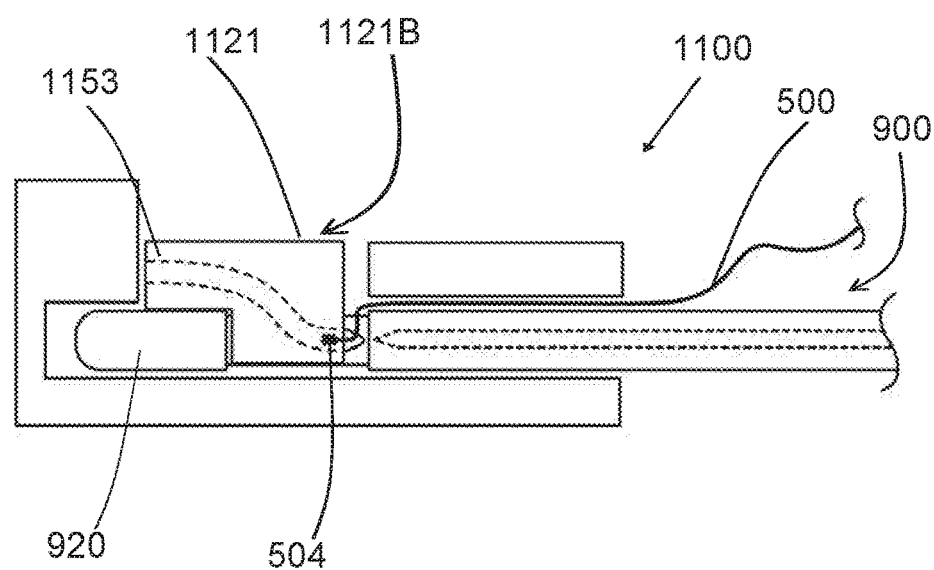
Figure 18C:
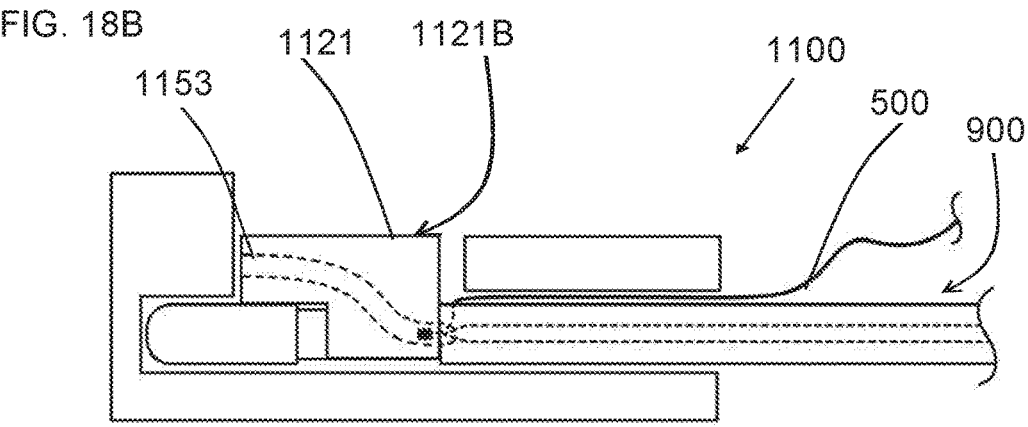
Figure 19A:
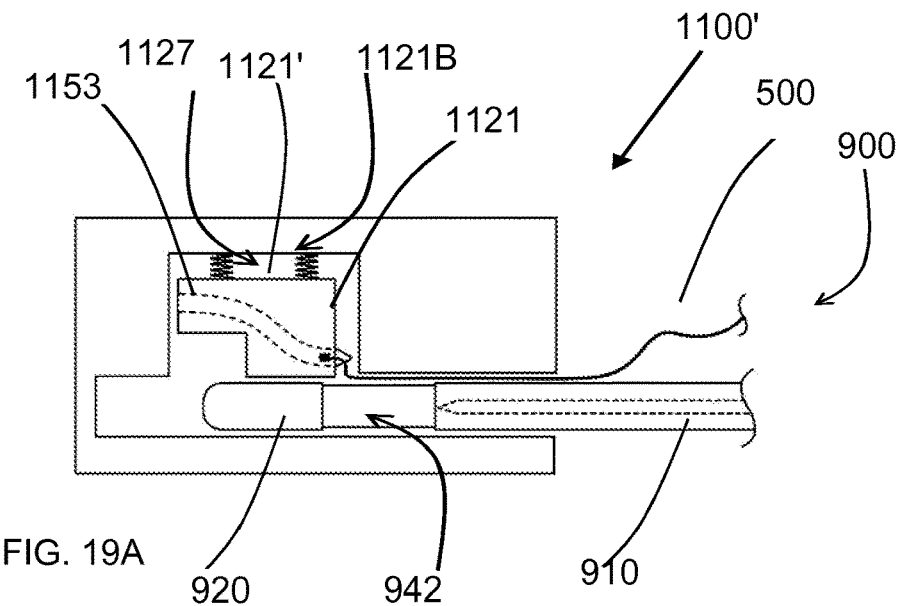
FIGS. 19A-19C illustrate an alignment mechanism of a cartridge and a method of using the same in accordance with an alternate embodiment of the present invention.
Figure 19B:
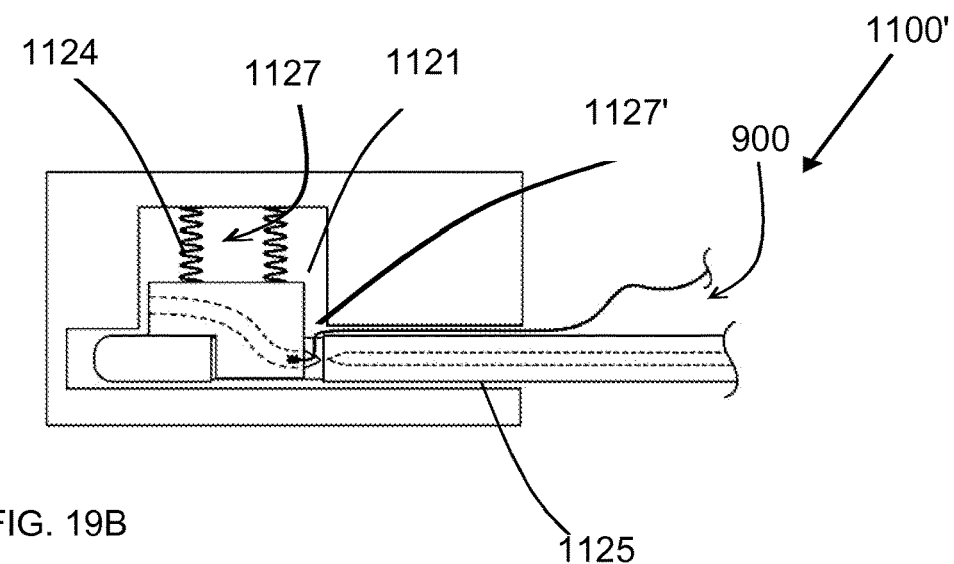
Figure 19C:
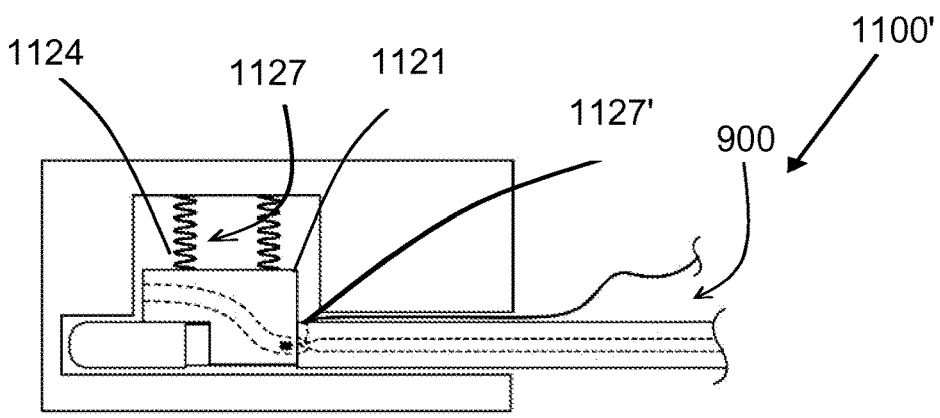

In some embodiments of the present invention, alternate alignment features may be provided. In some such embodiments, as shown in FIGS. 18A, 19A a side load mechanism 1100 is provided that for example that may be usable in examples 9 and 10 described herein above. The side load mechanism 1100 comprises a base 1120 comprising a magazine 1121 that is moveable within a magazine recess 1127. The magazine recess 1127 comprises a recess cavity 1127' that is configured to be aligned with tissue receiving recess 942 upon advancement of the suturing instrument 900. The magazine defines a seat 1122 for holding a suture end 504 of the suturing instrument 900. The magazine 1121 has a first position 1221A that is out of the way of a path of the advancing suturing instrument 900 along a base recess 1025 that functions to restrain the suturing instrument 900. As shown in FIGS. 18B and 19B, once the suturing instrument 900 is advanced distally such that the tissue receiving recess is aligned with the magazine cavity 1127', the magazine 1121 can be moveable sideways or laterally into its second position 1121A to align the seat 1122 and thus the suture passing member 930 such as needle 930' of the suturing instrument 900. As shown in FIGS. 18C and 19C the suturing instrument 900 can be advanced further with respect to the base 1120 such that the seat 1122 is in abutting contact with the needle 930'. In some such embodiments, the mechanism of loading suture using the cartridge comprises pulling the cartridge proximally over and along a portion of the suturing instrument 900.

In some embodiments as illustrated in FIGS. 18A-18C, the magazine 1121 is moveable manually into the magazine cavity 1127'. In other embodiments as illustrated in FIGS. 19A-19C, the side load alignment mechanism 1100' comprises a magazine 1121 that is automatically moveable into the magazine cavity 1127'. The magazine 1121 is biased towards the magazine cavity 1127' via a biasing mechanism 1121'. In one particular example, biasing mechanism 1121' comprises a spring biased mechanism 1124. In some examples, the spring biased mechanism may comprise two springs as shown. In some such embodiments, as illustrated in FIG. 19B, the magazine 1121 is automatically moveable into the magazine cavity 1127' upon advancement of the suturing instrument 900 within the cartridge.

In some such embodiments, the biasing mechanism 1121' allows the magazine 1121 to be configured such that it is moveable away from the magazine cavity 1127' upon advancement of the instrument distal portion 920 therethrough. Once the distal portion 920 has advanced past the magazine cavity 1127', the magazine 1121 is moveable into the magazine cavity 1127' upon movement of the tissue receiving gap 942 therein to allow alignment of the seat 1122 with instrument proximal portion 910.

Figure 21A:
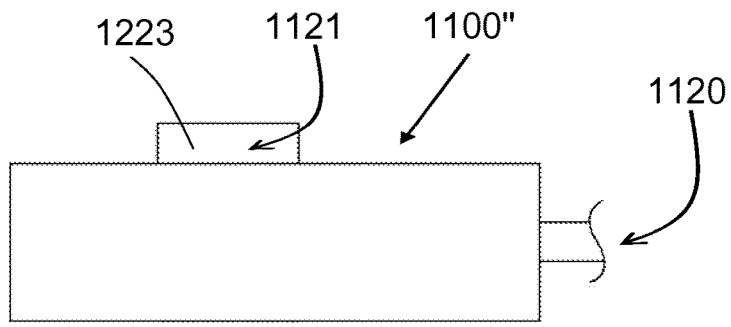
FIGS. 21A-21F illustrate an alignment mechanism of a cartridge and a method of using the same in accordance with an alternate embodiment of the present invention.
Figure 21B:
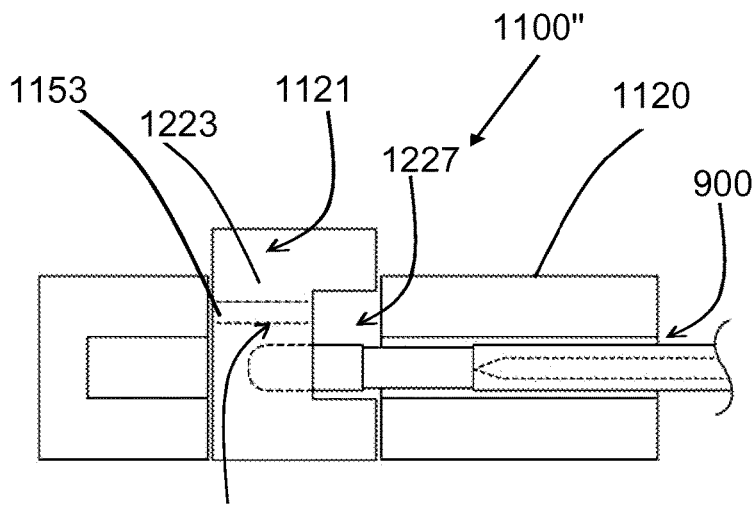
Figure 21C:
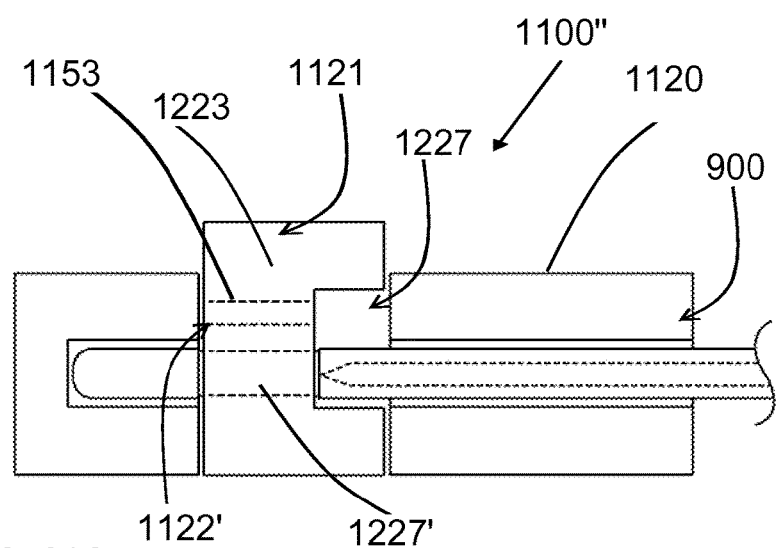
Figure 21D:
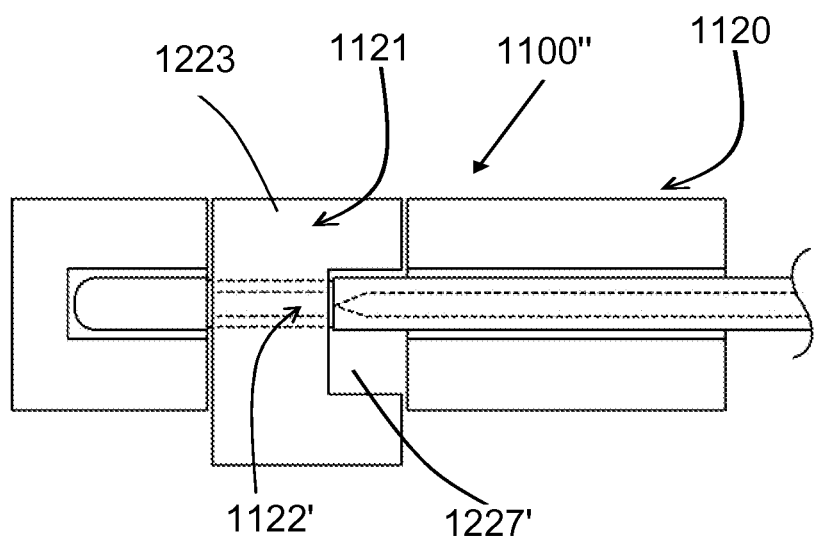
Figure 21E:
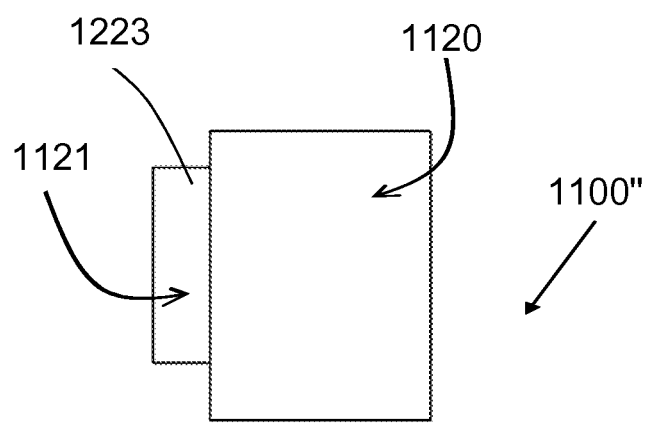
Figure 21F:
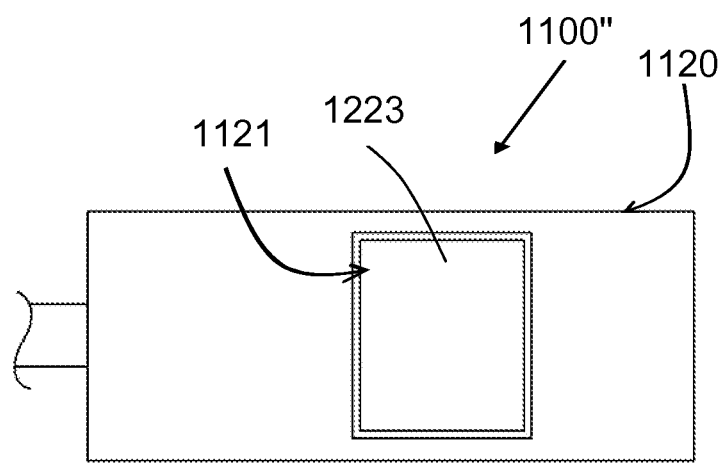

A further example of a side load alignment mechanism 1100" is shown in FIGS. 21A-21F. The magazine 1121 defines a button 1123 shown in its initial position 1121A (FIG. 21A, 21E) comprising a side loading sliding seat 1122' (as shown in FIG. 21B). The base 1120 defines a magazine recess 1227 defining a magazine cavity 1227', and the magazine 1121 is moveable within the magazine recess. Initially, the instrument is advanceable into the base recess 1025 that functions as a restraint to maintain the position of the suturing instrument 900 as it is advanced distally within the base 1120. Upon loading of the cartridge onto the suturing instrument, the magazine cavity 1227' corresponds to the tissue receiving gap 942, as shown in FIG. 21C. In other words, once the suturing instrument 900 is advanced within the base 1120, the tissue receiving gap 942 of the suturing instrument 900 is positioned within the magazine cavity 1227'. The magazine 1121 is then moveable sideways into the magazine cavity 1227' to align the seat 1122' with respect to the suturing instrument 900. FIG. 21E illustrates a side view of the base 1120 with the button in its depressed or second position 1121A.

Figure 20A:
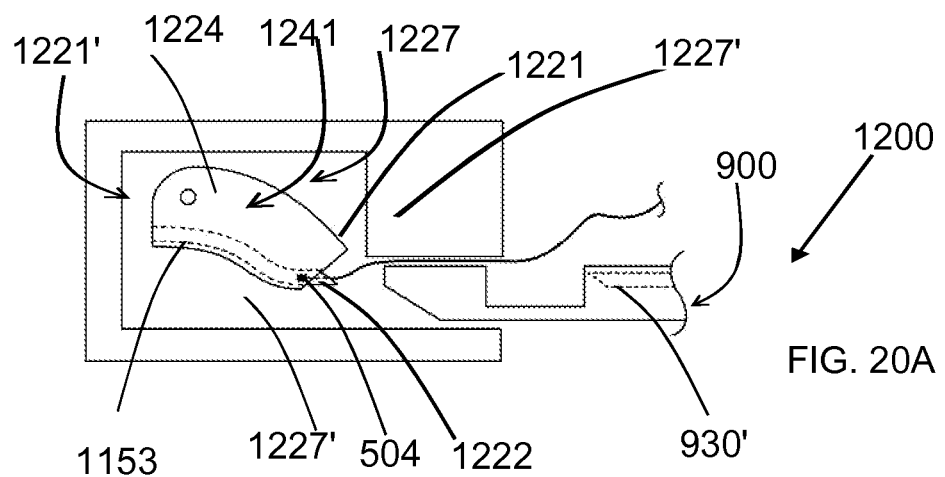
FIGS. 20A-20D illustrate an alignment mechanism of a cartridge and a method of using the same in accordance with an alternate embodiment of the present invention.
Figure 20B:
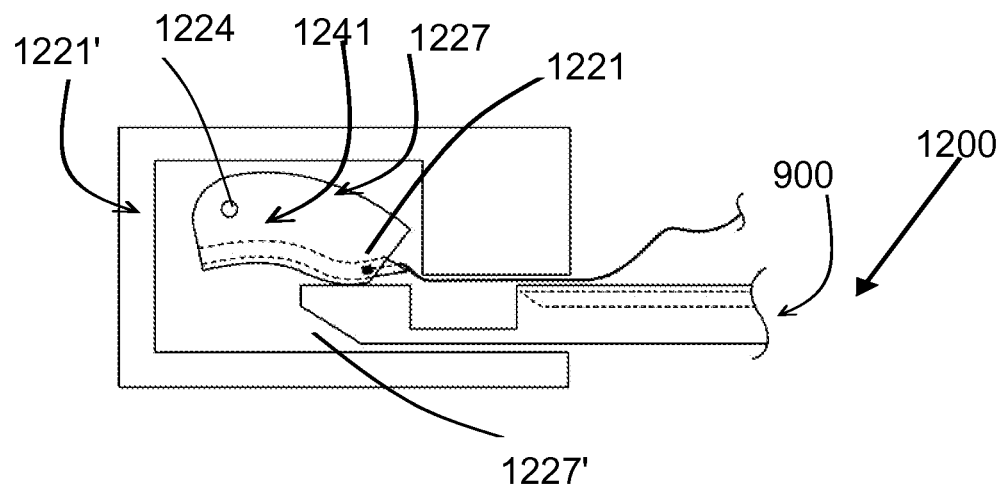
Figure 20C:
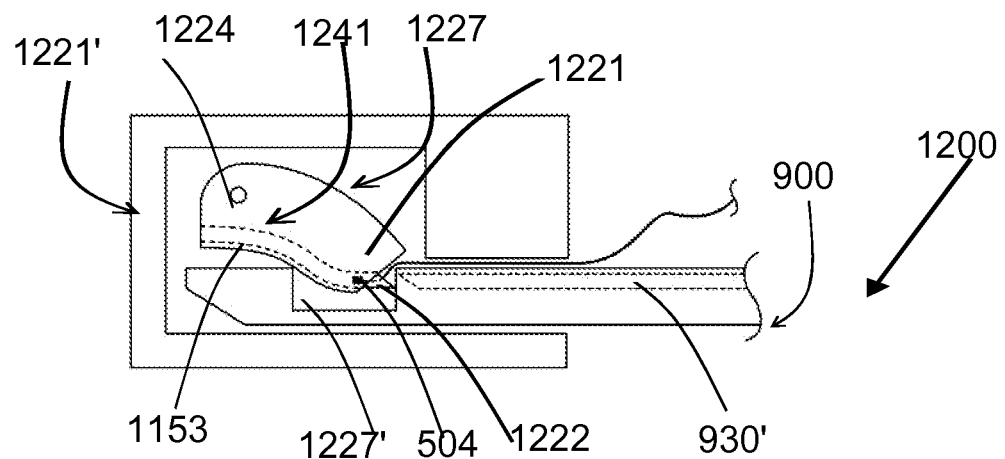
Figure 20D:
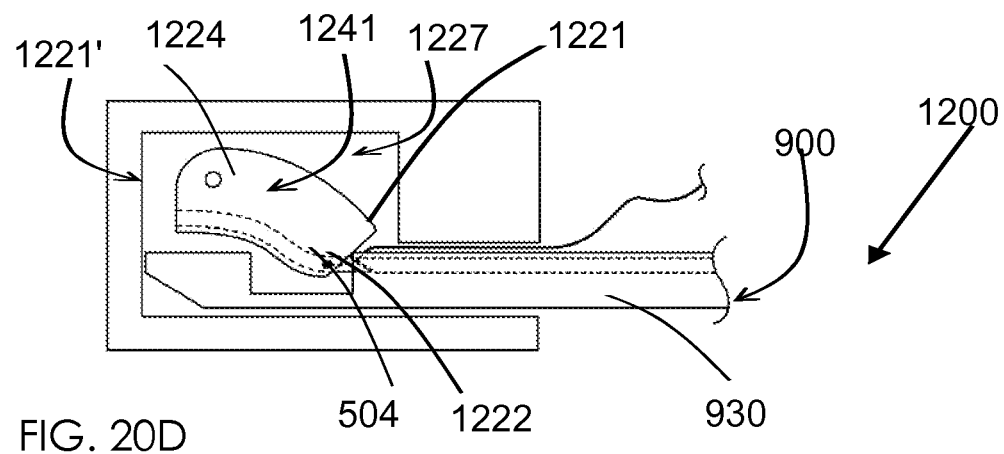

In additional embodiments, the loading mechanism may comprise a top load mechanism 1200'. In some such embodiments, the magazine is biased towards the cavity via a biasing mechanism. In some such embodiments, similar to examples 9, 10 discussed previously herein, the biasing mechanism 1221' comprises a pivoting mechanism 1224, as shown in FIGS. 20A-20D. In the particular example shown in FIG. 20A, the cartridge comprises a base 1220 with a magazine 1221 comprising a rocker 1241 that is coupled to the base 1220 via a pivotal connection and is housed within a magazine recess 1227. In some such embodiments, similar to the automatic side-load mechanism, the pivot-based biasing mechanism 1221' allows the magazine 1221 to be configured such that it is moveable away from the magazine cavity 1227' (as shown in FIG. 20B) to allow advancement of the instrument distal portion 920 there-through. The magazine 1221 is then moveable into the magazine cavity 1227' upon movement of the tissue receiving gap 942 therein (as shown in FIG. 20C) to allow alignment of the seat 1222 with instrument proximal portion 910. In other words, the rocker 1241 is configured to pivot up and out of the way of the suturing instrument 900 as the distal portion 920 of the suturing instrument 900 is advanced into the base 1220 of the cartridge, and is configured to pivot downwards into the tissue receiving gap 942 as the suturing instrument 900 (and thus the suture passing member 930 therein) is advanced further.

As such, the magazine 1221 is moveable transversally or downwards into the cavity, as shown in FIG. 20C. Furthermore, as illustrated in FIGS. 20A-20D, the magazine 1221 is automatically moveable into the magazine cavity 1227' to align the seat 1222, and thus the suture end 504 held therein, with the suturing instrument 900. The instrument 900 may be advanced further with respect to the base 1220 to dock the suture passing member 930 with the seat 1022 to facilitate transfer of the suture end 504 from the seat into a suture receiving passage of the suturing instrument.

Figure 22A:
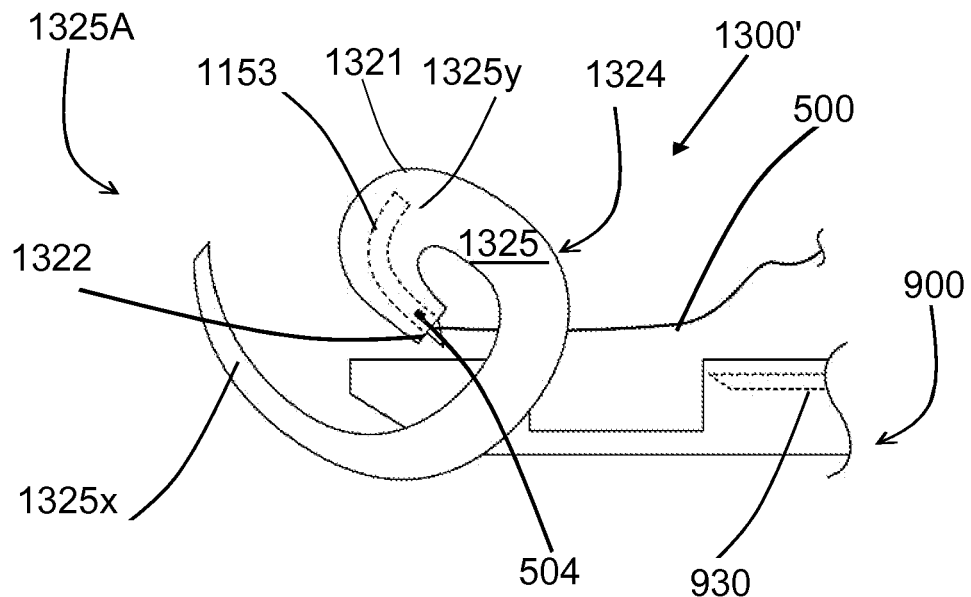
FIGS. 22A-22C illustrate an alignment mechanism of a cartridge and a method of using the same in accordance with an alternate embodiment of the present invention.
Figure 22B:
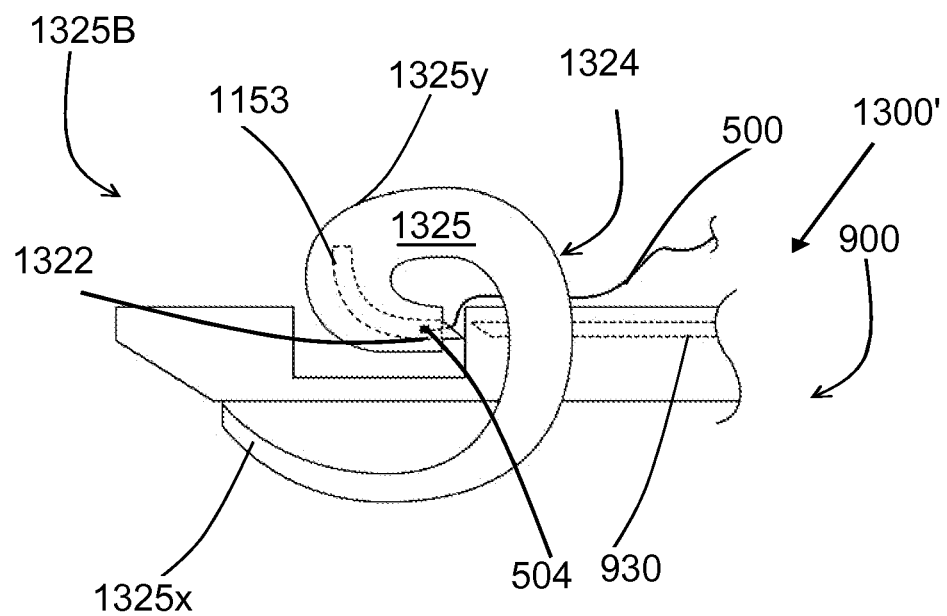
Figure 22C:
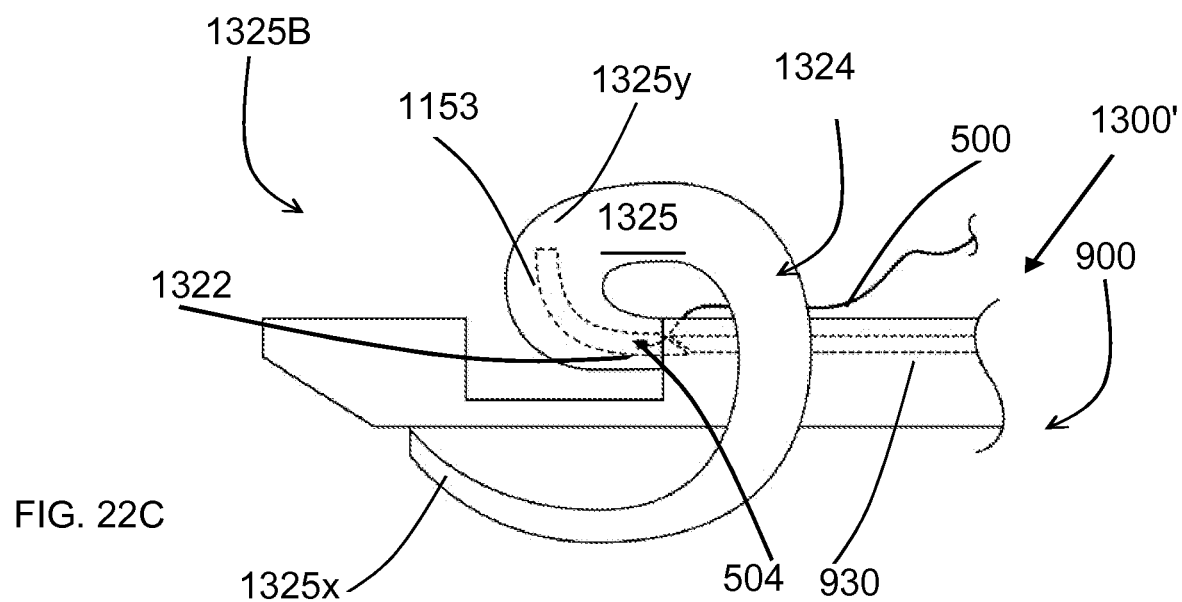

In an additional embodiment of the present invention, as shown in FIGS. 22A-22C, a top load mechanism 1300' is provided. More specifically, a magazine 1321 is provided that is biased via biasing mechanism 1321' that also comprises a pivoting mechanism. In one such example as shown in FIG. 22A, the magazine 1321 comprises a spiral configuration 1324 that is automatically moveable to align a seat 1322 with the suturing instrument 900. In the specific example shown in FIGS. 22A-22C, comprising a spiral 1325, the spiral 1325 defines a spiral first portion 1325$x$ and a spiral second portion 1325$y$ that defines a seat 1322. The spiral 1325 has a first configuration 1325A (as shown in FIG. 22A) and a second configuration 1325B (as shown in FIG. 22B). As shown in FIGS. 22B and 22C, the suturing instrument 900 is advanceable to engage the first portion 1325$x$ to pivot the spiral 1325 from its first position 1325A to its second position 1325B to align the seat 1322, and thus the suture end 504 of the suture 500 held therein, with a suture passing member 930 of the suturing instrument 900.

Figure 23A:
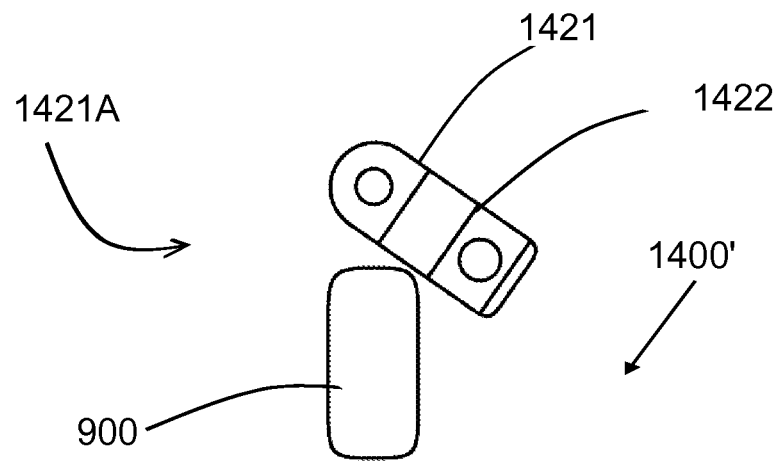
FIGS. 23A-23C illustrate an alignment mechanism of a cartridge and a method of using the same in accordance with an alternate embodiment of the present invention.
Figure 23B:
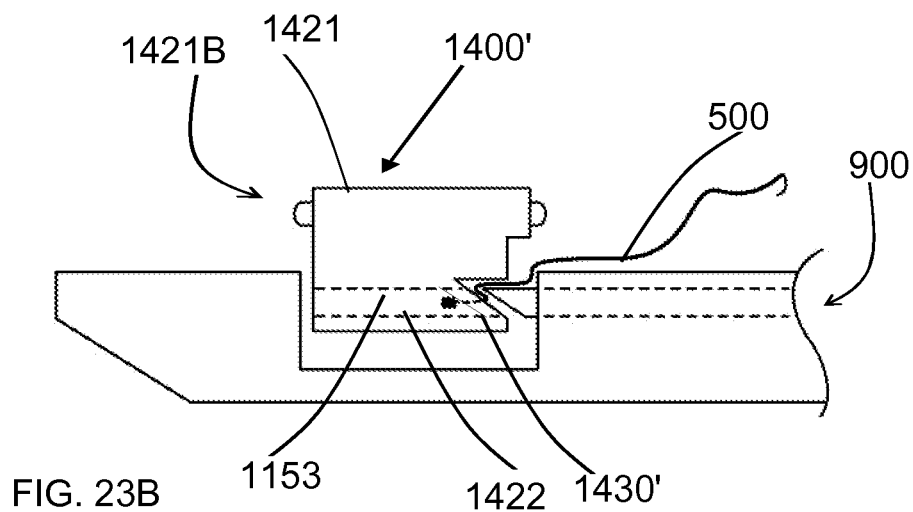

In some embodiments of the present invention, similar to embodiments described previously herein above with reference to FIGS. 9L and 9N, a cartridge is provided that comprises a magazine 1421 defining a seat 1422 (that comprises a seat recess or seat channel) for holding the suture end 504 of the suture 500 therein, and an alignment recess 1430' that is located adjacent the seat 1422. The alignment recess 1430' is configured for receiving the suture passing member 930, such as needle 930', in its needle-out configuration (where it is configured to be in a partially extended position, i.e. it extends partially distally from the shaft 910 of the suturing instrument 900 during loading to align the seat 1422 with the suture passing member 930 received within the alignment recess 1430' (as shown in FIG. 23B).

Figure 23C:
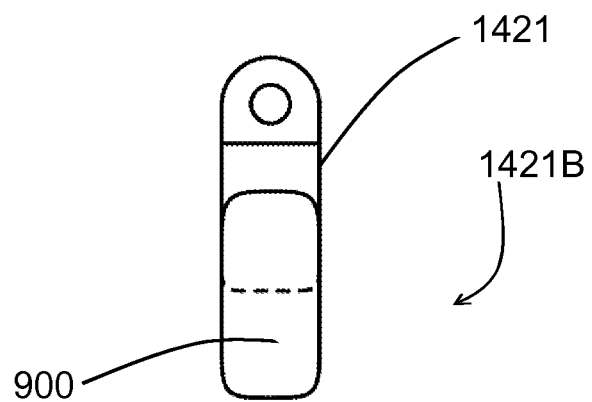

In one such embodiment, the cartridge comprises a side loading mechanism 1400' as shown. More specifically, as shown in FIGS. 23A-23C the side loading mechanism comprises a pivotal configuration 1421' as shown, where the magazine pivots sideways from a first configuration 1421A (shown in FIG. 23A) to a second configuration 1421B (shown in FIG. 23B) to receive the suture passing member 930 within the alignment recess 1430' to align the seat 1422 with the suture passing member 930. In one such embodiment, the suture passing member may be a needle 930' while it is in its partially extended position, as shown in FIG. 23B). In one example, the cartridge may be pulled further to dock the needle 930' with the seat 1422 to enable transfer of the suture end 504 into the suture receiving passage 932 of the suture passing member 930 (FIG. 23C). In one example, the pivotal configuration 1421' may comprise a molded spring that provides torsion. In other embodiments, other spring biased means may be used, such as torsion spring. Additionally, the seat may comprise a bevel to enable auto ejection. In other words, the seat comprises a bevel that enables the magazine 1421 to pivot out to the side as the instrument 900 is being removed from the cartridge 1000. This pivotal movement is caused by a proximal wall of the distal end 920 of the suturing instrument interacting with the bevel. In one such embodiment, a bevel is provided on a one side of the magazine to cause the rocker to pivot out. As such, the magazine 1421 facilitates retraction of the suturing instrument 900 from the cartridge.

Figure 24A:
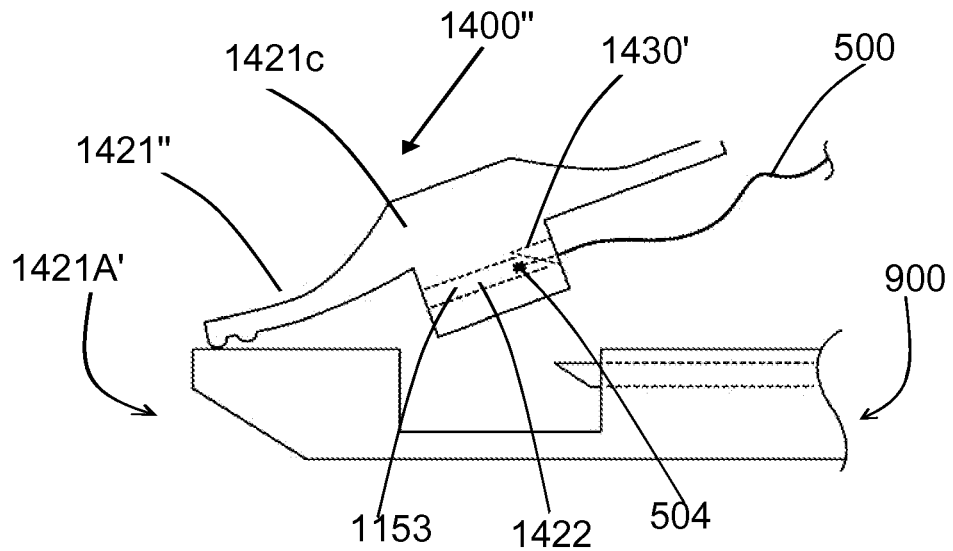
FIGS. 24A-24C illustrate an alignment mechanism of a cartridge and a method of using the same in accordance with an alternate embodiment of the present invention.
Figure 24B:
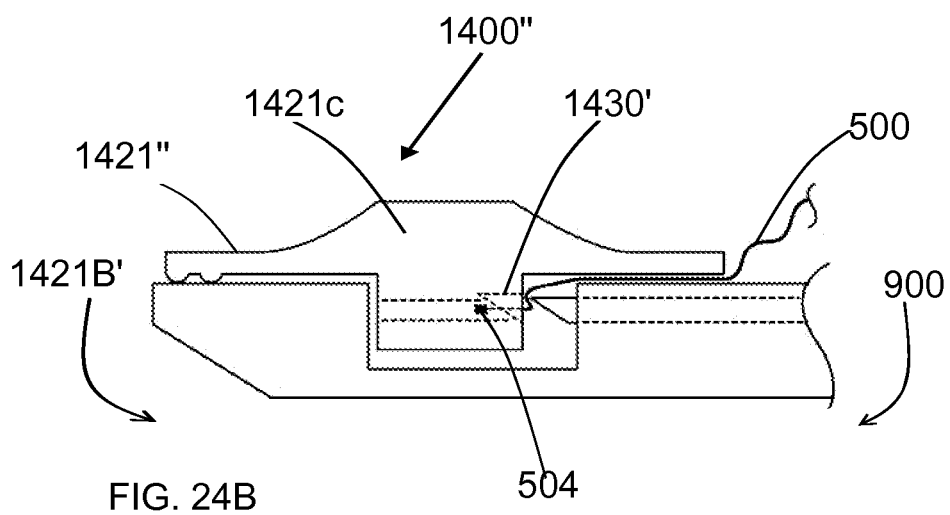
Figure 24C:
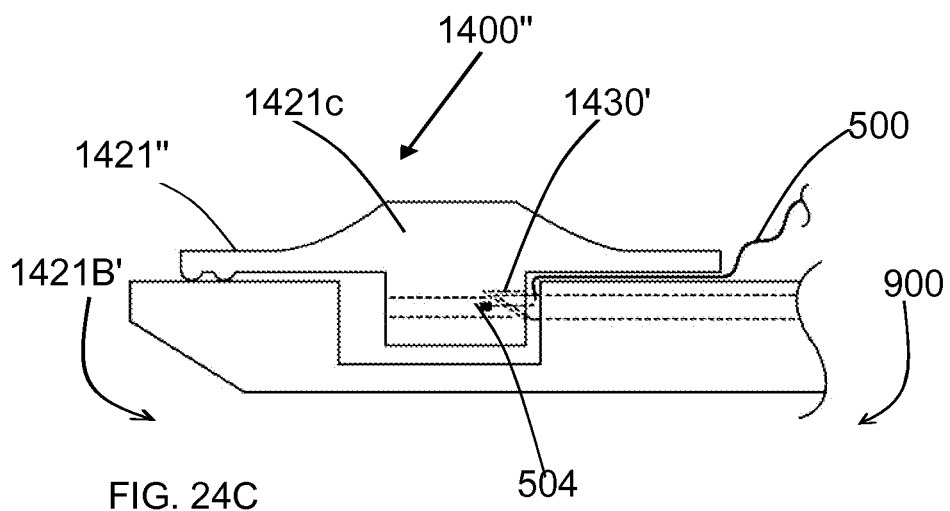

Alternatively, in one such embodiment a top-loading mechanism or configuration 1400" is provided that comprises a pivotal configuration 1421", as shown in FIGS. 24A-24C. A magazine 1421c is provided that pivots downwards from a first configuration 1421A' (as shown in FIG. 24A) to a second configuration 1421B' (as shown in FIG. 24B) to receive the suture passing member 930 within the alignment recess 1430' to align the seat 1422 with the suture passing member 930. The magazine 1421c may be configured to receive the suture passing member 930, such as needle 930', while the needle 930' is in its partially extended position, as shown. In one example, the suturing instrument 900 may be advanced relative to the cartridge (or in other words the cartridge may be pulled further) to dock the needle 930' with the seat 1422 to enable transfer of the suture end 504 into the suture receiving passage 932 of the suture passing member 930 (as shown in FIG. 24C). In one such example, in order to provide the pivotal configuration 1421", the magazine 421c is formed from a molded spring. In other examples, the mechanism may incorporate a cold or torsion spring. The mechanism provided in the embodiment outlined in FIGS. 24A-24C may be used for either a needle-in configuration, or a needle-out configuration of the cartridge.

In some embodiments as described herein with respect to FIGS. 18-24, the magazine may define a wire channel 1153 that is in communication with the seat 1122. The wire channel 1153 may be configured to receive a longitudinally extending wire therein for use with a push mechanism (as described with reference to example 10) to push the suture end 504 from the seat into the suture passing member 930 of the suturing instrument, using a suture transferring component of the cartridge. Alternatively, examples described in FIGS. 18-24 may be usable with a pull mechanism where the suture transferring component of the cartridge is usable to pull the suture end 504 to transfer it from the seat into the suture receiving passage of the suture passing member 930. In some examples, the suture transferring component applies tension to the suture, (for example a segment of the suture that is held in frictional engagement with it in order to apply tension of the suture end to transfer the suture end). As such the suture transferring component is operable to apply tension on the suture portion to pull the suture portion to transfer it to the suturing instrument.

Figure 25A:
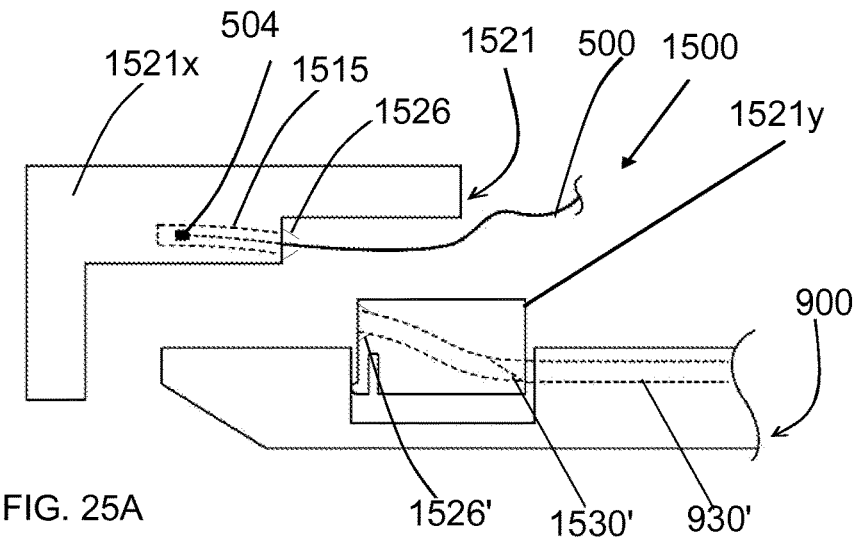
FIGS. 25A-25B illustrate a magazine for a cartridge and a method of using the same in accordance with an alternate embodiment of the present invention.
Figure 25B:
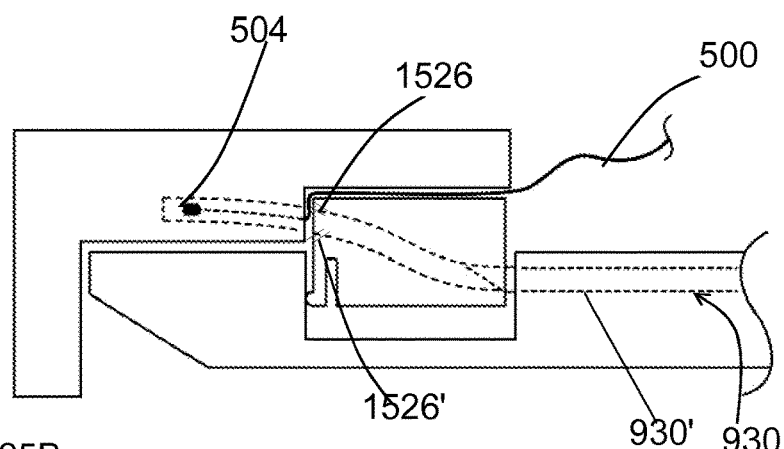

In an alternate embodiment of the present invention, as shown in FIGS. 25A and 25B, a cartridge 1500 is provided that comprises a base comprising a magazine 1521. As shown in FIG. 15A, the magazine 1521 comprises two components: a seat defining component 1521x that comprises the seat 1522, and an instrument mounted component 1521y. The instrument mounted component 1521y defines a suture passage 1515 adjacent an alignment recess 1530' that is aligned with and receives a suture passing member 930 of the suturing instrument 900. The instrument mounted component 1521y is mountable onto the suturing instrument 900. As shown in FIG. 25B, the seat defining component 1521x of the magazine 1521 is moveable to be brought into engagement with the instrument mounted component 1521y to align the seat 1522 with the suture passage 1515 to allow transfer of suture end 504 from the seat 1522 along the suture passage 1515 into the suture receiving passage 932 of the suturing instrument 900 that is within the alignment recess 930'. In some embodiments, the seat defining component 1521x of the magazine 1521 comprises a bevel 1526 that is receivable within a corresponding tapered opening 1526' within the instrument mounted component 1521y to be enageable therewith. This configuration facilitates transfer of the suture end from the bevel 1526 into the tapered opening 1526'. In some such embodiments, the instrument mounted component 1521y may be pre-shipped with the suturing instrument 900. In some embodiments, the instrument mounted component 1521y may be formed from a molded spring to positively press together the instrument mounted component 1521y and the needle 930'.

Figure 26A:
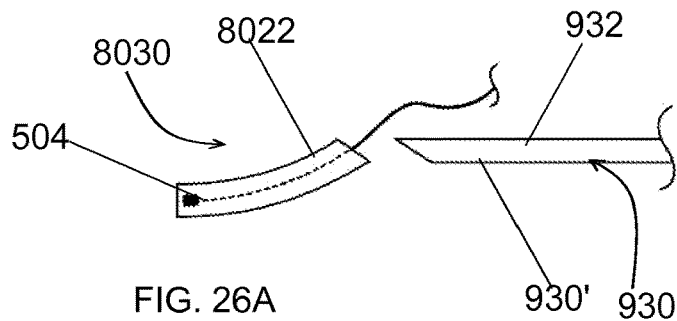
FIGS. 26A-26B illustrate an alignment mechanism and a method of using the same in accordance with an alternate embodiment of the present invention.
Figure 26B:
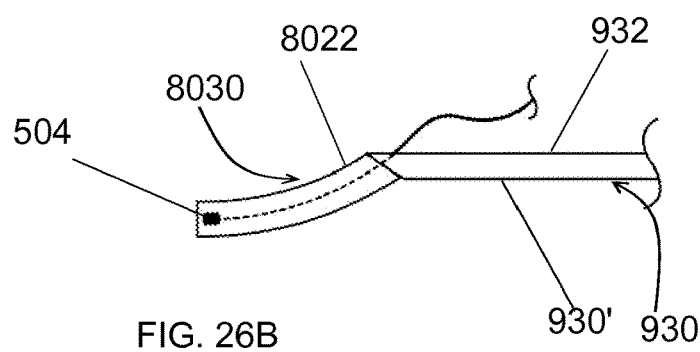

In an alternate embodiment, a cartridge is provided comprising a seat 8022 defined by a seat member, such as a projection 8030 within a magazine. As an alternative to approaching the suture passing member 930, such as the needle 930', perpendicularly to the bevel opening of the needle 930' as shown in FIG. 26A, the cartridge provides a configuration that enables the seat 8022 to approach the needle 930' from below. This alternative increases the projection area through which the suture end 504 has to find the inner diameter of the needle 930. In the example shown, the projection area increases in the Y-direction (i.e. transversally), and stays the same in X-direction (laterally). The increased projection area may help ensure that the suture end 504 finds the needle 930' and, as such, may reduce the risk of the suture end 504 not entering the needle 930' due to misalignments that may be introduced due to tolerance stack-up. As such, a larger projection area may provide the suture end 504 with additional room to find its way into the needle 930'. This may be beneficial in some cases where the seat 8022 and the needle 930' may be misaligned.

As outlined previously herein above with respect to FIGS. 9L and 9N, in some embodiments the magazine, for example the rocker 1041, comprises an alignment recess 1030' that is located adjacent to a seat 1022' that comprises a seat recess or channel for holding the suture end 504 in frictional engagement therein. The alignment recess 1030' is configured to receive the suture passing member 930 (such as needle 930') therein in a partially extended position during loading of the cartridge 1000 onto the suturing instrument 900, as shown in FIG. 9N, to allow suture end 504 to be transferred from the seat 1022' to the suture receiving passage 932 of the suture passing member 930. This may be referred to as the needle-out configuration of the cartridge, as the needle 930' is maintained in a partially extended position where a distal portion of the needle 930 extends distally outside the shaft 910 of the suturing instrument at the time of loading the cartridge 1000 onto the suturing instrument.

In some embodiments, a needle lock is provided that is mounted along the instrument proximal portion or shaft 910 of the suturing instrument 900. The needle lock is engageable with an aperture 935 (shown in FIG. 27A) within the needle 930' in its locking position to maintain the needle 930' in the partially extended position during loading of the cartridge onto the suturing instrument 900. The needle lock may be disengaged thereafter to allow the needle 930' to be retracted to its nominal position prior to use of the suturing instrument 900. As such, in some embodiments the surgical suturing instrument 900 comprises a needle lock for frictionally engaging the needle 930' to maintain the needle 930' in the partially extended position to facilitate alignment of the seat with the needle 930' upon loading of the cartridge onto the suturing instrument 900.

Figure 27A:
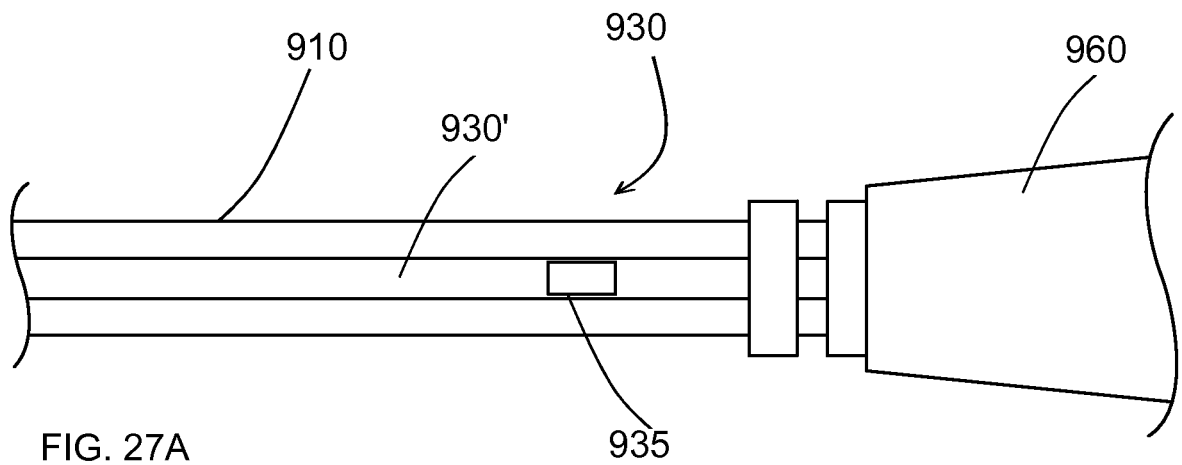
FIGS. 27A-27C illustrate a needle lock and a method of using the same in accordance with an alternate embodiment of the present invention.
Figure 27B:
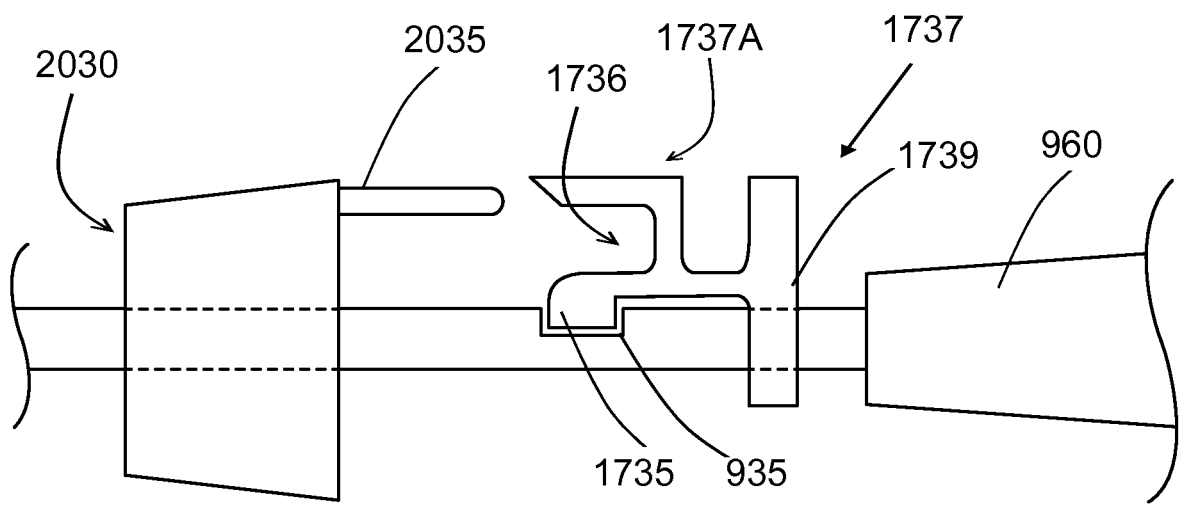
Figure 27C:
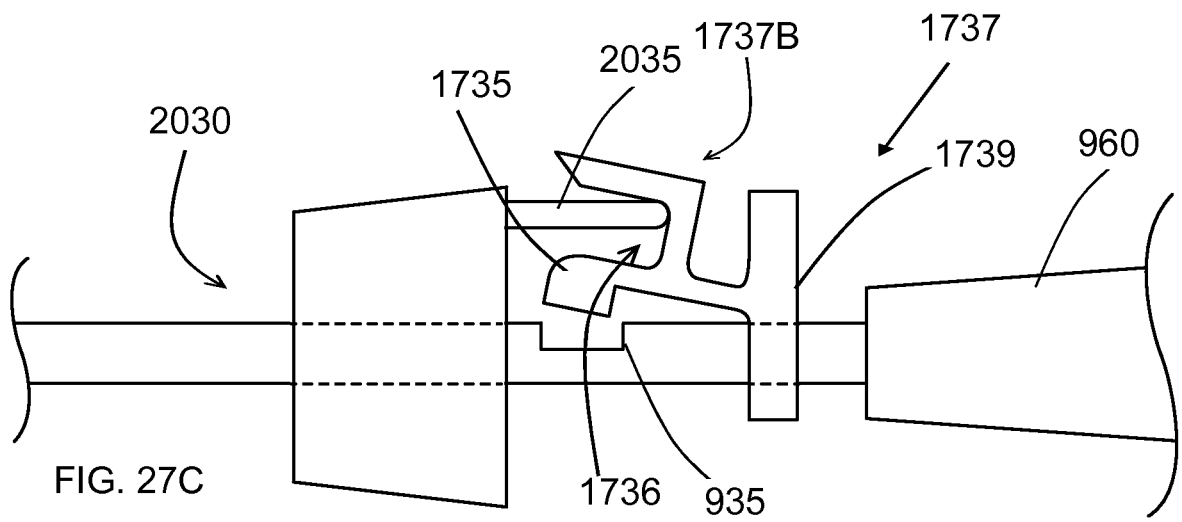

In one specific example, as shown in FIG. 27B, the needle lock comprises a resilient lock 1737 comprising a lock housing or body 1739 that is mounted on the instrument proximal portion or shaft 910. The lock housing or body 1739 comprises a flexible resilient arm 1735. In its locked position 1737A as shown, the resilient arm 1735 is engaged with the aperture 935 of the needle 930' preventing the needle 930' from retracting into the instrument proximal portion or shaft 910. As such, the resilient arm 1735 allows the needle 930' to remain in its partially extended position to allow the needle 930' to be received within the alignment recess 1030' of the cartridge 1000, which facilitates alignment and transfer of suture end from the seat 1022' into the needle 930'. In one such example, a component of the cartridge 1000, 2000, such as a component of the cartridge housing 1010', 2010', may be usable to disengage the resilient lock 1737. In one particular example, a knot slider such as the knot slider shown and described with reference to example 10, may be moveable proximally along the instrument proximal portion of shaft 910 to disengage the resilient lock 1737 moving it into its unlocked position 1737B. As the knot slider 2030 is advanced proximally, an unlocking tab 2035 of the knot slider 2030 is received within and engages with an opening 1736 of the lock housing or body 1739, which enables the resilient arm 1735 to flex up and out of the needle aperture 935, as shown in FIG. 27C. In other words, as the knot slider 2030 is pushed or moved back, it flips the lock on the needle up. As such, the knot slider 2030 moves the resilient lock 1737 into its unlocked position 1737B where it is disengaged from needle 930', allowing the needle 930' to retract back into the shaft or instrument proximal portion 910 into its unactuated/nominal position. In some such embodiments, the knot slider 2030 is moved further back to be coupled to the instrument proximal portion. In some examples of this, the needle lock may be consumed inside the knot slider 2030. In other words, the needle lock is received within the knot slider 2030 to be housed therein prior to the knot slider 2030 being coupled to the instrument proximal portion 960.

Figure 28A:
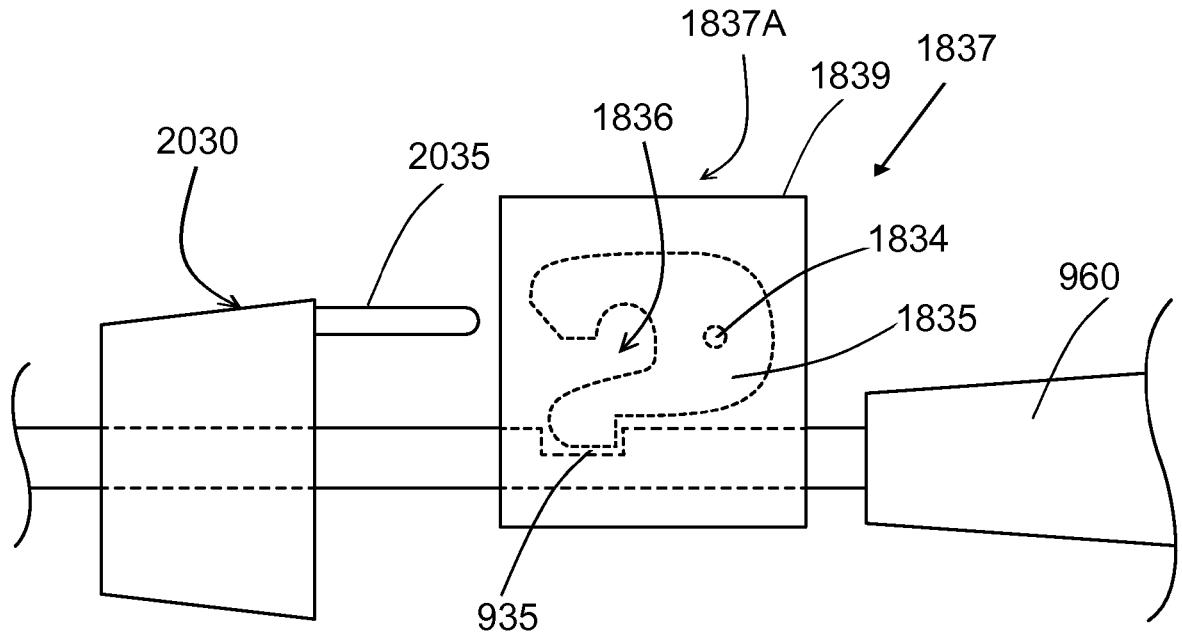
FIGS. 28A-28B illustrate a needle lock and a method of using the same in accordance with an alternate embodiment of the present invention.
Figure 28B:
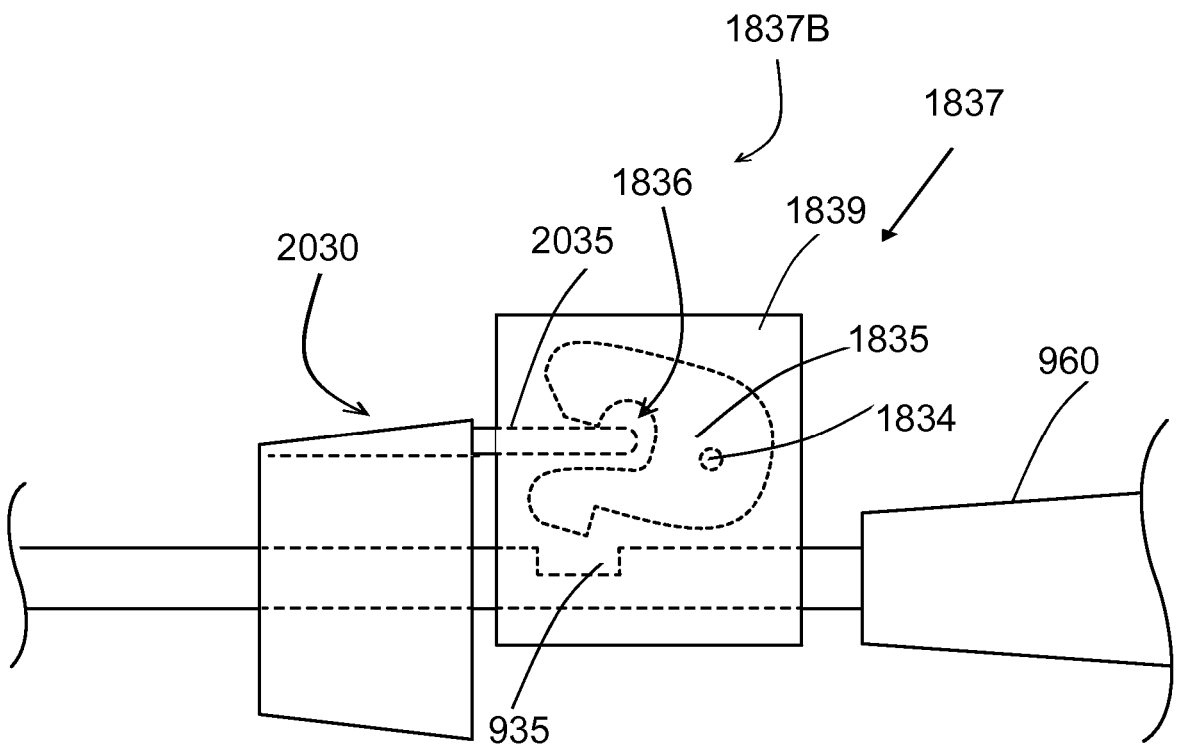

In an alternate embodiment as shown in FIG. 28A, the needle lock comprises a pivot-based needle lock 1837 comprising a lock housing or body 1839 that is mounted on the instrument proximal portion or shaft 910. The lock housing or body 1839 comprises a rotatable arm 1835 that is mounted on an over center pivot 1834 and is rotatable within the lock housing or body 1839. In its locked position 1837A as shown in FIG. 28A, the rotatable arm 1835 is engaged with the aperture 935 of the needle 930', preventing the needle 930' from retracting into the instrument proximal portion or shaft 910. As such, the rotatable arm 1835 allows the needle 930' to remain in its partially extended position to allow the needle 930' to be received within the alignment recess 1030' of the cartridge 1000 facilitating alignment and transfer of suture end form the seat 1022' into the needle 930'. In the present example, a knot slider, such as the knot slider 2030 described in example 10, may moveable proximally along the instrument proximal portion of shaft 910 to disengage the pivot-based needle lock 1837 moving it into its unlocked position 1837B. As the knot slider 2030 is advanced proximally, an unlocking tab 2035 of the knot slider 2030 is received within and engages with an opening 1836 of the lock housing or body 1839, which enables the rotatable arm 1835 to rotate clockwise out of engagement with the needle aperture 935, as shown in FIG. 28C. In other words, when the knot slider 2030 is pushed or moved back it moves the lock on the needle 930' up. In some such embodiments, since the needle 930' tries to retract back to its nominal retracted position in the locked position 1837A of the pivot-based needle lock 1837, it enables tighter engagement between the rotatable arm 1835 and the needle aperture 935. In some such embodiments, the knot slider 2030 exerts a sufficient force using the unlock tab 2035 and provides a sufficient mechanical advantage to push up the rotatable arm 1835 of the over center mechanism, as shown.

As such, the knot slider 2030 moves the pivot-based needle lock 1837 into its unlocked position 1837B, disengaging it from needle 930' allowing the needle 930' to retract back into the shaft or instrument proximal portion 910 into its unactuated/nominal position.

Figure 29A:
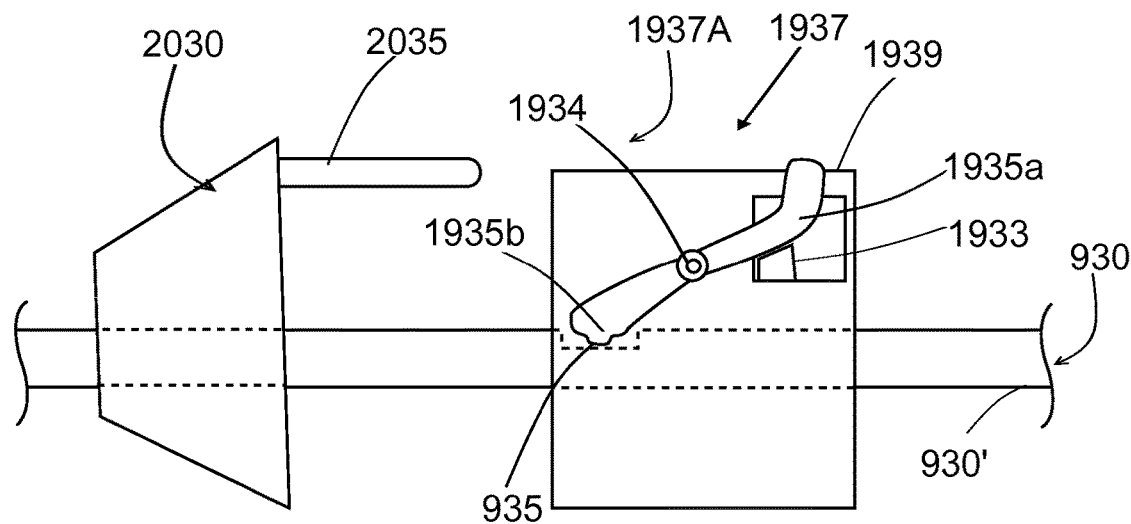
FIGS. 29A-29D illustrate a needle lock and a method of using the same in accordance with an alternate embodiment of the present invention.

In still a further alternative, as shown in FIG. 29A, the needle lock comprises a linkage-based needle lock 1937 comprising a lock housing or body 1939 that is mounted on the instrument proximal portion or shaft 910. The lock housing or body 1939 comprises a linkage 1935 that comprises first and second rotatable arms 1935a, 1935b that are mounted on a pivot 1934. In one specific example, the linkage 1935 comprises an over center linkage for example that forms a live hinge. In the locked position 1938A as shown in FIG. 29A, the linkage 1935 is locked with the first arm 1935a of the linkage resting on a support 1933 and the second arm 1935b of the linkage is engaged with the aperture 935 of the needle 930' preventing the needle 930' from retracting into the instrument proximal portion or shaft 910. As such, the second arm 1935b allows the needle 930' to remain in its partially extended position to allow the needle 930' to be received within the alignment recess 1030' of the cartridge 1000, facilitating alignment and transfer of suture end from the seat 1022' into the needle 930'. In some embodiments, the position of the linkage 1935 within the lock housing or body 1939 may be adjustable so that the needle tip extension distance can be tuned (i.e. how much the needle distal tip extends distally beyond the shaft 910).

Figure 29B:
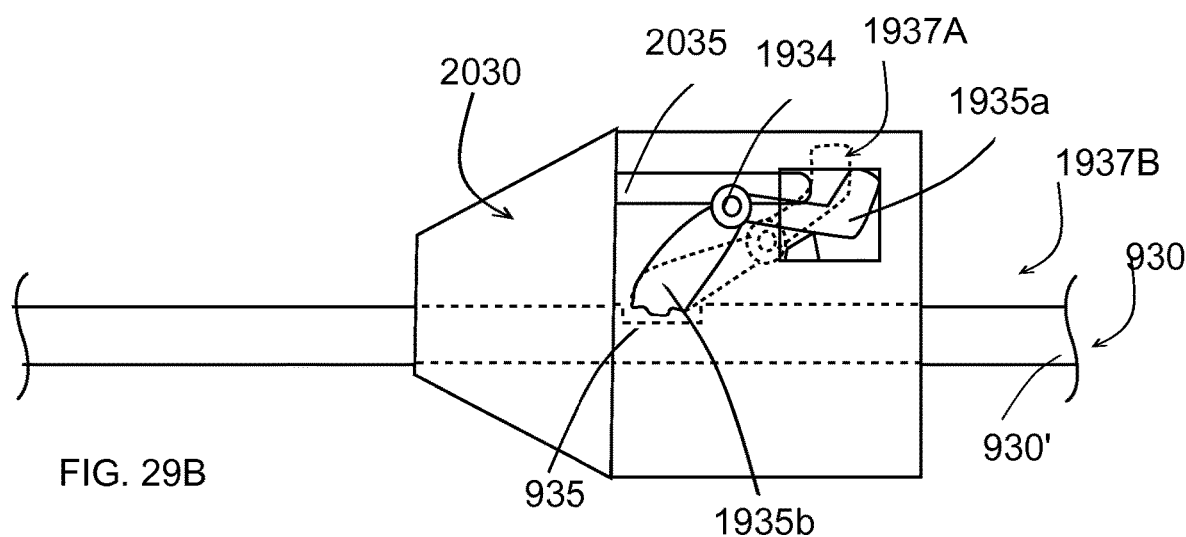
Figure 29C:
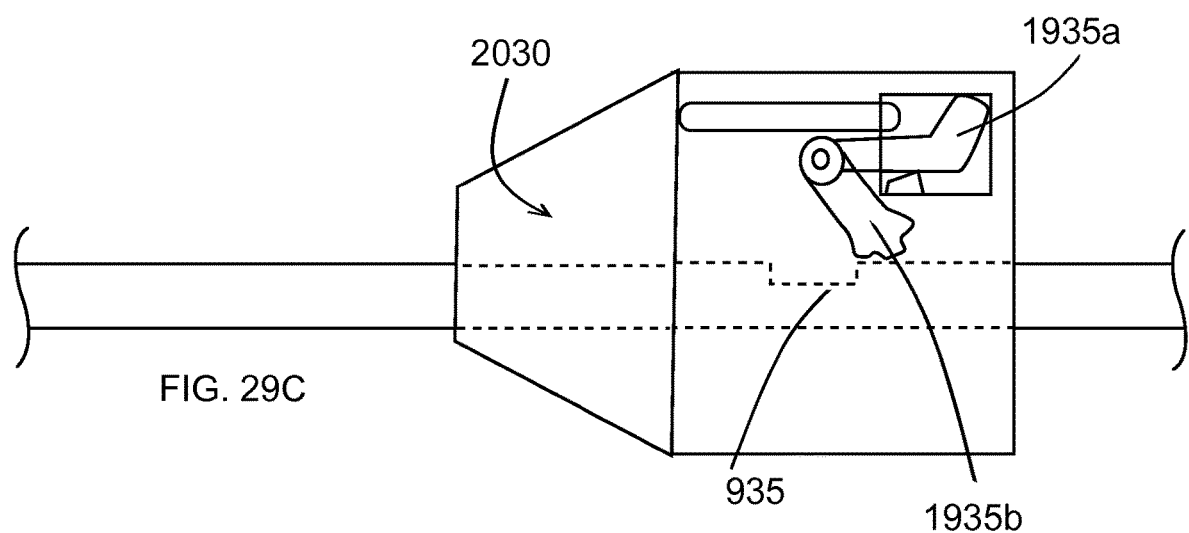

As shown in FIG. 29B, in the present embodiment a knot slider (such as the knot slider 2030 described in example 10) may moveable proximally along the instrument proximal portion of shaft 910 to disengage the linkage-based needle lock 1937 by moving the linkage and thus the needle lock into its unlocked position 1937B. As the knot slider 2030 is advanced proximally, the unlocking tab 2035 of the knot slider 2030 is received within the lock housing or body 1939 and it pushes against the first arm 1935a of the linkage 1935, which toggles the linkage 1935 back past the center to unlock the needle 9030'. More specifically, the unlocking tab 2035 moves the first arm 1935a clockwise which moves the pivot 1934 up. The upward movement of the pivot 1934, in conjunction with the proximal force exerted on the second arm 1935b by the needle aperture 935 as the needle 930' attempts to retract, enables the second arm 1935b of the linkage 1935 to move out of engagement with the needle aperture 935, as shown in FIG. 29C, which allows the needle 930' to retract to its nominal position where it is inside the instrument shaft 910. In other words, the movement of the unlocking tab 2035 to push the linkage 1935, and the proximal movement of the needle 930' at the same time, causes the linkage arms to move and enabling the second arm 1935b to move out of the way. As such the knot slider 2030 moves the linkage-based needle lock 1937 into its unlocked position 1937B, disengaging it from needle 930' allowing the needle 930' to retract back into the shaft or instrument proximal portion 910 into its unactuated/nominal position.

Figure 29D:
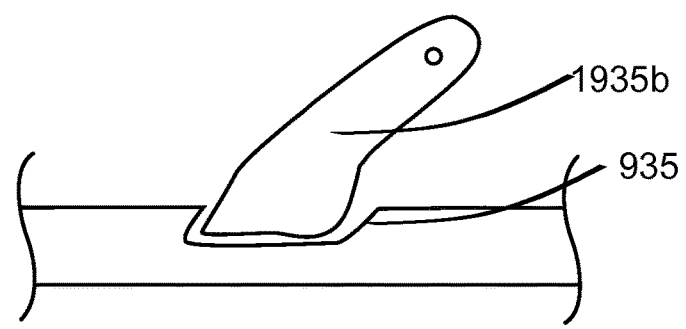

In some such embodiments, as shown in FIG. 29D, the needle slot 935 may be cut at an angle to achieve an under-cut, which may facilitate and enhance locking of the needle 930' in its partially extended position. In one such example, the needle 930' is locked using an over center linkage as described above in the linkage-based needle lock 1937.

Figure 30A:
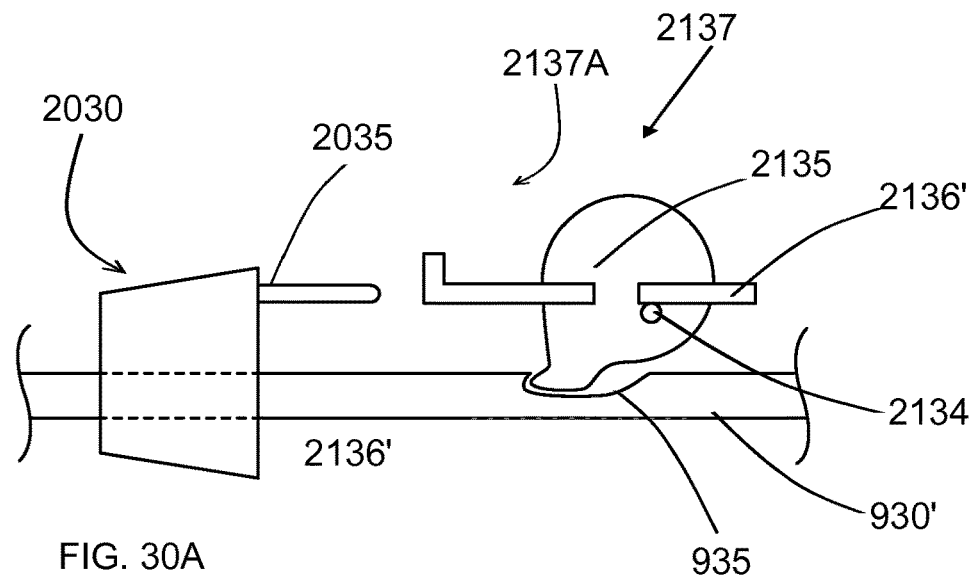
FIGS. 30A-30C illustrate a needle lock and a method of using the same in accordance with an alternate embodiment of the present invention.

In an alternate embodiment, as shown in FIG. 30A, the needle lock comprises a slider-based needle lock 2137 comprising a lock housing or body (not shown) that is mounted on the instrument proximal portion or shaft 910. The lock housing or body comprises a rotatable arm 2135 that is mounted on a pivot 2134 and is rotatable about the pivot 2134 within the lock housing or body 2139. The arm 2135 is additionally translatable along the lock housing or body in a vertical or transverse direction. The housing additionally comprises a slider 2136' defining a gap 2136 therein, the slider 2136' is moveable to unlock the locking mechanism of the needle lock. In the locked position 2137A, as shown in FIG. 30A, the rotatable arm 2135 engages with the aperture 935 of the needle 930' as the slider 2136' functions as a stop to prevent the arm 2135 from rotating. As such, the slider 2136' prevents the needle 930' from retracting into the instrument proximal portion or shaft 910. Thus, the slider 2136' and the arm 2135 co-operate to lock the needle 930' to keep it in its partially extended position to allow the needle 930' to be received within the alignment recess 1030' of the cartridge 1000 to facilitate alignment and transfer of suture end form the seat 1022' into the needle 930'.

Figure 30B:
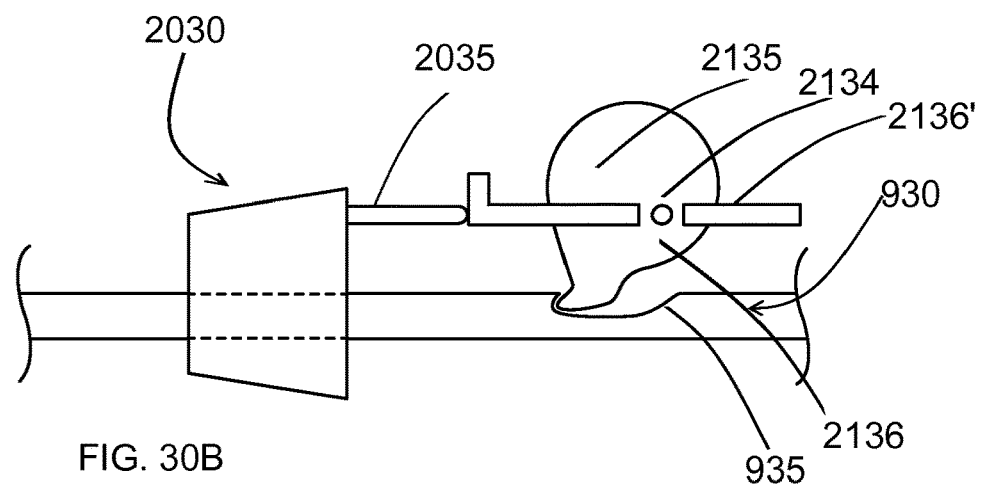
Figure 30C:
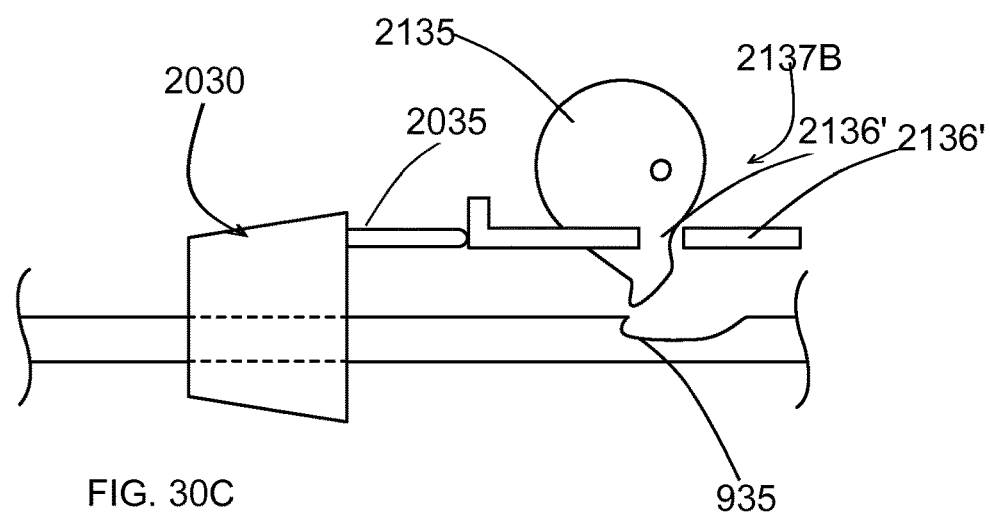

Similar to embodiments discussed herein above, in the present embodiment a knot slider 2030 (as described previously in example 10) is provided that is moveable proximally along the instrument proximal portion of shaft 910 to disengage the slider-based needle lock 2137. As the knot slider 2030 is advanced proximally, the unlocking tab 2035 of the knot slider 2030 pushes and translates the slider 2136' proximally such that the gap 2136 of the slider 2136' is now positioned above the pivot 2134 of the arm 2135. The gap 2136 enables the pivot 2134 to move vertically therein and as such allows the pivot 2134 and the arm 2135 attached thereto to rotate clockwise out of engagement with the needle aperture 935 (as shown in FIGS. 30B and 30C). Furthermore, as the arm 2135 translates vertically it is able to rotate as a result of the needle 930' moving proximally. In other words, as the arm 2135 translates vertically it allows the arm 2135 to complete the rotation to allow the arm 2135 to move out of engagement with the needle. This allows the slider-based needle lock 2137 to move into its unlocked position 2137B, disengaging it from needle 930' allowing the needle 930' to retract back into the shaft or instrument proximal portion 910 into its unactuated/nominal position.

Figure 31A:
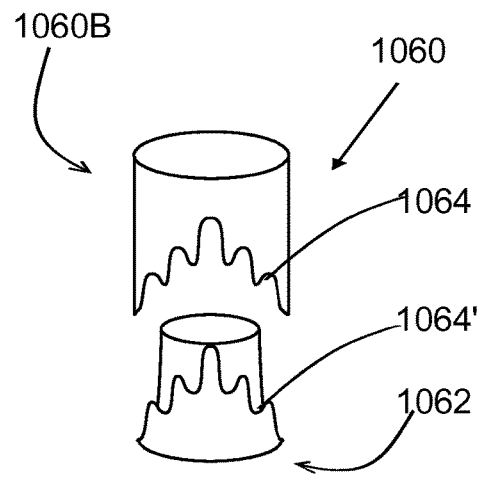
FIGS. 31A-31F illustrate alternate embodiments of a suture lock in accordance with various embodiments of the present invention.
Figure 31B:
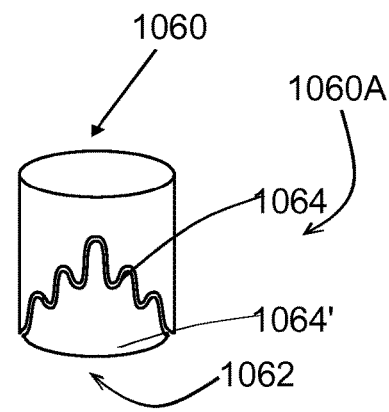

As outlined previously herein above with reference to FIGS. 13A-13B, 13E and additionally with reference now to FIGS. 31A and 31B, embodiments of the present invention provide a suture lock 1060 for coupling a portion of the suture 500, such a middle portion of the suture to the housing 1010' comprising the suture transferring component 1011. As such, in its locked configuration 1060A, as shown in FIG. 31B, the suture lock 1060 allows the suture transferring component 1011 to pull the suture that is coupled to it using the lock 1060 to be pulled along with it as it is translated proximally along the suturing instrument.

As discussed previously herein, in the initial locked configuration 1060A, the suture 500 is held between the teeth 1064 of the suture lock 1060 and corresponding teeth 1064' of the suture lock engaging component 1062. In order to release the lock 1060, the lock is moved into its second position 1060B as shown in FIGS. 13D and 13F, and additionally shown in FIG. 31A, which moves the teeth 1064, 1064' out of engagement with one another to release the suture held therein (for example a middle portion of the suture).

Figure 31C:
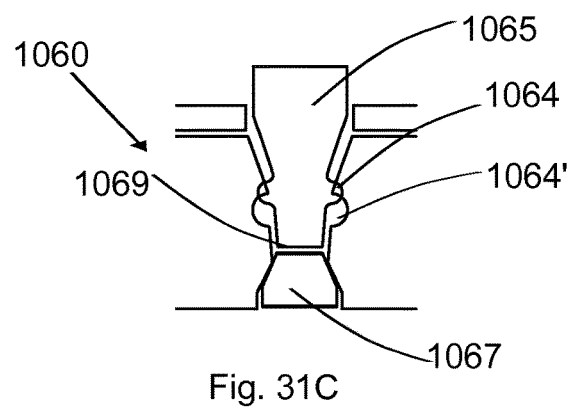

As shown in FIG. 31C, in some embodiments, the suture lock 1060 additionally comprises a release mechanism in order to unlock and release the suture 500 held therein. This is further illustrated in FIGS. 13B, 13D, and FIGS. 13E, 13F. The suture lock 1060 additionally provides a locking portion 1065 and a release portion 1067, where the locking portion 1065 is moveable for example by depressing it, to bring the teeth 1064 of the suture lock 1060 into engagement with the corresponding teeth 1064' of the suture lock engaging component 1062 with a segment of the suture (such as a middle segment of the suture) being held there-between. As such, the locking portion 1065 moves into the housing 1010' to bring the lock 1060 into its locked configuration 1060A, as is additionally shown in FIGS. 13B, 13E. Furthermore, in the locked configuration 1060A, the releasing portion 1067 is positioned substantially outside the housing 1010' and is visible on the outside and is now operable to release the suture lock 1060. In one such embodiment, the teeth 1064, 1064' provide a tortuous path for the suture and the suture is pressed against smooth but tightly fitted surfaces provided by the teeth 1064, 1064'. Additionally, when it is desired to release the suture 500, for example after the housing 1010' has been translated to pull the suture end into the suture passing member, the suture lock 1060 can be released. In one such example, the release portion 1067 of the suture lock 1060 may be depressed so that it is positioned within the housing 1010' as shown in FIG. 13D, bringing the teeth 1064 of the suture lock 1060 out of engagement with the corresponding teeth 1064' of the suture lock engaging component 1062, thus releasing the suture lock 1060 and the suture 500 held therein.

Figure 31D:
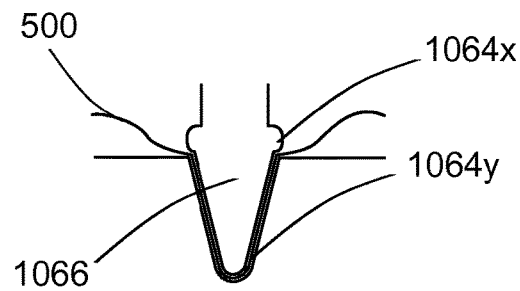

In still a further alternative of the suture lock, as shown in FIG. 31D, the suture lock comprises a Luer taper 1066 that provides a contoured surface 1064x that is engageable within a corresponding lock cavity 1066' that comprises a substantially matching contour 1064y, allowing the suture 500 to be press-fit there-between as shown. The Luer taper 1066 has a tip that is not too sharp, which allows suture to be press-fit along the sides of the Luer and/or at the bottom of the Luer, as shown in FIG. 31D.

In embodiments described herein above, the housing 1010' is translated along the suturing instrument 900, after having been disengaged from the base 1020, in order the suture end into the suture passing member 930. The housing 1010' may then be advanced further proximally after the suture lock is disengaged to be coupled to the handle or proximal portion of the suturing instrument 900 (for example in the case where the housing 1010' additionally has a pre-tied knot that is mounted onto the suturing instrument 900). In one such example, as the housing 1010' is translated proximally to load the suture end into the suturing instrument 900, the suture lock may disengage automatically (after the suture end has been transferred into the suturing instrument) allowing the housing 1010' to be moved independently from a portion of the suture (such as the suture end and the portion of the suture that was held within the suture lock 2060).

Figure 31E:
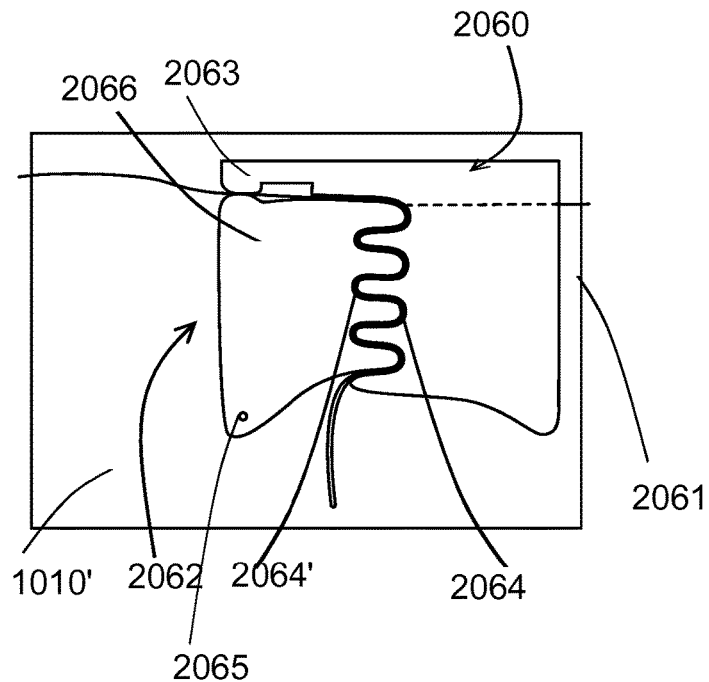
Figure 31F:
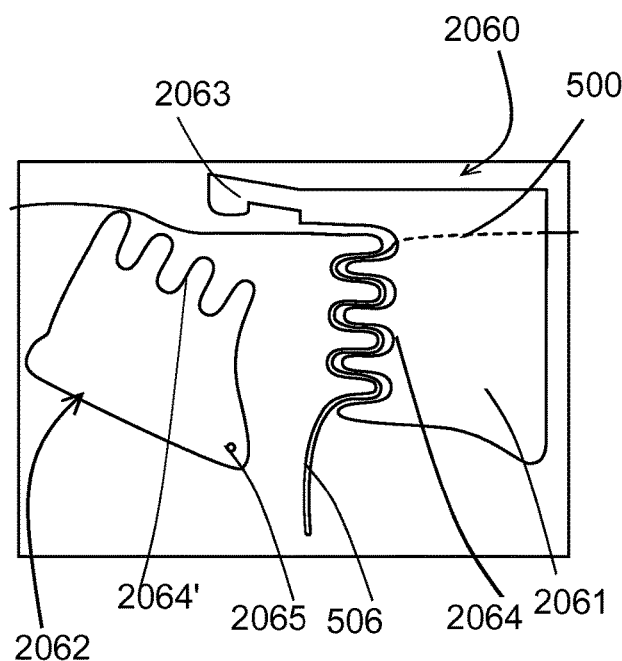

Thus, as a further alternative as shown in FIG. 31E, an automatic suture lock 2060 is shown that is mounted on a cartridge housing for example a cartridge 1010' as described with reference to example 9 herein above. In the specific example shown, the suture lock 2060 comprises a first member 2061 having fins 2064 and a second member 2062 having corresponding fins 2064'. The first and second members 2061, 2062 are coupled via an engagement arm 2063 of the first member 2061 that engages a locking tab 2066 of the second member 2062. In one such example, the fins 2064, 2064' are Luer lock fins. The suture 500 is held between the fins 2064, 2064', as shown. As housing 1010' is translated to transfer the suture into the suture passing member 930', it is then translated further. As the housing 1010' translates further, the suture 500 exerts a sufficient force to pull the engaging arm 2063 up and out, which disengages it from the lock tab 2066. As such, the second member 2062 disengages from the first member 2061, causing it to pivot out, and the suture loop 506 pulls up through the fins (to prevent the suture loop 506 from continually being pulled through the locking fins). In some such embodiments, the lock tab 2066 location may be moved further down to provide a greater mechanical advantage. This would require the suture to exert a greater pulling force to disengage the engaging arm 2063 from the lock tab 2066. In some embodiments, this may also provide a means for adjusting the release force required to disengage the engaging arm 2063.

Figure 32A:
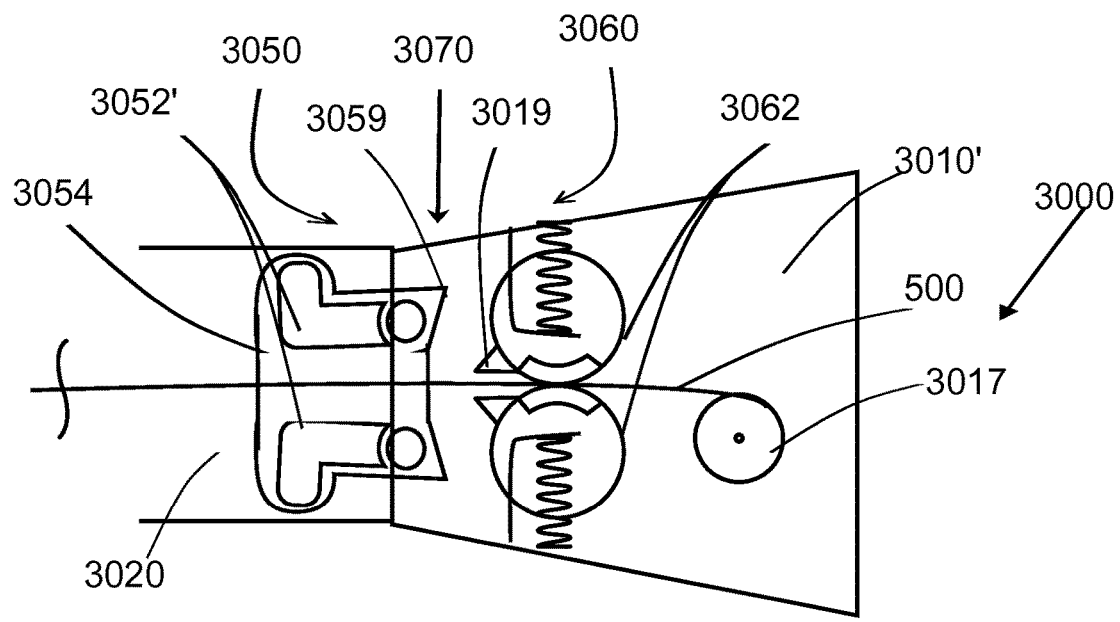
FIGS. 32A-32D illustrate alternate embodiments of a release mechanism for a cartridge in accordance with various embodiments of the present invention.

In an alternate embodiment of the present invention, as shown in FIG. 32A, a combined locking mechanism 3070 is provided that comprises a suture lock 3060 and an interlock 3050 that are both actuated simultaneously by the same mechanism. In the illustrated embodiment, a cartridge 3000 is provided that comprises a housing 3010' that is coupled to a base 3020. A suture spool 3017 holds the suture 500 that extends from the base 3020 into the housing 3010' where it passes between two biased friction rollers 3062 of the suture lock 3060 that hold the suture between them, before being routed into the suture spool 3017. In some such embodiments, the base 3020 has a feature that enables the entire cartridge assembly 3000 including the housing 3010' and the base 3020 to be retracted together to transfer the suture end and then may be pulled further proximally. As the cartridge 3000 is pulled back, the suture 500 is pulled out of the suture spool 3017, which exerts a force on the rollers 3062 forcing them to more apart and rotate outwards releasing the suture 500 from between them and as such the suture lock 3060 is disengaged. As the rollers rotate outwards, a wedge 3019 on the rollers engages an extension 3059 on rocking arms 3052' of the interlock 3050 that couples the base and the housing. This causes the rocking arms 3052' to rotate inwards within the space 3054 and out of engagement with a catch that holds them within the base 3020. Thus, the interlock 3050 is also disengaged, releasing the base 3020 from the housing 3010'. As such the housing 3010' can then be retracted pulled proximally independently from the base 3020 and independently from the suture portion that was previously held by the suture lock 3060.

Figure 32B:
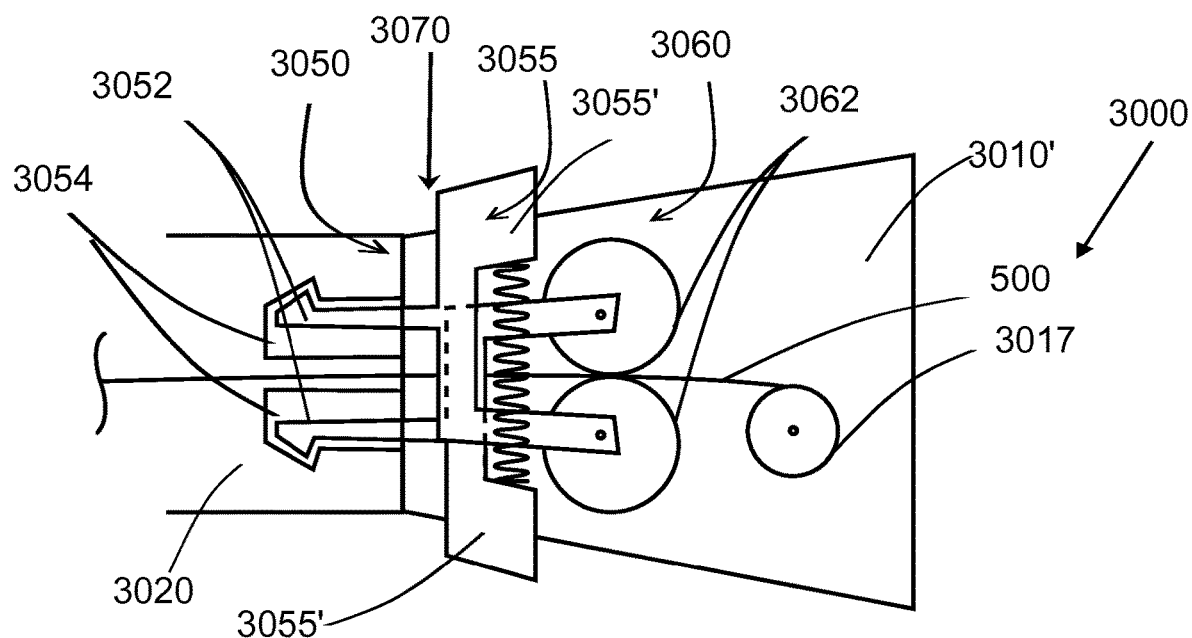

In one such embodiment, as shown in FIG. 32B, the release mechanism for the combined locking mechanism 3070 comprising interlock 3050 and the suture lock 3060 comprises a manual release button 3055 comprising legs 3055' that are biased away from one another via a spring 3056. Each of the legs 3055' is coupled to a moveable arm 3052 of the interlock 3050 as well as a roller 3062 of the suture lock 3060. As the manual release button is pressed, the legs 3055' are pressed and moved inwards towards each other, causing the rollers to move apart from each other releasing the suture 500 held there-between, while the legs 3055' additionally enable the moveable arms 3052 to move inwards within the space 3054. As such the manual release button 3055 enables the suture lock 3060 and the interlock 3050 of the combined locking mechanism 3070 to be disengaged simultaneously to permit the housing 3010' to be released from the base 3020, and to release the portion of the suture that was previously held within the suture lock 3060.

Figure 32C:
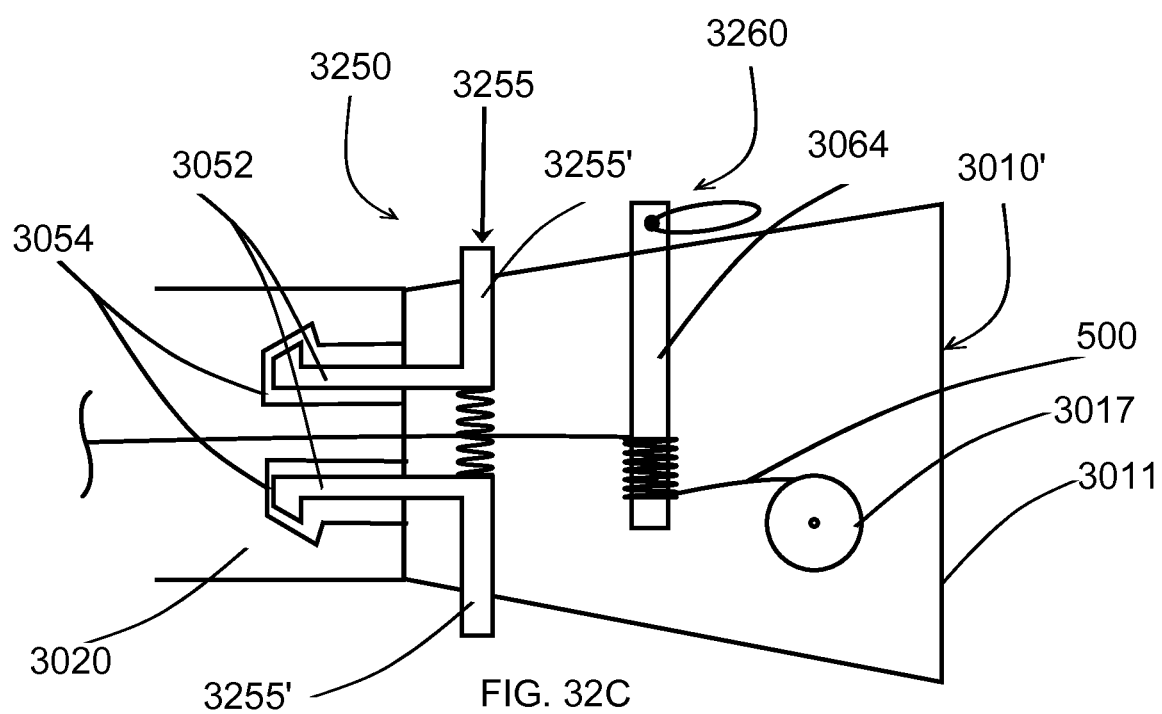
Figure 32D:
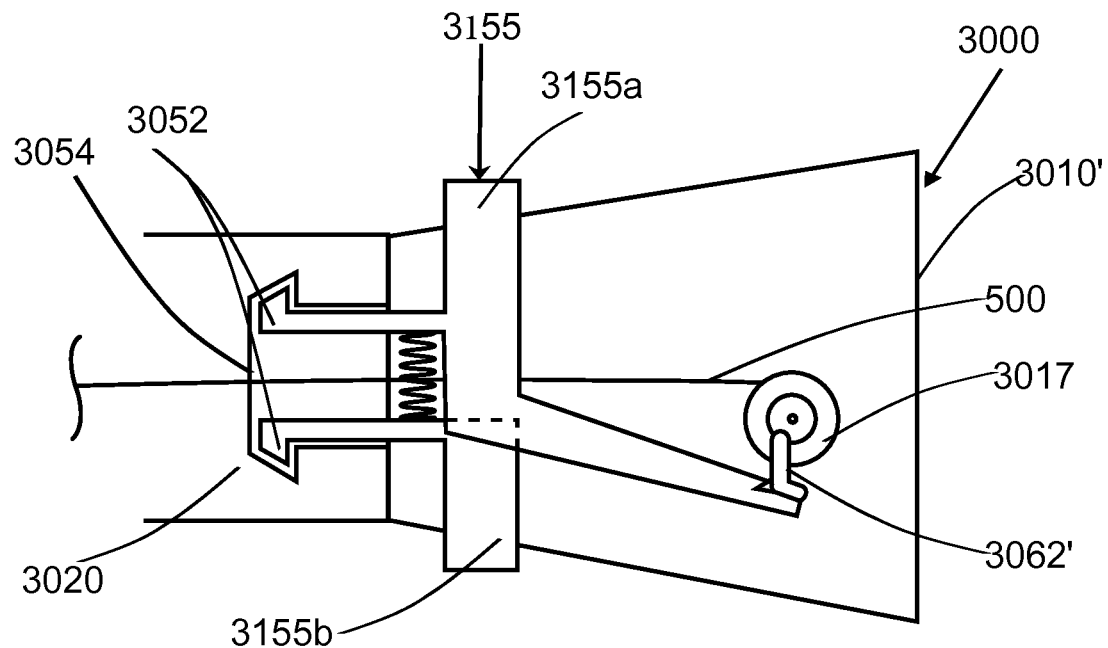

In another embodiment, as shown in FIG. 32D, the release mechanism for the combined locking mechanism 3070 comprises an interlock 3050 and a suture lock 3060 comprising a manual release button 3155 that comprises first and second legs 3155a, 3155b that are each coupled to the moveable arms 3052 of the interlock 3050. The first leg 3155a additionally engages a moveable tooth 3062' of the suture lock that frictionally engages the suture 500 on the suture reel 3017. As the manual release button 3155 is pressed, the legs 3155a, 3155b are pressed and moved inwards towards each other, enabling the moveable arms 3052 to move inwards within the space 3054. Furthermore, as the first arm moves inwards as the button 3155 is pressed, it causes the moveable tooth 3062' to move or flip over center to disengage the spool to release the suture 500. As such, the manual release button 3155 enables the suture lock 3060 and the interlock 3050 of the combined locking mechanism 3070 to be disengaged simultaneously to permit the housing 3010' to be released from the base 3020, and to release the portion of the suture that was previously held within the suture lock 3060.

In an alternate embodiment of the present invention as shown in FIG. 32C, the housing 3010' and the base 3020 of the housing comprise an interlock 3250 that operates independently from the suture lock 3260. The manual release mechanism for the interlock 3250 comprises a button 3255 comprising legs 3255' that are biased away from each other via a spring as shown. Each of the legs 3255' is coupled to a moveable arm 3052. Pressing the button 3255 moves the legs 3255' towards each other, which enables the moveable arms 3052 to move inwards within the space 3054, moving them out of engagement from a corresponding feature within the base 3020 disengaging the housing 3010' from the base 3020. This may allow the housing 3010' to be moved independently from the base 3020 (to function as a suture transferring component 3011) to transfer suture from a seat within the base into a suture passing member of the suturing instrument 900. Additionally, the suture lock 3060 may then be disengaged to allow the housing 3010' to move independently from the suture portion that was held within the suture lock 3060. In one such example, the suture lock 3060 comprises a suture release pin 3064 that has a portion of suture 500 wrapped around it after it exits the suture spool 3017. In one such embodiment, the suture release pin 3064 may then be removed to release the wrapped suture portion held thereabout, allowing the housing 3010' to be moved proximally separately from the wrapped suture portion for example to allow the housing 3010' to mount a pre-tied knot that it carries onto the suturing instrument 900 to be held adjacent the handle of the suturing instrument 900.

In alternative embodiments, a fully automatic mechanism is provided for aligning and transferring suture. In other embodiments, a more simple mechanical design may be provided that reduces the number of steps that the user is required perform in order to load the suture. In some embodiments, the mechanical design provides one or more steps that the user is required to perform to load the suture.

In alternative embodiments, with reference to example 10, a push rod interlock may be provided in the form of a button that the user presses in order to allow the push rod to move to push the suture end into the suturing instrument.

In some embodiments as described herein above with reference to example 10, the embodiment provides for automatic decoupling of the knot slider. In alternative embodiments, the knot slider may be manually decoupled from the cartridge base by the user at a specified time. In some such embodiments, a visual indicator window may be provided that shows the user when the suture end or Lobster has been loaded and when the suture knot slider can be released. In some embodiments, with reference now to example 9, a similar mechanism in the form of a visual indicator window may be provided that shows the user when the Lobster has been loaded and when the suture lock may be released.

In some embodiments of the present invention, a cartridge is provided that provides an additional means for providing an indication for when the suture has been loaded into the suture passing member. In some such embodiments, an interlock in the seat (i.e. a seat interlock) may be provided which senses when the suture has left the seat. Alternatively, the cartridge may provide clear or see-through components so the user can physically see when the suture has been loaded. Furthermore, in still a further alternative, optical sensors may be provided that detect when the suture has been loaded.

In still some additional embodiments, with reference to example 10, instead of a sliding tail hook on the knot slider, a fixed tail hook may be provided.

Methods for Loading Suture

In accordance with a broad embodiment of the present invention, a method is provided for loading a suture onto a surgical suturing instrument, the suture comprising suture loops and terminating in a suture end. The method involves mounting the suture loops onto a surgical suturing instrument positioned through the suture loops. The suture end is aligned with and transferred to the suture receiving passage of the suture passing member. The step of aligning the suture end may involve restraining the suturing instrument with respect to the suture end. The suture end may be aligned by moving the suture end with respect to the suturing passing member. In some examples, the step of aligning the suture end may comprise moving the suture passing member with respect to the suture end. In some embodiments, the method of loading the suture onto the suturing instrument is performed using a suture loading apparatus such as a cartridge. The cartridge may be used to both mount suture loops onto the surgical instrument and to align the suture end with the suture receiving passage of the suture passing member In a general embodiment of the present invention, a method is provided for suturing within an inter-vertebral disc. The method involves using a cartridge to load suture onto a suturing instrument, and then using the surgical suturing instrument to deliver the suture into the inter-vertebral disc. In some embodiments, the cartridge is used to load suture at the point of use, for example, by a physician just prior to using the suturing instrument within a patient. In a specific example of the method, the suturing instrument is used to pass or insert suture into a region of tissue surrounding a defect within the inter-vertebral disc and approximating the defect using the suture. In an instant of this example, approximating the defect involves forming a loop of suture around the defect using the suture to provide a 360 degree approximation of the defect. After the suture is used to approximate the defect a means is provided to secure the suture within the inter-vertebral disc, such as a knot. In some embodiments, the knot comprises a pre-tied knot and is deployed after the step of approximating the defect. In a particular example, the cartridge provides a pre-tied knot.

Examples 1A, 1B

In some embodiments, the method of loading the suture onto the suturing instrument is performed using a suture loading apparatus such as a cartridge. More specifically with reference now to FIGS. 1A-1F, a cartridge 100 is provided for loading suture 500 onto the suturing instrument 900. The suture 500 comprises suture loops or a pre-tied knot 502 that opens into a service loop 501 comprising a tug loop 507 that terminates in the suture end 504 held within the seat 122. Referring now to FIG. 1F, the distal tip 920 of suturing instrument 900 is inserted into the housing 10' through the channel 14 within the chamber 10 such that it is positioned through the suture loops or pre-tied knot 502 mounted on the housing 10'. The distal tip 920 of the suturing instrument 900 is then advanced distally through and past the channel 14 so that the housing 10' is now mounted onto the proximal portion or shaft 910 of the suturing instrument. Since the base 120 is flexibly coupled to the housing 10' via flexible tube 152, this allows the cartridge base 120 to be positioned to the side and out of the way (away from the longitudinal axis of the suturing instrument 900) to permit advancement of the suturing instrument 900. The flexible tube 152 bends to allow the cartridge base 120 to be kept off to the side from the path of the surgical suturing instrument 900 as it is advanced through the housing 10'. The suturing instrument 900 is positioned such that the distal tip 920 and the neck portion 940 as well as the tissue receiving gap 942, are positioned distal to the housing 10'.

The cartridge base 120 is then moved back towards the longitudinal axis of the suturing instrument 900 to be clipped into the surgical suturing instrument 900. In the example illustrated in FIG. 1A-1F, the restraint 25 comprises a locking recess 125 that corresponds to the shape of the suturing instrument 900. Specifically it is a recess that is shaped to accommodate the neck portion 940, and a segment of the proximal and distal portions 910, 920 of the suturing instrument 900. Referring again to FIG. 1F, the cartridge base 120 is then snapped to the suturing instrument 900. The suturing instrument 900 is received within the locking recess 125 such that the base 120 press-fits around it. The locking recess 125 functions to restrain the suturing instrument to help align the seat 122 and thus the suture end 504 held within the with the seat 122 with the suture receiving passage 932 of the suturing instrument 900.

As outlined previously, the cartridge base 120 additionally comprises an alignment recess 130 adjacent the seat 122 to further assist in aligning the seat 122 with the suture receiving passage 932 of the suturing instrument 900. The alignment recess 130 is dimensioned to receive the suture passing member 930 such as needle 930'. Once the movement of the suturing instrument 900 is constrained or restricted by the locking recess 125, the needle 930' is advanced (for example, by actuating a trigger) within the alignment recess 130 such that the needle 930' is positioned adjacent the seat 122.

As mentioned previously, the suture is routed through the base slot 128 that is in communication with the seat 122, as shown in FIG. 1B. Once the suturing instrument 900 is inserted within the locking recess 125 (in the position shown in FIG. 1F), the base slot 128 is aligned with the longitudinal opening 928 within the instrument proximal portion 910 and with the slit 938 within the needle 930'. The suture tug loop 507 that exits the cartridge 100 is then pulled (proximally) by tugging on it to draw the suture end 504 from the seat 122 and into the aligned suture receiving passage 932 of the suture passing member 930 to position the suture end 504 therein. As the tug loop 507 is pulled, the suture retention pin 165 holds a portion of the tug loop 507 to prevent the service loop 501 from being pulled out of the suture spool 160. The suture retaining component 165 may then be removed, releasing the suture 500. In one specific example where the trigger is actuated to advance the needle 930' within the recess, the trigger may be released at this point. Once, suture end 504 is loaded onto the suturing instrument 900, the cartridge housing 10' is then advanced proximally along the instrument proximal portion or shaft 910, for example till the handle of the suturing instrument 900 and coupled there. Once the housing 10' is advanced proximally the flexible tube 152 is detached from the housing 10', decoupling the base 120 from the housing' 10'. The cartridge base 120 can be removed from the suturing instrument by unsnapping the cartridge base 120 from the surgical suturing instrument 900. More specifically, the suturing instrument 900 is decoupled from the locking recess 125 of the base 120.

The suturing instrument 900 is then used to pass suture 500 through a region of tissue for example within an intervertebral disc of a patient's body to apply suture thereto, for example to close a defect within the inter-vertebral disc. As the suture 500 is passed through the inter-vertebral disc, the suturing instrument 900 is then pulled such that the suture 500 held within suture storage such as suture spool 160, is payed out. The tension within the suture 500 then decouples the housing 10' from the instrument proximal portion or shaft 910, allowing the housing 10' to slide distally along the suturing instrument 900 and deploy the pre-tied knot 502 within the inter-vertebral disc to secure the suture 500 passed through the disc.

The cartridge base 220 may be removed from the surgical instrument and discarded.

Example 2

In accordance with an alternate embodiment of the present invention, a method is provided for loading suture 500 onto the suturing instrument 900 using a cartridge 200, as shown in FIG. 2D. As outlined previously, the cartridge 200 comprises a base 220 that is coupled to the housing 10' via a flexible tube 152. In order to load the suture 500 onto the surgical instrument 900, the suturing instrument 900 is advanced through the channel 14 to be positioned through the chamber 10 within the housing 10'. As such, the suturing instrument 900 is positioned through the suture loops or pre-tied knot 502 mounted about the chamber 10. The suturing instrument 900 is then advanced until the suture receiving gap 942 of the surgical instrument is positioned distal to the housing 10'. The base 220 is then positioned within the tissue receiving gap 942 and slid proximally towards the instrument proximal portion or shaft 910. In some embodiments, a portion of the cartridge, such as base 220, axially receives a portion of a suturing instrument 900 in order to load the suture onto the surgical instrument 900. In other words, the base 220 permits axial advancement of the suturing instrument 900 relative to the base 220. As the base 220 is advanced proximally, a segment of the shaft 910 is received within the locking recess 225 (which is an alignment feature) in a friction fit engagement. The locking recess 225 is a restraint that functions to fix or constrain the suturing instrument 900 with respect to the cartridge base 220.

The cartridge base 220 is then slid proximally until the projection 230 which functions as an alignment feature abuts against the suture passing member 930 (such as needle 930'). More specifically, the bevel face 234 of the projection 230 abuts against the needle bevel 934 to assist in aligning the seat 222 (and suture end 504 held therein) with the suture receiving passage 932 of the needle 930'. Once the suture end 504 is aligned with the suture receiving passage 932, the suture end 504 is transferred into the suture receiving passage, for example, by pulling the tug loop 507, as shown in FIG. 2D. The suture retaining component 65 comprising suture retention pin 265 holds a portion of the tug loop 507 to prevent the service loop 501 from being pulled out from one of the suture payout tubes 260 that hold the extra suture 500, as shown in FIG. 2E.

The housing 10' is pulled proximally along the shaft 910 for example till the handle of the suturing instrument 900 to be positioned there. This detaches the tether 152, decoupling the base 220 from the housing 10'. The base 220 can then be removed. The suturing instrument 900 is then used to pass suture within a region of tissue, such as inter-vertebral disc. Once the suture is passed through the disc, for example, to provide 360 degree suturing of a defect, the suturing instrument 900 is pulled proximally. The extra suture held within the suture storage 60 and more specifically, the suture tubes 260 is payed out, which pulls on the housing 10' pulling it distally along the suturing instrument until it reaches the distal tip 920 of the suturing instrument, where it is stopped (for example, with a tab engaging with a portion of the suturing instrument 900). As the suturing instrument 900 is pulled, the pre-tied knot 502 is deployed to secure the suture 500 within the region of tissue such as the inter-vertebral disc, for example to close a defect.

Example 3

In accordance with an alternate embodiment of the present invention, a method is provided for loading suture 500 onto the suturing instrument 900 using a cartridge 300, as shown in FIGS. 3C-3D. The cartridge 300 comprises a housing 10' detachably coupled to the base 320 via a rigid coupling which is a snap 352. As shown in FIG. 3C, the cartridge 300 is loaded onto the suturing instrument 900 by inserting a segment of the suturing instrument 900 through the cartridge housing 10' and thus through the suture loops (or pre-tied knot) 502 mounted thereon. The suturing instrument 900 is then advanced distally through the instrument receiving recess 325' within the base 320 with the magazine 321 being in its first position 321A. In some embodiments, the cartridge 300 axially receives (or in other words permits axial advancement of) a portion of a suturing instrument 900 relative to the base in order to load the suture onto the surgical instrument 900. In other words, the cartridge 300 loads suture onto the surgical instrument 900 by allowing the surgical instrument 900 to be received axially through the cartridge 300. For example, the suturing instrument 900 may be advanced distally through the cartridge 300 or the cartridge 300 may be moved proximally along the suturing instrument 900.

Figure 3E:
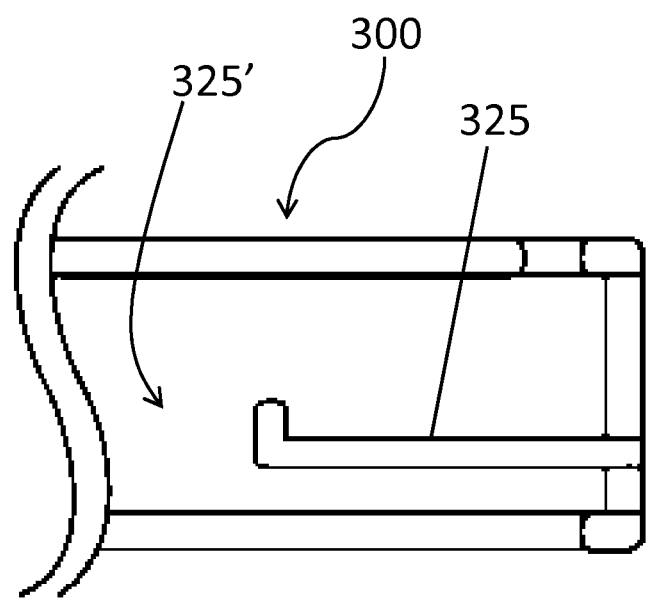
FIG. 3E shows a partial top view of a cartridge in accordance with an embodiment of the present invention.

In a particular example, with reference now to FIG. 3C, the suturing instrument 900 is advanced distally through the instrument receiving recess 325' (shown in FIG. 3A) until it is stopped or restrained by the tail hook 325 (also shown in FIG. 3E). The tail hook 325 engages or latches onto the end wall of the instrument shaft 910 in order to position the cartridge 300 such that the magazine 321 is aligned with the tissue receiving gap 942 of the suturing instrument, as illustrated in FIG. 3C.

As shown in FIG. 3D, the magazine 321 is then moved downwards towards the bottom of the cartridge 300 to position the magazine 321 within the tissue receiving gap 942 of the suturing instrument 900. The magazine 321, and thus seat 322, is moved to align it with the suture receiving passage 932. The magazine 321 is positioned so that the alignment recess 330 is in line with the suture passing member 930 (or more specifically needle 930'). The needle 930' is advanced, for example by actuating a trigger, so that it is received within the alignment recess 330 within the magazine 321, similar to the method described herein above with reference to cartridge 100. This aligns the seat 322 and suture end 504 held therein with the suture receiving passage 932. The suture tug loop 507 is then pulled to transfer the suture end 504 from the seat 322 into the suture receiving passage 932. The tug loop 507 is routed through the base slot 328 (shown in FIG. 3B) to provide clearance for the tug loop 507 to be manipulated or pulled to transfer the suture end 504. The trigger can then be released.

The housing 10' is advanced along the shaft 910 till the handle to be coupled thereto, detaching the base 320 from the housing 10' in the process. The base 320 can then be removed from the suturing instrument 900 by disengaging the snap 352 and discarded. The suture loops or pre-tied knot 502 can be deployed in a manner similar to the cartridge embodiments 100, 200 outlined previously herein above.
Example 4

In accordance with an alternate embodiment of the present invention, a method is provided for loading suture 500 onto the suturing instrument 900 using a cartridge 400, as shown in FIGS. 4A-4C. The cartridge comprises a housing 10' (for example of the type previously described) that is detachably coupled to the base 420. The cartridge is loaded onto the suturing instrument 900 by advancing the instrument 900 through the housing 10' and then through the instrument receiving recess 425' within the cartridge base 420 with the spring mounted magazine 421 (or interlock 421') being initially positioned in its first or initial position 421A, as shown in FIG. 4B. In some embodiments, the cartridge 400 axially receives (or in other words permits axial advancement of) a portion of a suturing instrument 900 relative to the base in order to load the suture onto the suturing instrument 900. In other words, the cartridge 400 permits loading suture onto the surgical instrument 900 by allowing the surgical instrument 900 to be received axially through the cartridge 400. For example, the suturing instrument 900 may be advanced distally through the cartridge 400 or the cartridge 400 may be moved proximally along the suturing instrument). In one example, the method provides for front end loading of the suturing instrument 900' using the cartridge 400.

In a particular example, as the instrument 900 is advanced distally through the cartridge base 420, a tapered section of the distal tip 920 engages a slant or incline 923 of the interlock 421' automatically moving the magazine 421 (and thus the seat 422) downwards and into the tissue receiving gap 942 of the suturing instrument 900 to align the seat 422 (and the suture end 504 held therein) with the suture receiving passage 932, as illustrated in FIG. 4C. The spring mounted magazine 421 (or interlock 421') is now positioned in its second position 421B. The movement of the magazine 421 into the tissue receiving gap 942, and the distal advancement of the suturing instrument 900 through the magazine 421, further functions as a restraining feature to lock or restrain the suturing instrument 900 with respect to the cartridge 400. In some embodiments the suturing instrument 900 is slid into the cartridge 400 until it stops.

Furthermore, as the magazine 421 moves downwards during distal advancement of the suturing instrument 900, the projection 430 moves into the shaft 910 such that bevel 434 of the projection 430 abuts against the needle bevel 934. This helps align the seat 422 (and suture end 504 held releasably within the seat channel 424) with the suture receiving passage 932 of the suturing instrument 900. Thus, the magazine 321 (as shown in FIG. 4C) is automatically moved into its second position to align the seat 422 with the suture passing member 930 upon relative movement between the cartridge base 420 and the instrument 900. In some embodiments, the housing 10' may be advanced proximally along the shaft 910 until it abuts against the instrument handle, decoupling the base 420 from the housing 910'. The base 420 can then be removed from the suturing instrument 900. In some embodiments, the base 420 can be automatically detached as the instrument 900 is withdrawn proximally and magazine 421 moves into its initial position 421A. The pre-tied knot 502 on the housing 10' may be deployed in the manner described previously for cartridge embodiments 100, 200.
Example 5

In some embodiments, as outlined in FIGS. 5A and 5B, the cartridge 500' is loaded onto the suturing instrument by advancing the surgical suturing instrument 900 through the channel 514 within the housing 510'. The channel 514 is wide enough to allow the suturing instrument 900 to be advanced distally through it, and thus through the pre-tied knot 502, without any hindrance. The suturing instrument 900 is therefore advanced distally straight through the channel 514 (along the bottom of the channel 514) such that the distal portion 920 of the suturing instrument is positioned distal to base 520. Furthermore, the neck 940 and the tissue receiving gap 942 are positioned within the cut-out 516 below the base 520. The cartridge 500' is then moved downwards (or the instrument is moved upwards) such that base 520 is positioned within the tissue receiving gap 942, to align the seat 522 and the suture receiving passage 932 of the suture passing member 930.

Thus, the suturing instrument 900 and the cartridge 500' (including base 520 and housing 510') are moved relative to each other to allow the base 520 to be positioned within the tissue receiving gap 942. The cartridge 500' is then moved proximally along the shaft 910 of the suturing instrument 900 such that the shaft 910 is received within the locking recess 525' to restrain the suturing instrument 900 relative to the cartridge 500' to further aid in aligning the seat 522 with the suture passing member 930. Once positioned therein the cartridge 500' is then advanced further proximally relative to the suturing instrument 900, to allow the projection 530 to abut against suture passing member 930, such as needle 930'. More specifically, the bevel 534 of the projection 530 rests against the bevel of the needle 930' to align the seat 522 with the suture receiving passage 932 to align the seat 522 and the suture end 504 held therein with the suture receiving passage 932. The suture end 504 may be loaded into the suture receiving passage 932, for example, by tugging the suture loop 507. In some embodiments, the base 520 may remain coupled to the housing 510' that is mounted on the suturing instrument 900, during use of the instrument 900 to pass suture through a region of tissue. The pre-tied knot 502 may be deployed as outlined previously with respect to embodiments described herein above.

Example 6

In accordance with an alternative embodiment of the present invention as illustrated in FIGS. 6A-6B, a suture loading apparatus (cartridge 600) is provided for loading a ferrule 70 onto a surgical suturing instrument 900'. The method provides for front end loading of the suturing instrument 900' using the cartridge 600. The method comprises moving the suturing instrument axially with respect the chamber 610. In some embodiments, the instrument is advanced distally through the channel or recess 614 within the chamber 610. In a particular example, the recess 614 functions as a restraint and helps to position the suturing instrument 900' received through the chamber 610 relative to the seat 622 for aligning the seat 622 with a ferrule receiving passage 933 of the suturing instrument 900. As illustrated in FIG. 6C, the suturing instrument 900' is advanced further until the distal tip 920 of the suturing instrument 900' abuts against the cap 621. The cap 621 functions as a restraint to position the suturing instrument 900' relative to the seat 622 to align the seat 622 with the ferrule receiving passage 933 of the suturing instrument 900'. Additionally, the projection 630 also helps to align the ferrule 70 with the ferrule receiving passage 933 as it is received therein. Once the ferrule 70 is positioned within the ferrule receiving passage 933, it is aligned with the longitudinal axis of the ferrule passing member 931 (such as a needle 931') to allow the ferrule 70 to be captured by the ferrule passing member 931 upon its advancement. Thus, the cartridge 600' further helps to align the ferrule 70 with the ferrule passing member 931.

In some embodiments, the cartridge 600' further provides a means for coupling the ferrule 70 to the distal tip 920 of the suturing instrument after the ferrule 70 has been positioned within the ferrule receiving passage 933. In some embodiments, the seat 622 is moveable relative to the suturing instrument 900' and the chamber 610 to enable locking of the ferrule 70 within the suturing instrument 900'. More specifically, as shown in FIG. 6D, the seat 622 is rotatable relative to the suturing instrument 900' as well as the chamber 610 to enable locking of the ferrule 70 to the suturing instrument 900'. For example, the rotation of the seat 622 enables rotation of the ferrule 70 to allow one or more recesses or indentations within the ferrule 70 to be received within teeth or projections 902 of the distal end (or distal tip) 920. In a particular example, the locking ring 620' of the base 620 (and thus base 620) is rotated 90 degrees anti-clockwise to allow for rotational coupling of the ferrule 70 to the ferrule receiving passage 933. In a specific example of this, where the base 620 had previously been rotatably locked to the housing 610' through a clockwise 90 degree rotation of the locking ring 620' with respect to the housing 610', the 90 degree anti-clockwise rotation also enables decoupling of the locking ring 620' from the housing 610'.

The base 620 (and thus the locking ring 620') may then be removed from the housing 610', as shown in FIG. 6E, leaving the housing 610' and ferrule 70 attached to the instrument distal portion 920. Removal of the base 620 allows the housing 610' to be advanced proximally along the suturing instrument 900' to be positioned along the instrument proximal portion or shaft 910, as shown in FIGS. 6F and 6G. As the housing 610' is advanced proximally along the shaft 910, it allows the pre-tied knot 502 that is mounted on it to be advanced past the tissue receiving gap 942 to be positioned about the shaft 910. The slot 628 within the housing 610' (for example, as shown in FIGS. 6B and 6I) provides clearance for routing the suture 500 to permit the housing 610' to be pulled proximally without getting caught on the suture 500. In some embodiments, the housing 610' may remain mounted on the shaft 910 during use of the suturing instrument 900' (to apply suture 500 within a region of tissue). Then the housing 610' may be slid distally along the instrument 900' past the tissue receiving gap 942 until it is positioned about the distal end 920. The knot 502 may be deployed off the housing 610' to secure the suture 500 within the region of tissue.

In an alternate embodiment, the base 620 of the cartridge 600' may remain coupled to the housing 610' during use of the cartridge 600'. As before, the cartridge 600' (including base 620 and housing 610') is mounted onto the device as shown in FIGS. 6A-6C. The base 620 (comprising the locking ring 620') is then rotated to lock the ferrule 70 within the ferrule receiving passage 933 of the suturing instrument 900', as illustrated in FIG. 6D.

In one such embodiment, the locking ring 620' (and base 620) may be rotated along with the housing 610'. In other words, the entire cartridge 600' may be rotated to lock the ferrule 70 within the ferrule receiving passage 933. With reference now to FIG. 6H, once the ferrule 70 has be loaded onto the suturing instrument 900', the suture loops or pre-tied knot 502 are then transferred to the instrument proximal portion or shaft 910. In a specific example, the pre-tied knot 502 may be peeled off the housing 610' and may be transferred manually onto the shaft 910. A slot 628 within the housing 610' (for example as shown in FIG. 6J) provides room for the suture 500 to exit the housing 610' to allow for removal of the cartridge 600' from the suturing instrument 900', as shown in FIG. 6H. In other words, the slot 628 provides clearance for the suture strand 500 to allow the cartridge 600' to be removed for example, by pulling the cartridge 600' distally.

Example 7

In accordance with an alternative embodiment of the present invention as illustrated in FIGS. 7A-7B, a suture loading apparatus (cartridge 700) is provided for loading a ferrule 70 onto a surgical suturing instrument 900'. The ferrule 70 has an end of a suture coupled to it (the suture is not shown for illustrative purposes). The method provides axial loading of the suturing instrument 900' using the cartridge 700. The method comprises moving the cartridge 700 such that the seat 722 carrying the ferrule 70 is dropped or positioned within the tissue receiving gap 742, with the instrument proximal portion or shaft 910 being received within recess 714 of the chamber 710, as shown in FIGS. 7C, 7D and 7E. More specifically, the recess 714 functions as a restraint and helps to position the suturing instrument 900' received within the chamber 710 with respect to seat 722 to align the seat 722 with the ferrule receiving passage 933. Thus, once the seat 722 is positioned within the tissue receiving gap 942 it is aligned with the ferrule receiving passage 933 within the distal tip 920 shown in FIG. 7E.

As shown in FIGS. 7F and 7I, the cartridge 700 is then advanced distally along the shaft 910 in sliding engagement with the shaft 910 such that the seat 722 travels axially within the tissue receiving gap 942 to be received within the ferrule receiving passage 933 to position the ferrule 70 therein. As the cartridge 700 is slid axially along the shaft 910, it remains in its initial configuration 700A. FIG. 7G illustrates a front end view of the cartridge 700 in its initial configuration 700A. FIG. 7L shows a cross-section of the housing 710' when the cartridge 700 is in its initial configuration. (For illustrative purposes, in FIGS. 7G and 7H, the cartridge is shown by itself and the suturing instrument 900' is not shown.)

The cartridge 700 is then rotated clockwise into its second configuration 700B, as shown in FIGS. 7I and 7M, to enable rotational locking of the ferrule 70 within the ferrule receiving chamber 933 of the suturing instrument 900. More specifically, in the embodiment shown, the cartridge 700 is rotated clockwise by about 90 degrees to couple the ferrule 70 mounted on the seat 722 to the ferrule receiving passage 933. FIGS. 7K and 7L show a front end view of the cartridge 700 and a cross-sectional view of the housing 710', respectively, when the cartridge 700 is rotated clockwise to be oriented in its second configuration 700B. (For illustrative purposes FIGS. 7K and 7L show the cartridge 700 on its own and the suturing instrument 900' is not shown.)

In further detail, as the cartridge 700 is rotated clockwise, it rotates the seat 722 and the ferrule 70. In a specific example as shown in FIG. 7G, the seat 722 comprises a D-shaped pin that forms the projection 730 for mounting the ferrule 70. The D-shaped pin allows the ferrule 70 to be rotated along with it as an interference fit is created between the pin and the ferrule 70 due to the matching D-shaped inner profile of the ferrule 70. As the ferrule 70 is rotated, it is locked within the instrument distal portion 920. For example, projections or teeth within the distal portion or tip 920 may be received within one or more recesses within the ferrule 70.

Figure 7N:
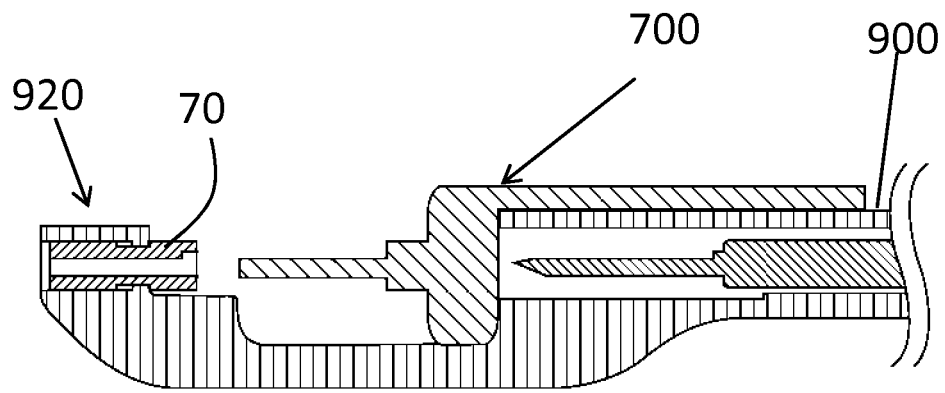
FIGS. 7N-7P illustrate steps of a method for loading suture onto a surgical suturing instrument using a cartridge in accordance with an embodiment of the present invention.
Figure 7O:
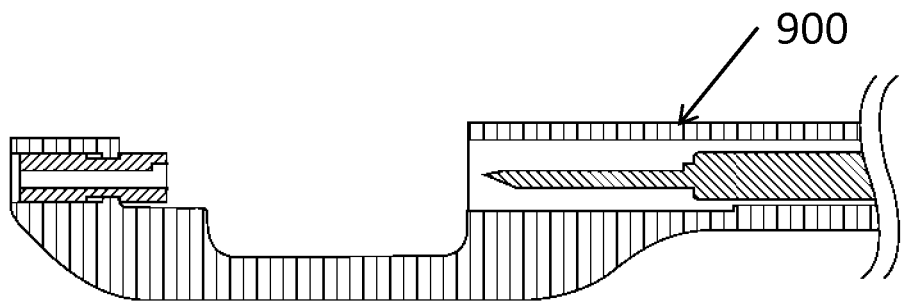
Figure 7P:
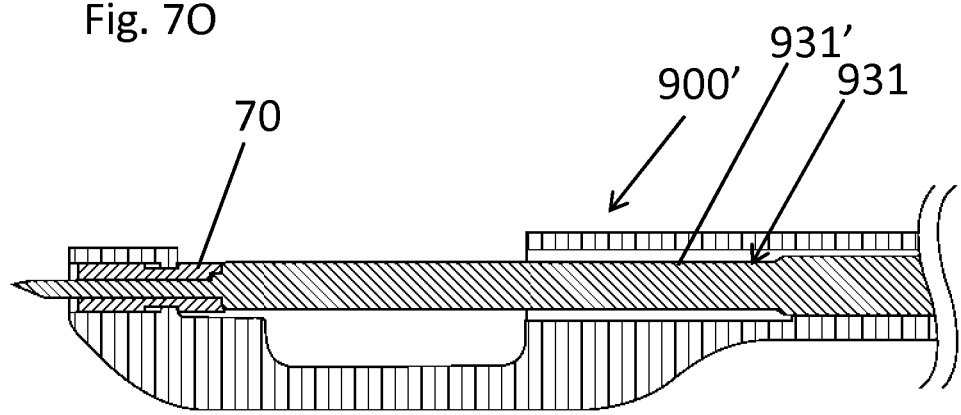

Once the cartridge 700 is used to position and lock the ferrule 70 within the ferrule receiving passage 733, the ferrule 70 is aligned with the longitudinal axis of the ferrule passing member 931 for example a needle 931', as shown in FIG. 7I. The cartridge 700 can then be withdrawn proximally, as shown in FIG. 7N. The cartridge 700 is moved axially with respect to the suturing instrument 900', with the chamber 710 being in sliding engagement with the shaft 910 and the seat being retracted axially into the tissue receiving gap 942. The cartridge 700 is then disengaged from the suturing instrument and removed, as shown in FIG. 7O. Since the ferrule 70 is aligned with the longitudinal axis of the ferrule passing member 931, the ferrule passing member 931 may then be advanced distally to be coupled to the ferrule 70 (that has a suture coupled thereto), which will allow the ferrule passing member 931 to pass suture through a region of tissue within the patient's body. In some embodiments, the housing 610' may additionally comprise a pre-tied knot to enable the pre-tied knot to be mounted onto the suturing instrument 900' to be deployed thereafter in order to secure suture that has been passed through tissue.

Example 8

With reference now to in FIGS. 8A-8G, in accordance with an alternative embodiment of the present invention, a suture loading apparatus (cartridge 800) is provided for loading one or more suture tabs 80 onto a surgical suturing instrument 900". The method provides for front end loading of the suturing instrument 900" using the cartridge 800.

Figure 8E:
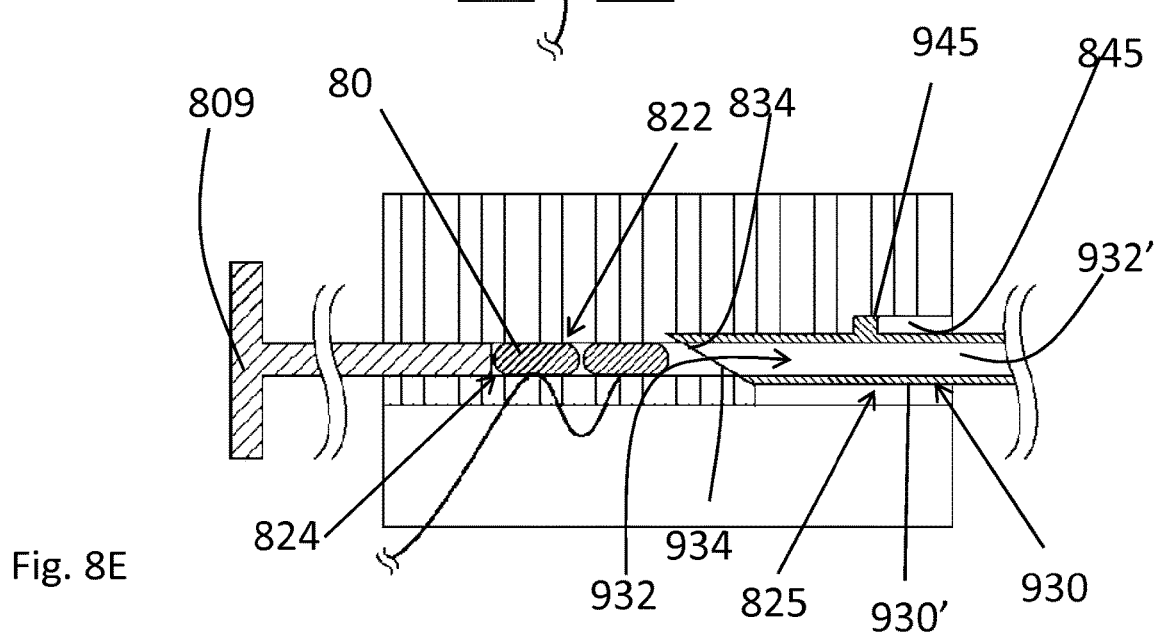
FIGS. 8E-8G illustrate cross-sectional views of a cartridge and the method of using the same to load suture onto a surgical suturing instrument in accordance with an embodiment of the present invention.

As a first step, the suturing instrument 900" (comprising suture passing member 930) is advanced axially with respect the chamber defined by the cartridge 800, as shown in FIG. 8E. In some embodiments, the suture passing member 930 comprises a needle 930', which is advanced distally through the chamber that defines the channel or recess 825. (The channel 825 is shown in FIG. 8B). Referring now to FIG. 8E, in a particular example, the channel 825 functions as a restraint and helps to position the needle 930' inserted through the channel 825, relative to the seat 822, for aligning the seat 822 with the suture receiving passage 932 (or in other words a tab receiving passage 932') of the suturing instrument. Additionally, the depth stop 945 of the needle 930' is received within a portion of the channel 825. In other words, the depth stop 945 is received within a portion of channel 825 that forms the depth stop cavity 845, rotationally aligning the needle 930' to the cartridge 800. This ensures that the cartridge slot 828 is aligned with the needle slot or longitudinal opening 928. (The depth stop cavity 845 is also shown in FIG. 8B).

Furthermore, as the needle 930' is advanced it is received within the alignment recess 830 (visible in FIG. 8B) to help align the seat 822 with the needle 930'. More specifically, the bevel face 834 defining the alignment recess 830 engages with the bevel face 934 of the needle 930' for docking the needle 930' to further align the suture receiving passage 932 of the needle 930' with the seat 822.

Figure 8F:
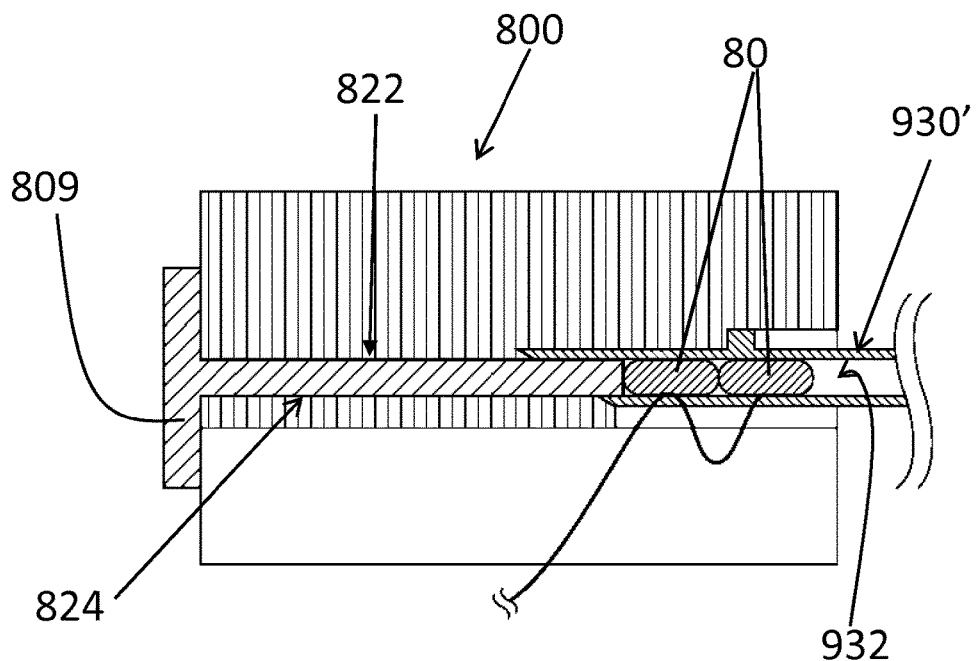

Once the needle 930' has been aligned with the seat 822, a plunger 809 is activated to push the tabs 80 into the suture receiving passage 932. The plunger 809 is pushed such that it moves proximally within the seat channel 824 to move the tabs 80 held within the seat channel 824 of the seat 822 into the suture receiving passage 932. As the tabs 80 are pushed into the suture receiving passage 932 of the needle 930', the suture 500 is also transferred from the slot 828 within the base 820 and into slot 928 of the needle 930', as shown in FIG. 8F. In this embodiment as illustrated in FIGS. 8A-8G, the suture receiving passage 932 may be referred to as the tab receiving passage 932', and is dimensioned to receive the tabs 80.

Figure 8G:
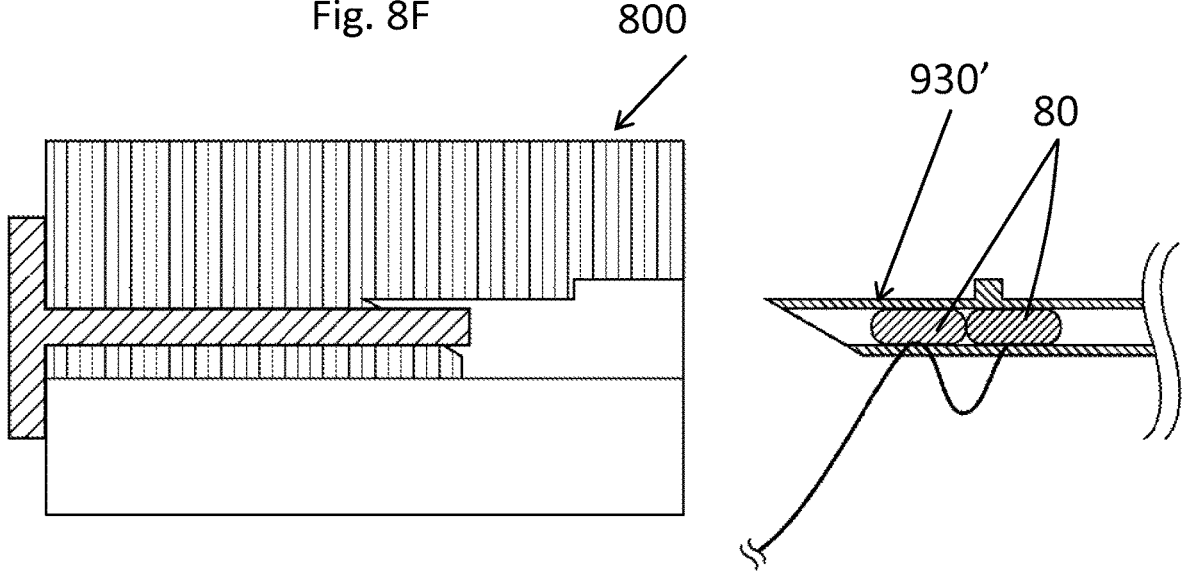

In some embodiments, the plunger 809 may be activated manually to push the tabs 80 into the suture receiving passage 932. Alternatively, the plunger 809 may be activated automatically. The plunger 809 may be coupled to/formed from an exterior housing. For example, after needle 930' has been advanced into the base 820 and positioned therein, an attempt may be made to advance the needle 930' distally, enabling distal movement of base 820 with respect to the exterior housing, which would allow the plunger 809 to advance proximally relative to the base 820 to push the tabs 80 to permit transfer of the tabs 80 (and the suture coupled thereto), from the seat 822 into the needle 930'. In an additional example, a rotatable pin may initially block the movement of the plunger 809, and as the needle 930' is advanced it may cause pin to pivot away from the path of the plunger 809. Then the needle 930' and the base 820 may be advanced distally with respect to the exterior housing to allow the plunger 809 to move automatically to push the tabs 80 into the needle 930'. The needle 930' (and the tabs 80 held therein) may then be removed from the cartridge 800, for example, by withdrawing the needle 930' proximally relative to the cartridge, as shown in FIG. 8G.

Example 9

Generally, embodiments of the present invention as outlined herein above provide a cartridge 1000 that permits axial loading of a suturing instrument 900 for example of the type described previously herein with reference to FIGS. 9A-9O. The suturing instrument 900 particularly provides a challenge as the instrument 900 defines an instrument distal portion 920 and an instrument proximal portion 910 defining a tissue receiving gap 942 there-between, where the suture passing member 930 that is to be loaded with suture is held within the instrument proximal portion 910.

Thus, in order to permit axial loading of the suturing instrument 900, the cartridge 1000 provides a means for aligning the suture with the suture passing member 930 by allowing the suture to remain out of the way of the advancing suturing instrument 900 to enable advancement of the instrument distal portion 920 without hindrance. Thus, the suture is kept out of the way of the suturing instrument 900 until the instrument distal portion 920 has advanced past the suture, allowing the suture to then be moved into the tissue receiving gap 942 thereafter to align the suture with the suture passing member 930 to transfer the suture therein.

In accordance with an embodiment of the present invention, with reference now to FIG. 10A, a method of use of the cartridge 1000 is disclosed for facilitating loading of suture 500 onto a surgical suturing instrument 900, for example, at the point of use. In some embodiments, a pivoting seat 1022 such as that defined by the rocker 1041 facilitates axial loading by enabling the rocker 1041 to remain out of the way of the path of the advancing suturing instrument 900 until the tissue receiving gap 942 is positioned within the rocker cavity 1027'. Once the suturing instrument 900 is in place, the cartridge 1000 enables the rocker 1041 to pivot down into the tissue receiving gap 942 such that the seat 1022 is positioned adjacent to and aligned with the suture passing member 930 such as a needle 930'.

As shown in FIG. 10A, the method provides for initially positioning the suturing instrument 900 within the cartridge 1000. The suturing instrument 900 is then passed axially through the cartridge 1000 to enable front end loading of the suturing instrument 900. More specifically, with reference to FIGS. 10A and 9C, the suturing instrument 900 is inserted into the opening 1016 within the housing 1010' and is guided by the beveled interior edge 1016' into the channel 1014 of the cartridge housing 1010' and advanced distally. As outlined above, channel 1014 extends longitudinally through the housing 1010' and is in communication with the base recess 1025 formed within the base 1020, forming a restraint 25. Thus, as the suturing instrument 900 is advanced through the cartridge 1000, it extends from the channel 1014 into the instrument receiving groove 1025a of the recess 1025 within the base 1020 that is in communication with the channel 1014. The restraint 25 constrains or limits the movement of the suturing instrument 900 in the transverse (i.e. up and down) and lateral directions, as well along a longitudinal path defined thereby. The restraint 25 enables the suturing instrument 900 to be advanced in sliding engagement therein to maintain the position to the suturing instrument 900 along a path that is in line with the final position of the seat 1022 to facilitate alignment therewith to enable transfer of suture into a portion of the suturing instrument. The suturing instrument 900 is then advanced further such that the distal portion or end 920 of the suturing instrument 900 exits recess 1025a of the base 1020. More specifically, in the illustrated embodiment as shown in FIG. 10A, as the suturing instrument 900 is advanced it passes through the instrument receiving groove 1025a of the base 1020 (shown in FIG. 9E) into the rocker recess 1027 of the base 1020, until it is received within the distal groove portion 1048 of the rocker 1041. As such, the suturing instrument 900 is positioned adjacent the suture 500 held within the suture groove 1025b (also shown in FIG. 9D). As outlined previously, the suture 500 is held within the cartridge 1000 such that the suture end 504 is held within the seat 1022 from where it exits into the pivot recess or cavity 1027, and is routed along the suture groove 1025b of the base recess 1025.

Referring again to FIG. 10A, the distal portion 920 of the suturing instrument 900 is initially received within the distal groove portion 1048 of the rocker groove 1044, with the rocker 1041 being in its initial or first position 1041A. As shown in FIG. 10B, upon advancement of the suturing instrument 900, the distal surface of the distal tip 920 then contacts and engages the bevel surface 1043 of the groove 1044 along the rear wall of the of the distal groove portion 1048. The instrument distal tip engages the bevel face 1043, exerting a force there-against to enable the rocker 1041 to move from its first position into its second position 1041B, as shown in FIGS. 10C(i), 10C(ii), and 10C(iii). More specifically, the distal portion 920 of the suturing instrument 900 is advanced with a sufficient force to enable the rocker 1041 to disengage from a location within the rocker recess 1027 where it is held in place in its initial position 1041A, as shown in FIG. 10A, for example by frictional engagement or a tab.

With reference again to FIGS. 10C(i), 10C(ii), 10C(iii), once rocker 1041 is released from engagement, it starts to pivot down. As the rocker 1041 pivots into position, the proximal portion 910 of the suturing instrument 900 is received into the proximal groove portion 1046. The pivotal movement of the rocker 1041 enables the suturing instrument 900 to be loaded axially by allowing the distal end 920 to advance past the seat 1022 of the rocker 1041 before the rocker 1041 pivots down into the tissue receiving gap 942 such that the seat 1022 is now positioned within the tissue receiving gap 942 of the suturing instrument 900. As shown in FIG. 10D, the surgical suturing instrument 900 is then advanced further into the base 1020 until the suture passing member 930 such as the needle 930' is in abutting contact with the seat 1022. Once the needle 930' abuts the projection 1030, it halts the movement of the suturing instrument 900 with respect to and within the cartridge 1000. More specifically, as shown in FIG. 10D and earlier with reference to FIG. 9M, the bevel face 934 of the needle 930' is in abutting contact with bevel face 1034 of the projection 1030 that defines the seat 1022, such that the needle slot 938 and the shaft slot 928 [behind the needle 930' and the projection 1030 that forms the seat 1022] are in line with and adjacent to the seat slot 1028. The shaft slot 928 and the needle slot 938 are visible in FIGS. 1D and 1E, as discussed earlier.

In some embodiments of the present invention, in order to align the suture 404 with a suture receiving feature of the suturing instrument 900 (such as suture receiving passage 932 within suture passing member 930) a magazine in the form of a rocker 1041 is provided. The rocker is operable to be mechanically interlocked with the suturing instrument such that when the suture cartridge is inserted over the suturing instrument and pressed, the rocker 1041 is configured to rotate down, aligning the suture end 504 with the suturing instrument. In some such embodiments, the rocker 1041 grabs onto the suturing instrument 900 to align the suture end 504 in the X-axis (laterally) and Y-axis (transverse/vertical or up and down directions) and constrains the rotation of the suture end in the X and Y rotational directions. Furthermore, the rocker 1041 mates with and is pushed proximally up to the suturing instrument 900 to align the suture in the Z-axis (linear or longitudinal directions).

Figure 12A:
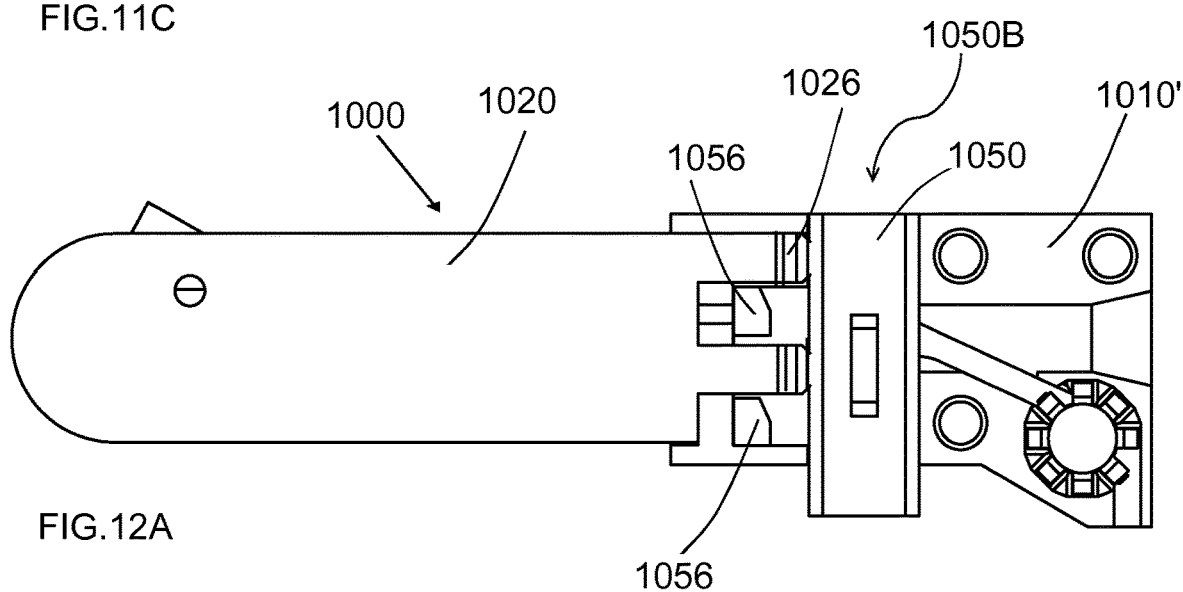
FIGS. 12A-12B illustrate views of an interlock mechanism of a cartridge in accordance with an embodiment of the present invention.
Figure 12B:
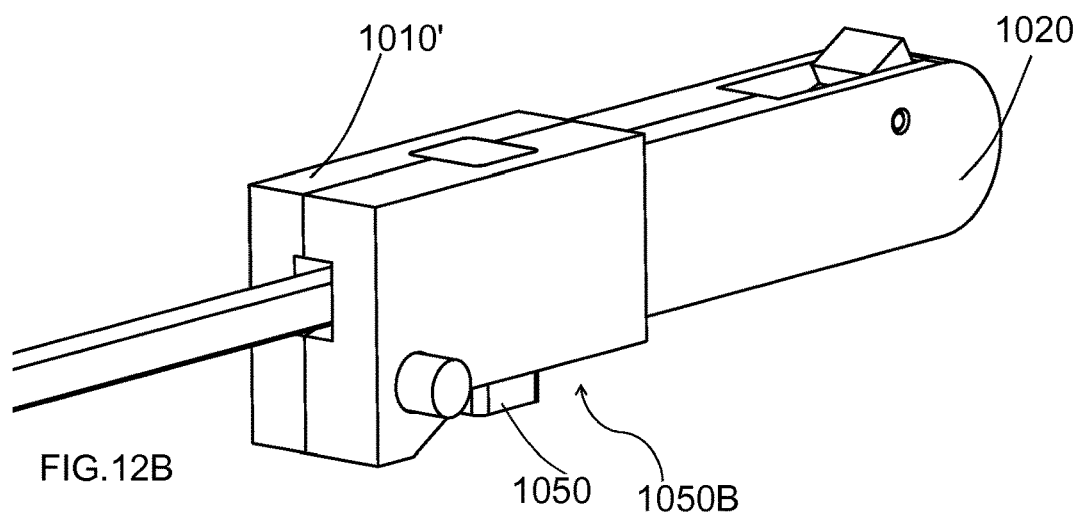

As outlined previously, up until this point the interlock 1050 remains in its initial locked position 1050A, which ensures that the base 1020 remains coupled to the housing 1010', as shown in FIGS. 11A and 11C. As further illustrated in FIG. 11B, in this position the interlock arms 1056 are positioned axially adjacent the locking arms 1026 of the base, and prevent the movement of the base 1020 relative to the housing 1010'. As such, the locking arms 1026 of the base 1020 are in engagement with the interlock arms 1056. However, once the seat 1022 and thus the suture end 504 has been aligned with the needle 930', the cartridge 1000 enables direct transfer of the suture end 504 into the needle 930' using the housing 1010'. In other words, when the seat 1022 is in alignment with and adjacent to the bevel face 934 of the needle 930', the suture end (held in a force fit inside the seat 1022) can then be transferred into the needle 930' (as shown in FIGS. 9M and 10D). As shown in FIGS. 12A and 12B, the interlock 1050 is then moved from its locked position 1050A to its unlocked position 1050B to disengage the housing 1010' (which defines a suture transferring component 1011 as discussed previously herein) from the base to transfer the suture onto the suturing instrument 900. More specifically, the housing 1010' and as such the suture transferring component 1011 defined thereby, is detached from the base 1020 allowing the housing 1010' to be pulled back such that the suture end 504 is transferred into the needle 930', as shown in FIG. 13A. The detached base 1020 may be removed thereafter as shown. As such, the cartridge 1000 of the present embodiment allows suture to be independently transferred from the cartridge 1000 into the suture passing instrument 900. In additional embodiments, where suture loops that form a partially pre-tied knot may be mounted about the housing 1010', the housing 1010' additionally provides for loading a partially pre-tied knot on the suturing instrument 900.

In some embodiments, once the suture end 504 has been loaded into the needle, the housing 1010' may then be removed. In other embodiments, where the housing provides a partially pre-tied knot and/or carries excess suture therein for example in a spool, the housing 1010' may remain mounted on the instrument proximal portion 910 to retain the partially pre-tied knot and or excess suture on the suturing instrument 900. In the embodiment illustrated in FIGS. 13A-13E, the suture lock 1060 may be disengaged to allow the housing 1010' and as such the suture transferring component 1011 defined thereby to be disengaged with the suturing instrument 900 after the suture end 504 has been loaded onto the suturing instrument 900. With reference now to FIGS. 13A-13B, 13E, which illustrate the lock in its initial locked configuration 1060A. As discussed previously, herein in the initial locked configuration 1060A, the suture 500 is routed through the suture lock engaging component 1062 of the housing 1010', and the suture lock 1060 is press fit in the suture lock engaging component 1062, thereby pressing the suture 500 between the teeth 1064 of the suture lock 1060 and the corresponding teeth 1064' of the suture lock engaging component 1062. As such, the suture 500 is coupled to the housing 1010'. In order to release the lock 1060, the lock is then moved into its second position 1060B, as shown in FIGS. 13D and 13F, moving the teeth 1064, 1064' out of engagement with one another and releasing the suture held therein. The housing 1010', and thus the suture transferring component 1011, may then be removed from the suturing instrument 900.

Thus, embodiments of the present invention provide a cartridge 1000 that provides a means to load suture into a suture passing instrument of the type as described herein (such as suturing instrument 900) having an instrument proximal portion 910 and an instrument distal end 920 defining a tissue receiving gap 942 there-between. The current embodiment additionally facilitates automatic alignment of suture 500 (for example end 504 of the suture 500) by allowing the rocker 1041 to pivot into the tissue receiving gap upon engagement with the instrument distal end 920 as it is being advanced into the cartridge 1000.

As such, in terms of a general overview of the embodiment described herein above in Example 9, in some embodiments, in order to facilitate insertion of the suture portion held within the cartridge, alignment of the suture portion may be required and three basic mechanical events may be configured to take place: (i) an applied force on the suture relative to the suture passer in one direction [for example, in a proximal direction]; (ii) relative motion between the suture and the suture passer in the same direction; and (iii) relative motion between the suture and the seat in the opposite direction.

In some such embodiments, a suture cartridge is provided that exerts a force on the end of the suture to load it into the surgical suturing instrument or the suture passer. In an example, all mechanical events achieved by the suture cartridge device are obtained in a single "pump" action performed by the user, and in some embodiments may not require actuation of the suture passer (suturing instrument) trigger. In some such embodiments, the single "pump" action maybe likened to that of a shotgun loading action.

As such, in some embodiments of the present invention, a suture cartridge is provided that uses a pulling force on the end of the suture to load it into the suture passer as outlined in Example 9 herein above. In some embodiments, a pull method may be used to insert suture into a suture passer that allows space for a generally straight-line pull of the suture in the direction of loading. In some situations, the pull method may be used when it may be required that the suture stay managed/in tension throughout the loading procedure.

In terms of a broad overview, a part of the cartridge that is independent from the seat locks onto the suture limb. The mechanical events to insert the suture occur in the following ways: (i) to apply the force to the end of the suture, the strand of suture is pulled in the middle by grasping the strand with the suture lock; (ii) to achieve relative motion between the suture and suture passer, the suture passer is fixed with respect to the suture such that when the applied pulling force is exerted onto the suture, the suture passer stays still and the suture moves towards and into the suture passer; and (iii) to achieve relative motion between the suture and the seat (in the Suture cartridge). The seat is also fixed with respect to the suture such that when the applied pulling force is exerted onto the suture, the seat stays still and the suture moves away from and out of the seat.

In some embodiments, a pull insertion mechanism is provided that has a suture lock which is a piece that can move independently from the cartridge base, and the suture passer that holds the suture proximally to the seat and is moved away from the seat, thus pulling the suture and creating the required force and relative motion.

In some embodiments, the suture lock automatically decouples from the cartridge base once the seat has fully aligned the suture (suture portion) with the suture passer.

This is done by way of an interlock that prevents the suture lock from moving relative to the cartridge base until the full alignment step has occurred (i.e. prevents the suture from being pulled before it is fully aligned).

In some embodiments, the pull insertion mechanism comprises a suture lock that automatically unlocks from the suture once the suture (e.g. suture end) has been successfully loaded into the suture passer. As such, unlocking of the suture allows the suture passer to pass the suture freely. In some examples, unlocking the suture lock is performed by way of an interlock which prevents unlocking to occur until the point at which the suture is successfully loaded into the suture passer. In one such example, the suture lock interlock may be force/displacement based using a spring to ensure that a given amount of force is exerted on the suture to obtain a given displacement of the suture lock (as shown in FIGS. 32A-32D). In some embodiments, the force may be calibrated to be much greater than the maximum theoretical/empirically derived force required to successfully load the suture. Once this force is achieved, a certain displacement may also be achieved, causing the interlock to unlock the suture.

In some such embodiments, a pre-tied knot is provided on a knot slider that is integrated with a suture lock and houses the suture strands. The knot slider remains on the suture passer after the suture cartridge is actuated to load the suture into the suture passer, and functions to release the suture knot to the surgical site once the suture passer is used.

Example 10

In accordance with an embodiment of the present invention, with reference now to FIGS. 15A(i)-16D(ii), a method of use of the cartridge 2000 is disclosed for facilitating loading of suture 500 onto a surgical suturing instrument 900, for example, at the point of use. In some embodiments, a pivoting seat 1022, such as that defined by the rocker 1041, facilitates axial loading by enabling the rocker 1041 to remain out of way of the path of the advancing suturing instrument 900 until the tissue receiving gap 942 is positioned substantially within the rocker cavity 1027'. Once the suturing instrument 900 is in place, the cartridge 1000 enables the rocker 1041 to pivot down into the tissue receiving gap 942 such that the seat 1022 is positioned adjacent to and aligned with the suture passing member 930 such as a needle 930'. The cartridge 2000 additionally provides a suture transferring component 2011 for transferring the suture end 504 from the seat 1022 into the suture receiving recess 932 of the suturing instrument 900. The cartridge 2000 additionally provides a knot slider 2030 that permits loading of a pre-tied knot 502 onto the suturing instrument 900.

In some embodiments, the method provides for initially positioning the suturing instrument 900 within the cartridge 2000. The method is described in reference to the advancement of the suturing instrument 900 within the cartridge 2000. However, in some such embodiments, the cartridge 2000 is loaded onto the suturing instrument 900 via a proximal movement of the cartridge 2000 over the suturing instrument 900. As such, the suturing instrument 900 and the cartridge 2000 are moveable relative to one another.

With reference now to FIG. 15A(i), the cartridge 300 is loaded proximally over the suturing instrument 900, with the suturing instrument 900 being passed axially through the cartridge 3000 to enable front end loading of the suturing instrument 900. More specifically, the suturing instrument 900 is inserted through the chamber 1010 of the housing 1010' defined by the knot slider 2030. The suturing instrument is guided by the beveled interior edge 2016' of the opening 2016 into the channel 2014 of the knot slider (as shown in FIG. 14D and FIG. 15A(iii)), and as such mounting the knot slider 2030 and the pre-tied knot mounted onto the suturing instrument. As the suturing instrument 900 is advanced further, it is received within the instrument receiving groove 2025a of the base recess 2025 within the base 2020. The base recess 2025 and the channel 1014, function as the restraint 25 to constraint or limit the movement of the suturing instrument 900 in the transverse (i.e. up and down) and lateral directions, as well as along a longitudinal path defined thereby. The restraint 25 enables the suturing instrument 900 to be advanced in sliding engagement therein to maintain the position to the suturing instrument 900 along a path that is in line with the final position of the seat 1022 to facilitate alignment therewith to enable transfer of suture into a portion of the suturing instrument. The instrument receiving groove 2025a guides the suturing instrument into the rocker recess 1027. As outlined previously, the suture 500 is held within the cartridge 2000 such that the suture end 504 is held within the seat 1022 from where it exits into the pivot recess or cavity 1027 and is routed along the suture groove 1025b of the base recess 1025. As such, the suturing instrument 900 is positioned adjacent the suture 500 held within the suture groove 1025b, also shown in FIGS. 14F(i), 14F(ii).

Referring again to FIG. 15A (i),(ii), the distal portion 920 of the suturing instrument 900 is initially received within the distal groove portion 1048 of the rocker groove 1044, with the rocker 1041 being in its initial or first position 1041A. Upon advancement, the instrument distal tip 920 contacts and engages the bevel surface 1043 along the rear wall of the of the distal groove portion 1048, exerting a force thereagainst to move the rocker 1041 to rom its first position 1041A into its second position 1041B, as shown in FIGS. 15B(i),(ii). More specifically, the distal portion 920 of the suturing instrument 900 is advanced with a sufficient force to enable the rocker 1041 to disengage from the friction tab 2029 within the rocker recess 1027 where it is held in place in its initial position 1041A, as shown in FIG. 15A(i).

With reference again to FIGS. 15B(i), 15B(ii), once rocker 1041 is released from engagement within the rocker recess 1027, it starts to pivot down into the rocker cavity 1027'. As the rocker 1041 pivots into position, the proximal portion 910 of the suturing instrument 900 is received into the proximal groove portion 1046. The pivotal movement of the rocker 1041 enables the suturing instrument 900 to be loaded axially by allowing the distal end 920 to advance past the seat 1022 of the rocker 1041 before the rocker 1041 pivots down into the rocker cavity 1027' that corresponds to the tissue receiving gap 942 such that the seat 1022 is now positioned within the tissue receiving gap 942 of the suturing instrument 900.

In some embodiments of the present invention, in order to align the suture 504 with a suture receiving feature of the suturing instrument 900 (such as suture receiving passage 932 within suture passing member 930) a magazine in the form of a rocker 1041 is provided that is operable to be mechanically interlocked with the suturing instrument such that when the suture cartridge is inserted over the suturing instrument and pressed, the rocker 1041 is configured to rotate down, aligning the suture end 504 with the suturing instrument. In some such embodiments, the rocker 1041 grabs onto the suturing instrument 900 to align the suture end 504 in the X-axis (laterally) and Y-axis (transverse/vertical or up and down directions) and constrains the rotation of the suture end in the X and Y rotational directions. Furthermore, the rocker 1041 mates with and is pushed proximally up to the suturing instrument 900 to align the suture in the Z-axis (linear or longitudinal directions).

As shown in FIG. 15B (i),(ii), the surgical suturing instrument 900 is then continued to be advanced into the base 2020, upto/until the suture passing member 930 such as the needle 930' is in abutting contact with the seat 1022. Once the needle 930' abuts the projection 1030, it halts the movement of the suturing instrument 900 with respect to and within the cartridge 1000. More specifically, as shown in FIG. 10D and earlier with reference to FIG. 9M, the bevel face 934 of the needle 930' is in abutting contact with bevel face 1034 of the projection 1030 that defines the seat 1022 such that the needle slot 938 and the shaft slot 928 [behind the needle 930' and the projection 1030 that forms the seat 1022] are in line with and adjacent to the seat slot 1028. The shaft slot 928 and the needle slot 938 are visible in FIGS. 1D and 1E, discussed earlier.

As outlined previously, up until this point the interlock 2050 remains in its initial locked position 1050A which ensures that the base 1020 remains coupled to the housing 1010', as shown in FIGS. 15A(i), 15A(ii). As further illustrated in FIGS. 15C(i), 15C(ii), in this position the interlock arm 2056 is positioned axially adjacent and distal to the base 2020. The interlock arm prevents the movement of the base 2020 relative to the housing 2010'. However, as the seat 1022 moves into the rocker cavity 1027' of the rocker recess 1027 (and thus the suture end 504 aligned with the needle 930') the rocker bar 2055 moves the interlock tab 2054 adjacent the base wall 2054' to be positioned out of way of the interlock 2050. As shown in FIGS. 15D(i), 15D(ii), the interlock 2050 is then moved from its locked position 2050A to its unlocked position 2050B to disengage the base 2020 from the housing 1010', which defines a suture transferring component 1011 as discussed previously herein. This allows the base 2020 and the knot slider 2030 attached thereto to slide distally as the housing sleeve 1011' is pulled proximally (FIGS. 15E(i), 15E(ii)). In the illustrated example, the interlock 2050 is moved by the user.

Upon relative movement of the suture transferring component 1011 proximally relative to the base 2020, the base 2020 moves distally and presses against the push sleeve hub 2012 that moves distally within the sleeve cavity 2012'. As the push sleeve hub 2012 is biased towards the base 2020 via a spring mechanism [that comprises two springs 2013], it functions to push the push rod hub 2057 upon translation of the suture transferring component 2011 with respect to the base 2020. The push rod hub 2057 translates proximally within push rod cavity 2057' (FIG. 15B(ii), FIG. 15E(ii)) causing the longitudinally extending wire 2053' to translate proximally within the wire channel 2053 in communication with the seat 1022 to push the suture end 504 held within the seat 1022 into the suture receiving passage 932 of the suturing instrument 900.

Figure 15F:
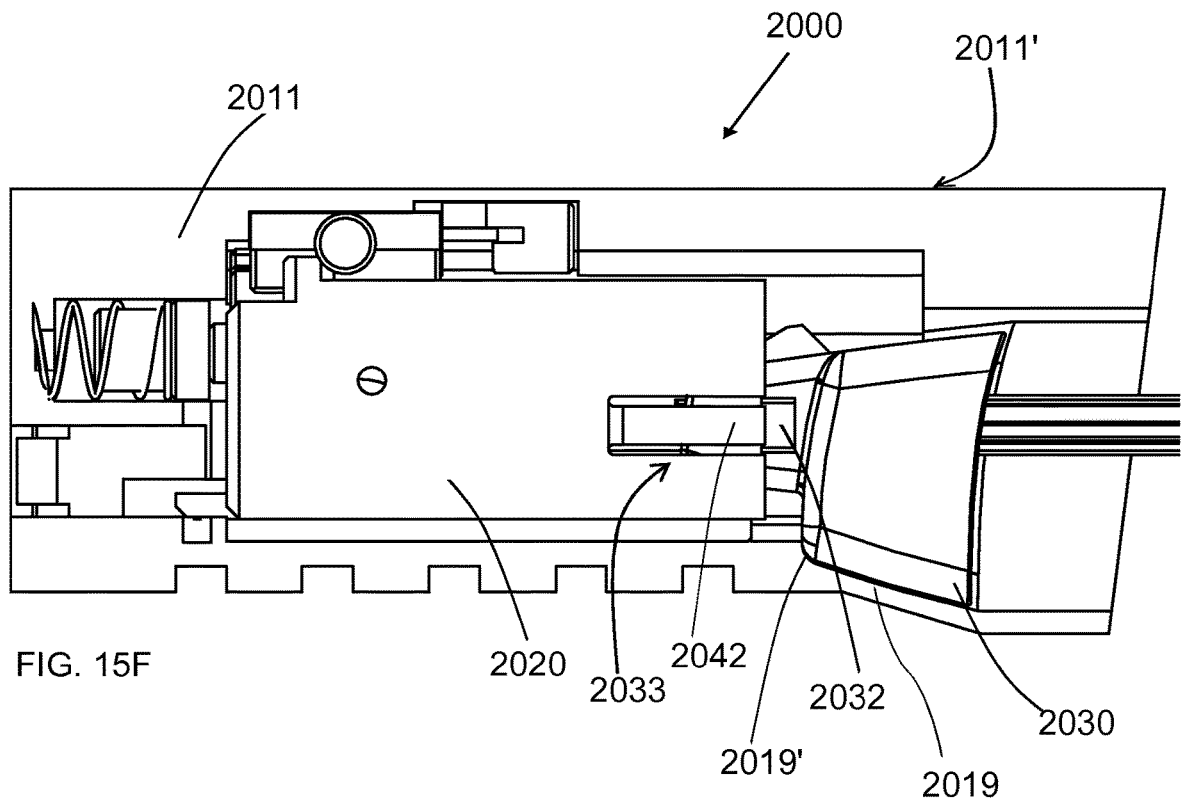

As the base 2020 is advanced distally, the knot slider 2030 is moveable with base 2020 the knot slider 2030 is moveable distally along the knot slider recess 2018 within the housing sleeve 2011' upon distal movement of the base 2020 within the housing sleeve 2011'. However, the wall of the housing sleeve 1011' adjacent the tapered inner wall 2019 (as shown in FIG. 14B) of the knot slider recess 2018 functions as a stop to prevent further distal movement of the knot slider 2030 to disengage snap arms 2042 of the base 2020 from the snap grooves of the knot slider 2030, as shown in FIG. 15F. As such, the knot slider release interlock 2033 is disengaged, releasing the knot slider 2030. In additional embodiments, where suture loops that form a partially pre-tied knot may be mounted about the housing 1010', the housing 1010' additionally provides for loading a partially pre-tied knot on the suturing instrument 900.

In some embodiments the suture is contained within tubing (for example inside a PTFE tube) mounted on the inside the knot slider 2030 (as shown in FIG. 27D), the cartridge additionally provides for loading or mounting the suture limbs within the knot slider 2030 on the suturing instrument 900 along with the partially pre-tied knot.

Figure 16A:
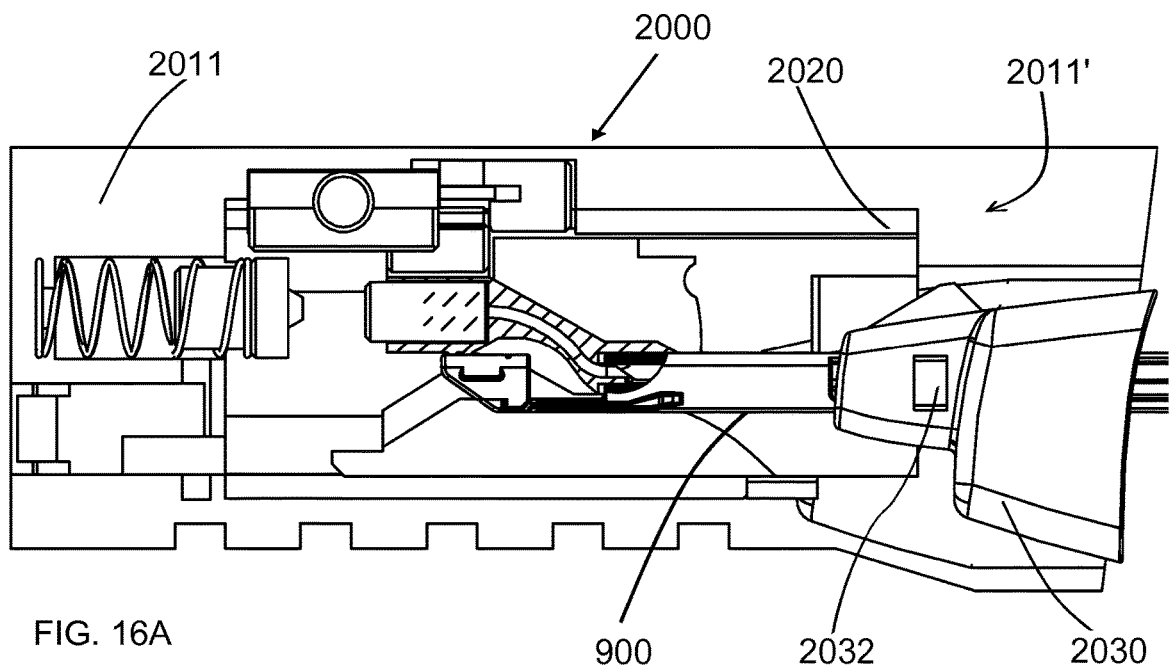
Figure 16B:
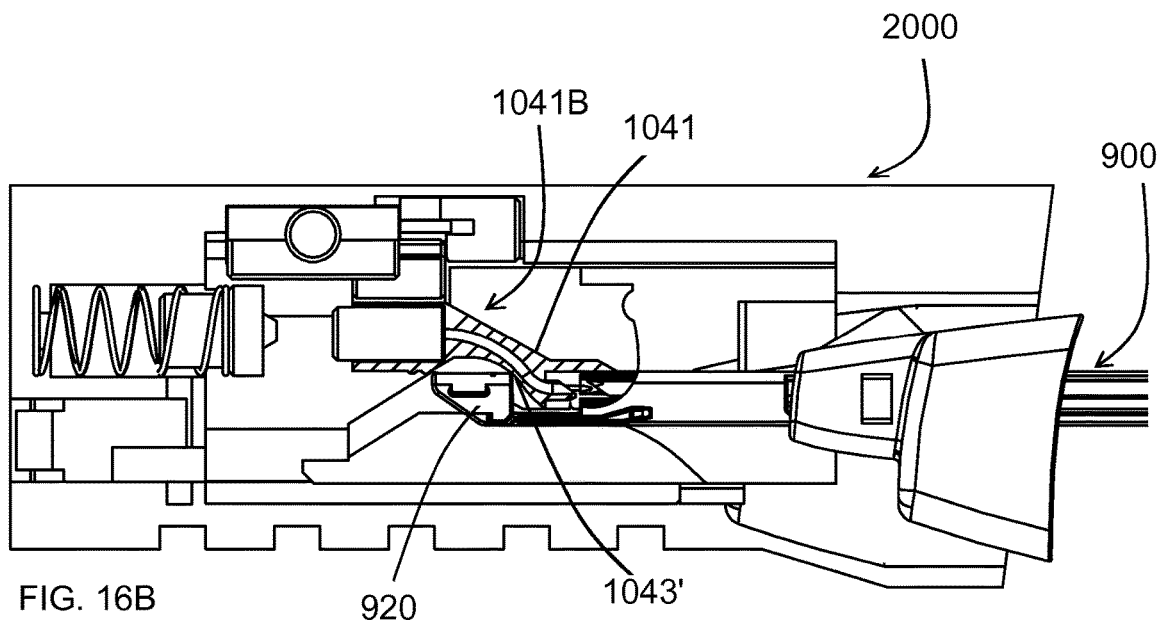
Figure 16C:
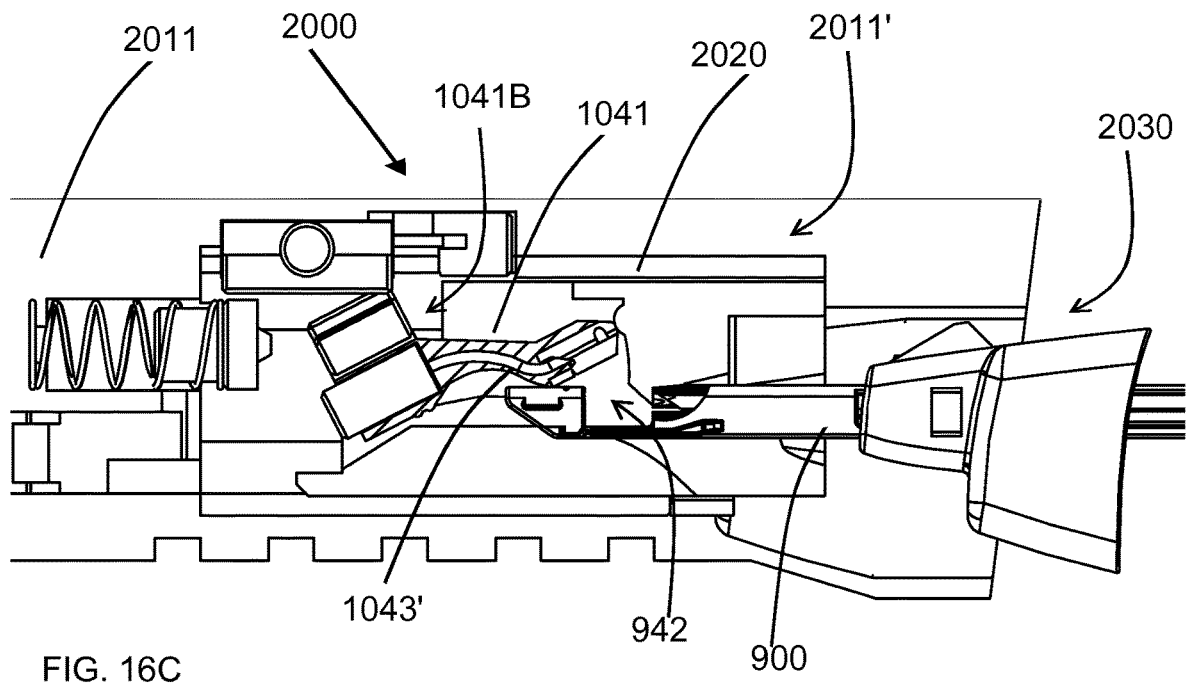

In some embodiments, once the suture end 504 has been loaded into the needle, the housing 1010' the cartridge 2000 may then be removed and may be pulled proximally. As such, in some embodiments the cartridge 2000 is loaded onto the suturing instrument 900 and removed thereafter using a pumping action. The relative movement of the suturing instrument with respect to the cartridge 2000 is in a proximal direction. As the suturing instrument 900 is pulled proximally, the knot slider 2030 remains mounted thereon and is removed with the suturing instrument 900 (as shown in FIG. 16A). As the suturing instrument 900 is retracted, the distal head 920 interacts with the bevel face 1043' of the rocker 1041 (FIG. 16B). This enables the rocker 1041 to move out from the tissue receiving gap 942, allowing the suturing instrument 900 to be removed without hindrance, as shown in FIG. 16C.

The knot slider arm 2034 is slidable along the instrument window or groove 965 in said inner position 2034A. The knot slider arm 2034 may remain in its initial position 2034A as it is slid proximally along the instrument proximal portion or shaft 910, for example to be attached with a handle portion 960 of the instrument 900 (as shown in FIG. 27A). Once the instrument 900 has been used to pass suture, the tissue the instrument 900 may be used thereafter to deploy the pre-tied knot 502. As the instrument 900 is pulled back proximally after suturing, the knot slider 2030 disengages from the handle portion of the suturing instrument and slides distally along the shaft proximal portion of the suturing instrument 900. As shown in FIG. 17B, as the knot slider slides distally along the shaft 910 it engages with a front wall 965' of the shaft groove 965, causing the knot slider arm 2034 to move out from the slider groove 2036 into said external position 2034B to enable positioning of said knot slider 2030 over the tissue receiving gap 942 (as shown in FIG. 17C) such that a cover arm 2038 of the knot slider is positioned over the tissue receiving gap 942. This enables deployment of the pre-tied knot 502 from the knot slider 2030 while maintaining engagement of the knot slider 2030 with the suturing instrument 900, and as such prevents the pre-tied knot from falling in or getting caught in the tissue receiving gap 942.

Thus, embodiments of the present invention additionally provide a cartridge 2000 that provides a means to load suture into a suture passing instrument 900 of the type as described herein having an instrument proximal portion 910 and an instrument distal end 920 defining a tissue receiving gap 942 there-between. The current embodiment additionally facilitates automatic alignment of suture 500 (for example end 504 of the suture 500) by allowing the rocker 1041 to pivot into the tissue receiving gap upon engagement with the instrument distal end 920 as it is being advanced into the cartridge 1000. Furthermore, cartridge 2000 provides a suture transferring component 2011 to transfer suture into the suture passing member and additionally provides a knot slider 2030 to mount a pre-tied knot 502 onto the suturing instrument 900.

As such in terms of general overview of the embodiment described herein above in example 10, in order to facilitate insertion of the suture portion held within the cartridge, alignment of the suture portion must have occurred and three basic mechanical events are configured to take place: (i) an applied force on the suture relative to the suture passer in one direction (for example proximally); (ii) relative motion between suture and suture passer in the same direction; and (iii) relative motion between the suture and the seat in the opposite direction.

In some such embodiments, a suture cartridge is provided that exerts a force on the end of the suture to load it into the surgical suturing instrument or the suture passer. All mechanical events achieved by the suture cartridge device are obtained in a single "pump" action performed by the user and in some embodiments may not require actuation of the suture passer (suturing instrument) trigger. In some such embodiments the single "pump" action maybe likened to that of a shotgun loading action.

In some such embodiments, a suture cartridge is provided that uses a pushing force on the end of the suture to load it into the suture passer, as outlined in example 10 herein above. In one such example, the cartridge applies a direct pushing force to the suture to load it onto the suture passer.

In some embodiments, the cartridge comprises a push rod which is a part of the cartridge independent from the seat and suture passer. The push rod exists inside the seat and, upon actuation, presses against the end of the suture to push it forwards in the seat.

In some embodiments, the mechanical events to insert the suture occur in the following ways: (i) to apply the force to the end of the suture, a flexible, moveable push rod exists in an S-shaped lumen that exists in the seat. The push rod has a tip that contacts the suture; (ii) to achieve relative motion between the suture and suture passer, the suture passer is fixed with respect to the suture such that when the applied pushing force is exerted onto the suture, the suture passer stays still and the suture moves towards and into the suture passer; (iii) to achieve relative motion between the suture and the seat (in the suture cartridge), the seat is also fixed with respect to the push rod and suture such that when the applied pushing force is exerted onto the suture, the seat stays still and the suture moves away from and out of the seat.

In some embodiments, once insertion of the suture has been achieved, a part of the cartridge that contains the suture limbs (such as the knot slider) detaches from the cartridge and remains attached to the suture passer. The remaining cartridge base is then discarded, leaving the suture passer fully loaded with suture and with the knot slider attached. In some embodiments, the push method can be used when a high loading force is required.

In some embodiments, the cartridge mechanism comprises a push rod that is a piece that can move independently from the cartridge base, seat, and suture passer. The push rod exists inside the seat and, upon actuation, presses against the end of the suture to push it forwards in the seat.

In some embodiments, the push insertion mechanism is configured such that the push rod pushes the suture once the seat has fully aligned the suture with the suture passer. This may be done by way of a series of interlocks that prevent the push rod from moving relative to the seat until the full alignment step has occurred (i.e. prevents the suture from being pushed before it is fully aligned). One such interlock is a rocker interlock to prevent the rocker from moving until shaft is inserted (tab or detent 2029 as shown in FIG. 14C). In some embodiments the rocker geometry may be such that it prevents the seat member from contacting the shaft during rocker rotation. For example, bevel 1043 in FIG. 15A(i) of the rocker and its location and configuration in reference to the seat ensures that the seat does not contact the shaft as the instrument is advanced. In some embodiments the interlock comprises a cartridge base (magazine) interlock (e.g. interlock 2050 discussed above) to prevent the cartridge base from moving before seat is aligned with the needle. In some embodiments the interlock comprises a push rod interlock to prevent the push rod from moving before the seat is aligned with the needle. Some embodiments comprise a push spring. In some embodiments, the push rod is actuated with a spring (as outlined above in example 10) to ensure that a given amount of force exerted on the suture results in a given displacement of the push rod. This force may be calibrated to be much greater than the maximum theoretical/empirically derived force required to successfully load the suture. Once this force is achieved, a certain displacement would also be achieved and the interlock would unlock the suture.

In some embodiments, as outlined previously herein above, the cartridge is configured for containing a pre-tied knot on a knot slider which also houses the suture strands. The knot slider (for example knot slider 2030 as described above) automatically detaches from the cartridge base and remains on the suture passer after the suture cartridge is actuated. The knot slider functions to release the suture knot to the surgical site once the suture passer is used.

In some embodiments an interlock may be provided, such as a knot slider release interlock (for example knot slider release interlock 2033 as described above, which prevents the knot slider from releasing until the suture has been loaded into the needle. In some embodiments, there may be an additional suture retention interlock that prevents the suture limb from moving until the shaft is removed from the cartridge.

In some embodiments of the present invention, the cartridge comprises suture storage. As outlined previously with reference to FIG. 17D, in some embodiments the cartridge stores the suture limbs within the knot slider inside a PTFE tube. The PTFE tube allows the suture to be released with a constant and small force. In some embodiments, a silicone O-Ring provides a dampening effect on the release of the suture to achieve a smoother, more constant force of release, and to retain tautness in the suture throughout the procedure.

Furthermore, as outlined in example 10, the cartridge comprises knot slider retention features on the shaft. In some embodiments, the cartridge has a knot slider that contains a tail hook that retains the knot slider on the suture passer shaft at the end of the procedure. As outlined previously, the tail hook is enclosed within the knot slider and once the knot slider slides to the end of the shaft, the tail hook slides out of the knot slider and hooks onto the shaft.

Thus, as described herein above, various embodiments of a cartridge, and methods of use thereof, are disclosed. These embodiments provide a cartridge for loading suture at the point-of-use onto a surgical suturing instrument such as a suture passing instrument or suture passer, where the suturing instrument includes a suture passing member onto/into which the suture is to be loaded, and where the application requires/benefits from a pre-tied knot. In some embodiments, a suture loading cartridge is provided with a feature for securing a pre-tied knot with the ability to deploy the pre-tied knot onto the suture passer (for example by passing the suturing instrument through a chamber of the cartridge that has the knot tied about it), as well as a second feature for aligning a suture end with the suture passing member of the suture passer to facilitate loading of the suture onto/into the suture passing member. In some embodiments, the second feature for aligning the suture may be movable with respect to the first feature (so that the suture passer can be inserted into the cartridge through the pre-tied knot after which a suture end loaded into the cartridge can be brought into alignment with the suture passing member).

In some embodiments, a restraint (means for restraining) may be provided for positioning a portion of the suturing instrument received through the chamber relative to the suture end for aligning the suture end with a suture receiving passage of the suture passing member. In some embodiments, a cartridge is structured to allow the seat to be brought into alignment with (a suture receiving passage of) a suture passing member received through/within the chamber. In some embodiments, the seat is movable relative to the chamber for aligning suture strand with a (suture receiving passage of a) suture passing member.

Furthermore, as described herein above, various embodiments of a cartridge, and methods of use thereof, are disclosed. In some embodiments, the method involves aligning an end of the suture strand with a suture receiving passage of a suture passing member of the suturing instrument to allow the suture strand to be received within the suture passing member to be coupled thereto.

Additionally, some embodiments of the present invention provide a method for suturing within an inter-vertebral disc, the method comprising the steps of loading a suture onto a surgical suturing instrument using a cartridge; and using the surgical suturing instrument to deliver the suture into the inter-vertebral disc. As a feature of this broad aspect, the step of loading the suture is performed at the point of use.

Further Examples

NOTE—in the following examples, the term "portion" as used in different examples may refer to the same or different portions of particular features or components.

In one example, embodiments of the present invention comprise a cartridge for loading a suture onto a suturing instrument and for loading a pre-tied knot formed from the suture onto the suturing instrument, the surgical suturing instrument being of the type having a suture passing member defining a suture receiving passage therein. The cartridge comprises a housing defining a chamber comprising a (means for securing/mounting) mount for securing a pre-tied knot about the chamber, the housing defining a channel to allow a portion of a surgical suturing instrument to be received through the knot to deploy the knot thereon. The cartridge further comprises a base coupled to the housing, the base defining a seat for releasably holding an end (a portion) of a suture, the seat being moveable relative to the chamber (housing) to bring the suture end into alignment with a suture receiving passage of a suture passing member when a portion the suturing instrument is received through the channel within the chamber for permitting transfer of the suture end from the seat within the cartridge into the suture receiving passage.

In another example, embodiments of the present invention comprise a cartridge for loading a suture onto a surgical suturing instrument and for loading a pre-tied knot formed from the suture onto the suturing instrument, the surgical suturing instrument of the type having a suture passing member defining a suture receiving passage therein. The cartridge comprises a housing defining a chamber comprising a (means for mounting/securing) mount for securing a pre-tied knot about the chamber, the housing defining a channel to allow a portion of a surgical suturing instrument to be received through the knot to deploy the knot thereon. The cartridge additionally provides a base coupled to the housing, defining a seat for releasably holding an end of a suture, the base comprising a restraint for positioning a portion of the suturing instrument received through the chamber relative to the seat for aligning the seat with a suture receiving passage of the suturing instrument.

In another example, embodiments of the present invention comprise a cartridge for loading a suture onto a surgical suturing instrument of the type having a suture receiving passage therein. The cartridge comprises a chamber defining a recess (aperture) for axially receiving a distal portion of a suturing instrument. The cartridge further comprises a seat adjacent to the recess for releasably holding a portion of a suture, and additionally provides a restraint (means for restraining) for positioning a portion of the suturing instrument received through the chamber relative to the seat for aligning the seat with a suture receiving passage of the suturing instrument to permit transfer of the suture portion from the seat into the suture receiving passage.

In an additional example, embodiments of the present invention comprise a method for loading suture onto a surgical suturing instrument, the suture comprising suture loops formed from the suture and for loading an end of the suture where the surgical suturing instrument is of the type having a suture passing member which defines a suture receiving passage. The method comprises the steps of: mounting the suture loops onto a surgical suturing instrument positioned there-through; aligning the suture end with the suture receiving passage of the suture passing member; and transferring the suture end into the suture receiving passage of the suture passing member.

In still another example, embodiments of the present invention comprise a method for suturing within an inter-vertebral disc, the method comprising the steps of: loading a suture onto a surgical suturing instrument using a cartridge; and using the surgical suturing instrument to deliver the suture into the inter-vertebral disc.

In an additional example, embodiments of the present invention comprise a cartridge for loading a ferrule with a suture coupled thereto, onto a surgical suturing instrument of the type having a ferrule receiving passage. The cartridge comprises a housing defining a chamber for holding a pre-tied knot about the chamber, the chamber defining a recess (aperture) for receiving a distal end of a suturing instrument. The cartridge additionally comprises a base detachably coupled to the housing. The base defines a seat adjacent to the recess for releasably holding a ferrule having one end of a suture attached thereto. In some embodiments, a cartridge is provided that is structured to allow the seat to be brought into alignment with a ferrule receiving passage of the suturing instrument when the suturing instrument is positioned within the recess for permitting transfer of the ferrule from the seat within the cartridge into the ferrule receiving passage.

In another example, embodiments of the present invention comprise a cartridge for loading a ferrule with a suture coupled thereto, onto a surgical suturing instrument of the type having a ferrule receiving passage. The cartridge comprises a chamber defining a recess (aperture) for receiving a portion of the suturing instrument for allowing axial movement between them. The cartridge additionally comprises a seat adjacent to the recess for releasably holding a ferrule having one end of a suture attached thereto. In some embodiments, the chamber and the suturing instrument are moveable with respect to each other to allow the seat to be to be brought into alignment with the ferrule receiving passage to permit transfer of the ferrule from the seat into the ferrule receiving passage.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A cartridge for loading suture onto a suture passing instrument, the cartridge comprising:
   a base comprising a seat configured for releasably holding a portion of the suture; and
   a housing coupled to the base wherein the housing includes a suture transferring component for transferring the suture portion from the seat onto the suture passing instrument;
   the cartridge being configured to allow relative movement between the seat and the housing for aligning the suture portion with the suture passing instrument;
   wherein the suture transferring component comprises a push mechanism operable to be moved towards the suture passing instrument received within the cartridge to push the suture into the suture passing instrument.

2. The cartridge of claim 1, wherein the housing defines a chamber for receiving the suture passing instrument there-through.

3. The cartridge of claim 2, further comprising a partially pre-tied knot releasably coupled to the chamber for deployment onto the suture passing instrument, the partially pre-tied knot being formed from the suture.

4. The cartridge of claim 3, wherein the housing is detachable from the base to be mounted onto the suture passing instrument for deploying the partially pre-tied knot about the suture passing instrument.

5. The cartridge of claim 2, wherein the seat comprises a moveable seat for permitting transfer of the suture portion from the seat into the suture passing instrument.

6. The cartridge of claim 2, wherein the seat is moveable relative to the chamber.

7. The cartridge of claim 2, wherein the base comprises a restraint for maintaining a position of the suture passing instrument received through the chamber relative to the seat for aligning the seat with a portion of the suture passing instrument.

8. The cartridge of claim 2, wherein the chamber includes a recess for axially receiving a distal portion of the suture passing instrument there-through, the seat being positioned substantially adjacent the recess.

9. The cartridge of claim 2, wherein the seat is configured to move automatically upon receipt of the suture passing instrument within the cartridge.

10. The cartridge of claim 2, wherein the chamber includes a longitudinally extending recess for receiving the suture passing instrument there-through.

11. The cartridge of claim 2, wherein the housing comprises a mount defining the chamber for holding a pre-tied knot about the chamber, whereby the suture passing instrument is receivable within the chamber for allowing the pre-tied knot to be mounted onto the suture passing instrument.

12. The cartridge of claim 1, wherein the seat is moveable relative to another section of the base.

13. The cartridge of claim 1, wherein the suture portion comprises an end of the suture.

14. The cartridge of claim 1, wherein the cartridge is configured to align and transfer the suture upon a single linear motion of the cartridge with respect to the suture passing instrument.

15. A cartridge for loading a suture onto a suturing instrument, the cartridge comprising:
   a housing comprising a chamber defining a recess for axially receiving a distal portion of the suturing instrument therethrough;
   a seat adjacent the recess for releasably holding a portion of the suture; and
   a restraint configured for constraining movement of the suturing instrument relative to the seat, for facilitating alignment of the seat with the suturing instrument received through the recess to permit transfer of the suture portion from the seat into the suturing instrument;
   the cartridge being configured to allow relative movement between the seat and the housing for aligning the suture portion with the suturing instrument;
   wherein the housing includes a suture transferring component for transferring the suture portion from the seat onto the suturing instrument, wherein the suture transferring component comprises a push mechanism operable to be moved towards the suturing instrument received within the cartridge to push the suture into the suturing instrument.

16. The cartridge of claim 15, wherein the suture portion comprises a knot.

17. A method of suturing an intervertebral disc, the method comprising the steps of:
   loading a suture onto a suturing instrument at a point of use comprising:
   inserting the suturing instrument into a cartridge, the cartridge comprising a base comprising a seat configured for releasably holding a portion of the suture, and a housing coupled to the base comprising a suture transferring component;
   aligning the portion of the suture with the suturing instrument by moving the seat relative to the housing;
   transferring the suture portion from the seat onto the suturing instrument, wherein the suture transferring component comprises a push mechanism operable to push a suture for transferring into the suturing instrument; and
   passing the suture through at least a portion of the intervertebral disc using the suturing instrument.

18. The method of claim 17, wherein the suture comprises suture loops and terminates in the suture end, the method comprising the steps of:

Using the cartridge to align the suture end with a suture receiving passage of the suturing instrument; and transferring the suture loops onto the suturing instrument.

19. The method of claim 17, wherein the step of aligning the suture portion with the suturing instrument further comprises causing the seat of the cartridge to move automatically to align the portion of the suture with a suture receiving passage of the suturing instrument.

20. The method of claim 17, wherein the intervertebral disc has a defect therein, the method further comprising the step of:

substantially approximating the defect in the intervertebral disc using the suture.

21. A suturing system comprising:

a suturing instrument defining a tissue receiving gap and comprising a suture passing member defining a suture receiving passage therein; and a cartridge, the cartridge comprising:
  a base comprising a seat configured for releasably holding a suture portion;
  a housing coupled to the base wherein the housing includes a suture transferring component for transferring the suture portion from the seat onto the suturing instrument;
  the cartridge being configured to allow relative movement between the seat and the housing for aligning the suture portion with the suturing instrument;
  wherein the suture transferring component comprises a push mechanism operable to be moved towards the suturing instrument received within the cartridge to push the suture portion into the suturing instrument.

22. The suturing system of claim 21, wherein the seat is automatically moveable upon advancement of the suturing instrument within the cartridge to align the suture portion with the suture receiving passage.

23. The suturing system of claim 22, wherein the suture passing member comprises a needle.

24. The suturing system of claim 23, wherein the seat is defined by a projection comprising a projection bevel face for engaging in abutting contact with a needle bevel face defined by the needle, the projection bevel face and the needle bevel face configured to cooperatively engage to dock the seat substantially adjacent the needle to enable transfer of the suture portion.

25. The suturing system of claim 21, wherein the cartridge comprises a knot slider.

* * * * *